US009809647B2

(12) United States Patent
Imai et al.

(10) Patent No.: US 9,809,647 B2
(45) Date of Patent: *Nov. 7, 2017

(54) NEUTRALIZING ANTI-CCL20 ANTIBODIES

(71) Applicant: Eisai R&D Management Co., Ltd., Tokyo (JP)

(72) Inventors: Toshio Imai, Kyoto (JP); James Bradford Kline, Morgantown, PA (US); Tetsu Kawano, Kobe (JP); Luigi Grasso, Bryn Mawr, PA (US); Yoshimasa Sakamoto, Nishinomiya (JP); Jared Spidel, Downingtown, PA (US); Miyuki Nishimura, Kobe (JP); Kenzo Muramoto, Tsukuba (JP); Tatsuo Horizoe, Moriya (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,989

(22) Filed: Aug. 3, 2015

(65) Prior Publication Data

US 2016/0046707 A1 Feb. 18, 2016

Related U.S. Application Data

(60) Continuation of application No. 13/924,433, filed on Jun. 21, 2013, now Pat. No. 9,133,273, which is a division of application No. 13/300,352, filed on Nov. 18, 2011, now Pat. No. 8,491,901.

(60) Provisional application No. 61/415,614, filed on Nov. 19, 2010.

(51) Int. Cl.
*C07K 16/24* (2006.01)
*G01N 33/68* (2006.01)
*A61K 39/00* (2006.01)

(52) U.S. Cl.
CPC ......... *C07K 16/24* (2013.01); *G01N 33/6863* (2013.01); *A61K 2039/505* (2013.01); *C07K 2317/24* (2013.01); *C07K 2317/33* (2013.01); *C07K 2317/34* (2013.01); *C07K 2317/76* (2013.01); *C07K 2317/92* (2013.01); *G01N 2333/521* (2013.01)

(58) Field of Classification Search
CPC ..................................................... C07K 16/24
See application file for complete search history.

(56) References Cited

U.S. PATENT DOCUMENTS

| 4,816,397 A | 3/1989 | Boss et al. |
|---|---|---|
| 4,816,567 A | 3/1989 | Cabilly et al. |
| 4,897,348 A | 1/1990 | Johnson et al. |
| 4,946,778 A | 8/1990 | Ladner et al. |
| 5,011,912 A | 4/1991 | Hopp et al. |
| 5,225,539 A | 7/1993 | Winter |
| 5,278,287 A | 1/1994 | Rollins et al. |
| 5,306,709 A | 4/1994 | Gewirtz |
| 5,346,686 A | 9/1994 | Lyle et al. |
| 5,413,778 A | 5/1995 | Kunkel et al. |
| 5,474,983 A | 12/1995 | Kuna et al. |
| 5,476,786 A | 12/1995 | Huston |
| 5,530,101 A | 6/1996 | Queen et al. |
| 5,585,089 A | 12/1996 | Queen et al. |
| 5,602,008 A | 2/1997 | Wilde et al. |
| 5,693,761 A | 12/1997 | Queen et al. |
| 5,693,762 A | 12/1997 | Queen et al. |
| 5,741,957 A | 4/1998 | Deboer et al. |
| 5,750,172 A | 5/1998 | Meade et al. |
| 5,756,687 A | 5/1998 | Denman et al. |
| 5,821,337 A | 10/1998 | Carter et al. |
| 5,827,690 A | 10/1998 | Meade et al. |
| 5,859,205 A | 1/1999 | Adair et al. |
| 5,929,212 A | 7/1999 | Jolliffe et al. |
| 5,936,068 A | 8/1999 | Wilde et al. |
| 5,959,177 A | 9/1999 | Hein et al. |
| 5,981,230 A | 11/1999 | Li et al. |
| 6,001,649 A | 12/1999 | Caput et al. |
| 6,046,037 A | 4/2000 | Hiatt et al. |
| 6,054,297 A | 4/2000 | Carter et al. |
| 6,057,426 A | 5/2000 | Lesslauer et al. |

(Continued)

FOREIGN PATENT DOCUMENTS

| EP | 0125023 | 6/1991 |
|---|---|---|
| EP | 0120694 | 7/1993 |
| EP | 0194276 | 8/1993 |
| EP | 0239400 | 8/1994 |
| EP | 0 460 171 | 6/1995 |
| EP | 0 460 167 | 10/1995 |
| EP | 0 451 216 | 1/1996 |
| EP | 0 460 178 | 10/1997 |
| EP | 0 538 030 | 8/1998 |
| EP | 0 939 127 | 9/1999 |

(Continued)

OTHER PUBLICATIONS

EP 0 807 439, search report, dated Jan. 23, 1998, SmithKline Beecham Corporation.
EP 1 006 188, search report, dated Apr. 14, 2000, Human Genome Sciences, Inc.
GenBank Accession No. D17181 (Jun. 21, 1993).
GenBank Accession No. T27336 (Dec. 6, 1994).
GenBank Accession No. T27433 (Dec. 6, 1994).
GenBank Accession No. D31065 (Feb. 8, 1995).
GenBank Accession No. 164134 (Feb. 17, 1995).

(Continued)

*Primary Examiner* — Prema Mertz
(74) *Attorney, Agent, or Firm* — Foley & Lardner LLP; Karen Mangasarian; Gitanjali Chimalakonda

(57) ABSTRACT

The present invention relates to novel humanized, chimeric and murine antibodies that have binding specificity for the human CC chemokine ligand 20 (CCL20). The present invention further relates to heavy chains and light chains of said antibodies. The invention also relates to isolated nucleic acids, recombinant vectors and host cells that comprise a sequence which encodes a heavy chain and/or a light chain of said antibodies, and to a method of preparing said antibodies. The anti-CCL20 antibodies of the invention can be used in therapeutic applications to treat, for example, inflammatory and autoimmune disorders and cancer.

7 Claims, 50 Drawing Sheets

(56) References Cited

U.S. PATENT DOCUMENTS

| | | | |
|---|---|---|---|
| 6,096,300 A | 8/2000 | Hromas | |
| 6,174,995 B1 | 1/2001 | Li et al. | |
| 6,180,370 B1 | 1/2001 | Queen et al. | |
| 6,331,415 B1 | 12/2001 | Cabilly et al. | |
| 6,407,213 B1 | 6/2002 | Carter et al. | |
| 6,417,429 B1 | 7/2002 | Hein et al. | |
| 6,458,349 B1 | 10/2002 | Li et al. | |
| 6,537,794 B1 | 3/2003 | Lesslauer et al. | |
| 6,548,640 B1 | 4/2003 | Winter | |
| 6,632,927 B2 | 10/2003 | Adair et al. | |
| 6,639,055 B1 | 10/2003 | Carter et al. | |
| 6,645,491 B1 | 11/2003 | Oldham et al. | |
| 6,673,344 B1 | 1/2004 | Li et al. | |
| 6,719,971 B1 | 4/2004 | Carter et al. | |
| 6,750,325 B1 | 6/2004 | Jolliffe et al. | |
| 6,800,738 B1 | 10/2004 | Carter et al. | |
| 6,921,645 B2 | 7/2005 | Li et al. | |
| 7,022,500 B1 | 4/2006 | Queen et al. | |
| 7,241,877 B2 | 7/2007 | Adair et al. | |
| 7,244,615 B2 | 7/2007 | Adair et al. | |
| 7,244,832 B2 | 7/2007 | Adair et al. | |
| 7,262,050 B2 | 8/2007 | Adair et al. | |
| 7,264,806 B2 | 9/2007 | Carr et al. | |
| 7,282,338 B2 | 10/2007 | Wei et al. | |
| 7,375,192 B2 | 5/2008 | Rosen et al. | |
| 7,396,653 B2 | 7/2008 | Wei et al. | |
| 7,442,512 B2 | 10/2008 | Burns et al. | |
| 7,468,253 B2 | 12/2008 | Wei | |
| 7,566,771 B1 | 7/2009 | Adair et al. | |
| 7,662,623 B2 | 2/2010 | Fang et al. | |
| 7,943,741 B2 | 5/2011 | Rosen et al. | |
| 8,491,901 B2 * | 7/2013 | Imai | C07K 16/24 424/141.1 |
| 2003/0049683 A1 | 3/2003 | Bowdish et al. | |
| 2003/0103976 A1 | 6/2003 | Serizawa et al. | |
| 2005/0069541 A1 | 3/2005 | Karlik et al. | |
| 2005/0123534 A1 | 6/2005 | Adair et al. | |
| 2006/0029593 A1 | 2/2006 | Adair et al. | |
| 2006/0073136 A1 | 4/2006 | Adair et al. | |
| 2006/0073137 A1 | 4/2006 | Adair et al. | |
| 2006/0228349 A1 | 10/2006 | Acton et al. | |
| 2006/0251658 A1 | 11/2006 | Ledbetter et al. | |
| 2006/0263364 A1 | 11/2006 | Vicari et al. | |
| 2007/0238644 A1 | 10/2007 | Li et al. | |
| 2009/0162931 A1 | 6/2009 | Bristol et al. | |
| 2010/0016556 A1 | 1/2010 | Carter et al. | |
| 2010/0056764 A1 | 3/2010 | Ursø et al. | |

FOREIGN PATENT DOCUMENTS

| | | |
|---|---|---|
| EP | 0 940 468 | 9/1999 |
| EP | 0 488 900 | 2/2001 |
| EP | 0 626 390 | 11/2001 |
| EP | 0 807 439 | 4/2003 |
| EP | 0 566 647 | 10/2003 |
| EP | 0 590 058 | 11/2003 |
| EP | 1 386 932 | 2/2004 |
| EP | 0 777 494 | 3/2004 |
| EP | 1 400 536 | 3/2004 |
| EP | 1 477 497 | 11/2004 |
| EP | 0519596 | 2/2005 |
| EP | 1 006 188 | 12/2006 |
| EP | 1 417 488 | 12/2006 |
| GB | 2209757 | 5/1989 |
| JP | 7089866 | 4/1995 |
| WO | WO 86/01533 | 3/1986 |
| WO | WO 89/07142 | 8/1989 |
| WO | WO 90/006321 | 6/1990 |
| WO | WO 90/007861 | 7/1990 |
| WO | WO 91/004274 | 4/1991 |
| WO | WO 91/009966 | 7/1991 |
| WO | WO 91/009967 | 7/1991 |
| WO | WO 91/009968 | 7/1991 |
| WO | WO 91/012815 | 9/1991 |
| WO | WO 92/01047 | 1/1992 |
| WO | WO 92/03918 | 3/1992 |
| WO | WO 92/005198 | 4/1992 |
| WO | WO 92/011018 | 7/1992 |
| WO | WO 92/020372 | 11/1992 |
| WO | WO 92/022653 | 12/1992 |
| WO | WO 93/06213 | 4/1993 |
| WO | WO 94/04679 | 3/1994 |
| WO | WO 94/26087 | 11/1994 |
| WO | WO 94/29351 | 12/1994 |
| WO | WO 95/017092 | 6/1995 |
| WO | WO 95/031467 | 11/1995 |
| WO | WO 95/031468 | 11/1995 |
| WO | WO 96/006169 | 2/1996 |
| WO | WO 96/009062 | 3/1996 |
| WO | WO 96/14328 | 5/1996 |
| WO | WO 96/016979 | 6/1996 |
| WO | WO 96/34095 | 10/1996 |
| WO | WO 96/005856 | 12/1996 |
| WO | WO 96/039520 | 12/1996 |
| WO | WO 96/039521 | 12/1996 |
| WO | WO 96/039522 | 12/1996 |
| WO | WO 97/015594 | 5/1997 |
| WO | WO 97/015595 | 5/1997 |
| WO | WO 97/031098 | 8/1997 |
| WO | WO 97/33899 | 9/1997 |
| WO | WO 97/33904 | 9/1997 |
| WO | WO 97/035982 | 10/1997 |
| WO | WO 98/001557 | 1/1998 |
| WO | WO 98/06842 | 2/1998 |
| WO | WO 98/07880 | 2/1998 |
| WO | WO 98/009171 | 3/1998 |
| WO | WO 98/011226 | 3/1998 |
| WO | WO 98/014573 | 4/1998 |
| WO | WO 98/017800 | 4/1998 |
| WO | WO 98/18921 | 5/1998 |
| WO | WO 98/021330 | 5/1998 |
| WO | WO 98/30693 | 7/1998 |
| WO | WO 98/30694 | 7/1998 |
| WO | WO 98/32856 | 7/1998 |
| WO | WO 98/41629 | 9/1998 |
| WO | WO 98/52976 | 11/1998 |
| WO | WO 98/54202 | 12/1998 |
| WO | WO 98/56892 | 12/1998 |
| WO | WO 99/047674 | 9/1999 |
| WO | WO 00/09560 | 2/2000 |
| WO | WO 00/34317 | 6/2000 |
| WO | WO 00/046248 | 8/2000 |
| WO | WO 01/66754 | 9/2001 |
| WO | WO 02/032456 | 4/2002 |
| WO | WO 02/101350 | 12/2002 |
| WO | WO 03/047420 | 6/2003 |
| WO | WO 03/48731 | 6/2003 |
| WO | WO 03/092597 | 11/2003 |
| WO | WO 07/083759 | 7/2007 |
| WO | WO 09/156994 | 12/2009 |
| WO | WO 10/037837 | 4/2010 |
| WO | WO 13/005649 | 1/2013 |

OTHER PUBLICATIONS

GenBank Accession No. T64262 (Feb. 17, 1995).
GenBank Accession No. U46767 (Jan. 22, 1996).
GenBank Accession No. CAA66950 (Jun. 4, 1996).
GenBank Accession No. X98306 (Jun. 4, 1996).
GenBank Accession No. AAB61534.1 (Jul. 17, 1996).
GenBank Accession No. CAB01111 (Jul. 30, 1996).
GenBank Accession No. CAB01112 (Jul. 30, 1996).
GenBank Accession No. Z77650 (Jul. 30, 1996).
GenBank Accession No. Z77651 (Jul. 30, 1996).
GenBank Accession No. CAA04888 (Sep. 10, 1996).
GenBank Accession No. W44398 (Oct. 11, 1996).
GenBank Accession No. AAC50943.1 (Oct. 31, 1996).
GenBank Accession No. U77035 (Oct. 31, 1996).
GenBank Accession No. AAB38703 (Dec. 16, 1996).
GenBank Accession No. I35613 (Feb. 22, 1997).
GenBank Accession No. D86955 (Mar. 6, 1997).

(56) References Cited

OTHER PUBLICATIONS

GenBank Accession No. AA297433 (Apr. 18, 1997).
GenBank Accession No. AA403048 (May 16, 1997).
GenBank Accession No. AA404346 (May 16, 1997).
GenBank Accession No. U64197 (Jun. 25, 1997).
GenBank Accession No. AJ000979 (Jun. 30, 1997).
GenBank Accession No. AC002482 (Aug. 21, 1997).
GenBank Accession No. AJ001634 (Sep. 10, 1997).
GenBank Accession No. AA426245 (Oct. 16, 1997).
GenBank Accession No. AA739063 (Jan. 14, 1998).
GenBank Accession No. W61279 (Sep. 24, 1998).
GenBank Accession No. AI735669 (Jun. 14, 1999).
GenBank Accession No. AI925360 (Sep. 2, 1999).
GenBank Accession No. AAR29479 (Sep. 3, 2003).
GenBank Accession No. AAW57475 (Aug. 18, 2004).
Genbank Accession No. AAW56690 (Nov. 18, 2004).
Geneseq Accession No. AAR29479 (Apr. 22, 1993).
Geneseq Accession No. AAR93087 (Aug. 27, 1996).
Geneseq Accession No. R95690 (Dec. 20, 1996).
Geneseq Accession No. W17660 (Dec. 16, 1997).
Geneseq Accession No. AAW22670 (Mar. 19, 1998).
Geneseq Accession No. T90880 (May 21, 1998).
Geneseq Accession No. T90883 (May 21, 1998).
Geneseq Accession No. W30191 (May 21, 1998).
Geneseq Accession No. W44398 (Jun. 11, 1998).
Geneseq Accession No. V28591 (Aug. 17, 1998).
Geneseq Accession No. W56087 (Aug. 17, 1998).
Abiko et al., "Expression of MIP-3alpha/CCL20, a macrophage inflammatory protein in oral squamous cell carcinoma," *Arch. Oral Biol.*, 48(2):171-175 (2003).
Adema et al., "A dendritic-cell-derived C-C chemokine that preferentially attracts naive T cells," *Nature*, 387:713-717 (1997).
Akahoshi et al., "Production of macrophage inflammatory protein 3 (MIP-3) (CCL20) and MIP-3 (CCL 19) by human peripheral blood neutrophils in response to microbial pathogens," *Infect. Immun.*, 71(1):524-526 (2003).
Altschul et al., "Basic local alignment search tool," J. Mol. Biol., 215:403-410 (1990).
Altschul et al., "Gapped Blast and PSI-Blast: a new generation of protein database search programs," Nucleic Acids Res., 25:3389-3402 (1997).
Ambrosini et al., "Astrocytes are the major intracerebral source of macrophage inflammatory protein-3alpha/CCL20 in relapsing experimental autoimmune encephalomyelitis and in vitro," *Glia*, 41(3):290-300 (2003).
Amit et al., "Three-dimensional structure of an antigen-antibody complex at 2.8 A resolution," *Science*, 233:747-753 (1986).
Annunziato, "Type 17 T helper cells-origins, features and possible roles in rheumatic disease," *Nat. Rev. Rheumatol.* 5(6):325-331 (2009).
Aoki et al., "Dysregulated generation of follicular helper T cells in the spleen triggers fatal autoimmune hepatitis in mice," Gastroenterology, 140(4):1322-1333 (2011).
Beider et al., "Interaction between CXCR4 and CCL20 pathways regulates tumor growth," *PloS One*, 4(4):e5125 (2009).
Bennouna et al., "Cross-talk in the innate immune system: neutrophils instruct recruitment and activation of dendritic cells during microbial infection," *J. Immunol.*, 171:6052-6058 (2003).
Berger, "Isolation of Monocyte Chemotactic Protein-4," *Clinical Res.*, 42(2):305A (1994).
Bird et al., "Single-chain antigen-binding proteins," Science, 242:423-426 (1988).
Bischoff et al., "Monocyte Chemotactic Protein 1 Is a Potent Activator of Human Basophils," *J. Exp. Med.*, 175:1271-1275 (1992).
Blum et al., "Three Human Homologs of a Murine Gene Encoding an Inhibitor of Stem Cell Proliferation," *DNA and Cell Biol.*, 9(8):589-602 (1990).

Bowie et al., "Deciphering the message in protein sequences: tolerance to amino acid substitutions," *Science*, 247:1306-1310 (1990).
Brown et al., "A Family of Small Inducible Proteins Secreted by Leukocytes are Members of a New Superfamily that Includes Leukocyte and Fibroblast-Derived Inflammatory Agents, Growth Factors, and Indicators of Various Activation Processes," *J. Immunol.*, 142(2):679-687 (1989).
Brown et al., "Tolerance of single, but not multiple, amino acid replacements in antibody VH CDR 2: a means of minimizing B cell wastage from somatic hypermutation?" J Immunol, 156:3285-3291 (1996).
Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 111:2129-2138 (1990).
Caberg et al., "Increased migration of Langerhans cells in response to HPV16 E6 and E7 oncogene silencing: role of CCL20," *Cancer Immunology Immunotherapy* 58(1):39-47 (2009).
Caruso et al., "A functional role for interleukin-21 in promoting the synthesis of the T-cell chemoattractant, MIP-3alpha, by gut epithelial cells," *Gastroenterology*, 132(1):166-175 (2007).
Charbonnier et al., "Macrophage inflammatory protein 3alpha is involved in the constitutive trafficking of epidermal Langerhans cells," *J. Exp. Med.*, 190(12):1755-68 (1999).
Chevrel et al., Interleukin-17 increases the effects of IL-1 beta on muscle cells: arguments for the role of T cells in the pathogenesis of myositis, Journal of Neuroimmunology, 137(1-2): 125-133 (2003).
Chothia et al., "Canonical Structures for the Hypervariable Regions of Immunoglobulins," J. Mol. Biol., 196:901-917 (1987).
Clements et al., "Biological and Structural Properties of MIP-1a Expressed in Yeast," *Cytokine*, 4(1):76-82 (1992).
Craddock et al., "Antibodies to VLA4 integrin mobilize long-term repopulating cells and augment cytokine-induced mobilization in primates and mice," *Blood*, 90(12):4779-4788 (1997).
Crane-Godreau et al., "Exposure to Cigarette Smoke Disrupts CCL20-Mediated Antimicrobial Activity in Respiratory Epithelial Cells," *Open Immunology Journal*, 2:86-93 (2009).
Cremel et al., "Characterization of CCL20 secretion by human epithelial vaginal cells: involvement in Langerhans cell precursor attraction," *Journal of Leukocyte Biology*, 78(1):158-166 (2005).
Crittenden et al., "Expression of inflammatory chemokines combined with local tumor destruction enhances tumor regression and long-term immunity," *Cancer Res.*, 63:5505-5512 (2003).
Cruse et al., "Illustrated Dictionary of Immunology," 1995 by CRC Press, p. 241.
Dailey et al., "Sequences in the polyomavirus DNA regulatory region involved in viral DNA replication and early gene expression," J. Virol. 54:739-749 (1985).
Daugherty et al., "Polymerase chain reaction facilitates the cloning, CDR-grafting, and rapid expression of a murine monoclonal antibody directed against the CD18 component of leukocyte integrins," Nucleic Acids Res., 19:2471-2476 (1991).
Davies et al., "Affinity improvement of single antibody VH domains: residues in all three hypervariable regions affect antigen binding," Immunotechnology, 2:169-179 (1996).
Dereeper et al., "Phylogeny.fr: robust phylogenetic analysis for the non-specialist," Nucleic Acids Res., 1:W465-469 (2008).
Derynck et al., "Recombinant Expression, Biochemical Characterization, and Biological Activities of the Human MGSA/gro Protein," *Biochem.*, 29(44):10225-10233 (1990).
Dieu-Nosjean et al., "Macrophage inflammatory protein 3 is expressed at inflamed epithelial surfaces and is the most potent chemokine known in attracting Langerhans cell precursors," *J. Exp. Med.*, 192(5):705-717 (2000).
Dohlman et al., "The CCR6/CCL20 axis mediates Th17 cell migration to the ocular surface in dry eye disease," *Invest Ophthalmol Vis Sci.*, 54:4081-4091 (2013).

(56) References Cited

OTHER PUBLICATIONS

Elliott et al., "Fine-Structure Epitope Mapping of Antierythropoietin Monoclonal Antibodies Reveals a Model of Recombinant Human Erythropoietin Structure," Blood, 87:2702-2713 (1996).
Fahy et al., "Control of *Salmonella dissemination* in vivo by macrophage inflammatory protein (MIP)-3alpha/CCL20," *Laboratory Investigation*, 84(11):1501-1511 (2004).
Furuta et al., "Production and Characterization of Recombinant Human Neutrophil Chemotactic Factor," *J. Biochem.*, 106:436-441 (1989).
Fushimi et al., "Macrophage inflammatory protein 3alpha transgene attracts dendritic cells to established murine tumors and suppresses tumor growth," *J. Clin. Invest.*, 105(10):1383-1393 (2000).
Garcia-Zepeda et al., "Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3," *J. Immunol.*, 157(12):5613-5626 (1996).
George et al., "Current Methods in Sequence Comparison and Analysis, Macromolecular Sequencing & Synthesis," Alan R. Liss, Inc. Ch. 12, pp. 127-149 (1988).
Giuliani et al., "CC-chemokine ligand 20/macrophage inflammatory protein-3α and CC-chemokine receptor 6 are overexpressed in myeloma microenvironment related to osteolytic bone lesions," *Cancer Research*, 68(16):6840-6850 (2008).
Giusti et al., "Somatic diversification of S107 from an antiphosphocholine to an anti-DNA autoantibody is due to a single base change in its heavy chain variable region," Proc Natl Acad Sci USA, 84:2926-2930 (1987).
Glover, David M., "Gene Cloning: The Mechanics of DNA Manipulation," Chapman and Hall, London and New York, Ch.1-8, pp. 1-218 (1984).
Gonnet et al., "Exhaustive matching of the entire protein sequence database," Science 256:1443-1445 (1992).
Graham et al., "SCI/MIP-1 Alpha: A Potent Stem Cell Inhibitor with Potential Roles in Development," *Develop. Biol.*, 151:377-381 (1992).
Griffiths et al., "Comparison of ustekinumab and etanercept for moderate-to-severe psoriasis," *N. Engl. J. Med.*, 362(2):118-28 (2010).
Griffiths et al., "Human anti-self antibodies with high specificity from phage display libraries," EMBO J., 12:725-734 (1993).
Griswold et al., "Effect of inhibitors of eicosanoid metabolism in murine collagen-induced arthritis," Arthritis & Rheumatism, 31:1406-1412 (1988).
Harper et al., "Th17 cytokines stimulate CCL20 expression in keratinocytes in vitro and in vivo: implications for psoriasis pathogenesis," *J. Invest. Dermatol.* 129(9):2175-83 (2009).
Hedrick et al., "CCR6 is required for IL-23-induced psoriasis-like inflammation in mice," J. Clin. Invest., 119:2317-2329 (2009).
Hieshima et al., "A Novel Human CC Chemokine PARC That Is Most Homologous to Macrophage-Inflammatory Protein-1α /LD78 Alpha and Chemotactic for T Lymphocytes, but Not for Monocytes," *J. Immunol.*, 159:1140-1149 (1997).
Hieshima et al., "Molecular Cloning of a Novel Human CC Chemokine Liver and Activation-regulated Chemokine (LARC) Expressed in Liver," *J. Biol. Chem.*, 272(9):5846-5853 (1997).
Holliger et al., "Diabodies": small bivalent and bispecific antibody fragments, Proc. Natl. Acad. Sci. USA, 90:6444-6448 (1993).
Holt et al., "Domain antibodies: proteins for therapy," Trends Biotechnol, 21:484-490 (2003).
Homey et al., "Up-regulation of macrophage inflammatory protein-3/CCL20 and CC chemokine receptor 6 in psoriasis," *J. Immunol.*, 164:6621-6632 (2000).
Hoover et al., "The structure of human macrophage inflammatory protein-3alpha/CCL20-linking antimicrobial and CC chemokine receptor-6-binding activities with human beta-defensins," *J. Biol. Chem.*, 277(40):37647-37654 (2002).
Hosokawa et al., "Macrophage inflammatory protein 3alpha-CC chemokine receptor 6 interactions play an important role in CD4+ T-cell accumulation in periodontal diseased tissue," *Clin. Exp. Immunol.*, 128(3):548-554 (2002).
Hromas et al., "Cloning and Characterization of Exodus, a Novel β-Chemokine," *Blood*, 89(9):3315-3322 (1997).
Hung et al., "Promoting dendritic cell migration by airway epithelial cells through interleukin-17A-induced CCL20 Expression," FASEB Journal, Experimental Biology Meeting 2010 (Abstract only).
Huston et al., "Protein engineering of antibody binding sites: recovery of specific activity in an anti-digoxin single-chain Fv analogue produced in *Escherichia coli*," Proc. Natl. Acad. Sci. USA, 85:5879-5883 (1988).
Ill et al., "Design and construction of a hybrid immunoglobulin domain with properties of both heavy and light chain variable regions," Protein Eng., 10:949-957 (1997).
Inoue et al., "Effect of etodolac on type-II collagen-induced arthritis in mice," Agents Actions, 39:187-194 (1993).
Iwamoto et al., "IFN-γ is reciprocally involved in the concurrent development of organ-specific autoimmunity in the liver and stomach," Autoimmunity, 45(2):186-198 (2012).
Iwamoto et al., "TNF-α is essential in the induction of fatal autoimmune hepatitis in mice through upregulation of hepatic CCL20 expression," Clinical Immunology,146(1):15-25 (2012).
Jespers et al., "Aggregation-resistant domain antibodies selected on phage by heat denaturation," Nature Biotechnology, 22:1161-1165 (2004).
Jia et al., "A novel method of Multiplexed Competitive Antibody Binning for the characterization of monoclonal antibodies," J. Immunol. Methods, 288:91-98 (2004).
Jose et al., "Eotaxin: A Potent Eosinophil Chemoattractant Cytokine Detected in a Guinea Pig Model of Allergic Airways Inflammation," *J. Exp. Med.*, 179: 881-887 (1994).
Kamman et al.,"Rapid insertional mutagenesis of DNA by polymerase chain reaction (PCR)," Nucl. Acids Res., 17:5404 (1989).
Katchar et al., "MIP-3alpha neutralizing monoclonal antibody protects against TNBS-induced colonic injury and inflammation in mice," Am J Physiol Gastrointest Liver Physiol, 292:G1263-G1271 (2007).
Keller et al.,"T cell-regulated neutrophilic inflammation in autoinflammatory diseases," *J. Immunol*, 175(11):7678-86 (2005).
Kettleborough, "Humanization of a mouse monoclonal antibody by CDR-grafting: the importance of framework residues on loop conformation," Protein Engineering, 4:773-783 (1991).
Kim et al., "Macrophage inflammatory protein 3alpha deficiency in atopic dermatitis skin and role in innate immune response to vaccinia virus," *Journal of Allergy and Clinical Immunology* 119(2):457-463 (2007).
Kitagawa et al., "Inhibition of CCL20 increases mortality in models of mouse sepsis with intestinal apoptosis," *Surgery*, 154:78-88 (2013).
Kleeff et al., "Detection and localization of Mip-3alpha/LARC/ exodus, a macrophage proinflammatory chemokine, and its CCR6 receptor in human pancreatic cancer," *Int. J. Cancer*, 81(4):650-657 (1999).
Kodelja et al., "Alternative Macrophage Activation-Associated CC-Chemokine-1, a Novel Structural Homologue of Macrophage Inflammatory Protein-1a with a TH2-Associated Expression Pattern," *J. Immunol.*, 160(3):1411-1418 (1998).
Kohler et al., "A role for macrophage inflammatory protein-3alpha/ CC chemokine ligand 20 in immune priming during T cell-mediated inflammation of the central nervous system," *J. Immunol.*, 170:6298-6303 (2003).
Kolbinger, "Humanization of a mouse anti-human IgE antibody: a potential therapeutic for IgE-mediated allergies," Protein Engineering, 8:971-980 (1993).
Kuna et al., "Monocyte Chemotactic and Activating Factor Is a Potent Histamine-releasing Factor for Human Basophils," *J. Exp. Med.*, 175:489-493 (1992).
Kurdowska et al., "Biological and Kinetic Characterization of Recombinant Human Macrophage Inflammatory Peptides 2 Alpha

(56) References Cited

OTHER PUBLICATIONS and Beta and Comparison with the Neutrophil Activating Peptide 2 and Interleukin 8," *Cytokine*, 6(2):124-134 (1994).
Kussie et al., "A single engineered amino acid substitution changes antibody fine specificity," J Immunol, 152:146-152 (1994).
Kwon et al., "cDNA sequences of two inducible T-cell genes," *PNAS USA*, 86:1963-1967 (1989).
Kwon et al., "Colonic epithelial cells are a major site of macrophage inflammatory protein 3alpha (MIP-3alpha) production in normal colon and inflammatory bowel disease," *Gut*, 51(6):818-826 (2002).
Lamkhioued et al., "Monocyte chemoattractant protein (MCP)-4 expression in the airways of patients with asthma," *J Respir Grit Care Med.*, 162:723-732 (2000).
Laterveer et al., "Rapid mobilization of hematopoietic progenitor cells in rhesus monkeys by a single intravenous injection of interleukin-8," *Blood*, 87(2):781-788 (1996).
Laterveer, L. et al., "Improved survival of lethally irradiated recipient mice transplanted with circulating progenitor cells mobilized by IL-8 after pretreatment with stem cell factor," *Exp. Hemet.*, 24:1387-1393 (1996).
Lazar et al., "Transforming growth factor alpha: mutation of aspartic acid 47 and leucine 48 results in different biological activities," *Mol. Cell. Biol.*, 8(3):1247-1252 (1988).
Lerner, Richard A., "Tapping the immunological repertoire to produce antibodies of predetermined specificity," *Nature*, 299:592-596 (1982).
Leung et al., "Thymopentin therapy reduces the clinical severity of atopic dermatitis," J. Allergy Clin. Immunol., 85:927-933 (1990).
Lewis et al., "Immunoglobulin complementarity-determining region grafting by recombinant polymerase chain reaction to generate humanised monoclonal antibodies," Gene,101:297-302 (1991).
Liao et al., "Human B cells become highly responsive to macrophage-inflammatory protein-3 alpha/CC chemokine ligand-20 after cellular activation without changes in CCR6 expression or ligand binding," J. Immunol., 168:4871-4880 (2002).
Lin et al., "Selective early production of CCL20, or macrophage inflammatory protein 3alpha, by human mast cells in response to Pseudomonas aeruginosa," *Infect. Immun.*, 71(1):365-373 (2003).
Liu et al., "The granulocyte colony-stimulating factor receptor is required for the mobilization of murine hematopoietic progenitors into peripheral blood by cyclophosphamide or interleukin-8 but not fit-3 ligand," *Blood*, 90(7):2522-2528 (1997).
Liu et al., "Fine mapping of the antigen-antibody interaction of scFv215, a recombinant antibody inhibiting RNA polymerase II from *Drosophila melanogaster*," J Mol Recognit, 12:103-111 (1999).
Lukacs et al., "The Role of Macrophage Inflammatory Protein 1a in Schistosoma mansoni," *J. Exp. Med.*, 177:1551-1559 (1993).
Malik et al., "Structure of human MIP-3alpha chemokine," Acta Cryst Sec F. Struct Biol Cryst Commun., 62:631-634 (2006).
Martin et al., "The affinity-selection of a minibody polypeptide inhibitor of human interleukin-6," EMBO J.,13:5303-5309 (1994).
Matsui et al., "Selective recruitment of CCR6-expressing cells by increased production of MIP-3 alpha in rheumatoid arthritis," *Clin. Exp. Immunol.*, 125(1):155-161 (2001).
Matsushima et al., "Purification and Characterization of a Novel Monocyte Chemotactic and Activating Factor Produced by a Human Myelomonocytic Cell Line," *J. Exp. Med.*, 169:1485-1490 (1989).
Maynard et al., "Antibody engineering," Annu Rev Biomed Eng, 2:339-376 (2000).
McCafferty et al., "Phage antibodies: filamentous phage displaying antibody variable domains," Nature, 348:552-554 (1990).
Nakao et al., "Structures of Human Genes Coding for Cytokine LD78 and Their Expression," *Molec. Cell. Biol.*, 10(7):3646-3658 (1990).
Nakayama et al., "Inducible expression of a CC chemokine liver- and activation-regulated chemokine (LARC)/macrophage inflammatory protein (MIP)-3 alpha/CCL20 by epidermal keratinocytes and its role in atopic dermatitis," *Int Immunol.*, 13(1):95-103 (2001).
Ngo et al., "The Protein Folding Problem and Tertiary Structure Prediction", Merz, et al. (eds.), Birkhauser, Boston, MA, pp. 433 and 492-495 (1994).
Nishi et al., "Involvement of myeloid dendritic cells in the development of gastric secondary lymphoid follicles in helicobacter pylori-infected neonatally thymectomized BALB/c mice," *Infect. Immun.*, 71(4):2153-2162 (2003).
Obaru et al., "A cDNA Clone Used to Study mRNA Inducible in Human Tonsillar Lymphocytes by a Tumor Promoter," *J. Biochem.*, 99(3):885-894 (1986).
Opdennaker et al., "Human monocyte chemotactic protein-3 (MCP-3): molecular cloning of the cDNA and comparison with other chemokines," *Biochem. Biophys. Res. Commun.*, 191(2):535-542 (1993).
Orloff et al., "The future of drug development: advancing clinical trial design," *Nat. Rev. Drug Discov.*, 8:949-957 (2009).
Osbourn et al., "From rodent reagents to human therapeutics using antibody guided selection," Methods, 36:61-68 (2005).
Panka et al., "Variable region framework differences result in decreased or increased affinity of variant anti-digoxin antibodies," *Proc. Natl. Acad. Sci. USA*, 85:3080-3084 (1988).
Patel et al., "Molecular and functional characterization of two novel human C-C chemokines as inhibitors of two distinct classes of myeloid progenitors," *J. Exp. Med.*, 185(7):1163-1172 (1997).
Pear et al., "Production of high-titer helper-free retroviruses by transient transfection," Proc. Natl. Acad. Sci., 90:8392-8396 (1993).
Pearson, "Flexible sequence similarity searching with the FASTA3 program package," Methods Mol. Biol., 132:185-219 (2000).
Pearson, "Rapid and sensitive sequence comparison with FASTP and FASTA," Methods Enzymol. 183:63-98 (1990).
Pearson, "Using the FASTA program to search protein and DNA sequence databases," Methods Mol. Biol., 243:307-31 (1994).
Pène et al., "Chronically inflamed human tissues are infiltrated by highly differentiated Th17," *J. Immunol.*, 180(11):7423-30 (2008).
Pini et al., "Design and use of a phage display library. Human antibodies with subnanomolar affinity against a marker of angiogenesis eluted from a two-dimensional gel," J Bio Chem, 273:21769-21776 (1998).
Power et al., "Cloning and characterization of a specific receptor for the novel CC chemokine MIP-3alpha from lung dendritic cells," *J. Exp. Med.*, 186(6):825-35 (1997).
Quan et al., "Genome-wide association study for vitiligo identifies susceptibility loci at 6q27 and the MHC," Nature Genetics, 42(7): 614-618 (2010).
RD_system_MAB360, Human CCL20/MIP-3a Antibody, Oct. 7, 2010, [online]. [Retrieved on Feb. 29, 2012]. Retrieved from the Internet: <URL: http://www.mdsystems.com/pdf/mab360.pdf> Specificity; Source; and Background.
Rich et al., "Advancements in the treatment of psoriasis: role of biologic agents," *J. Managed Care Pharmacy*, 10(4):318-325 (2004).
Rudikoff et al., "Single amino acid substitution altering antigen-binding specificity," *Proc. Natl. Acad. Sci. USA*, 79:1979-1983 (1982).
Ruth et al., "Role of macrophage inflammatory protein-3alpha and its ligand CCR6 in rheumatoid arthritis," *Lab. Invest.*, 83(4):579-588 (2003).
Sandhu, "Protein Engineering of Antibodies," *Critical Rev. in Biotechnol.*, 12:437-445 (1992).
Sato et al., "Reshaping a human antibody to inhibit the interleukin 6-dependent tumor cell growth," Cancer Research, 53:851-856 (1993).
Scapini et al., "Neutrophils produce biologically active macrophage inflammatory protein-3alpha (MIP-3alpha)/CCL20 and MIP-3beta/CCL19," *European Journal of Immunology*, 31(7):1981-1988 (2001).
Schall et al., "Molecular cloning and expression of the murine RANTES cytokine: structural and functional conservation between mouse and man," *Eur. J. Immunol.*, 22:1477-1481 (1992).

(56) References Cited

OTHER PUBLICATIONS

Schall, Thomas J., "Biology of the RANTES/SIS Cytokine Family," *Cytokine*, 3(3):165-183 (1991).
Schildbach et al., "Contribution of a single heavy chain residue to specificity of an anti-digoxin monoclonal antibody," Protein Sci, 3:737-749 (1994).
Schildbach et al., "Heavy chain position 50 is a determinant of affinity and specificity for the anti-digoxin antibody 26-10," J Bio Chem, 268:21739-21747 (1993).
Schutyser et al., "The CC chemokine CCL20 and its receptor CCR6," *Cytokine Growth Factor Rev.*, 14(5):409-26 (2003).
Seffernick et al., "Melamine deaminase and atrazine chlorohydrolase: 98 percent identical but functionally different," *J. Bacteriology*, 183:2405-2410 (2001).
Shimizu et al., "CC-chemokine receptor 6 and its ligand macrophage inflammatory protein 3alpha might be involved in the amplification of local necroinflammatory response in the liver," Hepatology, 34(2):311-319 (2001).
Sierro et al., "Flagellin stimulation of intestinal epithelial cells triggers CCL20-mediated migration of dendritic cells," *Proc. Natl. Acad. Sci. USA*, 98(24):13722-13727 (2001).
Skolnick et al., "Structural genomics and its importance for gene function analysis," *Nature Biotechnol.*, 18:283-287 (2000).
Skolnick et al., "From genes to protein structure and function; novel applications of computational approaches in the genomic era," *Trends in Biotech.*, 18:34-39 (2000).
Soga et al., "Use of amino acid composition to predict epitope residues of individual antibodies," Protein Eng Des Sel, 23:441-448 (2010).
Sudo et al., "2058 Expressed Sequence Tags (ESTs) from a Human Fetal Lung cDNA Library," *Genomics*, 24:276-279 (1994).
Sun, "Expression of macrophage inflammatory protein-3alpha in an endometrial epithelial cell line, HHUA, and cultured human endometrial stromal cells," *Mol Hum Reprod.*, 8(10):930-3 (2002).
Taha et al., "Eotaxin and monocyte chemotactic protein-4 mRNA expression in small airways of asthmatic and nonasthmatic individuals," *J Allergy Clin Immunol.*, 103(3, part 1):476-483 (1999).
Taha et al., "Increased expression of the chemoattractant cytokines eotaxin, monocyte chemotactic protein-4, and interleukin-16 in induced sputum in asthmatic patients," *Chest*, 120:595-601 (2001).
Tao et al., "Up-regulation of CC chemokine ligand 20 and its receptor CCR6 in the lesional skin of early systemic sclerosis," European Journal of Dermatology, 21(5):731-736 (2011.
Taub et al., "Chemokines, inflammation and the immune system," *Ther. Immunol.*, 1(4):229-246 (1994).
Teramoto et al., "Increased lymphocyte trafficking to colonic microvessels is dependent on MAdCAM-1 and C-C chemokine mLARC/CCL20 in DSS-induced mice colitis," *Clinical and Experimental Immunology*, 139(3):421-428 (2005).
Terao et al., "Macrophage inflammatory protein-3alpha plays a key role in the inflammatory cascade in rat focal cerebral ischemia," *Neuroscience Research*, 64(1):75-82 (2009).
Tournadre et al., "Expression of Toll-like receptor 3 and Toll-like receptor 7 in muscle is characteristic of inflammatory myopathy and is differentially regulated by Th1 and Th17 cytokines," Arthritis and Rheumatism, 62(7): 2144-2151 (2010).

Traunecker et al., "Bispecific single chain molecules (Janusins) target cytotoxic lymphocytes on HIV infected cells," EMBO J.,10:3655-3659 (1991).
Traunecker et al., "Janusin: new molecular design for bispecific reagents," Int. J. Cancer Suppl., 7:51-52 (1992).
Truchetet et al., "Increased frequency of circulating Th22 in addition to Th17 and Th2 lymphocytes in systemic sclerosis: association with interstitial lung disease," Arthritis Research & Therapy, 13(5):R166 (2011).
Uguccioni et al., "Monocyte Chemotactic Protein 4 (MCP-4), a Novel Structural and Functional Analogue of MCP-3 and Eotaxin," *J. Exp. Med.*, 183:2379-2384 (1996).
Urlaub et al., "Isolation of Chinese hamster cell mutants deficient in dihydrofolate reductase activity," Proc. Natl. Acad. Sci. 77:4216-4220 (1980).
Vajdos et al., "Comprehensive functional maps of the antigen-binding site of an anti-ErbB2 antibody obtained with shotgun scanning mutagenesis," J Mol Bio, 320:415-428 (2002).
Vaughan et al., "Human antibodies with sub-nanomolar affinities isolated from a large non-immunized phage display library," Nature Biotech., 14:309-314 (1996).
Vongsa et al., "CCR6 regulation of the actin cytoskeleton orchestrates human beta defensin-2- and CCL20-mediated restitution of colonic epithelial cells," J Biol Chem., 284:10034-10045 (2009).
Wells, "Additivity of mutational effects in proteins," *Biochemistry*, 29(37):8509-8517 (1990).
Widmer et al., Genomic Cloning and Promoter Analysis of Macrophage Inflammatory Protein (MIP)-2, MIP-1a, and MIP-1β, Members of the Chemokine Superfamily of Proinflammatory Cytokines, *J. Immunol.*, 150(11):4996-5012 (1993).
Wolpe et al., "Identification and characterization of macrophage inflammatory protein 2," *Proc. Natl. Acad. Sci. USA*, 86:612-616 (1989).
Wolpe et al., "Macrophage inflammatory proteins 1 and 2: members of a novel superfamily of cytokines," *FASEB J.*, 3:2565-2573 (1989).
Wolpe et al., "Macrophages secrete a novel heparin-binding protein with inflammatory and neutrophil chemokinetic properties," *J. Exp. Med.*, 167:570-581 (1988).
Xiang et al., "Study of B72.3 combining sites by molecular modeling and site-directed mutagenesis," Protein Eng, 13:339-344 (2000).
Yabe et al., "Treatment of cerebellar granule cell neurons with the neurotrophic factor pigment epithelium-derived factor in vitro enhances expression of other neurotrophic factors as well as cytokines and chemokines," *Journal of Neuroscience Research*, 77(5):642-652 (2004).
Yang et al., "Many chemokines including CCL20/MIP-3alpha display antimicrobial activity," *J. Leukoc. Biol.*, 74(3):448-455 (2003).
Yoshimura et al., "Production and characterization of mouse monoclonal antibodies against human monocyte chemoattractant protein-1," *J Immunol.*, 147:2229-2233 (1991).
Zipfel et al., "Mitogenic Activation of Human T Cells Induces Two Closely Related Genes Which Share Structural Similarities with a New Family of Secreted Factors," *J. Immunol.*, 142(5):1582-1590 (1989).

* cited by examiner

```
Heavy chain_36
Kabat definition         <----------FWR1----------->  <CDR1>  <-----FWR2----->  <------CDR2------>  <----
Chothia definition                                    <--CDR1-->                <--CDR2-->
mouse 36P7C10  1  QVQLQQPGAELVKPGASVRMSCKASGYTFT  NYWMH  WVKQRPGQGLEWIG  VIDPSDSYTTYNQKFKG  KATL  70
HC2            1  QVQLVQSGAEVKKPGASVKVSCKASGYTFT  NYWMH  WVRQAPGQGLEWMG  VIDPSDSYTTYAQKFQG  RVTM  70
HC3            1  QVQLVQSGAEVKKPGASVKVSCKASGYTFT  NYWMH  WVKQAPGQGLEWIG  VIDPSDSYTTYNQKFKG  KATM  70
36HKK3         1  QVQLVQSGAEVKKPGASVKVSCKASGYTFT  NYWMH  WVRQAPGQGLEWMG  VIDPSDSYTTYNQKFKG  KATL  70
ABM67212       1  QVQLVQSGAEVKKPGASVKVSCKASGYTFT  SYYMH  WVRQAPGQGLEWMG  IINPSGGSTSYAQKFQG  RVTM  70
IGHV1-46*03    1  QVQLVQSGAEVKKPGASVKVSCKASGYTFT  SYYMH  WVRQAPGQGLEWMG  IINPSGGSTSYAQKFQG  RVTM  70

Kabat definition         <---------FWR3---------->  <---CDR3--->  <----FWR4--->
Chothia definition                                  <---CDR3--->
mouse 36P7C10  71  TVDTSSSTAYMQLSSLTSEDSAVYYCTR  GNYGVDYAMDY  WGQGTSVTVSS  120
HC2           71  TVDTSTSTVYMELSSLRSEDTAVYYCTR  GNYGVDYAMDY  WGQGTLVTVSS  120
HC3           71  TRDTSTSTVYMELSSLRSEDTAVYYCTR  GNYGVDYAMDY  WGQGTSVTVSS  120
36HKK3        71  TVDTSTSTAYMELSSLRSEDTAVYYCTR  GNYGVDYAMDY  WGQGTLVTVSS  120
ABM67212      71  TRDTSTSTVYMELSSLRSEDTAVYYCAR  EGDGYIQAFDY  WGQGTLVTVSS  120
IGHV1-46*03   71  TRDTSTSTVYMELSSLRSEDTAVYYCAR                            98
JH4            1                                    YFDY          WGQGTLVTVSS  15

Bold; different residues between mouse and human
Underline; grafted CDRs
Bold Italic; substituted  residues with mouse residues
```

FIG. 6A

```
Heavy chain_42
Kabat definition          <------FWR1------->  <CDR1>  <----FWR2----->  <---CDR2------>
Chothia definition                             <-CDR1->                 <--CDR2-->
mouse 42G5B10    1  QVQLQQPGAELVKPGASVKMSCKASGYTFT  SYWMH  WVKQRPGQGLEWIG  LIDPSDKYTNYNQKFKG  KATL   70
42HKK1           1  QVQLVQSGAEVKKPGASVKVSCKASGYTFT  SYWMH  WVRQAPGQGLEWMG  LIDPSDKYTNYNQKFKG  RVTL   70
42HKK2           1  QVQLVQSGAEVKKPGASVKVSCKASGYTFT  SYWMH  WVRQAPGQGLEWMG  LIDPSDKYTNYNQKFKG  RVTL   70
42HKK3           1  QVQLVQSGAEVKKPGASVKVSCKASGYTFT  SYWMH  WVRQAPGQGLEWMG  LIDPSDKYTNYNQKFKG  KATL   70
ABM67212         1  QVQLVQSGAEVKKPGASVKVSCKASGYTFT  SYYMH  WVRQAPGQGLEWMG  IINPSGGSTSYAQKFQG  RVTM   70
IGHV1-46*03      1  QVQLVQSGAEVKKPGASVKVSCKASGYTFT  SYYMH  WVRQAPGQGLEWMG  IINPSGGSTSYAQKFQG  RVTM   70

Kabat definition     <------FWR3------>  <---CDR3--->  <---FWR4--->
Chothia definition                       <--CDR3-->
mouse 42G5B10   71  TVDTSSSTAYMQLSSLTSEDSAVYYCTR  GNYGVDYGMDY  WGQGTSVTVSS  120
42HKK1          71  TRDTSTSTVYMELSSLRSEDTAVYYCAR  GNYGVDYGMDY  WGQGTLVTVSS  120
42HKK2          71  TVDTSTSTVYMELSSLRSEDTAVYYCTR  GNYGVDYGMDY  WGQGTLVTVSS  120
42HKK3          71  TVDTSSSTAYMELSSLRSEDTAVYYCTR  GNYGVDYGMDY  WGQGTLVTVSS  120
ABM67212        71  TRDTSTSTVYMELSSLRSEDTAVYYCAR  EDGYIQAFDY  WGQGTLVTVSS  120
IGHV1-46*03     71  TRDTSTSTVYMELSSLRSEDTAVYYCAR                            98
JH4              1                              YFDY  WGQGTLVTVSS   15
```

Bold; different residues between mouse and human
<u>Underline</u>; grafted CDRs
*Bold italic*; substituted residues with mouse residues

FIG. 6B

Light chain

| Kabat definition | | <------FWR1------> | <--CDR1--> | <----FWR2----> | <--CDR2> | |
|---|---|---|---|---|---|---|
| Chothia definition | | | <--CDR1--> | | <--CDR2> | |
| mouse 36F7C10 | 1 | DIQMTQSPASLSASVGETVTITC | GASENIYGALN | WYQRKQGKSPQLLIY | GATNLAD | GMSSRFSGSGSGRQ 70 |
| LC3 | 1 | DIQMTQSPSSLSASVGDRVTITC | RASENIYGALN | WYQQKPGKAPKLLIY | GATNLAD | GVPSRFSGSGSGRQ 70 |
| LK3 | 1 | DIQMTQSPSSLSASVGDRVTITC | GASENIYGALN | WYQRKPGKAPKLLIY | GATNLAD | GVPSRFSGSGSGRD 70 |
| BAH04867.1 | 1 | DIQMTQSPSSLSASVGDRVTITC | RASQSISSYLN | WYQQKPGKAPKLLIY | AASSLQS | GVPSRFSGSGSGTD 70 |
| IGKV1D-39*01 | 1 | DIQMTQSPSSLSASVGDRVTITC | RASQSISSYLN | WYQQKPGKAPKLLIY | AASSLQS | GVPSRFSGSGSGTD 70 |

| Kabat definition | | -FWR3----------> | <--CDR3--> | <--FWR4--> | |
|---|---|---|---|---|---|
| Chothia definition | | | <--CDR3--> | | |
| mouse 36F7C10 | 71 | YSLKISSLHPDDVATYYC | QNVLITPYT | FGGGTKLEIK | 107 |
| LC3 | 71 | YSLTISSLQPEDFATYYC | QNVLITPYT | FGGGTKLEIK | 107 |
| LK3 | 71 | YTLTISSLQPEDFATYYC | QNVLITPYT | FGGGTKLEIK | 107 |
| BAH04867.1 | 71 | FTLTISSLQPEDFATYYC | QQSYSTFYT | FGQGTKLEIK | 107 |
| IGKV1D-39*01 | 71 | FTLTISSLQPEDFATYYC | QQSYSTPP | | 96 |

Bold; different residues between mouse and human
Underline; grafted CDRs
*Bold Italic; substituted residues with mouse residues*
*Underline Italic; substituted residues with human residues*

FIG. 6C

| IC50 (nM, mean±SD) | | | | |
|---|---|---|---|---|
| OR: out of range | | | | |
| If no SD value is shown, the assay was single. | | | | |
| | | Heavy chain | | |
| | | 36HCM1 | 40HCM1 | 42HCM1 |
| Light chain | 36LM1 | 3.297±2.303 | 15.483±12.423 | 1.903±0.707 |
| | 40LM1 | OR | 3.423±0.975 | 8.580±1.858 |
| | 42LM1 | OR | OR | 3.297±1.330 |
| | | Heavy chain | | |
| | | 36HKK1 | 36HKK2 | 36HKK3 |
| Light chain | 36LK1 | 1.870±0.281 | 1.323±0.258 | 0.987±0.219 |
| | 36LK2 | 2.513±0.828 | 1.220±0.474 | 1.107±0.474 |
| | 36LK3 | 1.240±0.192 | 1.233±0.075 | 1.313±0.245 |
| | | Heavy chain | | |
| | | 42HKK1 | 42HKK2 | 42HKK3 |
| Light chain | 42LK1 | 13.51 | 18.22 | 18.97 |
| | 42LK2 | 9.72 | 13.35 | 13.6 |
| | 42LK3 | 2.38 | 1.99 | 3.09 |
| | | Heavy chain | | |
| | | 42HKK1 | 42HKK2 | 42HKK3 |
| Light chain | 36LK1 | 1.39 | 2.62 | 1.86 |
| | 36LK2 | 1.33 | 1.08 | 1.59 |
| | 36LK3 | 1.357±0.250 | 1.663±0.475 | 1.467±0.160 |
| | | Heavy chain | | |
| | | 36HKK3 | 36HC2 | 36HC3 |
| Light chain | 36LK3 | 1.210±0.306 | 1.014±0.330 | 1.128±0.041 |
| | 36LC3 | 1.265±0.266 | 1.117±0.193 | 1.327±0.346 |

FIG. 7A

| IC90 (nM, mean±SD) | | | | |
|---|---|---|---|---|
| OR: out of range | | | | |
| | | | | |
| | | Heavy chain | | |
| | | 36HCM1 | 40HCM1 | 42HCM1 |
| Light chain | 36LM1 | OR | OR | 28.173±18.382 |
| | 40LM1 | OR | OR | OR |
| | 42LM1 | OR | OR | OR |
| | | | | |
| | | Heavy chain | | |
| | | 36HKK1 | 36HKK2 | 36HKK3 |
| Light chain | 36LK1 | 34.300±12.049 | 21.040±12.576 | 6.957±1.059 |
| | 36LK2 | OR | OR | 16.360±4.492 |
| | 36LK3 | 8.75±1.121 | 5.613±0.882 | 4.130±1.769 |
| | | | | |
| | | Heavy chain | | |
| | | 42HKK1 | 42HKK2 | 42HKK3 |
| Light chain | 42LK1 | OR | OR | OR |
| | 42LK2 | OR | OR | OR |
| | 42LK3 | 40.74 | 53.08 | OR |
| | | | | |
| | | Heavy chain | | |
| | | 42HKK1 | 42HKK2 | 42HKK3 |
| Light chain | 36LK1 | 8.74 | 44.04 | 15.99 |
| | 36LK2 | 14.31 | 25.33 | 18.65 |
| | 36LK3 | 4.857±0.403 | 6.540±2.040 | 5.647±1.107 |
| | | | | |
| | | Heavy chain | | |
| | | 36HKK3 | 36HC2 | 36HC3 |
| Light chain | 36LK3 | 4.376±0.651 | 4.564±1.928 | 4.603±1.521 |
| | 36LC3 | 4.327±0.816 | 5.251±0.591 | 6.339±0.614 |

FIG. 7B

| iC95 (nM, mean±SD) | | | | |
|---|---|---|---|---|
| OR: out of range | | | | |
| | | | | |
| | | Heavy chain | | |
| | | 36HCM1 | 40HCM1 | 42HCM1 |
| Light chain | 36LM1 | OR | OR | OR |
| | 40LM1 | OR | OR | OR |
| | 42LM1 | OR | OR | OR |
| | | | | |
| | | Heavy chain | | |
| | | 36HKK1 | 36HKK2 | 36HKK3 |
| Light chain | 36LK1 | OR | OR | OR |
| | 36LK2 | OR | OR | OR |
| | 36LK3 | OR | OR | 7.587±3.511 |
| | | | | |
| | | Heavy chain | | |
| | | 42HKK1 | 42HKK2 | 42HKK3 |
| Light chain | 42LK1 | OR | OR | OR |
| | 42LK2 | OR | OR | OR |
| | 42LK3 | OR | OR | OR |
| | | | | |
| | | Heavy chain | | |
| | | 42HKK1 | 42HKK2 | 42HKK3 |
| Light chain | 36LK1 | OR | OR | OR |
| | 36LK2 | 32.31 | 54.83 | 60.93 |
| | 36LK3 | 9.020±0.762 | 15.337±9.599 | 10.780±3.938 |
| | | | | |
| | | Heavy chain | | |
| | | 36HKK3 | 36HC2 | 36HC3 |
| Light chain | 36LK3 | 6.886±1.274 | 8.972±4.417 | 8.381±4.053 |
| | 36LC3 | 9.747±3.758 | (11.77, >66.7, 10.33) | OR |

FIG. 7C 37.5% identity in 56 residues overlap; Score: 106.0; Gap frequency: 5.4%

```
CCL16,   37  CCLKYTEKVLPRRLVVGYRKAL---NCHLPAIIFVTKRNREVCTNPNDDWVQEYIK
CCL20,   32  CCLGYTDRILHPKFIVGFTRQLANEGCDINAIIFHTKKKLSVCANPKQTWVKYIVR
             ***   *      *   *  *     * *  ** *        ** **  * **
```

FIG. 12

```
86.5% identity in 96 residues overlap; Score: 441.0; Gap frequency:  0.0% hum_CCL20      1 MCCTKSLLLAALMSVLLLHLCGESEAASNFDCCLGYTDRILHPKFIVGFTRQLANEGCDI
rhe_CCL20      1 MCCTKSLLLAALMSVLLLYLCSESEAASNFDCCLRYTDRILHPKFIVGFTQQLANETCDI
                 ****  *****   ************* ************ hum_CCL20     61 NAIIFHTKKKLSVCANPKQTWVKYTVRLLSKKVKNM
rhe_CCL20     61 NAVVFHTKKGLSVCANPKQTWVKLIVRRLSKKINKM
                 **  ***** ************  **  **** **

97.9% identity in 96 residues overlap; Score: 497.0; Gap frequency:  0.0% rhe_CCL20      1 MCCTKSLLLAALMSVLLLYLCSESEAASNFDCCLRYTDRILHPKFIVGFTQQLANETCDI
cyn_CCL20      1 MCCSKSLLLAALMSVLLLYLCSESEAASNFDCCLRYTDRILHPKFIVGFTQQLANETCDI
                 * ************************************************* rhe_CCL20     61 NAVVFHTKKGLSVCANPKQTWVKLIVRRLSKKINKM
cyn_CCL20     61 NAVIFHTKKGLSVCANPKQTWVKLIVRRLSKKINKM
                 *** ********************************

64.2% identity in 95 residues overlap; Score: 310.0; Gap frequency:  0.0% hum_CCL20      2 CCTKSLLLAALMSVLLLHLCGESEAASNFDCCLGYTDRILHPKFIVGFTRQLANEGCDIN
mou_CCL20      3 CSGKRLLFLALAWVLLAHLCSQAEAAASNYDCCLSYIQTFLPSRAIVGFTRQMADEACDIN
                 *  *     *  *  **** **  *   *  * ** hum_CCL20     62 AIIFHTKKKLSVCANPKQTWVKYTVRLLSKKVKNM
mou_CCL20     63 AIIFHTKRKKSVCADPKQNWVKRAVNLLSLRVKKM
                 ******* * *** *** *** *   **  **
```

FIG. 14

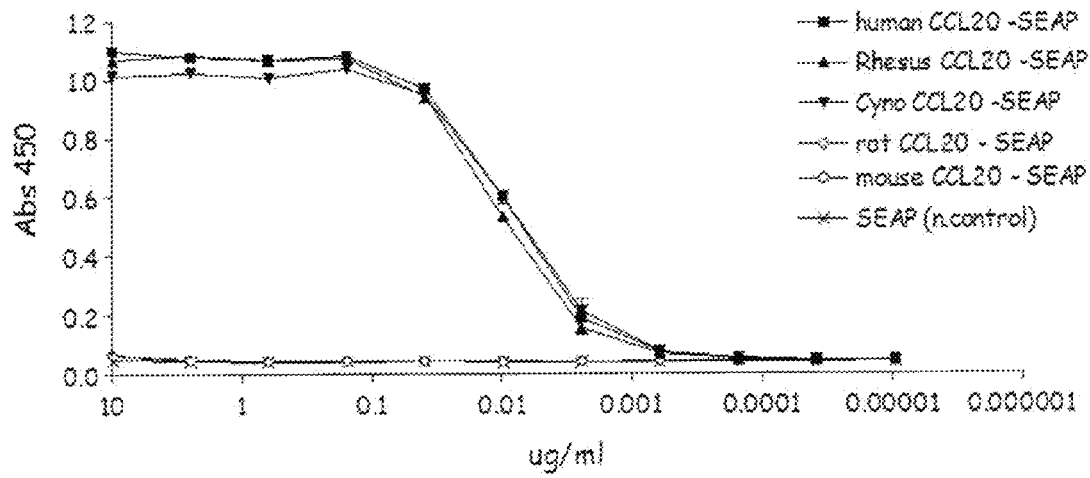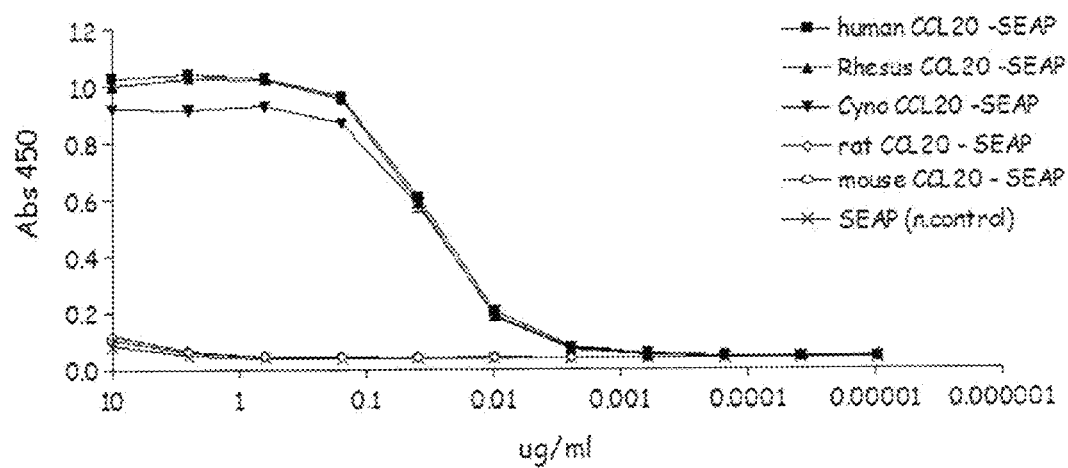
FIG. 17A

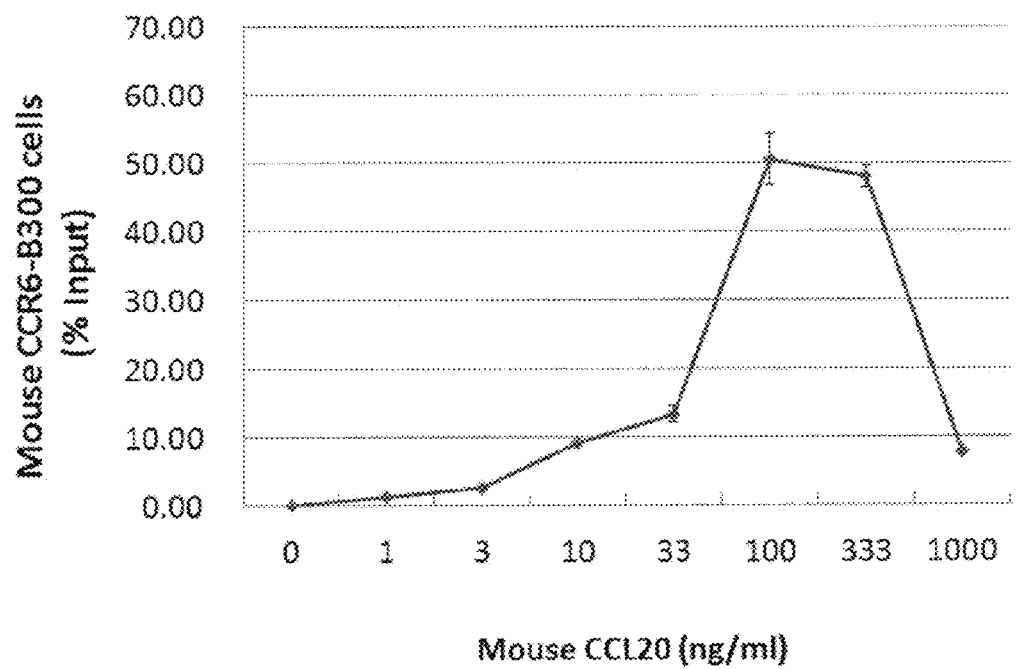
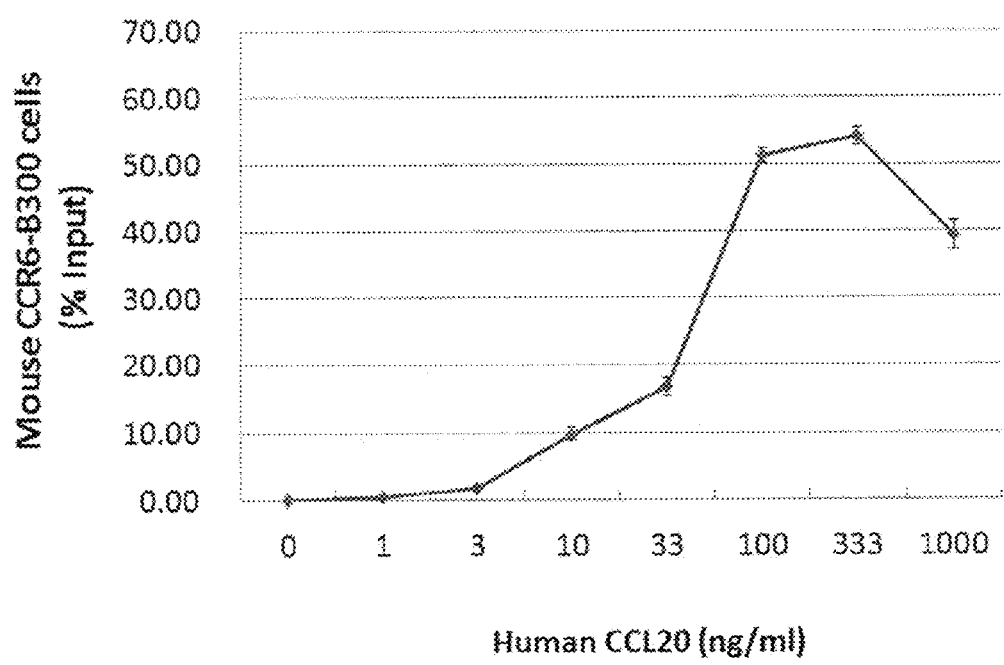
FIG. 19

| | | | | | | Day | | | | | | |
|---|---|---|---|---|---|---|---|---|---|---|---|---|
| Control IgG | | | | | | | | | | | | |
| Animal | 6 | 7 | 8 | 10 | 13 | 14 | 15 | 16 | 17 | | | |
| 1 | 1 | 1 | 2 | 2 | 9 | 9 | 10 | 10 | 10 | | | |
| 2 | 2 | 2 | 4 | 5 | 6 | 7 | 7 | 7 | 7 | | | |
| 3 | 3 | 6 | 7 | 8 | 8 | 8 | 8 | 8 | 8 | | | |
| 4 | 2 | 3 | 3 | 5 | 5 | 6 | 5 | 4 | 5 | | | |
| 5 | 3 | 3 | 5 | 9 | 11 | 12 | 12 | 12 | 12 | | | |
| 6 | 2 | 3 | 5 | 6 | 6 | 6 | 6 | 6 | 6 | | | |
| Average | 2.2 | 3.0 | 4.3 | 5.8 | 7.5 | 8.0 | 8.0 | 7.8 | 8.0 | | | |
| ST DEV | 0.3 | 0.7 | 0.7 | 1.0 | 0.9 | 0.9 | 1.1 | 1.2 | 1.1 | | | |
| 2F5-5 | | | | | | | | | | | | |
| Animal | | | | | | | | | | | | |
| 1 | 3 | 3 | 3 | 4 | 5 | 5 | 6 | 6 | 6 | | | |
| 2 | 3 | 2 | 2 | 2 | 2 | 3 | 3 | 3 | 3 | | | |
| 3 | 3 | 3 | 4 | 4 | 3 | 3 | 4 | 3 | 3 | | | |
| 4 | 1 | 1 | 2 | 3 | 3 | 3 | 3 | 3 | 3 | | | |
| 5 | 2 | 2 | 1 | 2 | 3 | 3 | 3 | 3 | 3 | | | |
| 6 | 1 | 0 | 0 | 0 | 1 | 1 | 1 | 1 | 1 | | | |
| Average | 2.2 | 1.8 | 2.0 | 2.5 | 2.8 | 3.0 | 3.3 | 3.2 | 3.2 | | | |
| ST DEV | 0.4 | 0.5 | 0.6 | 0.6 | 0.5 | 0.5 | 0.7 | 0.7 | 0.7 | | | |

FIG. 22

| | 1 | 2 | 3 | 4 | | 5 | 6 | 7 | | 8 | 9 | 10 | 11 |
|---|---|---|---|---|---|---|---|---|---|---|---|---|---|
| | | | | | CIA with IFA (Incomplete Freund adjuvant) | | | | CIA with CFA (Complete Freund adjuvant) | | | | |
| A | 1 | normal_1 | | Hamster control IgG | anti-CCL20 (2F5-5) | | | | Hamster control IgG | | anti-CCL20 (2F5-5) | | |
| B | 2 | normal_2 | | Hamster control IgG | anti-CCL20 (2F5-5) | | | | Hamster control IgG | | anti-CCL20 (2F5-5) | | |
| C | 3 | normal_3 | | Hamster control IgG | anti-CCL20 (2F5-5) | | | | Hamster control IgG | | anti-CCL20 (2F5-5) | | |
| D | 4 | normal_4 | | Hamster control IgG | anti-CCL20 (2F5-5) | | | | Hamster control IgG | | anti-CCL20 (2F5-5) | | |
| E | 5 | normal_5 | | Hamster control IgG | anti-CCL20 (2F5-5) | | | | Hamster control IgG | | anti-CCL20 (2F5-5) | | |
| F | 6 | normal_6 | | Hamster control IgG | anti-CCL20 (2F5-5) | | | | | | | | |
| G | Calibrator U/L | 0 | 0.9 | 0.45 | 0.22 | | 0.11 | 0.055 | | blank | blank | blank | blank |
| H | | | | | | | | | | blank | blank | blank | blank |

| | 1 | 2 | 3 | 4 | 5 | 6 | 7 | 8 | 9 | 10 | 11 |
|---|---|---|---|---|---|---|---|---|---|---|---|
| A | 1 | 0.669 | 0.637 | 0.504 | 0.483 | 0.558 | 0.585 | 0.508 | 0.512 | 0.552 | 0.566 |
| B | 2 | 0.577 | 0.559 | 0.493 | 0.468 | 0.541 | 0.552 | 0.442 | 0.445 | 0.614 | 0.618 |
| C | 3 | 0.592 | 0.550 | 0.559 | 0.484 | 0.551 | 0.566 | 0.475 | 0.482 | 0.520 | 0.549 |
| D | 4 | 0.551 | 0.537 | 0.460 | 0.432 | 0.512 | 0.523 | 0.437 | 0.461 | 0.513 | 0.524 |
| E | 5 | 0.600 | 0.557 | 0.515 | 0.480 | 0.481 | 0.487 | 0.529 | 0.518 | 0.554 | 0.581 |
| F | 6 | 0.589 | 0.577 | 0.431 | 0.400 | 0.518 | 0.538 | 0.443 | 0.456 | 0.537 | 0.561 |
| G | Calibrator OD450 | 0.800 | 0.250 | 0.360 | 0.450 | 0.575 | 0.692 | 0.848 | 0.840 | 0.855 | 0.897 |
| H | | 0.807 | 0.257 | 0.361 | 0.456 | 0.581 | 0.706 | 0.873 | 0.890 | 0.876 | 0.941 |

OD450 values were obtained by regular colorimetric assay

FIG. 25B

NEUTRALIZING ANTI-CCL20 ANTIBODIES

This application is a continuation application of U.S. application Ser. No. 13/924,433, filed Jun. 21, 2013 (now pending), which is a divisional application of U.S. patent application Ser. No. 13/300,352, filed Nov. 18, 2011 (now U.S. Pat. No. 8,491,901), which claims priority from U.S. Provisional Patent Application No. 61/415,614, filed Nov. 19, 2010. The disclosures of all the aforementioned priority applications are incorporated by reference in their entirety herein.

The instant application contains a Sequence Listing that has been submitted in ASCII format via EFS-Web and is hereby incorporated by reference in its entirety. This Sequence Listing electronic file, created on Jul. 31, 2015, is named "106806-0008-103_Sequence_Listing.TXT" and is 113,622 bytes in size.

FIELD OF THE INVENTION

The present invention relates to novel humanized, chimeric and murine antibodies specifically directed against the human CC chemokine ligand 20 (CCL20). The humanized antibodies of the invention are particularly well-suited as therapeutics for the treatment of inflammatory and autoimmune diseases.

BACKGROUND OF THE INVENTION

The immune system is a highly sophisticated bio-circuit used by the body to discriminate non-self (e.g., foreign organisms or substances) from self. The detection of non-self in the body can result in inflammation, in which various cellular and molecular components are orchestrated to respond to potentially harmful events caused by the non-self organism or substance. Although the inflammatory process helps to protect the body from foreign attack, de-regulation of the immune system can lead to negative consequences such as self attack, e.g., autoimmune disease. By altering the function of inflammatory molecules such as chemokines, it may be possible to reduce the initiation and progression of disorders relating to immune/inflammatory responses.

Chemokines are a family of small (8-10 kDa) proteins that play a pivotal role in inflammation. During the inflammatory process, chemokines are produced locally at the site of the noxious stimulus and work as central players to recruit immune cells that express their cognate receptors, seven trans-membrane G protein-coupled receptors (GPCRs). CCL20, alternatively named liver and activation-regulated chemokine (LARC), macrophage inflammatory protein-3 alpha (MIP-3α), or Exodus-1, is a soluble chemokine that is expressed by epithelial cells. Epithelial keratinocytes and synovium-lining cells are known to produce large amounts of CCL20 during homeostatic as well as inflammatory and pathological conditions such as cancer, psoriasis, and rheumatoid arthritis. The cognate receptor for CCL20 is CC chemokine receptor 6 (CCR6); CCL20 is the only chemokine known to interact with CCR6. In response to the CCL20 signal, immune cells possessing CCR6, such as immature dendritic cells (DC), effector/memory T-cells, and B-cells, migrate and infiltrate the surrounding tissues, thus activating the inflammatory cascade.

Because CCL20 expression is significantly enhanced in inflammation induced by inflammatory cytokines such as interleukin 1β (IL-1β) and tumor necrosis factor α (TNF-α), the CCL20-CCR6 interaction is thought to play a role in pathological inflammatory processes.

Rheumatoid Arthritis (RA) is one of the most common autoimmune diseases. The first sign of RA is often synovitis, which manifests as a swollen, painful joint. Although the specific factors that initiate synovitis remain unknown, synovium lining epithelial cells and synovial fibroblasts are thought to be primary inducers of the inflammatory reaction. Synovial fluid from RA patients effectively chemo-attracts human monocytes and pro-inflammatory T helper 17 (Th17) cells, which then induce and exacerbate the RA inflammatory process. Because reactive synovial cells are capable of producing large amounts of CCL20 (particularly under the influence of IL-1β and TNF-α), while CCR6 is the major receptor of Th17 cells, the CCL20-CCR6 interaction is thought to play a key role in the inflammatory process.

The CCL20-CCR6 interaction may also play an important role in certain types of dermatitis. Psoriasis, for example, initiates with a noxious psoriatic event in the skin (induced by environmental and/or genetic factors) followed by infiltration of Th17 cells. Because CCR6 is expressed on the surface of Th17 cells, B cells, dendritic cells, and tissue damaging effector T cells, CCL20 may represent the main chemoattractant for these cell types in psoriasis. Further evidence for the importance of the CCL20-CCR6 interaction can be found in studies using an interleukin 23 (IL-23)-induced mouse model of psoriasis (Hedrick et al., *J. Clin. Invest.* 119:2317-2329 (2009)). In this model, injection of IL-23 causes interleukin 22 (IL-22)-dependent psoriatic inflammation. However, Ccr6$^{-/-}$ mice did not exhibit psoriasis-like symptoms when injected with IL-23, indicating that CCR6 is required for the development of psoriasis.

Human keratinocytes can produce large amounts of CCL20, especially under the influence of the Th17-derived cytokines interleukin 17 (IL-17), IL-22, and TNF-α. While CCL20 and CCR6 are rarely detected in normal skin, both exhibit increased expression levels in atopic dermatitis and pustular psoriasis. Strong induction of CCL20 and accumulation of CCR6+ cells can be observed in microscopic immunohistochemical analysis of human dermatitis lesions. These observations provide additional evidence for the role of CCL20 and CCR6 in the dermatitis inflammatory process.

Currently available MAb biologics for treating immune disorders can be roughly classified into three groups: inhibitors of immunostimulatory cytokines (e.g., anti-TNF-α MAbs), immune cell eliminators (e.g., anti-CD20 MAbs), and blockers of accessory molecules (e.g. Abatacept). These biologics may be useful in the treatment of inflammatory diseases; however, due to primary non-responsiveness or a gradual decline in response rate to these treatments, there is an urgent need for alternative biologics with novel mechanisms of action to meet the medical needs of patients with, e.g., CCL20/CCR6-mediated disorders. The antibodies of the subject invention represent such alternative biologics.

SUMMARY OF THE INVENTION

The present invention relates to neutralizing anti-CCL20 antibodies, or antigen-binding portions thereof. In certain embodiments, the anti-CCL20 antibody is a humanized anti-human CCL20 antibody, which may comprise the complementarity determining regions (CDRs) of mouse anti-human CCL20 antibodies. In some embodiments, the anti-CCL20 antibody is a mouse or chimeric anti-human CCL20 antibody or an antigen-binding portion thereof.

In some embodiments, the anti-CCL20 antibody or antigen-binding portion thereof binds to human CCL20. In some embodiments, the antibody or portion does not bind to human CCL16.

The antibodies of the invention specifically bind CCL20. In some embodiments, the anti-CCL20 antibody or antigen-binding portion thereof binds to cynomolgus and/or rhesus CCL20 as well as human CCL20. In some embodiments, the anti-CCL20 antibody or antigen-binding portion thereof does not bind to mouse and/or rat CCL20. In one embodiment, the anti-CCL20 antibody or antigen-binding portion binds to human, cynomolgus, and rhesus CCL20, but not to mouse and rat CCL20.

In some embodiments, the anti-CCL20 antibody or antigen-binding portion thereof has a binding affinity ($K_D$) for human CCL20 of less than:

1 nM, 500 pM, 100 pM, 90 pM, 80 M, 70 pM, 60 pM, or 50 pM using a monovalent surface plasmon resonance assay, or 1 nM, 500 pM, 100 pM, 75 pM, 50 pM, 25 pM, 20 pM, 15 pM, 14 pM, 13 pM, 12 pM, 11 pM, 10 pM, 9 pM, 8 pM, 7 pM, 6 pM, or 5 pM using a bivalent surface plasmon resonance assay.

In certain embodiments, the antibody or portion has a binding affinity for human CCL20 greater than that of human CCR6.

In some embodiments, the anti-CCL20 antibody or antigen-binding portion thereof has a $k_a$ for human CCL20 of less than 100, 90, 80, 70, 60, 50, 40, or 30 ($\times 10^5$ $M^{-1}$ $sec^{-1}$), as determined by bivalent surface plasmon resonance. In some embodiments, the anti-CCL20 antibody or antigen-binding portion thereof has a $k_d$ for human CCL20 of less than 10, 9, 8, 7, 6, 5, 4, or 3 ($\times 10^{-5}$ $sec^{-1}$), as determined by bivalent surface plasmon resonance.

In some embodiments, the anti-CCL20 antibody or antigen-binding portion thereof has a $k_a$ for rhesus CCL20 of less than 100, 90, 80, 70, 60, 50, 40, or 30 ($\times 10^5$ $M^{-1}$ $sec^{-1}$), as determined by bivalent surface plasmon resonance. In some embodiments, the anti-CCL20 antibody or antigen-binding portion thereof has a $k_d$ for rhesus CCL20 of less than 50, 40, 30, 20, 10, 9, 8, 7, 6, 5, 4, 3, or 2 ($\times 10^{-5}$ $sec^{-1}$), as determined by bivalent surface plasmon resonance. In some embodiments, the anti-CCL20 antibody or antigen-binding portion thereof has a $K_D$ for rhesus CCL20 of less than 100, 90, 80, 70, 60, 50, 40, 30, 20, or 10 pM, as determined by bivalent surface plasmon resonance.

In some embodiments, the anti-CCL20 antibody or antigen-binding portion thereof has a $k_a$ for cynomolgus CCL20 of less than 500, 400, 300, 200, 100, 90, 80, 70, 60, 50, 40, or 30 ($\times 10^5$ $M^{-1}$ $sec^{-1}$), as determined by bivalent surface plasmon resonance. In some embodiments, the anti-CCL20 antibody or antigen-binding portion thereof has a $k_d$ for cynomolgus CCL20 of less than 50, 40, 30, 20, 19, 18, 17, 16, 15, 14, 13, 12, 11, 10, 9, 8, 7, or 6 ($\times 10^{-5}$ $sec^{-1}$), as determined by bivalent surface plasmon resonance. In some embodiments, the anti-CCL20 antibody or antigen-binding portion thereof has a $K_D$ for cynomolgus CCL20 of less than 100, 90, 80, 70, 60, 50, 40, 30, 20, 19, 18, 17, 16, or 15 pM, as determined by bivalent surface plasmon resonance.

In some embodiments, the anti-CCL20 antibody or antigen-binding portion thereof binds to human CCL20 with an $EC_{50}$ of less than 100, 90, 80, 70, 60, 50, 40, 39, 38, 37, 36, 35, or 34 pM. In some embodiments, the anti-CCL20 antibody or antigen-binding portion thereof binds to rhesus CCL20 with an $EC_{50}$ of less than 500, 400, 300, 200, 150, 140, 130, 120, 110, 100, 90, 80, 70, 65, 60, 59, 58, 57, 56, 55, 54, 53, 52, 51, or 50 pM. In some embodiments, the anti-CCL20 antibody or antigen-binding portion thereof binds to cynomolgus CCL20 with an $EC_{50}$ of less than 500, 400, 350, 300, 250, 200, 190, 180, 170, 160, 150, 140, 130, 120, 110, 109, 108, 107, 106, 105, 104, 103, or 102 pM.

In some embodiments, the anti-CCL20 antibody or antigen-binding portion thereof has a selectivity for human CCL20 over other human chemokines, including but not limited to CX3CL1, CXCL1, CXCL2, CXCL4, CXCL8, CXCL9, CXCL10, CXCL12, CXCL13, CXCL16, CCL1, CCL2, CCL3, CCL4, CCL5, CCL7, CCL11, CCL13, CCL16, CCL17, CCL19, CCL21, CCL22, CCL24, CCL25, CCL27, CCL28, and/or XCL1. In certain embodiments, the anti-CCL20 antibody or antigen-binding portion has a selectivity for human CCL20 over all of said chemokines.

In some embodiments, the anti-CCL20 antibody or antigen-binding portion thereof reduces human CCL20-induced chemotaxis of human or mouse CCR6+ cells with an $IC_{50}$ of less than 20, 19, 18, 17, 16, 15, 14, 13, 12, 11, 10, 9, 8, 7, 6, 5, 4, 3, 2, 1.7, 1.6, 1.5, 1.4, 1.3, 1.2, or 1.1 nM. In certain embodiments, the anti-CCL20 antibody or antigen-binding portion thereof reduces human CCL20-induced chemotaxis of human or mouse CCR6+ cells with an $IC_{50}$ of less than 1.7, 1.6, 1.5, 1.4, 1.3, 1.2, or 1.1 nM. In some embodiments, the anti-CCL20 antibody or antigen-binding portion thereof reduces human CCL20-induced chemotaxis of human or mouse CCR6+ cells with an $IC_{90}$ of less than 45, 40, 35, 30, 25, 20, 19, 18, 17, 16, 15, 14, 13, 12, 11, 10, 9, 8, 7, 6, 5.5, 5.4, 5.3, 5.2, 5.1, 4.9, 4.8, 4.7, or 4.6 nM. In certain embodiments, the anti-CCL20 antibody or antigen-binding portion thereof reduces human CCL20-induced chemotaxis of human or mouse CCR6+ cells with an $IC_{90}$ of less than 6, 5.5, 5.4, 5.3, 5.2, 5.1, 4.9, 4.8, 4.7, or 4.6 nM. In some embodiments, the anti-CCL20 antibody or antigen-binding portion thereof reduces human CCL20-induced chemotaxis of human or mouse CCR6+ cells with an $IC_{95}$ of less than 70, 65, 60, 55, 50, 45, 40, 35, 30, 25, 20, 15, 10, 9, 8, or 7 nM. In certain embodiments, the anti-CCL20 antibody or antigen-binding portion thereof reduces human CCL20-induced chemotaxis of human or mouse CCR6+ cells with an $IC_{95}$ of less than 10, 9.9, 9.8, 9.7, 9.6, 9.5, 9.4, 9.3, 9.2, 9.1, or 9 nM.

In some embodiments, the anti-CCL20 antibody or antigen-binding portion thereof reduces human CCL20-induced chemotaxis of human or mouse CCR6+ cells in vitro.

In some embodiments, the anti-CCL20 antibody or antigen-binding portion thereof reduces human CCL20-induced chemotaxis of human or mouse CCR6+ cells in vivo.

In some embodiments, the anti-CCL20 antibody or antigen-binding portion thereof reduces the progression of arthritis symptoms (such as articular lesions of the extremities distal to the elbow or knee and degree of erythema and swelling) in a subject, e.g., in a collagen-induced arthritis (CIA) and/or a glucose-6-phosphate isomerase (G6PI)-induced arthritis mouse model. In some embodiments, the antibody or antigen-binding portion thereof reduces bone lesions in a subject, including osteoporosis, bone erosion, and/or new bone formation, e.g., in a CIA model. In some embodiments, the antibody or antigen-binding portion reduces cartilage oligomeric matrix protein (COMP) serum levels in a subject, e.g., in a CIA model. In some embodiments, the antibody or antigen-binding portion thereof reduces mRNA levels of receptor activator for nuclear factor κB ligand (RANKL), receptor activator for nuclear factor κB (RANK), tartrate resistant acid phosphatase (TRAP), and/or cathepsin K in a subject, e.g., in mouse paws in a CIA model. In some embodiments, the antibody or antigen-binding portion thereof reduces atopic dermatitis symptoms (e.g., dryness, scale, erythema, oozing/crusting, and/or excoriation) in a subject, for example, symptoms of oxazolone-induced atopic dermatitis in NC/Nga strain mice. In some embodiments, the antibody or antigen-binding portion reduces allergic contact dermatitis symptoms in a subject, for example, symptoms of dinitrofluorobenzene (DNFB)-induced allergic contact dermatitis in a mouse model.

In some embodiments, the anti-CCL20 antibody or antigen-binding portion thereof comprises a heavy chain whose CDR3 (H-CDR3) comprises the sequence of SEQ ID NO: 67 or 68.

In some embodiments, the anti-CCL20 antibody or antigen-binding portion thereof comprises a light chain whose CDR3 (L-CDR3) comprises the sequence of SEQ ID NO 75.

In certain embodiments, the anti-CCL20 antibody or antigen-binding portion thereof comprises an H-CDR3 whose sequence comprises SEQ ID NO: 67 and an L-CDR3 whose sequence comprises SEQ ID NO: 75; or an H-CDR3 whose sequence comprises SEQ ID NO: 68 and an L-CDR3 whose sequence comprises SEQ ID NO: 75.

In some embodiments, the anti-CCL20 antibody or antigen-binding portion thereof comprises a heavy chain whose CDR1 (H-CDR1), CDR2 (H-CDR2), and CDR3 (H-CDR3) respectively comprise the sequences of:
  SEQ ID NOS: 60, 63, and 67;
  SEQ ID NOS: 60, 64, and 67;
  SEQ ID NOS: 61, 65, and 68;
  SEQ ID NOS: 77, 79, and 67; or
  SEQ ID NOS: 78, 80, and 68.

In some embodiments, the anti-CCL20 antibody or antigen-binding portion thereof comprises a light chain whose CDR1 (L-CDR1), CDR2 (L-CDR2), and CDR3 (L-CDR3) respectively comprise the sequences of
  SEQ ID NOS: 70, 73, and 75; or
  SEQ ID NOS: 71, 73, and 75.

In some embodiments, the anti-CCL20 antibody or antigen-binding portion thereof comprises:
  an H-CDR1 comprising a sequence selected from the group consisting of SEQ ID NOS: 60-62, 77, and 78;
  an H-CDR2 comprising a sequence selected from the group consisting of SEQ ID NOS: 63-66 and 79-81;
  an H-CDR3 comprising the sequence of SEQ ID NO: 67 or 68;
  an L-CDR1 comprising a sequence selected from the group consisting of SEQ ID NOS: 70-72;
  an L-CDR2 comprising the sequence of SEQ ID NO: 73 or 74; or
  an L-CDR3 comprising SEQ ID NO: 75;
  or any combination thereof.

In certain embodiments, the anti-CCL20 antibody or antigen-binding portion thereof comprises an H-CDR1, H-CDR2, H-CDR3, L-CDR1, L-CDR2, and L-CDR3 respectively comprising the sequences of:
  SEQ ID NOS: 60, 63, 67, 70, 73, and 75;
  SEQ ID NOS: 60, 64, 67, 70, 73, and 75;
  SEQ ID NOS: 61, 65, 68, 70, 73, and 75;
  SEQ ID NOS: 77, 79, 67, 70, 73, and 75;
  SEQ ID NOS: 78, 80, 68, 70, 73, and 75;
  SEQ ID NOS: 60, 63, 67, 71, 73, and 75;
  SEQ ID NOS: 60, 64, 67, 71, 73, and 75;
  SEQ ID NOS: 61, 65, 68, 71, 73, and 75;
  SEQ ID NOS: 77, 79, 67, 71, 73, and 75; or
  SEQ ID NOS: 78, 80, 68, 71, 73, and 75.

In some embodiments, the anti-CCL20 antibody or antigen-binding portion thereof comprises a heavy chain variable domain comprising a sequence selected from the group consisting of SEQ ID NOS: 9-14. In some embodiments, the anti-CCL20 antibody or antigen-binding portion thereof comprises a heavy chain variable domain comprising a sequence selected from the group consisting of SEQ ID NOS: 39, 41, and 43.

In some embodiments, the anti-CCL20 antibody or antigen-binding portion thereof comprises a light chain variable domain comprising the sequence of SEQ ID NO: 15 or 16. In some embodiments, the anti-CCL20 antibody or antigen-binding portion thereof comprises a light chain variable domain comprising a sequence selected from the group consisting of SEQ ID NOS: 40, 42, and 44.

In certain embodiments, the anti-CCL20 antibody or antigen-binding portion thereof comprises a heavy chain variable domain and a light chain variable domain respectively comprising the sequences of:
  SEQ ID NO: 9 and SEQ ID NO: 15;
  SEQ ID NO: 10 and SEQ ID NO: 15;
  SEQ ID NO: 11 and SEQ ID NO: 15;
  SEQ ID NO: 12 and SEQ ID NO: 15;
  SEQ ID NO: 13 and SEQ ID NO: 15;
  SEQ ID NO: 14 and SEQ ID NO: 15;
  SEQ ID NO: 9 and SEQ ID NO: 16;
  SEQ ID NO: 10 and SEQ ID NO: 16;
  SEQ ID NO: 11 and SEQ ID NO: 16;
  SEQ ID NO: 12 and SEQ ID NO: 16;
  SEQ ID NO: 13 and SEQ ID NO: 16; or
  SEQ ID NO: 14 and SEQ ID NO: 16.

In certain embodiments, the anti-CCL20 antibody or antigen-binding portion thereof comprises a heavy chain variable domain and a light chain variable domain respectively comprising the sequences of:
  SEQ ID NO: 39 and SEQ ID NO: 40;
  SEQ ID NO: 39 and SEQ ID NO: 42;
  SEQ ID NO: 39 and SEQ ID NO: 44;
  SEQ ID NO: 41 and SEQ ID NO: 40;
  SEQ ID NO: 41 and SEQ ID NO: 42;
  SEQ ID NO: 41 and SEQ ID NO: 44;
  SEQ ID NO: 43 and SEQ ID NO: 40;
  SEQ ID NO: 43 and SEQ ID NO: 42; or
  SEQ ID NO: 43 and SEQ ID NO: 44.

In some embodiments, the anti-CCL20 antibody or antigen-binding portion thereof comprises a heavy chain having a sequence selected from the group consisting of SEQ ID NOS: 1-6 and 108 without the signal sequence (if present), and optionally without the C-terminal lysine. In some embodiments, the anti-CCL20 antibody or antigen-binding portion thereof comprises a light chain having a sequence selected from the group consisting of SEQ ID NOS: 7, 8, 110, and 112 without the signal sequence (if present). In certain embodiments, the anti-CCL20 antibody comprises a heavy chain and a light chain respectively having the sequences of:
  SEQ ID NO: 1 and SEQ ID NO: 7;
  SEQ ID NO: 2 and SEQ ID NO: 7;
  SEQ ID NO: 3 and SEQ ID NO: 7;
  SEQ ID NO: 4 and SEQ ID NO: 7;
  SEQ ID NO: 5 and SEQ ID NO: 7;
  SEQ ID NO: 6 and SEQ ID NO: 7;
  SEQ ID NO: 1 and SEQ ID NO: 8;
  SEQ ID NO: 2 and SEQ ID NO: 8;
  SEQ ID NO: 3 and SEQ ID NO: 8;
  SEQ ID NO: 4 and SEQ ID NO: 8;
  SEQ ID NO: 5 and SEQ ID NO: 8;
  SEQ ID NO: 6 and SEQ ID NO: 8;
  SEQ ID NO: 108 and SEQ ID NO: 110; or
  SEQ ID NO: 108 and 112;
  both of said sequences without the signal sequence, SEQ ID NOS: 1-6 and 108 optionally without the C-terminal lysine.

The present invention also provides an anti-CCL20 antibody or an antigen-binding portion thereof that comprises a heavy chain variable domain encoded by a sequence selected from the group consisting of SEQ ID NOS: 25-30. In some embodiments, the anti-CCL20 antibody or antigen-binding portion thereof comprises a heavy chain variable domain encoded by a sequence selected from the group consisting of SEQ ID NOS: 51, 53, and 55.

Further, the present invention provides an anti-CCL20 antibody or an antigen-binding portion thereof that comprises a light chain variable domain encoded by the sequence of SEQ ID NO: 31 or 32. In some embodiments, the anti-CCL20 antibody or antigen-binding portion thereof comprises a light chain variable domain encoded by a sequence selected from the group consisting of SEQ ID NOS: 52, 54, and 56.

In certain embodiments, the anti-CCL20 antibody or antigen-binding portion thereof comprises a heavy chain variable domain and a light chain variable domain respectively encoded by the sequences of:
SEQ ID NO: 25 and SEQ ID NO: 31;
SEQ ID NO: 26 and SEQ ID NO: 31;
SEQ ID NO: 27 and SEQ ID NO: 31;
SEQ ID NO: 28 and SEQ ID NO: 31;
SEQ ID NO: 29 and SEQ ID NO: 31;
SEQ ID NO: 30 and SEQ ID NO: 31;
SEQ ID NO: 25 and SEQ ID NO: 32;
SEQ ID NO: 26 and SEQ ID NO: 32;
SEQ ID NO: 27 and SEQ ID NO: 32;
SEQ ID NO: 28 and SEQ ID NO: 32;
SEQ ID NO: 29 and SEQ ID NO: 32; or
SEQ ID NO: 30 and SEQ ID NO: 32.

In certain embodiments, the anti-CCL20 antibody or antigen-binding portion thereof comprises a heavy chain variable domain and a light chain variable domain respectively encoded by the sequences of:
SEQ ID NO: 51 and SEQ ID NO: 52;
SEQ ID NO: 51 and SEQ ID NO: 54;
SEQ ID NO: 51 and SEQ ID NO: 56;
SEQ ID NO: 53 and SEQ ID NO: 52;
SEQ ID NO: 53 and SEQ ID NO: 54;
SEQ ID NO: 53 and SEQ ID NO: 56;
SEQ ID NO: 55 and SEQ ID NO: 52;
SEQ ID NO: 55 and SEQ ID NO: 54; or
SEQ ID NO: 55 and SEQ ID NO: 56.

In some embodiments, the anti-CCL20 antibody or antigen-binding portion thereof comprises a heavy chain encoded by a sequence selected from the group consisting of SEQ ID NOS: 17-22 and 109, said sequence lacking the sequence encoding a signal sequence (if present) and optionally lacking the sequence encoding the C-terminal lysine. In some embodiments, the anti-CCL20 antibody or antigen-binding portion thereof comprises a light chain encoded by a sequence selected from the group consisting of SEQ ID NOS: 23, 24, 111, and 113, said sequence lacking the sequence encoding a signal sequence (if present). In certain embodiments, the anti-CCL20 antibody comprises a heavy chain and a light chain respectively encoded by the sequences of:
SEQ ID NO: 17 and SEQ ID NO: 23;
SEQ ID NO: 18 and SEQ ID NO: 23;
SEQ ID NO: 19 and SEQ ID NO: 23;
SEQ ID NO: 20 and SEQ ID NO: 23;
SEQ ID NO: 21 and SEQ ID NO: 23;
SEQ ID NO: 22 and SEQ ID NO: 23;
SEQ ID NO: 17 and SEQ ID NO: 24;
SEQ ID NO: 18 and SEQ ID NO: 24;
SEQ ID NO: 19 and SEQ ID NO: 24;
SEQ ID NO: 20 and SEQ ID NO: 24;
SEQ ID NO: 21 and SEQ ID NO: 24;
SEQ ID NO: 22 and SEQ ID NO: 24;
SEQ ID NO: 109 and SEQ ID NO: 111; or
SEQ ID NO: 109 and SEQ ID NO: 113;
both of said sequences lacking the sequence encoding a signal sequence (if present), SEQ ID NOS: 17-22 and 109 optionally lacking the sequence encoding the C-terminal lysine.

In some embodiments, the anti-CCL20 antibody or antigen-binding portion thereof is humanized or chimeric. In some embodiments, the framework regions of the heavy chain of the humanized anti-CCL20 antibody or portion utilize an IGHV1-46*03 human germline gene (See, e.g., Altschul et al., "Gapped BLAST and PSI-BLAST: a new generation of protein database search programs", Nucleic Acids Res. 25:3389-3402 (1997)). In certain embodiments, the heavy chain framework regions have at least 50% homology to the framework regions of the IGHV1-46*03 human germline gene. For example, the heavy chain framework regions may be at least 50%, at least 60%, at least 70%, at least 80%, at least 90%, at least 95%, at least 98%, at least 99%, or even 100% identical to the framework regions of the IGHV1-46*03 human germline gene. In some embodiments, the framework regions of the light chain of the humanized anti-CCL20 antibody or portion utilize an IGKV1D-39*01 human germline gene (see Altschul et al., supra). In certain embodiments, the light chain framework regions have at least 50% homology to the framework regions of the IGKV1D-39*01 human germline gene. For example, the light chain framework regions may be at least 50%, at least 60%, at least 70%, at least 80%, at least 90%, at least 95%, at least 98%, at least 99%, or even 100% identical to the framework regions of the IGKV1D-39*01 human germline gene.

In some embodiments, the anti-CCL20 antibody or antigen-binding portion thereof (to the extent that said portion comprises at least part of a heavy chain constant region) is an IgG, an IgM, an IgE, an IgA, or an IgD molecule. In certain embodiments, the anti-CCL20 antibody or antigen-binding portion thereof is of the IgG1, IgG2, IgG3, or IgG4 subtype.

In some embodiments, the anti-CCL20 antibody is a monoclonal antibody.

The present invention also provides an anti-CCL20 antibody or an antigen-binding portion thereof that binds to an epitope of human CCL20 located in the N-loop and/or β2-β3 hairpin region of the molecule. In some embodiments, said anti-CCL20 antibody or portion binds to the same epitope on human CCL20 as an antibody or portion as described herein. Further, the present invention provides an anti-CCL20 antibody or an antigen-binding portion thereof that competes or cross-competes for binding to human CCL20 with an antibody or portion described herein.

In some embodiments, the human CCL20 epitope bound by the antibody or antigen-binding portion thereof of the invention comprises one or more amino acid sequences selected from the group consisting of:
residues 7-9 of SEQ ID NO: 84;
residues 10-19 of SEQ ID NO: 84;
residues 20-21 of SEQ ID NO: 84; and
residues 20-22 of SEQ ID NO: 84,
or the residues of wild-type human CCL20 corresponding to said residues of SEQ ID NO: 84.

In some embodiments, said human CCL20 epitope further comprises one or more amino acid sequences selected from the group consisting of:

residues 39-55 of SEQ ID NO: 84;
residues 39-57 of SEQ ID NO: 84;
residues 56-67 of SEQ ID NO: 84; and
residues 61-70 of SEQ ID NO: 84,
or the residues of wild-type human CCL20 corresponding to said residues of SEQ ID NO: 84.

In certain embodiments, said human CCL20 epitope comprises any combination of the amino acid sequences consisting of residues 7-9, 10-19, 20-22, 39-55, 56-57, and 61-70 of SEQ ID NO: 84, or the residues of wild-type human CCL20 corresponding to said residues of SEQ ID NO: 84.

In certain embodiments, said human CCL20 epitope comprises residues 7-9, 10-19, and 20-22 of SEQ ID NO: 84, or the residues of wild-type human CCL20 corresponding to said residues of SEQ ID NO: 84. In certain embodiments, said human CCL20 epitope comprises residues 7-9, 10-19, 20-22, 39-55, 56-57, and 61-70 of SEQ ID NO: 84, or the residues of wild-type human CCL20 corresponding to said residues of SEQ ID NO: 84. In certain embodiments, said human CCL20 epitope comprises residues 7-9, 10-19, 20-22, 39-57, and 61-70 of SEQ ID NO: 84, or the residues of wild-type human CCL20 corresponding to said residues of SEQ ID NO: 84.

In certain embodiments, said human CCL20 epitope comprises residues 7-9, 10-19, and 20-21 of SEQ ID NO: 84, or the residues of wild-type human CCL20 corresponding to said residues of SEQ ID NO: 84. In certain embodiments, said human CCL20 epitope comprises residues 7-9, 10-19, 20-21, 39-55, 56-67, and 61-70 of SEQ ID NO: 84, or the residues of wild-type human CCL20 corresponding to said residues of SEQ ID NO: 84. In certain embodiments, said human CCL20 epitope comprises residues 7-9, 10-19, 20-21, 39-57, and 61-70 of SEQ ID NO: 84, or the residues of wild-type human CCL20 corresponding to said residues of SEQ ID NO: 84.

In some embodiments, the human CCL20 epitope bound by the antibody or antigen-binding portion thereof comprises one or more amino acid residues of SEQ ID NO: 84 (or the residues of wild-type human CCL20 corresponding to said residues of SEQ ID NO: 84) selected from residues 7, 8, 9, 10, 11, 12, 13, 14, 15, 16, 17, 18, 19, 20, 21, 22, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70, or any combination thereof.

The present invention also provides an antigen-binding portion of any of the anti-CCL20 antibodies described herein. Said antigen-binding portion may be, e.g., a single chain antibody, Fv, Fab, Fab', F(ab')$_2$, Fd, single chain Fv molecule (scFv), bispecific single chain Fv dimer, polyvalent single chain Fv multimer, diabody, domain-deleted antibody, or single domain antibody (dAb).

The present invention also provides a variant of an antibody or antigen-binding portion as described herein, wherein said variant differs from the antibody or portion by 1, 2, 3, 4, 5, 6, 7, 8, 9 or 10 amino acid substitutions.

In one aspect, the present invention provides an antibody directed against human CCL20, wherein the heavy chain variable domain and the light chain variable domain of said antibody respectively comprise the sequences of:
SEQ ID NOS: 9 and 15;
SEQ ID NOS: 9 and 16;
SEQ ID NOS: 10 and 16;
SEQ ID NOS: 11 and 15;
SEQ ID NOS: 11 and 16;
SEQ ID NOS: 12 and 16;
SEQ ID NOS: 13 and 16; or
SEQ ID NOS: 14 and 16.

In one aspect, the present invention provides an antibody whose heavy chain comprises SEQ ID NO: 1 and whose light chain comprises SEQ ID NO: 7, wherein said amino acid sequences lack signal sequences.

In another aspect, the present invention provides an antibody whose heavy chain comprises SEQ ID NO: 1 without the C-terminal lysine and whose light chain comprises SEQ ID NO: 7, wherein said amino acid sequences lack signal sequences.

In one aspect, the present invention provides an antibody whose heavy chain comprises SEQ ID NO: 1 and whose light chain comprises SEQ ID NO: 8, wherein said amino acid sequences lack signal sequences.

In another aspect, the present invention provides an antibody whose heavy chain comprises SEQ ID NO: 1 without the C-terminal lysine and whose light chain comprises SEQ ID NO: 8, wherein said amino acid sequences lack signal sequences.

In one aspect, the present invention provides an antibody whose heavy chain comprises SEQ ID NO: 2 and whose light chain comprises SEQ ID NO: 8, wherein said amino acid sequences lack signal sequences.

In another aspect, the present invention provides an antibody whose heavy chain comprises SEQ ID NO: 2 without the C-terminal lysine and whose light chain comprises SEQ ID NO: 8, wherein said amino acid sequences lack signal sequences.

In one aspect, the present invention provides an antibody whose heavy chain comprises SEQ ID NO: 3 and whose light chain comprises SEQ ID NO: 7, wherein said amino acid sequences lack signal sequences.

In another aspect, the present invention provides an antibody whose heavy chain comprises SEQ ID NO: 3 without the C-terminal lysine and whose light chain comprises SEQ ID NO: 7, wherein said amino acid sequences lack signal sequences.

In one aspect, the present invention provides an antibody whose heavy chain comprises SEQ ID NO: 3 and whose light chain comprises SEQ ID NO: 8, wherein said amino acid sequences lack signal sequences.

In another aspect, the present invention provides an antibody whose heavy chain comprises SEQ ID NO: 3 without the C-terminal lysine and whose light chain comprises SEQ ID NO: 8, wherein said amino acid sequences lack signal sequences.

In one aspect, the present invention provides an antibody whose heavy chain comprises SEQ ID NO: 4 and whose light chain comprises SEQ ID NO: 8, wherein said amino acid sequences lack signal sequences.

In another aspect, the present invention provides an antibody whose heavy chain comprises SEQ ID NO: 4 without the C-terminal lysine and whose light chain comprises SEQ ID NO: 8, wherein said amino acid sequences lack signal sequences.

In one aspect, the present invention provides an antibody whose heavy chain comprises SEQ ID NO: 5 and whose light chain comprises SEQ ID NO: 8, wherein said amino acid sequences lack signal sequences.

In another aspect, the present invention provides an antibody whose heavy chain comprises SEQ ID NO: 5 without the C-terminal lysine and whose light chain comprises SEQ ID NO: 8, wherein said amino acid sequences lack signal sequences.

In one aspect, the present invention provides an antibody whose heavy chain comprises SEQ ID NO: 6 and whose light chain comprises SEQ ID NO: 8, wherein said amino acid sequences lack signal sequences.

In another aspect, the present invention provides an antibody whose heavy chain comprises SEQ ID NO: 6 without the C-terminal lysine and whose light chain comprises SEQ ID NO: 8, wherein said amino acid sequences lack signal sequences.

In one aspect, the present invention provides an antibody whose heavy chain comprises SEQ ID NO: 108 and whose light chain comprises SEQ ID NO: 110.

In another aspect, the present invention provides an antibody whose heavy chain comprises SEQ ID NO: 108 without the C-terminal lysine and whose light chain comprises SEQ ID NO: 110.

In one aspect, the present invention provides an antibody whose heavy chain comprises SEQ ID NO: 108 and whose light chain comprises SEQ ID NO: 112.

In another aspect, the present invention provides an antibody whose heavy chain comprises SEQ ID NO: 108 without the C-terminal lysine and whose light chain comprises SEQ ID NO: 112.

In another aspect, the present invention provides one or more nucleic acid molecules, e.g., isolated nucleic acid molecules, encoding a heavy chain or an antigen-binding portion thereof or a light chain or an antigen-binding portion thereof, wherein said heavy chain and light chain or antigen-binding portions thereof may associate to form an anti-CCL20 antibody or an antigen-binding portion thereof. In some embodiments, the nucleic acid molecule encoding the heavy chain or an antigen-binding portion thereof comprises a nucleotide sequence selected from the group consisting of SEQ ID NOS: 17-22, 25-30, and 109, or said nucleotide sequence without the sequence encoding a signal sequence, if present. The nucleotide sequences of SEQ ID NOS: 17-22 and 109 may also optionally lack the sequence encoding the C-terminal lysine, if present. In some embodiments, the nucleic acid molecule encoding the light chain or an antigen-binding portion thereof comprises a nucleotide sequence selected from the group consisting of SEQ ID NOS: 23, 24, 31, 32, 111, and 113, or said nucleotide sequence without the sequence encoding a signal sequence, if present. In some embodiments, the one or more nucleic acid molecules encode the heavy chain or an antigen-binding portion thereof and the light chain or an antigen-binding portion thereof of an antibody or portion as described herein. In certain embodiments, one nucleic acid molecule encodes both said heavy chain or an antigen-binding portion thereof and said light chain or an antigen-binding portion thereof.

In one embodiment, the nucleic acid molecule encoding the heavy chain or an antigen-binding portion thereof, the nucleic acid molecule encoding the light chain or an antigen-binding portion thereof, or nucleic acid molecule(s) encoding the heavy chain and the light chain or antigen-binding portions thereof, are used for treating a subject in need thereof.

In another aspect, the present invention provides a vector comprising nucleic acid sequence(s) encoding the heavy chain or an antigen-binding portion thereof, the light chain or an antigen-binding portion thereof, or both, of an antibody or portion as described herein.

In another aspect, the present invention provides a cell expressing the heavy chain or an antigen-binding portion thereof, the light chain or an antigen-binding portion thereof, or both, of an antibody or portion as described herein.

In another aspect, the present invention provides a method for making an antibody or portion as described herein, comprising maintaining a cell as described herein under conditions appropriate for expression of the antibody or portion. In some embodiments, the method comprises the step of isolating the antibody or portion.

The present invention also provides a method of producing a hybridoma that secretes an anti-CCL20 antibody. In certain embodiments, the hybridoma produces an antibody that binds to wild-type human CCL20. The invention also provides a hybridoma produced by the methods of the invention. Optionally, the monoclonal antibody secreted by the hybridoma is collected and can be further purified (e.g., substantially purified, isolated). In other embodiments, the method further comprises determining the nucleotide sequence of the monoclonal antibody secreted by the hybridoma.

In another aspect, the present invention provides a composition comprising an antibody or portion as described herein and a pharmaceutically acceptable vehicle or carrier.

In one aspect, the antibody or portion as described herein is used as a medicament. In certain embodiments, the antibody or portion as described herein is used for treating a subject in need thereof. In particular embodiments, the antibody or portion is used to treat a CCR6-associated condition, a CCL20 associated condition or both. Such conditions include but are not limited to inflammatory and autoimmune diseases, particularly arthritis, especially rheumatoid arthritis, atopic or allergic dermatitis, and psoriasis. In another particular embodiment, the antibody or portion is used to treat cancer. The antibody or portion may be used to treat, e.g., Grave's disease, vitiligo, hyperthyroidism, rheumatoid arthritis, psoriasis, atopic dermatitis, contact dermatitis, Crohn's disease, inflammatory bowel disease, B-cell malignancies, breast adenocarcinoma, chronic hepatitis, contact dermatitis, glioblastoma, hepatocellular carcinoma, human papillomavirus infection of the cervix, mycosis fungoides, pancreatic adenocarcinoma, periodontal disease, thyroid papillary carcinoma, pustulosis palmaris et plantaris, conditions associated with maculopapular exanthema, epidermolysis bullosa, alopecia areata, multiple sclerosis, polymyositis, dermatomyositis, Behcet's disease, acute generalized exanthematous pustulosis, vasculitides, juvenile idiopathic arthritis, sarcoidosis, bronchial asthma, allergic rhinitis, renal allograft rejection, graft-versus-host disease, liver allograft rejection, chronic obstructive pulmonary disease, cystic fibrosis, glomerulonephritis, respiratory syncytial virus infection, multiple myeloma, and/or Langerhans cell histiocytosis.

In some embodiments, the anti-CCL20 antibody or portion is used to reduce CCL20-mediated chemotaxis of CCR6+ cells in a subject in need thereof.

In some embodiments, the present invention provides:
1. A monoclonal anti-human CCL20 antibody or an antigen-binding portion thereof, wherein said antibody comprises a heavy chain whose complementarity determining region 3 (CDR3) comprises SEQ ID NO: 67 or 68.
2. The monoclonal antibody or antigen-binding portion of embodiment 1, wherein the complementarity determining region 1 (CDR1), complementarity determining region 2 (CDR2), and complementarity determining region 3 (CDR3) of said heavy chain respectively comprise amino acid sequences selected from the group consisting of:
   a) SEQ ID NOS: 60, 64, and 67;
   b) SEQ ID NOS: 60, 63, and 67;
   c) SEQ ID NOS: 61, 65, and 68;
   d) SEQ ID NOS: 77, 79, and 67; and
   e) SEQ ID NOS: 78, 80, and 68.
3. A monoclonal anti-human CCL20 antibody or an antigen-binding portion thereof, wherein said antibody comprises a light chain whose complementarity determining region 3 (CDR3) comprises SEQ ID NO: 75.
4. The monoclonal antibody or antigen-binding portion of embodiment 3, wherein the complementarity determining region 1 (CDR1), complementarity determining region 2 (CDR2), and complementarity determining region 3 (CDR3) of said light chain respectively comprise amino acid sequences selected from the group consisting of:
   a) SEQ ID NOS: 70, 73, and 75; and
   b) SEQ ID NOS: 71, 73, and 75.
5. The antibody or antigen-binding portion of embodiment 1 or 3, wherein the heavy chain of said antibody comprises a CDR3 comprising SEQ ID NO: 67 or 68 and the light chain of said antibody comprises a CDR3 comprising SEQ ID NO: 75.
6. The antibody or antigen-binding portion according to embodiment 2 or 4, wherein said heavy chain CDR1, CDR2, and CDR3 and said light chain CDR1, CDR2, and CDR3 respectively comprise amino acid sequences selected from the group consisting of:
   a) SEQ ID NOS: 60, 64, 67, 70, 73, and 75;
   b) SEQ ID NOS: 60, 64, 67, 71, 73, and 75;
   c) SEQ ID NOS: 60, 63, 67, 70, 73, and 75;
   d) SEQ ID NOS: 60, 63, 67, 71, 73, and 75;
   e) SEQ ID NOS: 61, 65, 68, 70, 73, and 75;
   f) SEQ ID NOS: 61, 65, 68, 71, 73, and 75;
   g) SEQ ID NOS: 77, 79, 67, 70, 73, and 75;
   h) SEQ ID NOS: 77, 79, 67, 71, 73, and 75;
   i) SEQ ID NOS: 78, 80, 68, 70, 73, and 75; and
   j) SEQ ID NOS: 78, 80, 68, 71, 73, and 75.
7. A monoclonal anti-human CCL20 antibody or an antigen-binding portion thereof, wherein said antibody comprises a heavy chain whose variable domain comprises an amino acid sequence selected from SEQ ID NOS: 9-14.
8. A monoclonal anti-human CCL20 antibody or an antigen-binding portion thereof, wherein said antibody comprises a light chain whose variable domain comprises SEQ ID NO: 15 or 16.
9. The antibody or antigen-binding portion according to embodiment 7 or 8, wherein said heavy chain variable domain and said light chain variable domain respectively comprise amino acid sequences selected from the group consisting of:
   a) SEQ ID NOS: 9 and 15;
   b) SEQ ID NOS: 9 and 16;
   c) SEQ ID NOS: 10 and 16;
   d) SEQ ID NOS: 11 and 15;
   e) SEQ ID NOS: 11 and 16;
   f) SEQ ID NOS: 12 and 16;
   g) SEQ ID NOS: 13 and 16; and
   h) SEQ ID NOS: 14 and 16.
10. A monoclonal anti-human CCL20 antibody whose heavy chain comprises an amino acid sequence selected from the group consisting of SEQ ID NOS: 1-6 without the signal sequence and SEQ ID NO: 108.
11. A monoclonal anti-human CCL20 antibody whose heavy chain comprises an amino acid sequence selected from the group consisting of SEQ ID NOS: 1-6 without the signal sequence and SEQ ID NO: 108, wherein said amino acid sequence lacks the C-terminal lysine.
12. A monoclonal anti-human CCL20 antibody whose light chain comprises an amino acid sequence selected from the group consisting of SEQ ID NOS: 7 and 8 without the signal sequence and SEQ ID NOS: 110 and 112.
13. The antibody according to any one of embodiments 10-12, wherein said heavy chain and said light chain respectively comprise amino acid sequences selected from the group consisting of:
   a) SEQ ID NOS: 1 and 7;
   b) SEQ ID NOS: 1 and 8;
   c) SEQ ID NOS: 2 and 8;
   d) SEQ ID NOS: 3 and 7;
   e) SEQ ID NOS: 3 and 8;
   f) SEQ ID NOS: 4 and 8;
   g) SEQ ID NOS: 5 and 8;
   h) SEQ ID NOS: 6 and 8;
   i) SEQ ID NOS: 108 and 110; and
   j) SEQ ID NOS: 108 and 112;
   wherein said amino acid sequences lack signal sequences, if present, and wherein SEQ ID NOS: 1-6 optionally lack the C-terminal lysine.
14. A monoclonal antibody whose heavy chain comprises SEQ ID NO: 108 and whose light chain comprises SEQ ID NO: 110.
15. A monoclonal antibody whose heavy chain comprises SEQ ID NO: 108 without the C-terminal lysine and whose light chain comprises SEQ ID NO: 110.
16. A monoclonal antibody whose heavy chain comprises SEQ ID NO: 108 and whose light chain comprises SEQ ID NO: 112.
17. A monoclonal antibody whose heavy chain comprises SEQ ID NO: 108 without the C-terminal lysine and whose light chain comprises SEQ ID NO: 112.
18. A monoclonal anti-human CCL20 antibody, or an antigen-binding portion thereof, that binds to the same epitope of human CCL20 as the monoclonal antibody or antigen-binding portion of any one of embodiments 1-17.
19. A monoclonal anti-human CCL20 antibody, or an antigen-binding portion thereof, that competes for binding to human CCL20 with the monoclonal antibody or antigen-binding portion of any one of embodiments 1-17.
20. A monoclonal anti-human CCL20 antibody, or an antigen-binding portion thereof, that cross-competes for binding to human CCL20 with the monoclonal antibody or antigen-binding portion of any one of embodiments 1-17.
21. The monoclonal antibody or antigen-binding portion of any one of embodiments 1-12, wherein the antibody is a humanized antibody.
22. The monoclonal antibody or antigen-binding portion of any one of embodiments 1-6, wherein the framework regions of said heavy chain utilize a IGHV1-46*03 human germline sequence, and wherein the framework regions of said light chain utilize a IGKV1D-39*01 human germline sequence.
23. The monoclonal antibody of any one of embodiments 1-9 and 18-22, wherein said antibody comprises a human IgG1, IgG2, IgG3, or IgG4 constant domain.
24. A monoclonal anti-human CCL20 antibody, or an antigen-binding portion thereof, whose heavy chain comprises a variable domain comprising an amino acid sequence selected from the group consisting of SEQ ID NOS: 39, 41, and 43.
25. A monoclonal anti-human CCL20 antibody, or an antigen-binding portion thereof, whose light chain comprises a variable domain comprising an amino acid sequence selected from the group consisting of SEQ ID NOS: 40, 42, and 44.
26. The antibody or antigen-binding portion of embodiment 24 or 25, wherein said heavy chain comprises an amino acid sequence selected from the group consisting of SEQ ID NOS: 39, 41, and 43 and wherein said light chain comprises an amino acid sequence selected from the group consisting of SEQ ID NOS: 40, 42, and 44.

27. The antibody of embodiment 26, wherein said heavy chain and said light chain respectively comprise amino acid sequences selected from the group consisting of:
   a) SEQ ID NOS: 39 and 40;
   b) SEQ ID NOS: 41 and 42; and
   c) SEQ ID NOS: 43 and 44.
28. A monoclonal anti-human CCL20 antibody, or an antigen-binding portion thereof, wherein said antibody comprises a heavy chain comprising SEQ ID NO: 39 and a light chain comprising SEQ ID NO: 40.
29. The monoclonal antibody or antigen-binding portion of any one of embodiments 24-28, wherein said antibody is a chimeric antibody.
30. The antigen-binding portion of any one of embodiments 1-9, 18-22, and 24-28, wherein said portion is a single chain antibody, Fv, Fab, Fab', F(ab')$_2$, Fd, single chain Fv molecule (scFv), bispecific single chain Fv dimer, diabody, domain-deleted antibody or single domain antibody (dAb).
31. The monoclonal antibody or antigen-binding portion according to any one of embodiments 1-30, wherein said antibody or antigen-binding portion has one or more properties selected from the group consisting of:
   a) does not bind to human CCL16;
   b) binds to cynomolgus or rhesus CCL20, but not to mouse or rat CCL20;
   c) has a binding affinity for human CCL20 of 70 pM or less using a monovalent surface plasmon resonance assay;
   d) has a binding affinity for human CCL20 of 12 pM or less using a bivalent surface plasmon resonance assay;
   e) has a binding affinity for human CCL20 greater than that of human CCR6;
   f) has a selectivity for human CCL20 over human CX3CL1, CXCL1, CXCL2, CXCL4, CXCL8, CXCL9, CXCL10, CXCL12, CXCL13, CXCL16, CCL1, CCL2, CCL3, CCL4, CCL5, CCL7, CCL11, CCL13, CCL16, CCL17, CCL19, CCL21, CCL22, CCL24, CCL25, CCL27, CCL28, or XCL1;
   g) reduces human CCL20-induced chemotaxis of CCR6+ cells with an IC$_{50}$ of 1.7 nM or less;
   h) reduces human CCL20-induced chemotaxis of CCR6+ cells in vivo;
   i) reduces human CCL20-induced chemotaxis of CCR6+ cells in vitro;
   j) reduces progression of arthritis symptoms in a subject;
   k) reduces osteoporosis, bone erosion, or new bone formation in a subject;
   l) reduces cartilage oligomeric matrix protein (COMP) serum levels in a subject;
   m) reduces mRNA levels of RANKL, RANK, TRAP, or cathepsin K in a subject;
   n) reduces progression of atopic dermatitis in a subject; and
   o) reduces progression of allergic contact dermatitis in a subject.
32. A monoclonal anti-human CCL20 antibody, or an antigen-binding portion thereof, that binds to an epitope of human CCL20 comprising one or more amino acid sequences selected from the group consisting of:
   a) residues 7-9 of SEQ ID NO: 84;
   b) residues 10-19 of SEQ ID NO: 84; and
   c) residues 20-22 of SEQ ID NO: 84.
33. The monoclonal antibody or antigen-binding portion of embodiment 32, wherein said epitope comprises residues 7-9, 10-19, and 20-22 of SEQ ID NO: 84.
34. The monoclonal antibody or antigen-binding portion of embodiment 32, wherein said epitope further comprises one or more amino acid sequences selected from the group consisting of:
   a) residues 39-55 of SEQ ID NO: 84;
   b) residues 56-67 of SEQ ID NO: 84; and
   c) residues 61-70 of SEQ ID NO: 84.
35. The monoclonal antibody or antigen-binding portion of embodiment 34, wherein said epitope comprises residues 7-9, 10-19, 20-22, 39-55, 56-67, and 61-70 of SEQ ID NO: 84.
36. An isolated nucleic acid molecule encoding the heavy chain or an antigen-binding portion thereof of an antibody or portion according to any one of embodiments 1-35.
37. An isolated nucleic acid molecule encoding the light chain or an antigen-binding portion thereof of an antibody or portion according to any one of embodiments 1-35.
38. An isolated nucleic acid molecule encoding the heavy chain or an antigen-binding portion thereof, and the light chain or an antigen-binding portion thereof, of an antibody or portion according to any one of embodiments 1-35.
39. An isolated nucleic acid molecule encoding the heavy chain or an antigen-binding portion thereof of a monoclonal anti-human CCL20 antibody, wherein said nucleic acid molecule comprises a nucleotide sequence selected from the group consisting of SEQ ID NOS: 17-22, 25-30, and 109, or said nucleotide sequence without the sequence encoding a signal sequence, if present.
40. An isolated nucleic acid molecule encoding the light chain or an antigen-binding portion thereof of a monoclonal anti-human CCL20 antibody, wherein said nucleic acid molecule comprises a nucleotide sequence selected from the group consisting of SEQ ID NOS: 23, 24, 31, 32, 111, and 113, or said nucleotide sequence without the sequence encoding a signal sequence, if present.
41. The isolated nucleic acid molecule of embodiment 39 or 40, wherein said nucleic acid molecule comprises a nucleotide sequence selected from the group consisting of SEQ ID NOS: 17-22, 25-30, and 109, or said nucleotide sequence without the sequence encoding a signal sequence if present; and wherein said nucleic acid molecule further comprises a nucleotide sequence selected from the group consisting of SEQ ID NOS: 23, 24, 31, 32, 111, and 113, or said nucleotide sequence without the sequence encoding a signal sequence if present.
42. Use of (1) a nucleic acid sequence encoding the heavy chain or an antigen-binding portion thereof, (2) a nucleic acid sequence encoding the light chain or an antigen-binding portion thereof, or (3) both, of an antibody or portion according to any one of embodiments 1-35, as a medicament.
43. A recombinant vector comprising (1) a nucleic acid sequence encoding the heavy chain or an antigen-binding portion thereof, (2) a nucleic acid sequence encoding the light chain or an antigen-binding portion thereof, or (3) both, of an antibody or portion according to any one of embodiments 1-35.
44. A host cell comprising a first nucleic acid sequence encoding the heavy chain or an antigen-binding portion thereof of an antibody or portion according to any one of embodiments 1-35, said first nucleic acid sequence operably linked to an expression control element, and a second nucleic acid sequence encoding the light chain or an antigen-binding portion thereof of said antibody or portion, said second nucleic acid sequence operably linked to an expression control element.

45. A method of making an anti-human CCL20 antibody or an antigen-binding portion thereof, comprising maintaining the host cell of embodiment 44 under conditions appropriate for expression of the antibody or portion.

46. The method of embodiment 45, further comprising isolating the antibody or portion.

47. A composition comprising the monoclonal antibody or antigen-binding portion of any one of embodiments 1-35 and a pharmaceutically acceptable vehicle or carrier.

48. A method for treating a subject in need thereof, comprising administering to the subject an effective amount of the antibody or antigen-binding portion of any one of embodiments 1-35 or the composition of embodiment 47.

49. A method for treating a condition in a subject in need thereof, comprising administering to the subject an effective amount of the antibody or antigen-binding portion of any one of embodiments 1-35 or the composition of embodiment 47.

50. The method of embodiment 49, wherein said condition is a CCR6-associated condition.

51. The method of embodiment 49, wherein said condition is an autoimmune or inflammatory condition.

52. The method of embodiment 49, wherein said condition is rheumatoid arthritis, psoriasis, atopic dermatitis, contact dermatitis, Crohn's disease, inflammatory bowel disease, Grave's disease, vitiligo, hyperthyroidism, chronic hepatitis, human papillomavirus infection of the cervix, mycosis fungoides, osteoporosis, or periodontal disease.

53. A method for treating cancer, comprising administering to a subject an effective amount of the antibody or antigen-binding portion of any one of embodiments 1-35 or the composition of embodiment 47.

54. The method of embodiment 53, wherein said cancer is a B-cell malignancy, breast adenocarcinoma, glioblastoma, hepatocellular carcinoma, pancreatic adenocarcinoma, or thyroid papillary carcinoma.

55. A method for reducing CCL20-mediated chemotaxis of CCR6+ cells in a subject in need thereof, comprising administering to the subject the antibody or antigen-binding portion of any one of embodiments 1-35 or the composition of embodiment 47.

56. A method for reducing CCL20-mediated chemotaxis of CCR6+ cells in vitro, using the antibody or antigen-binding portion of any one of embodiments 1-35 or the composition of embodiment 47.

57. A method for treating a condition in a subject, comprising administering to the subject the antibody or antigen-binding portion of any one of embodiments 1-35 or the composition of embodiment 47, wherein said condition is selected from the group consisting of:
a) articular lesions of extremities distal to the elbow or knee;
b) erythema;
c) swelling;
d) increased cartilage oligomeric matrix protein (COMP) serum levels;
e) increased mRNA levels of receptor activator for nuclear factor κB ligand (RANKL), receptor activator for nuclear factor κB (RANK), tartrate resistant acid phosphatase (TRAP), or cathepsin K;
f) atopic dermatitis; and
g) allergic contact dermatitis.

58. Use of the antibody or antigen-binding portion of any one of embodiments 1-35 or the composition of embodiment 47 for the manufacture of a medicament.

59. Use of the antibody or antigen-binding portion of any one of embodiments 1-35 or the composition of embodiment 47 as a medicament.

BRIEF DESCRIPTION OF THE DRAWINGS

FIGS. 6A-C depict sequence alignments of variable domains of antibodies of the invention (SEQ ID NOS: 9-16) with those of mouse anti-human antibodies 36F7C10 (VH: SEQ ID NO: 39; VL: SEQ ID NO: 40) and 42G5B10 (VH: SEQ ID NO: 43) and with germline sequences IGHV1-46*03 (SEQ ID NO: 57), JH4 (SEQ ID NO: 58), and IGKV1D-39*01 (SEQ ID NO: 59). Kabat and Chothia definitions of each CDR are indicated. ABM67212 (SEQ ID NO: 82) and BAH04867.1 (SEQ ID NO: 83) are human antibodies from which the framework regions of the shown humanized antibody chains were derived. See Example 3.

FIGS. 7A-C are tables depicting the inhibition of in vitro chemotaxis by different combinations of humanized anti-human CCL20 antibody chains. Data represent three trials, except where indicated. See Example 4.

FIG. 12 shows an amino acid sequence alignment between a56-residue overlap portion of CCL20 (SEQ ID NO: 114) and CCL16 (SEQ ID NO: 115). See Example 6.

FIG. 14 shows amino acid sequence alignments between human (first disclosure is SEQ ID NO: 85 and second disclosure is residues 2-96 of SEQ ID NO: 85), rhesus (SEQ ID NO: 86), cynomolgus (SEQ ID NO: 87), and mouse (SEQ ID NO: 88) CCL20 orthologs. See Example 7.

FIG. 19 is a pair of graphs demonstrating that mouse CCR6-transduced B300 cells migrate toward both mouse and human CCL20. See Example 10.

FIG. 22 is a table of individual animal clinical scores demonstrating that 2F5-5 MAb reduces progression of collagen-induced arthritis symptoms. See Example 11.

FIGS. 25A-C show measurements of a marker of cartilage destruction, serum cartilage oligomeric matrix protein (COMP), in a collagen-induced arthritic mouse model. A) Calibrator data with a COMP standard. X axis, units/liter; Y axis, optical density at 450 nm. B) Plate template and raw data for mice treated with a hamster control IgG or 2F5-5 MAb. C) Data from individual animals demonstrates reduced COMP levels in animals treated with 2F5-5 MAb compared to animals treated with control IgG antibodies. See Example 11.

DETAILED DESCRIPTION OF THE INVENTION

Figure 1:
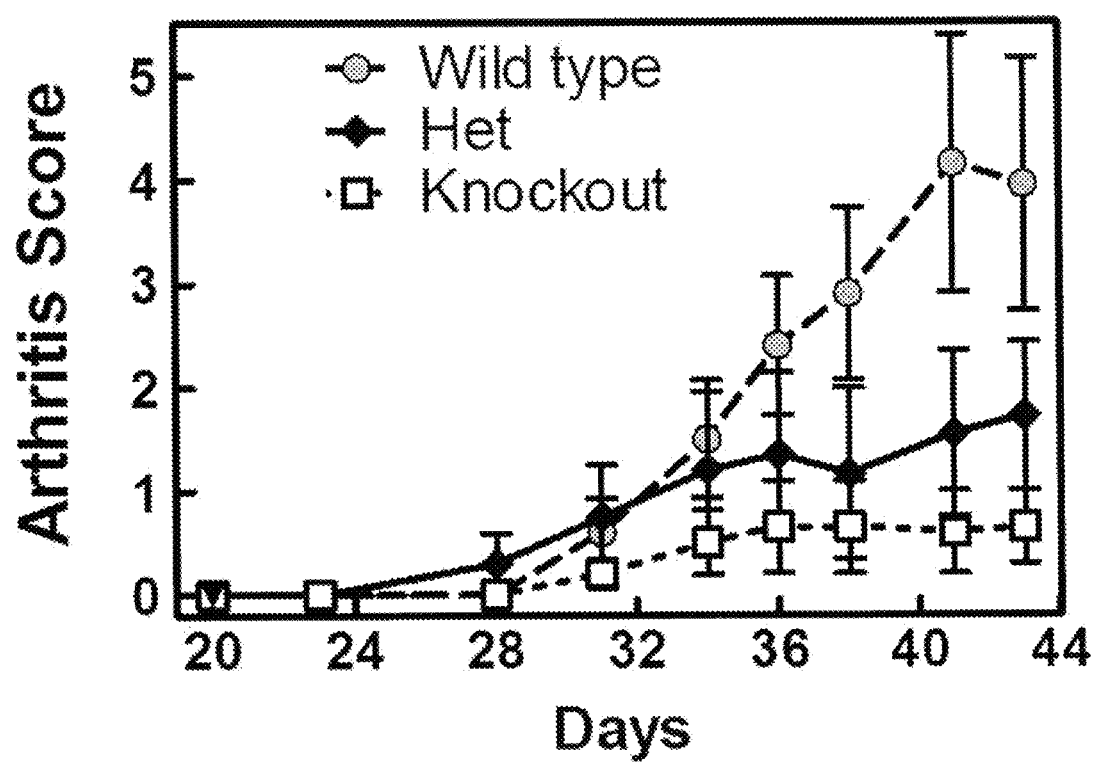
FIG. 1 is a graph showing that CCR6 deficient mice are less sensitive to collagen-induced arthritis than wild-type mice. Wild type, $CCR6^{+/+}$ mice; Het, $CCR6^{+/-}$ mice; Knockout, $CCR6^{-/-}$ mice. See Example 1.

This invention is directed to antibodies that specifically bind to CCL20 or a portion thereof (e.g., an antigenic portion thereof). The invention is also directed to antigen-binding portions of said antibodies. In one embodiment, the antibodies neutralize one or more activities of CCL20. An antibody is said to bind specifically to CCL20 if it does not substantially bind to non-CCL20 molecules. Substantial binding is, for example, binding with a $K_D$ of <100 nM, preferably < than 10 nM, 1 nM, 100 pM, 50 pM, 40 pM, or 35 pM as determined by Biacore™ (in bivalent format). In one embodiment, the antibodies or portions bind specifically to human CCL20 or a portion thereof, to some sequence variants of human CCL20 such as allelic variants, and may also cross-react with CCL20 from other species. In one embodiment, the antibodies or portions have binding specificity for a wild-type (also referred to as naturally occurring or endogenous) human CCL20. Unless otherwise indicated, "human CCL20" refers to wild-type human CCL20. The amino acid sequence of a wild-type human CCL20 with the signal sequence is shown in FIG. 14 (SEQ ID NO: 85). The amino acid sequence of a wild-type human CCL20 without the signal sequence (residues 1-26 of SEQ ID NO: 85) is found in SEQ ID NO: 99 (see Table 18). FIG. 18 depicts a variant of human CCL20 without the signal sequence (SEQ ID NO: 84) wherein the next to last residue is a D instead of the N as in the wild-type sequence (SEQ ID NO: 85). In some embodiments, the antibodies or portions bind to wild-type human CCL20, or human CCL20 wherein the next to last residue is a D instead of the N shown in the wild-type sequence, either sequence with or without the signal sequence (e.g., SEQ ID NO: 84, 85, or 99). In a particular embodiment, the antibodies or portions bind specifically to human, rhesus, and cynomolgus CCL20 but do not bind to mouse or rat CCL20.

The antibodies and antigen-binding portions thereof described herein can be purified and/or isolated using known techniques. Antibodies or portions that are "purified" or "isolated" have been separated away from molecules (e.g., peptides) of their source of origin (e.g., the supernatant of cells; in a mixture such as in a mixture of antibodies in a library; etc.), and include antibodies obtained by methods described herein or other suitable methods. Isolated antibodies include substantially pure (e.g., essentially pure)

antibodies, as well as antibodies produced by chemical synthesis, recombinant techniques and a combination thereof.

More specifically, the invention relates to anti-human CCL20 antibodies, antigen-binding portions (i.e., portions) of the antibodies, the light chains of the antibodies, the heavy chains of the antibodies, and portions of these light chains or heavy chains. The invention also relates to antibodies lacking the heavy and/or light chain signal sequences and glycosylated antibodies. The invention also relates to precursor antibodies, nonglycosylated antibodies, and antibodies whose heavy and/or light chains comprise signal sequences. The invention also relates to nucleic acid molecules that encode any of the antibody heavy chains and/or light chains, or portions thereof described herein; to vectors and host cells that comprise such nucleic acids; to methods of producing any of the antibody heavy and/or light chains or portions thereof described herein; and to methods of using the antibodies, antibody chains, or portions.

The antibodies and antigen-binding portions thereof of this invention can be used to treat a subject in need thereof (e.g., a human patient) to reduce CCL20 binding to CCR6, CCL20-mediated inflammation, and/or CCL20-mediated chemotaxis of CCR6+ cells as needed.

Antibodies of the invention include traditional antibodies comprising two heavy chains and two light chains. In some embodiments, one or more of the heavy and/or light chains comprises a variable domain (also referred to herein as a "variable region") and a constant domain (also referred to herein as a "constant region"). Complete variable domains, where present, comprise four framework regions (FRs) and three complementarity determining regions (CDRs), arranged, proceeding from the amino terminus, in the order FR1, CDR1, FR2, CDR2, FR3, CDR3, FR4. Visual inspection and sequence analysis can be carried out to identify the CDR boundaries. For this invention, the CDR sequences are defined by using the Kabat system (Kabat, E. A. et al., *Sequences of Proteins of Immunological Interest*, Fifth Edition, U.S. Department of Health and Human Services, U.S. Government Printing Office (1991)) and/or the Chothia system (Chothia & Lesk, *Canonical Structures for the Hypervariable Regions of Immunoglobulins, J. Mol. Biol.* 196:901-917 (1987)), as indicated in, e.g., FIG. 6.

Embodiments of the present invention that comprise a human heavy chain constant region may comprise a human constant region of any isotype, including IgG, IgM, IgA, IgD and IgE, in which the heavy chains are of the gamma (γ), mu (μ), alpha (α), delta (δ) or epsilon (ε) type, respectively, and any subclasses including IgG1, IgG2, IgG3, IgG4, IgA1 and IgA2, in which the heavy chains are of the γ1, γ2, γ3, γ4, α1 and α2 type, respectively. Embodiments comprising human light chains may comprise a human kappa (κ) or a human lambda (λ) light chain.

As used herein, the term "antibody" refers to a complete antibody (comprising two full-length heavy chains and two full-length light chains). The term "antigen-binding fragment" is used interchangeably herein with the term "antigen-binding portion" unless otherwise indicated. Antigen-binding portions of antibodies can be in the format of, for example, single chain antibodies, Fv fragments, Fab fragments, Fab' fragments, F(ab')$_2$ fragments, Fd fragments, single chain Fv molecules (scFv), bispecific single chain Fv dimers (PCT/US92/09665), diabodies, domain-deleted antibodies and single domain antibodies (dAbs). See, e.g., Jespers et al., *Nature Biotechnology* 22(9): 1161-1165 (2004)). Also within the invention are antigen-binding molecules comprising a VH and/or a VL. In the case of a VH, the molecule may also comprise one or more of a CH1, hinge, CH2 and CH3 region.

Antibody portions can be produced by enzymatic cleavage or by recombinant techniques. For instance, papain or pepsin cleavage can be used to generate Fab or F(ab')$_2$ fragments, respectively. Antibodies also can be produced in a variety of truncated forms using antibody genes in which one or more stop codons have been introduced upstream of the natural stop site. For example, a recombinant construct encoding the heavy chain of an F(ab')$_2$ fragment can be designed to include DNA sequences encoding the CH$_1$ domain and hinge region of the heavy chain.

In another embodiment, a fusion antibody or immunoadhesin may be made that comprises all or a portion of an anti-CCL20 antibody of the invention linked to another polypeptide. In one embodiment, only the variable domains of the anti-CCL20 antibody are linked to the polypeptide. In another embodiment, the V$_H$ domain of an anti-CCL20 antibody is linked to a first polypeptide, while the V$_L$ domain of an anti-CCL20 antibody is linked to a second polypeptide that associates with the first polypeptide in a manner such that the V$_H$ and V$_L$ domains can interact with one another to form an antigen binding site. In yet another embodiment, the V$_H$ domain is separated from the V$_L$ domain by a linker such that the V$_H$ and V$_L$ domains can interact with one another (see below under Single Chain Antibodies). The V$_H$-linker-V$_L$ antibody is then linked to the polypeptide of interest. In addition, fusion antibodies can be created in which two (or more) single-chain antibodies are linked to one another, to create a divalent or polyvalent antibody on a single polypeptide chain, or to create a bispecific antibody.

To create a single chain antibody of the invention, the V$_H$- and V$_L$-encoding DNA fragments are operatively linked to another fragment encoding a flexible linker, e.g., encoding the amino acid sequence (Gly$_4$-Ser)$_3$ (SEQ ID NO: 116), such that the V$_H$ and V$_L$ sequences can be expressed as a contiguous single-chain protein, with the V$_L$ and V$_H$ domains joined by the flexible linker. See, e.g., Bird et al., *Science* 242:423-426 (1988); Huston et al., *Proc. Natl. Acad. Sci. USA* 85:5879-5883 (1988); McCafferty et al., *Nature* 348:552-554 (1990); etc. In some embodiments, the single chain antibody is monovalent (only a single V$_H$ and V$_L$ are used), bivalent (two V$_H$ and V$_L$ are used), or polyvalent (more than two V$_H$ and V$_L$ are used). The invention also contemplates bispecific or polyvalent antibodies that bind specifically to human CCL20 and to another molecule.

In other embodiments, other modified antibodies may be prepared using anti-CCL20 antibody-encoding nucleic acid molecules. For instance, "Kappa bodies" (Ill et al., *Protein Eng.* 10:949-57 (1997)), "Minibodies" (Martin et al., *EMBO J.* 13:5303-9 (1994)), "Diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

In another aspect, the invention provides a variant of an antibody exemplified herein, or an antigen-binding portion of said variant antibody, wherein said variant antibody binds to human CCL20 specifically but differs in sequence from the exemplified antibody by 1, 2, 3, 4, 5, 6, 7, 8, 9, 10, or more amino acid substitutions (for example, in a CDR region, a FR region, and/or a constant domain). According to the invention, the variant antibody may be at least 80%, at least 85%, at least 90%, at least 91%, at least 92%, at least 93%, at least 94%, at least 95%, at least 96%, at least 97% at least 98% or at least 99% identical to the reference antibody in the heavy chain, the heavy chain variable domain, the light chain, the light chain variable domain, the six CDRs, or the eight FRs.

As used herein, sequence similarity for polypeptides, which is also referred to as sequence identity, is typically measured using sequence analysis software, which matches similar sequences using measures of similarity assigned to various substitutions, deletions and other modifications, including conservative amino acid substitutions. For instance, the Genetics Computer Group (GCG) Sequence Analysis Package contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences can also be compared with FASTA, a program in GCG Version 6.1., using default or recommended parameters. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). Another algorithm used when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997); herein incorporated by reference.

According to the invention, one or more cysteines in the antibody, which may be chemically reactive, may be changed to another residue, such as, without limitation, alanine or serine. In one embodiment, a non-canonical cysteine is substituted. The substitution can be made in a CDR or framework region of a variable domain or in the constant domain of an antibody. In some embodiments, the cysteine is canonical. In some embodiments, potential proteolytic sites in the antibody are removed. Such sites may occur in a CDR or framework region of a variable domain or in the constant domain of an antibody. Substitution of cysteine residues and removal of proteolytic sites may decrease the risk of heterogeneity in the antibody product and thus increase its homogeneity. In some embodiments, asparagine-glycine pairs, which form potential deamidation sites, are eliminated by altering one or both of the residues. In some embodiments, the antibody is deimmunized to reduce its immunogenicity. Techniques for reducing the immunogenicity of an antibody are well known in the art. See, e.g., PCT Publication Nos. WO 98/52976 and WO 00/34317.

In some embodiments, the antibody has one or more conservative amino acid substitutions when compared with an exemplified antibody of the invention. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g., Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan. 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

In certain embodiments, amino acid substitutions to an antibody or antigen-binding portion of the invention are those which: (1) reduce susceptibility to proteolysis, (2) reduce susceptibility to oxidation, (3) alter binding affinity for forming protein complexes, for example, to enhance ADCC and CDC activity of the antibody, (4) confer or modify other physicochemical or functional properties of such analogs, but still retain specific binding to human CCL20, (5) remove C-terminal lysine, and (6) add or remove glycosylation sites.

In one aspect, the invention provides a new and novel polypeptide that is the heavy or light chain of an antibody of this invention, or that is a variable domain-containing portion of the heavy or light chain. Such a polypeptide is useful because it can partner with a light or heavy antibody chain, respectively, to form an anti-CCL20 antibody.

Described herein are novel humanized neutralizing anti-CCL20 antibodies comprising the CDRs of novel mouse anti-human CCL20 antibodies, and antigen-binding portions of said humanized antibodies. The term "humanized anti-CCL20 antibody" as used herein refers to an antibody that comprises one or more CDRs (CDR1, CDR2 and CDR3) of an anti-CCL20 antibody of non-human origin, also referred to herein as the donor antibody (e.g., a mouse anti-CCL20 antibody), and at least a portion from a human sequence. The human antibody portion may be one or more framework regions (e.g., all of the framework regions), and/or all or part of a constant region. In some embodiments, the human sequence framework region comprises a germline sequence, but may include non-germline mutations. A CDR-grafted anti-CCL20 antibody in which the six CDRs of a non-human anti-CCL20 antibody are grafted into a human framework is an example of a humanized anti-CCL20 antibody of the invention. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird et al., Science 242:423-426 (1988)). In some embodiments, humanized antibodies are de-immunized antibodies. See, e.g., Carr et al., U.S. Pat. No. 7,264,806, regarding de-immunized antibodies that have been modified to reduce the number of potential T-cell epitopes, thereby reducing the propensity for the antibody to elicit an immune response upon administration to a human.

In particular embodiments, the humanized antibody comprises one or more light chain CDRs and/or one or more heavy chain CDRs of one or more of the following murine monoclonal anti-human CCL20 antibodies: 36F7C10, 42G5B10, and 40-1C10B9, wherein the CDRs are identified according to the Kabat system, the Chothia system, or any combination thereof. In some embodiments, the humanized antibody comprises all three heavy chain CDRs and all three light chain CDRs of antibody 36F7C10, 42G5B10, or 40-1C10B9.

In another embodiment, the humanized antibodies have the binding specificity of a murine anti-human CCL20 antibody of the invention (e.g., specificity for human CCL20, the same or similar epitopic specificity) and/or have a neutralizing activity. The humanized antibodies can have the binding specificity, epitopic specificity, and/or neutralizing activity of a murine, chimeric, or humanized anti-human CCL20 antibody described herein. For example, a humanized antibody of the invention can compete with the murine, chimeric, or humanized anti-human CCL20 antibody for binding to human CCL20, and/or it can have the neutralizing function of the murine, chimeric, or humanized anti-human CCL20 antibody. In a particular embodiment, the humanized antibody has the binding specificity, epitopic specificity and/or neutralizing activity of any one of mouse antibodies 36F7C10, 42G5B10, and 40-1C10B9.

The human sequence portion of the humanized antibody (e.g., framework region; constant region) can be from any suitable human antibody. For example, a human constant region or portion thereof in a humanized or chimeric antibody can be encoded by a human κ or λ light chain gene, and/or by a human γ (e.g., γ1, γ2, γ3, γ4), μ, α (e.g., α1, α2), δ or ε heavy chain gene, including allelic variants. A particular human constant region isotype (e.g., IgG1; IgG2), variant or portion thereof can be selected to tailor effector function. For example, a mutated constant region (i.e., a variant) can be incorporated into the antibody to reduce binding to an Fc receptor and/or ability to fix complement. (See e.g., Winter et al., GB 2,209,757 B; Morrison et al., WO 89/07142; Morgan et al., WO 94/29351).

As used herein, the term "germline" refers to the nucleotide sequences and amino acid sequences of the antibody genes and gene segments as they are passed from parents to offspring via the germ cells. This germline sequence is distinguished from the nucleotide sequences encoding a particular antibody in a B cell, which has been altered by recombination and hypermutation events during the course of affinity maturation. An antibody that "utilizes" a particular germline has a nucleotide or amino acid sequence that most closely aligns with the germline nucleotide sequence or with the amino acid sequence that it specifies as compared to other germline sequences. Such antibodies may be encoded by or comprise a sequence that is mutated compared with the germline sequence.

In some embodiments, the human framework has minimal variation from germline sequence, for example, less than 3, 4, 5, 6, 7, 8, 9, or 10 acceptor framework residues have been replaced to improve one or more properties of the antibody. In some embodiments, acceptor framework residues are replaced with donor framework residues, e.g., to improve binding affinity (see, e.g., Queen et al., U.S. Pat. No. 5,530,101). In a particular embodiment, a limited number of amino acids in the framework of a humanized antibody chain (e.g., 1, 2, 3, 4, 5, 6, 7, 8, 9, or 10 amino acids) are chosen to be the same as the amino acids at those positions in the donor sequence (i.e., "back-mutated"), rather than in the acceptor sequence, to increase the affinity of an antibody comprising the humanized antibody chain for human CCL20.

Human framework regions (e.g., of the heavy and/or light chain variable regions) are preferably obtained or derived from a human germline sequence having sequence similarity to the analogous or equivalent region (e.g., heavy or light chain variable regions) of the antigen-binding region of the donor antibody (e.g., murine anti-CCL20 antibody). Other sources of framework regions for human sequence portions of a humanized antibody include human variable region consensus sequences (See e.g., Kettleborough et al., *Protein Engineering* 4:773-783 (1991); Carter et al., WO 94/04679; Carter U.S. Pat. No. 6,407,213)). For example, the region of the donor sequence of the antibody (e.g., the sequence of the variable region) used to obtain the nonhuman portion can be compared to human sequences as described in Kabat, E. A. et al. *Sequences of Proteins of Immunological Interest*, Fifth Edition, U.S. Department of Health and Human Services, U.S. Government Printing Office (1991) to select a particular source of the human portions of the humanized antibody, e.g., a source of the framework regions.

In one embodiment, the framework regions of the humanized antibody chains are obtained, or derived, from a human Ig variable region having at least about 50%, at least about 55%, at least about 60%, at least about 65%, at least about 70%, at least about 75%, at least about 80%, at least about 85%, at least about 90% or at least about 95% overall sequence identity, with the variable region of the nonhuman donor. In a particular embodiment, the framework regions of the humanized antibody chains are obtained or derived from human variable region framework regions having at least about 50%, at least about 55%, at least about 60%, at least about 65%, at least about 70%, at least about 75%, at least about 80%, at least about 85%, at least about 90%, or at least about 95% overall sequence identity with the framework regions of the variable region of the nonhuman donor antibody.

In one embodiment, at least one of the framework regions (FR) of the humanized antibody is obtained or derived from one or more chains of a human sequence. Thus, the FR can include a FR1 and/or FR2 and/or FR3 and/or FR4 obtained or derived from one or more human sequence antibodies (e.g., from a human antibody chain, from a human consensus sequence).

It will be appreciated by one of skill in the art that in some cases residues flanking the one or more CDRs of the murine anti-CCL20 antibod(ies) may contribute, and in some cases, may be essential, either directly or indirectly, to function (e.g., binding). Accordingly, in some embodiments, one or more amino acids flanking one or more CDRs (e.g., 1, 2, 3, 4, 5, 6, 7, 8, 9, 10, or more flanking amino acids) of the murine framework are also included in the humanized antibody.

In some embodiments, the human heavy chain framework regions of the humanized antibodies of this invention utilize the human IGHV1-46*03 germline sequence. In some embodiments, the human light chain framework regions of the humanized antibodies of this invention utilize the human IGKV1D-39*01 germline sequence. Mutations (e.g., back mutations) may optionally be made in these FR regions, e.g., at one or more of the residues as described in the Examples below to improve CCL20-binding affinity of the humanized antibody.

"Affinity" is a term of art that describes the strength of a binding interaction and typically refers to the overall strength of binding of the antibody to the antigen. The affinity of the antibody for the antigen is typically expressed as the binding affinity equilibrium constant ($K_D$) of a particular antibody-antigen interaction.

In some embodiments, the antibody binds to human CCL20 with an affinity ($K_D$; $K_D=K_{off}(kd)/Kon(ka)$) of 500 pM or less, 400 pM or less, 300 pM or less, 200 pM or less, 100 pM or less, 90 pM or less, 80 pM or less, 70 pM or less, 60 pM or less, 50 pM or less, or 45 pM or less as determined by monovalent surface plasmon resonance; or 12 pM or less, 10 pM or less, 8 pM or less, 6 pM or less, or 5 pM or less as determined by bivalent surface plasmon resonance. In some embodiments, the antibody binds to human CCL20 with a $k_a$ of $1000\times10^5$ $M^{-1}$ $sec^{-1}$ or less, $900\times10^5$ $M^{-1}$ $sec^{-1}$ or less, $800\times10^5$ $M^{-1}$ $sec^{-1}$ or less, $700\times10^5$ $M^{-1}$ $sec^{-1}$ or less, $600\times10^5$ $M^{-1}$ $sec^{-1}$ or less, $500\times10^5$ $M^{-1}$ $sec^{-1}$ or less, $400\times10^5$ $M^1$ $sec^{-1}$ or less, $300\times10^5$ $M^{-1}$ $sec^{-1}$ or less, $240\times10^5$ $M^{-1}$ $sec^{-1}$ or less, $200\times10^5$ $M^{-1}$ $sec^{-1}$ or less, $190\times10^5$ $M^{-1}$ $sec^{-1}$ or less, $180\times10^5$ $M^{-1}$ $sec^{-1}$ or less, $170\times10^5$ $M^{-1}$ $sec^{-1}$ or less, $160\times10^5$ $M^{-1}$ $sec^{-1}$ or less, or $150\times10^5$ $M^{-1}$ $sec^{-1}$ or less, as determined by monovalent surface plasmon resonance (Biacore™). In some embodiments, the antibody binds to human CCL20 with a $k_d$ of $1000\times10^{-5}$ $sec^{-1}$ or less, $900\times10^{-5}$ $sec^{-1}$ or less, $800\times10^{-5}$ $sec^{-1}$ or less, $700\times10^{-5}$ $sec^{-1}$ or less, $600\times10^{-5}$ $sec^{-1}$ or less, $500\times10^{-5}$ $sec^{-1}$ or less, $400\times10^5$ $sec^{-1}$ or less, $300\times10^{-5}$ $sec^{-1}$ I or less, $240\times10^{-5}$ $sec^{-1}$ or less, $200\times10^{-5}$ $sec^{-1}$ or less, $190\times10^{-5}$ $sec^{-1}$ or less, $180\times10^{-5}$ $sec^{-1}$ or less, $170\times10^{-5}$ $sec^{-1}$ or less, $160\times10^{-5}$ $sec^{-1}$ or less, $150\times10^{-5}$ $sec^{-1}$ or less, $140\times10^{-5}$ $sec^{-1}$ or less, $130\times10^{-5}$ $sec^{-1}$ or less, $120\times10^{-5}$ $sec^{-1}$ or less, $100\times10^{-5}$ $sec^{-1}$ or less, $90\times10^{-5}$ $sec^{-1}$ or less, $80\times10^{-5}$ $sec^{-1}$ or less, $70\times10^{-5}$ $sec^{-1}$ or less, or $65\times10^{-5}$ $sec^{-1}$ or less as determined by monovalent surface plasmon resonance (Biacore™).

As is apparent to one of skill in the art, a variety of methods can be used to confirm that antibodies and antigen-binding portions thereof produced according to methods provided herein and known in the art have the requisite specificity (e.g., binding specificity, epitopic specificity). For example, the binding function of a humanized anti-CCL20 antibody or portion of the invention having binding specificity for human CCL20 can be detected using any suitable method, e.g., assays which monitor formation of a complex between the humanized antibody or portion and human CCL20 (or, e.g., a peptide having an amino acid sequence of CCL20 or a solid support comprising human CCL20).

The ability of an antibody or an antigen-binding portion thereof of the invention (e.g., a humanized antibody or portion of the invention) to bind to the same epitope on human CCL20 as a particular murine, chimeric, or humanized monoclonal antibody disclosed herein, or to bind to an epitope on human CCL20 which overlaps with the epitope on human CCL20 to which a particular murine, chimeric, or humanized monoclonal antibody disclosed herein binds, can be readily determined using a variety of techniques known to those of skill in the art, including e.g., competitive binding assays. These may involve the use of a labeled form of said particular antibody, and a measurement of the binding of that labeled antibody to human CCL20 in the presence and in the absence of an antibody of the invention.

An "epitope" as used herein includes any protein determinant capable of specific binding to an antibody. Methods for characterizing the epitope to which an antibody binds are known in the art. One method of characterizing an epitope bound by an anti-CCL20 antibody of the invention is described in Example 9. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. For example, the skilled worker may conduct competition studies to find antibodies that competitively bind with one another, i.e., antibodies that compete for binding to the antigen.

In one embodiment, to determine if a test antibody or antigen-binding portion thereof binds to the same or overlapping epitope as a humanized antibody of this invention, one allows the anti-CCL20 antibody of the invention to bind to CCL20 under saturating conditions and then measures the ability of the test antibody to bind to CCL20. If the test antibody is able to bind to CCL20 at the same time as the reference anti-CCL20 antibody, then the test antibody may bind to a different epitope than the reference anti-CCL20 antibody. However, if the test antibody is not able to bind to CCL20 at the same time, then the test antibody may bind to the same epitope, an overlapping epitope, or an epitope that is in close proximity to the epitope bound by the anti-CCL20 antibody of the invention. This experiment can be performed using, e.g., ELISA, RIA, Biacore™, or flow cytometry. To test whether an anti-CCL20 antibody cross-competes with another anti-CCL20 antibody, one may use the competition method described above in two directions, i.e., determining if the reference antibody blocks the test antibody and vice versa. In some embodiments, the experiment is performed using Biacore™.

Epitope binning also can be useful to characterize the antibodies of this invention. The term "binning" refers to a method to group antibodies based on their antigen binding characteristics. A high throughput process for "binning" antibodies based upon their cross-competition is described in International Patent Application No. WO 03/48731. The "epitope binning" can be investigated by allowing an unlabeled form of an anti-CCL20 antibody "A" to bind to a synthetic peptide corresponding to the sequence of CCL20 or to CCL20 positive cells. Subsequently a labeled second anti-CCL20 antibody "B" is added and one can assess the amount of labeled antibody that can bind relative to a control sample where the cells or synthetic peptide have not been exposed previously to anti-CCL20 antibody "A." Alternatively, anti-CCL20 antibodies "A" and "B" can both be labeled with different fluorochromes or chemicals enabling detection, and one can measure the quantities of both labeled antibodies that can engage the CCL20 peptide at the same time using a device capable of detecting the label or measure the amounts of both antibodies that simultaneously engage CCL20 positive cells by flow cytometry. Biacore™ and Octet technologies enable one to investigate the competitive binding of unlabelled forms of antibodies. This use of unlabelled forms of antibodies is desired as the chemical modification of some antibodies can compromise the binding activity. See also the technology described in Jia et al., *J. Immunol. Methods* 288:91-98 (2004), which is useful in performing epitope binning as well.

Also provided herein are portions of the anti-CCL20 antibodies of the invention, such as light chains, heavy chains, and portions of light and heavy chains. These antibody portions can be obtained or derived from antibodies (e.g., by reduction and/or cleavage), or produced or expressed by nucleic acids encoding a portion of an antibody or chain thereof having the desired property (e.g., binds human CCL20, sequence similarity). They can also be prepared by e.g., de novo synthesis of the relevant portion. Humanized antibodies comprising the desired portions (e.g., antigen-binding region, CDR, FR, C region) of human and nonhuman origin can be produced using synthetic and/or recombinant nucleic acids to prepare constructs (e.g., cDNA) encoding the desired humanized chain. For example, to prepare a portion of an antibody (e.g., a portion of a chain), one or more stop codons can be introduced at the desired position in the nucleic acid sequence. Nucleic acid (e.g., DNA) sequences coding for humanized variable regions can be constructed using PCR mutagenesis methods to alter existing DNA sequences (see e.g., Kamman et al., *Nucl. Acids Res.* 17:5404 (1989)). PCR primers coding for the new CDRs can be hybridized to a DNA template of a previously humanized variable region which is based on the same, or a very similar, human variable region (Sato et al., *Cancer Research* 53:851-856 (1993)). If a similar DNA sequence is not available for use as a template, a nucleic acid comprising a sequence encoding a variable region sequence can be constructed from synthetic oligonucleotides (see e.g., Kolbinger, *Protein Engineering* 8:971-980 (1993)). A sequence encoding a signal peptide ("signal sequence") can also be incorporated into the nucleic acid (e.g., on synthesis, upon insertion into a vector). If a signal peptide sequence is unavailable (e.g., not typically present), a signal peptide sequence from another antibody can be used (see, e.g., Kettleborough, *Protein Engineering* 4:773-783 (1991)). Using these methods, methods described herein or other suitable methods, variants can readily be produced.

As used herein, the acronym "mAb" (or "MAb") refers to a monoclonal antibody, which may be, e.g., an antibody synthesized by a clonal population of cells or a humanized antibody. A clonal population that produces a monoclonal antibody can be a clonal population of immortalized cells. In some embodiments, the immortalized cells in the clonal population are hybrid cells—hybridomas—typically produced by the fusion of individual B lymphocytes from an immunized animal with individual cells from a lymphocytic tumour.

The invention relates in part to a humanized antibody or antigen-binding portion thereof that has binding specificity for human CCL20 and comprises a humanized light chain and a humanized heavy chain and/or portions thereof. In one embodiment, the humanized antibody comprises a light chain comprising one or more CDRs (e.g., all three CDRs) of SEQ ID NO: 7 and a heavy chain comprising one or more CDRs (e.g., all three CDRs) of SEQ ID NO: 1; a light chain comprising one or more CDRs (e.g., all three CDRs) of SEQ ID NO: 7 and a heavy chain comprising one or more CDRs (e.g., all three CDRs) of SEQ ID NO: 2; a light chain comprising one or more CDRs (e.g., all three CDRs) of SEQ ID NO: 7 and a heavy chain comprising one or more CDRs (e.g., all three CDRs) of SEQ ID NO: 3; a light chain comprising one or more CDRs (e.g., all three CDRs) of SEQ ID NO: 7 and a heavy chain comprising one or more CDRs (e.g., all three CDRs) of SEQ ID NO: 4; a light chain comprising one or more CDRs (e.g., all three CDRs) of SEQ ID NO: 7 and a heavy chain comprising one or more CDRs (e.g., all three CDRs) of SEQ ID NO: 5; a light chain comprising one or more CDRs (e.g., all three CDRs) of SEQ ID NO: 7 and a heavy chain comprising one or more CDRs (e.g., all three CDRs) of SEQ ID NO: 6; a light chain comprising one or more CDRs (e.g., all three CDRs) of SEQ ID NO: 8 and a heavy chain comprising one or more CDRs (e.g., all three CDRs) of SEQ ID NO: 1; a light chain comprising one or more CDRs (e.g., all three CDRs) of SEQ ID NO: 8 and a heavy chain comprising one or more CDRs (e.g., all three CDRs) of SEQ ID NO: 2; a light chain comprising one or more CDRs (e.g., all three CDRs) of SEQ ID NO: 8 and a heavy chain comprising one or more CDRs (e.g., all three CDRs) of SEQ ID NO: 3; a light chain comprising one or more CDRs (e.g., all three CDRs) of SEQ ID NO: 8 and a heavy chain comprising one or more CDRs (e.g., all three CDRs) of SEQ ID NO: 4; a light chain comprising one or more CDRs (e.g., all three CDRs) of SEQ ID NO: 8 and a heavy chain comprising one or more CDRs (e.g., all three CDRs) of SEQ ID NO: 5; or a light chain comprising one or more CDRs (e.g., all three CDRs) of SEQ ID NO: 8 and a heavy chain comprising one or more CDRs (e.g., all three CDRs) of SEQ ID NO: 6.

In one embodiment, a humanized antibody of the invention comprises heavy chain (H)-CDR1, H-CDR2, H-CDR3, light chain (L)-CDR1, L-CDR2, and L-CDR3 whose amino acid sequences are:
a) SEQ ID NOS: 60, 64, 67, 70, 73, and 75, respectively;
b) SEQ ID NOS: 60, 64, 67, 71, 73, and 75, respectively;
c) SEQ ID NOS: 60, 63, 67, 70, 73, and 75, respectively;
d) SEQ ID NOS: 60, 63, 67, 71, 73, and 75, respectively;
e) SEQ ID NOS: 61, 65, 68, 70, 73, and 75, respectively;
f) SEQ ID NOS: 61, 65, 68, 71, 73, and 75, respectively;
g) SEQ ID NOS: 77, 79, 67, 70, 73, and 75, respectively;
h) SEQ ID NOS: 77, 79, 67, 71, 73, and 75, respectively;
i) SEQ ID NOS: 78, 80, 68, 70, 73, and 75, respectively; and
j) SEQ ID NOS: 78, 80, 68, 71, 73, and 75, respectively.

In another embodiment, a humanized antibody of this invention comprises an H-CDR3 whose sequence is SEQ ID NO: 67 or 68. In certain embodiments, a humanized antibody of this invention comprises H-CDR3 and L-CDR3 whose sequences are SEQ ID NOS: 67 and 75, respectively; or SEQ ID NOS: 68 and 75, respectively.

In another embodiment, the humanized antibody has binding specificity for human CCL20 and comprises a light chain comprising one or more CDRs selected from the group consisting of SEQ ID NOS: 70 or 71; 73; and 75, or a combination thereof; and a heavy chain comprising one or more CDRs selected from the group consisting of SEQ ID NOS: 60, 61, 77, or 78; 63, 64, 65, 79, or 80; and 67 or 68; or a combination thereof.

In another embodiment, the humanized antibody that has a binding specificity for human CCL20 comprises a light chain comprising one or more CDRs (e.g., all three CDRs) of SEQ ID NO: 7, 8, 110, or 112, and a heavy chain comprising one or more CDRs (e.g., all three CDRs) of SEQ ID NO: 1, 2, 3, 4, 5, 6, or 108.

The invention also relates to a humanized antibody light chain of the humanized antibody described herein. In one embodiment, the humanized antibody light chain comprises one or more CDRs selected from the group consisting of 70 or 71; 73; and 75, or a combination thereof. For example, the humanized antibody has L-CDR1, L-CDR2, and L-CDR3 whose amino acid sequences are 70, 73, and 75 respectively; or 71, 73, and 75, respectively.

The invention also relates to a humanized antibody heavy chain of the humanized antibody described herein. In one embodiment, the humanized antibody heavy chain comprises one or more CDRs selected from the group consisting of 60, 61, 77, or 78; 63, 64, 65, 79, or 80; and 67 or 68; or a combination thereof. For example, the humanized antibody has H-CDR1, H-CDR2, and H-CDR3 whose amino acid sequences are:
a) SEQ ID NOS: 60, 63, and 67;
b) SEQ ID NOS: 60, 64, and 67;
c) SEQ ID NOS: 61, 65, and 68;
d) SEQ ID NOS: 77, 79, and 67; or
e) SEQ ID NOS: 78, 80, and 68.

In one embodiment, a humanized antibody of this invention comprises a light chain comprising a variable domain (V$_L$) sequence of SEQ ID NO: 15 or 16. In a related embodiment, the humanized antibody comprises a light chain whose amino acid sequence comprises or consists of one of SEQ ID NOS: 7, 8, 110, and 112. In one embodiment, the humanized antibody comprises a light chain whose amino acid sequence comprises or consists of SEQ ID NO: 7 or 8 without the signal sequence.

In one embodiment, a humanized antibody of this invention comprises a heavy chain comprising a variable domain (V$_H$) sequence of one of SEQ ID NOS: 9-14. In a related embodiment, the humanized antibody comprises a heavy chain whose amino acid sequence comprises or consists of one of SEQ ID NOS: 1-6 and 108. In one embodiment, the humanized antibody comprises a heavy chain whose amino acid sequence comprises or consists of one of SEQ ID NOS: 1-6 without the signal sequence, and optionally without the C-terminal lysine. In one embodiment, the humanized antibody comprises a heavy chain whose amino acid sequence comprises or consists of SEQ ID NO: 108 without the C-terminal lysine.

In some embodiments, a humanized antibody of this invention comprises a V$_H$ and a V$_L$ whose amino acid sequences comprise or consist of
a) SEQ ID NO: 9 and SEQ ID NO: 15;
b) SEQ ID NO: 10 and SEQ ID NO: 15;
c) SEQ ID NO: 11 and SEQ ID NO: 15;
d) SEQ ID NO: 12 and SEQ ID NO: 15;
e) SEQ ID NO: 13 and SEQ ID NO: 15;
f) SEQ ID NO: 14 and SEQ ID NO: 15;
g) SEQ ID NO: 9 and SEQ ID NO: 16;
h) SEQ ID NO: 10 and SEQ ID NO: 16;
i) SEQ ID NO: 11 and SEQ ID NO: 16;
j) SEQ ID NO: 12 and SEQ ID NO: 16;
k) SEQ ID NO: 13 and SEQ ID NO: 16; or
l) SEQ ID NO: 14 and SEQ ID NO: 16.

In one embodiment, a humanized antibody of this invention comprises a light chain (LC) and a heavy chain (HC) whose amino acid sequences comprise or consist of
a) SEQ ID NO: 1 and SEQ ID NO: 7;
b) SEQ ID NO: 2 and SEQ ID NO: 7;
c) SEQ ID NO: 3 and SEQ ID NO: 7;
d) SEQ ID NO: 4 and SEQ ID NO: 7;
e) SEQ ID NO: 5 and SEQ ID NO: 7;
f) SEQ ID NO: 6 and SEQ ID NO: 7;
g) SEQ ID NO: 1 and SEQ ID NO: 8;
h) SEQ ID NO: 2 and SEQ ID NO: 8;
i) SEQ ID NO: 3 and SEQ ID NO: 8;
j) SEQ ID NO: 4 and SEQ ID NO: 8;
k) SEQ ID NO: 5 and SEQ ID NO: 8;
l) SEQ ID NO: 6 and SEQ ID NO: 8,
m) SEQ ID NO: 108 and SEQ ID NO: 110; and
n) SEQ ID NO: 108 and SEQ ID NO: 112;
wherein the amino acid sequences lack the signal sequence, if present, and wherein SEQ ID NOS: 1-6 and SEQ ID NO: 108 optionally lack the C-terminal lysine.

The present invention provides any combination comprising an exemplified humanized heavy chain or an antigen-binding portion thereof, and an exemplified humanized light chain or an antigen-binding portion thereof, of the invention; in other words, the heavy and light chains can be "mixed and matched." It is understood that any such combination is likely to retain binding to human CCL20 as well as chemotaxis neutralizing activity. These functional properties can readily be tested using methods described herein. Indeed, FIG. 7 demonstrates the neutralizing activity of several combinations of exemplified humanized heavy and light chains of the invention.

This invention also provides anti-human CCL20 antibodies or antigen-binding portions thereof that bind to the same epitope as, and/or compete or cross-compete with, an antibody exemplified herein. These antibodies can be, for example, humanized, chimeric, or mouse antibodies. For example, the invention provides anti-human CCL20 antibodies and portions that bind to the same epitope as, and/or compete or cross-compete with, one of mouse anti-CCL20 antibodies 36F7C10, 40-1C10B9, and 42G5B10, or humanized or chimeric versions of these mouse antibodies. The ability of an antibody to bind to the same epitope as, or compete or cross-compete with, a reference antibody, can be determined as described herein. By way of nonlimiting example, any antibody or portion comprising the three heavy chain CDRs and the three light chain CDRs from mouse antibody 36F7C10 would be expected to bind to the same epitope as, compete with, and cross-compete with mouse antibody 36F7C10. Such antibodies may include, e.g., antibodies whose heavy chain comprises any one of SEQ ID NOS: 9-11 and whose light chain comprises SEQ ID NO: 15 or 16. In some embodiments, such antibodies may further include, e.g., antibodies whose heavy chain comprises any one of SEQ ID NOS: 12-14 and whose light chain comprises SEQ ID NO: 15 or 16.

If desired, for example, for diagnostic or assay purposes (e.g., imaging to allow, for example, monitoring of therapies), the humanized antibody (or an antigen-binding portion thereof) can comprise a detectable label. Suitable detectable labels and methods for labeling a humanized antibody or antigen-binding portion thereof are well known in the art. Suitable detectable labels include, for example, a radioisotope (e.g., as Indium-111, Technetium-99m or Iodine-131), positron emitting labels (e.g., Fluorine-19), paramagnetic ions (e.g., Gadlinium (III), Manganese (II)), an epitope label (tag), an affinity label (e.g., biotin, avidin), a spin label, an enzyme, a fluorescent group or a chemiluminescent group. When labels are not employed, complex formation (e.g., between a humanized antibody and human CCL20) can be determined by surface plasmon resonance, ELISA, FACS, or other suitable methods.

Anti-CCL20 antibodies or antigen-binding portions thereof used in the invention also may be conjugated, for example, via chemical reactions or genetic modifications, to other moieties (e.g., pegylation moieties) that improve the antibodies' pharmacokinetics such as half-life. In some embodiments, the anti-CCL20 antibodies used in this invention can be linked to a suitable cytokine, e.g., via chemical conjugation or genetic modifications (e.g., appending the coding sequence of the cytokine in frame to an antibody coding sequence, thereby creating an antibody:cytokine fusion protein).

The invention also relates to immunoconjugates in which the humanized antibody (or an antigen-binding portion thereof) of the invention is coupled to another therapeutic agent, such as a bioactive compound (e.g., a cytokine, a superantigen, a cytotoxic agent or a toxin). For example, the humanized antibody that has binding specificity for human CCL20 (or an antigen binding portion thereof) can be coupled to a biological protein, a molecule of plant or bacterial origin (or derivative thereof), an interleukin-2 antibody or diphtheria toxin antibodies.

As described herein, mouse monoclonal antibodies having binding specificity for human CCL20 have been produced. Humanized and chimeric antibodies of this invention can be derived from the mouse monoclonal antibodies of this invention. That is, in some embodiments, humanized and chimeric anti-CCL20 antibodies of the invention comprise sequences taken from a mouse monoclonal antibody of the invention, such as one or more CDR sequences (e.g., all six CDR sequences) or one or more variable domains (e.g., the heavy chain variable domain and the light chain variable domain).

As used herein, the term "mouse monoclonal antibody" refers to an antibody containing light chain CDRs (L-CDR1, L-CDR2 and L-CDR3) and heavy chain CDRs (H-CDR1, H-CDR2 and H-CDR3) of a murine antibody, and framework and constant regions of murine origin.

The invention relates to the mouse monoclonal antibodies described herein, as well as antigen-binding portions of the mouse monoclonal antibodies, the light chains of the mouse monoclonal antibodies, the heavy chains of the mouse monoclonal antibodies, and portions of these heavy and light chains. In a particular embodiment, the mouse monoclonal antibody is 36F7C10, 40-1C10B9, or 42G5B10. The invention relates to mouse monoclonal antibodies lacking the heavy and light chain signal sequences and mouse monoclonal antibodies that are glycosylated. The invention also relates to precursor antibodies, nonglycosylated antibodies, and antibodies whose heavy and/or light chains comprise signal sequences. The invention also relates to nucleic acid molecules that encode any of the above mouse antibody heavy chains, light chains, or portions thereof; to vectors and host cells that comprise such nucleic acids; to methods of producing any of the above mouse heavy or light chains or portions thereof; and to methods of using the mouse antibodies or antigen-binding portions thereof.

The binding function of a mouse monoclonal antibody or antigen-binding portion thereof having binding specificity for human CCL20 can be detected using any suitable method, for example using assays which monitor formation of a complex between a mouse monoclonal antibody or portion and human CCL20 (or, e.g., a peptide having an amino acid sequence of CCL20 or a solid support comprising human CCL20).

Also provided herein are portions of the murine antibodies which include light chains, heavy chains and portions of light and heavy chains. These antibody portions can be obtained or derived, e.g., by means described herein for humanized antibody portions.

In one embodiment, a mouse monoclonal antibody of this invention comprises a light chain comprising SEQ ID NO: 40, 42, or 44 and further comprises a heavy chain comprising SEQ ID NO: 39, 41, or 43. In a certain embodiment, the mouse monoclonal antibody comprises a light chain comprising SEQ ID NO: 40 and a heavy chain comprising SEQ ID NO: 39; a light chain comprising SEQ ID NO: 42 and a heavy chain comprising SEQ ID NO: 41; or a light chain comprising SEQ ID NO: 44 and a heavy chain comprising SEQ ID NO: 43.

In another embodiment, the invention also relates to a mouse monoclonal antibody that has binding specificity for human CCL20, comprising the light chain variable region in a sequence selected from the group consisting of SEQ ID NOS: 40, 42, and 44; and a heavy chain variable region in a sequence selected from the group consisting of SEQ ID NOS: 39, 41, and 43.

The invention also relates to a mouse monoclonal antibody whose light chain comprises the variable region in SEQ ID NO: 40, 42, or 44.

The invention also relates to a mouse monoclonal antibody whose heavy chain comprises the variable region in SEQ ID NO: 39, 41, or 43.

If desired, for example, for diagnostic or assay purposes (e.g., imaging), the mouse monoclonal antibody or antigen binding portion thereof can comprise a detectable label e.g., as described herein for humanized antibodies. All suitable methods and techniques described herein for humanized antibodies of this invention can also be used for mouse monoclonal antibodies of the invention.

As described herein, chimeric antibodies having binding specificity for human CCL20 have been produced. As used herein, the term "chimeric antibody" refers to a recombinant protein that contains the variable domains of an antibody derived from one species while the constant domains of the antibody are derived from a different species. In one embodiment, the chimeric antibody with binding specificity for human CCL20 comprises variable domains from a mouse anti-human CCL20 monoclonal antibody. In one embodiment, the chimeric antibody with binding specificity for human CCL20 comprises constant domains from a human antibody. In a particular embodiment, the chimeric antibody comprises variable domains from a mouse anti-human CCL20 monoclonal antibody and constant domains from a human antibody.

The invention relates to the chimeric antibodies described herein, as well as antigen-binding portions of the chimeric antibodies, the light chains and heavy chains of the chimeric antibodies, and portions of these light and heavy chains. The invention relates to chimeric antibodies lacking the heavy and light chain signal sequences and chimeric antibodies that are glycosylated. The invention also relates to precursor antibodies, nonglycosylated antibodies, and antibodies whose heavy and/or light chains comprise signal sequences. The invention also relates to nucleic acid molecules that encode any of the above chimeric antibody heavy chains, light chains, or portions thereof; to vectors and host cells that comprise such nucleic acids; to methods of producing these any of the above chimeric antibody heavy or light chains or portions thereof; and to methods of using the chimeric antibodies.

The binding function of a chimeric antibody having binding specificity for human CCL20 can be detected using any suitable method, for example using assays which monitor formation of a complex between a chimeric antibody and human CCL20 (or, e.g., a peptide having an amino acid sequence of CCL20 or a solid support comprising human CCL20).

Also provided herein are portions of the chimeric antibodies which include light chains, heavy chains and portions of light and heavy chains. These antibody portions can be obtained or derived, e.g., by means described herein for humanized antibody portions.

In one embodiment, a chimeric antibody of this invention comprises the light chain variable region of SEQ ID NO: 40 and the heavy chain variable region of SEQ ID NO: 39; the light chain variable region of SEQ ID NO: 42 and the heavy chain variable region of SEQ ID NO: 41; or the light chain variable region of SEQ ID NO: 44 and the heavy chain variable region of SEQ ID NO: 43.

The invention also relates to a chimeric antibody that has binding specificity for human CCL20, comprising a light chain variable region sequence selected from the group consisting of: the light chain variable region in SEQ ID NO: 40, 42, or 44; and further comprising a heavy chain variable region sequence selected from the group consisting of: the heavy chain variable region in SEQ ID NO: 39, 41, or 43.

The invention also relates to a chimeric light chain comprising the variable region in SEQ ID NO: 40, 42, or 44.

The invention also relates to a chimeric heavy chain comprising the variable region in SEQ ID NO: 39, 41, or 43.

If desired, for example, for diagnostic or assay purposes (e.g., imaging), the chimeric antibody or antigen-binding portion thereof can comprise a detectable label, e.g., as described herein for humanized antibodies. All suitable methods and techniques described herein for humanized antibodies of this invention can also be used for chimeric antibodies of the invention.

In some embodiments, the anti-CCL20 antibody of the invention is a fully human antibody. As used herein, the term "human antibody" means any antibody in which the variable and constant domain sequences are human sequences. The term encompasses antibodies with sequences derived from human genes, but which have been changed, e.g. to decrease possible immunogenicity, increase affinity, eliminate cysteines that might cause undesirable folding, etc. The term also encompasses such antibodies produced recombinantly in non-human cells, which might impart glycosylation not typical of human cells. Methods for preparing fully human antibodies are known in the art. For example, human anti-CCL20 antibodies may be identified through in vitro methods, such as phage display, ribosome display (CAT), yeast display, and the like, or may be produced from a human B-cell or a human hybridoma cell. Alternatively, human antibodies may be produced by immunizing with a CCL20 antigen any of a number of non-human, transgenic animals comprising within their genomes some or all of human immunoglobulin heavy chain and light chain loci. In some embodiments, the non-human animal comprising human immunoglobulin genes is an animal that has a human immunoglobulin "minilocus" (e.g., GenPharm International, Inc.). In some embodiments, human anti-CCL20 antibodies are produced using a XENOMOUSE® (Abgenix, Inc., Fremont, Calif.), a HuMAb-Mouse® (Medarex, Inc.), a VelocImmune® mouse (Regeneron Pharmaaceuticals, Inc.), an AlivaMab Mouse (Ablexis, LLC), a KM™ mouse (Kirin Pharma USA, Inc.), or the like.

The present invention also relates to isolated and/or recombinant nucleic acids comprising sequences which encode a humanized antibody or a light chain or heavy chain thereof, mouse monoclonal antibody or a light chain or heavy chain thereof, chimeric antibody or a light chain or heavy chain thereof, or antigen-binding portions of any of the above, of the present invention. In some embodiments, the present invention provides a nucleic acid sequence selected from the group consisting of SEQ ID NOS: 17-32, 51-56, 109, 111, and 113.

In some embodiments, the nucleic acid molecules of the invention include nucleic acid sequences that hybridize under highly stringent conditions, or that are at least 70%, 75%, 80%, 85%, 90%, 95%, 97%, 98% or 99% identical, to one or more of the nucleic acid sequences recited herein or to a nucleic acid sequence encoding the amino acid sequence of any of the provided $V_H$ or $V_L$ sequences.

Nucleic acids referred to herein as "isolated" or "purified" are nucleic acids which have been separated away from the nucleic acids of the genomic DNA or cellular RNA of their source of origin (e.g., as they exist in cells or in a mixture of nucleic acids such as a library), and include nucleic acids obtained by methods described herein or other suitable methods. In some embodiments, the isolated nucleic acids are essentially pure nucleic acids, nucleic acids produced by chemical synthesis, nucleic acids produced by combinations of biological and chemical methods, or recombinant nucleic acids which are isolated (see, e.g., Daugherty et al., *Nucleic Acids Res.* 19(9):2471-2476 (1991); Lewis and Crowe, *Gene* 101:297-302 (1991)).

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric, possibly isolated, form of nucleotides of at least 10 bases in length, either ribonucleotides or deoxynucleotides or a modified form of either type of nucleotide. The term includes single and double stranded forms.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. In some embodiments, the recombinant nucleic acids result from recombination events that occur through the natural mechanisms of cells, but are selected for after the introduction into the cells of nucleic acids designed to allow and make probable a desired recombination event.

The present invention also relates more specifically to isolated and/or recombinant nucleic acids comprising a nucleotide sequence which encodes a humanized antibody, mouse antibody or chimeric antibody, or an antigen-binding portion of said antibody, that has binding specificity for human CCL20. In some embodiments, the antibody is a mouse antibody of the present invention, a humanized antibody of the present invention in which the nonhuman portion(s) are derived from a murine anti-CCL20 monoclonal antibody; or a chimeric antibody of the present invention in which the nonhuman portion(s) are derived from a murine anti-CCL20 monoclonal antibody.

In some embodiments, nucleic acids of the invention are used to produce humanized antibodies having binding specificity for human CCL20, mouse antibodies having binding specificity for human CCL20, and chimeric antibodies having binding specificity for human CCL20. For example, a nucleic acid (e.g., DNA (such as cDNA) or RNA) or one or more nucleic acids encoding a humanized antibody, mouse antibody or chimeric antibody of the present invention can be incorporated into a suitable construct (e.g., a recombinant vector) for further manipulation of sequences or for production of the encoded antibodies in suitable host cells.

Constructs or vectors suitable for the expression of a humanized antibody having binding specificity for human CCL20, mouse antibody having binding specificity for human CCL20 or chimeric antibody having binding specificity for human CCL20 are also provided. A variety of vectors are available, including vectors which are maintained in single copy or multiple copies in a host cell, or which become integrated into the chromosome(s) of a host cell. The constructs or vectors can be introduced into a suitable host cell, and cells which express a humanized antibody, mouse antibody or chimeric antibody of the present invention, can be produced and maintained in culture. A single vector or multiple vectors can be used for the expression of a humanized antibody, mouse antibody or chimeric antibody having binding specificity for human CCL20.

Suitable expression vectors, for example mammalian cell expression vectors, can also contain a number of components, including, but not limited to, one or more of the following: an origin of replication; a selectable marker gene; one or more expression control elements such as a transcriptional control element (e.g., a promoter, an enhancer, a terminator), one or more translation signals; and/or a signal sequence or leader sequence (encoding a "signal peptide")

for membrane targeting or secretion. In a construct or vector, a signal sequence can be provided by the construct or vector or other source. For example, transcriptional and/or translational signals can be used to direct expression.

In some embodiments, a promoter is provided for expression of an antibody or antibody chain of the invention in a suitable host cell. In some embodiments, the promoter is constitutive. In some embodiments, the promoter is inducible. The promoter may be operably linked to a nucleic acid encoding an antibody or antibody chain, or an antigen-binding portion of said antibody or chain, such that it directs expression of the encoded polypeptide. A variety of suitable promoters for prokaryotic (e.g., lac, tac, T3, T7 promoters for *E. coli*) and eukaryotic (e.g., yeast alcohol dehydrogenase (ADH1), SV40, CMV) hosts are available. Those of skill in the art will be able to select the appropriate promoter for expressing an anti-CCL20 antibody or antigen-binding portion thereof of the invention.

In some embodiments the vector encoding an antibody or antibody chain of the invention comprises a selectable marker for selection of host cells carrying the vector. In some embodiments, the selectable marker is a gene encoding a product that confers antibiotic or drug resistance that may be used in prokaryotic cells (e.g., β-lactamase gene (ampicillin resistance), Tet gene (tetracycline resistance), etc.) and eukaryotic cells (e.g., neomycin (G418 or geneticin), gpt (mycophenolic acid), ampicillin, or hygromycin resistance genes). In some embodiments, the selectable marker is dihydrofolate reductase, permitting selection with methotrexate in a variety of hosts. In some embodiments, the selectable marker is a gene encoding an auxotrophic marker of the host (e.g., LEU2, URA3, HIS3), e.g., for use in yeast. In some embodiments, the vector is a viral (e.g., baculovirus) or phage vector. In one embodiment, the vector is capable of integrating into the genome of the host cell (e.g., retroviral vector). In some embodiments, the vector is a replicable vector and comprises an origin of replication.

The invention thus relates to isolated nucleic acid molecules that encode the humanized antibody, humanized light chain, humanized heavy chain, mouse antibody, mouse antibody light chain, mouse antibody heavy chain, chimeric antibody, chimeric light chain, or chimeric heavy chain of this invention. The invention also relates to isolated nucleic acid molecules that encode an antigen-binding portion of any of these antibodies or their chains. Polypeptide sequences encoded by the nucleic acids of this invention are described above and in the following Examples.

In some embodiments, a nucleic acid or vector of this invention encodes a heavy chain (or an antigen-binding portion thereof) or a light chain (or an antigen-binding portion thereof) of the invention. A host cell containing both the heavy chain-encoding nucleic acid and the light chain-encoding nucleic acid, or nucleic acids encoding antigen-binding portions of said heavy chain and said light chain, can be used to make an antibody comprising a heavy and a light chain (or an antigen-binding portion of the antibody). The heavy chain-encoding nucleic acid and the light chain-encoding nucleic acid can be placed on separate expression vectors. They can also be placed on a single expression vector under the same or different expression control. See, e.g., U.S. Pat. Nos. 6,331,415 and 7,662,623.

Another aspect of the invention relates to a method of making an anti-human CCL20 antibody or an antigen-binding portion thereof of the invention. The antibody or portion can be produced, for example, by the expression of one or more recombinant nucleic acids encoding the antibody or portion in a suitable host cell. The host cell can be produced using any suitable method. For example, one or more expression constructs described herein can be introduced into a suitable host cell, and the resulting cell can be maintained under conditions suitable for expression of the construct(s) or vector(s). In some embodiments, the resulting cell is maintained in culture, in an animal, or in a plant. Suitable host cells can be prokaryotic, including bacterial cells such as *E. coli* (e.g., strain DH5α™ (Invitrogen, Carlsbad, Calif.)), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schneider S2 cells, Sf9 insect cells (WO 94/26087 (O'Connor), TN5B1-4 (HIGH 5) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096). CHO DG44 (Urlaub and Chasin., *Proc. Natl. Acac. Sci. USA* 77(7):4216-4220 (1980)), 293 (ATCC Accession No. CRL-1573), HeLa (ATCC Accession No. CCL-2), CV1 (ATCC Accession No. CCL-70), WOP (Dailey et al., *J. Virol.* 54:739-749 (1985)), 3T3, 293T (Pear et al., *Proc. Natl. Acad. Sci. U.S.A.* 90:8392-8396 (1993)), NS0 cells, SP2/0 cells, HuT 78 cells and the like)), or plants (e.g., tobacco, *lemna* (duckweed), and algae). (See, for example, Ausubel et al., eds. *Current Protocols in Molecular Biology*, Greene Publishing Associates and John Wiley & Sons Inc. (1993)). In some embodiments, the host cell is not part of a multicellular organism (e.g., plant or animal). In certain embodiments, the host cell is an isolated host cell or is part of a cell culture.

The present invention also relates to cells comprising a nucleic acid or a vector of the invention. In some embodiments, the vector is an expression vector. In some embodiments, one or more nucleic acids encoding the heavy and light chains of a humanized antibody or antigen-binding portion thereof, the heavy and light chains of a mouse antibody or antigen-binding portion thereof, or the heavy and light chains of a chimeric antibody or antigen-binding portion thereof, said antibody or portion having binding specificity for human CCL20, or one or more constructs comprising such nucleic acid(s), can be introduced into a suitable host cell by a method appropriate to the host cell selected. In some embodiments, the method of introduction is, e.g., transformation, transfection, electroporation, or infection. In some embodiments, the nucleic acid(s) are operably linked to one or more expression control elements. In certain embodiments, the nucleic acid(s) are in a vector, in a construct created by processes in the cell, or integrated into the host cell genome. Host cells can be maintained under conditions suitable for expression. In some embodiments, these conditions comprise the presence of an inducer, or of suitable media (supplemented with, e.g., appropriate salts, growth factors, antibiotic, nutritional supplements, etc.), whereby the encoded polypeptide(s) are produced. These processes encompasses expression in a host cell (e.g., a mammary gland cell) of a transgenic animal or plant (e.g., tobacco) (see e.g., WO 92/03918). In some embodiments, the antibodies or portions are isolated from the host cells, culture medium, or milk.

The invention also relates to fusion proteins in which an antibody or portion of the invention (e.g., a humanized antibody or portion) is linked to another moiety (e.g., a moiety which does not occur in antibodies as found in nature) in an N-terminal location, C-terminal location or internal to the fusion protein. In some embodiments, the fusion protein can be produced by the insertion of a nucleic acid encoding an antibody sequence(s) into a suitable expression vector, such as a pET vector (e.g., pET-15b, Novagen), a phage vector (e.g., pCANTAB 5 E, Pharmacia), or other vector (e.g., pRIT2T Protein A fusion vector, Pharmacia). The resulting construct can be introduced into a suitable host cell for expression. In some embodiments, the expressed fusion proteins are isolated or purified from a cell lysate by means of a suitable affinity matrix (see, e.g., *Current Protocols in Molecular Biology* (Ausubel et al., Eds., Vol. 2, Suppl. 26, pp. 16.4.1-16.7.8 (1991))).

The invention relates to a host cell that comprises recombinant nucleic acid(s) encoding an antibody or portion, or heavy and/or light chains thereof, provided herein (e.g., a humanized antibody, a humanized light chain or a humanized heavy chain, a mouse antibody, a mouse light chain or a mouse heavy chain, a chimeric antibody, or a chimeric heavy chain or a chimeric light chain, of the invention). The invention also relates to a host cell that comprises recombinant nucleic acid(s) encoding an antigen-binding portion of the antibody or its chains. In some embodiments, the host cell comprises a recombinant vector of the invention as referred to herein. In some embodiments, said recombinant vector is an expression vector. In certain embodiments, said recombinant vector is a mammalian cell expression vector.

The invention also relates to a method of preparing an antibody or portion, or a heavy or light chain thereof, of this invention. In one embodiment, the method comprises maintaining a host cell of the invention as described herein under conditions appropriate for expression of the antibody or portion or heavy and/or light chain thereof. In some embodiments, the host cell contains one or more isolated nucleic acids that encode the antibody or portion, or heavy and/or light chain thereof, of the invention. In some embodiments, the host cell is cultured on a substrate or in suspension. In some embodiments, the method further comprises the step of purifying or isolating the antibody or antibody chain.

The invention further relates to a method of preparing antibodies or antigen-binding portions thereof through phage display. In some embodiments, a naïve antibody phage display library on CCL20 antigen is panned. In some embodiments, a method of preparing antibodies through guided selection is used (see, e.g., U.S. Patent Publication No. US 2006-0251658 A1). In certain embodiments, a custom library built around, for example, a fixed heavy chain (and/or light chain) CDR3 region of a known anti-CCL20 antibody is created. The CDR1 and CDR2 regions of the heavy and light chains can be derived from a naïve repertoire (Osburn et al., *Methods* 36:61-68 (2005)). In one embodiment, anti-CCL20 scFvs are generated from scFv naïve antibody libraries which are used to obtain mouse-human chimeric antibodies with the desired binding properties. These libraries may be screened for antibodies with the desired binding properties. In some embodiments, scFv phage libraries are used. In certain embodiments, scFvs which recognize human CCL20 are isolated from scFv guided selection libraries following a series of repeated selection cycles on recombinant human CCL20 essentially as described in Vaughan et al. *Nature Biotech.* 14:309-314 (1996). In brief, following incubation with the library, the immobilized antigen, which is pre-coupled to paramagnetic beads, and bound phage can be recovered by magnetic separation while unbound phage is washed away. Bound phage can then be rescued as described by Vaughan et al. (1996; supra) and the selection process repeated.

In a particular embodiment, a library is constructed consisting of the entire variable domain of the heavy chain of a mouse anti-CCL20 antibody fused in a single chain format to a repertoire of naïve human light chain variable regions. After selection, the human light chain variable regions that complement the mouse heavy chain variable regions are identified. A library is then constructed consisting of the repertoire of human light chain variable regions selected as described above fused in a single chain format to a chimeric heavy chain variable region consisting of naïve human CDR1 and CDR2 regions and a fixed CDR3 region from the mouse anti-CCL20 antibody heavy chain variable domain. After selection for CCL20 binders, the best binding clones are selected. Five of the six CDR regions can be human in origin while the CDR3 of the heavy chain variable region can be identical to the original CDR3 of the mouse heavy chain variable domain.

In some embodiments, selections are performed using CCL20 coupled to DYNABEADS M-270 amine (Dynal) according to the manufacturer's recommendations. In some embodiments, selections using biotinylated CCL20 can be prepared using the primary amine specific reagent succinimidyl-6-(biotinamido) hexanoate following the manufacturer's instructions (EZ link NHS LC Biotin, Pierce).

In some embodiments outputs from selections are tested as periplasmic preparations in high throughput screens based on competition assays which measure the ability of the scFvs present in the periplasmic preparation to compete for binding to CCL20.

Samples that are able to compete in the high throughput screens may be subjected to DNA sequencing as described in Vaughan et al. (1996; supra) and Osburn et al. (2005; supra). Clones may then be expressed and purified as scFvs or IgGs and assessed for their ability to bind CCL20, neutralize CCL20 or a combination thereof, e.g., using assays such as antibody-dependent cell mediated cytotoxicity (ADCC) assay and complement dependent cytotoxicity (CDC) assay. Purified scFv preparations can then be prepared as described in Example 3 of WO 01/66754. Protein concentrations of purified scFv preparations were determined using the BCA method (Pierce). Similar approaches can be used to screen for an optimal partner (the opposite chain) of a fixed full-length antibody heavy or light chain or heavy or light chain variable domain.

In another embodiment, an anti-human CCL20 antibody or an antigen-binding portion thereof, as described herein, is first used to select heavy and light chain sequences having similar binding activity toward CCL20, using the epitope imprinting methods described in PCT Publication No. WO 93/06213, incorporated herein by reference. In certain embodiments, the antibody libraries used in this method are scFv libraries prepared and screened as described in PCT Publication No. WO 92/01047, McCafferty et al., *Nature* 348:552-554 (1990); and Griffiths et al., *EMBO J.* 12:725-734 (1993), all incorporated herein by reference. In certain embodiments, the scFv antibody libraries are screened using human CCL20 as the antigen.

Once initial $V_L$ and $V_H$ domains are selected, "mix and match" experiments can be performed, in which different pairs of the initially selected $V_L$ and $V_H$ segments are screened for CCL20 binding to select preferred $V_L/V_H$ pair combinations. Additionally, to further improve the quality of the antibody, the $V_L$ and $V_H$ segments of the preferred $V_L/V_H$ pair(s) can be randomly mutated in a process analogous to the in vivo somatic mutation process responsible for affinity maturation of antibodies during a natural immune response. In some embodiments, the random mutations occur within the CDR3 region of $V_H$ and/or $V_L$. In certain embodiments, this in vitro affinity maturation is accomplished by, e.g., amplifying $V_H$ and $V_L$ domains using PCR primers complimentary to the $V_H$ CDR3 or $V_L$ CDR3, respectively, wherein the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be re-screened for binding to CCL20.

Following screening and isolation of an anti-CCL20 antibody of the invention from a recombinant antibody display library, nucleic acids encoding the selected antibody can be recovered from the display package (e.g., from the phage genome) and subcloned into other expression vectors by standard recombinant DNA techniques. In some embodiments, the nucleic acid is further manipulated to create other antibody forms of the invention, as described herein. In certain embodiments, to express a recombinant human antibody isolated by screening of a combinatorial library, the DNA encoding the antibody is cloned into a recombinant expression vector and introduced into mammalian host cells, as described herein.

In a particular embodiment, the invention provides a method of producing a hybridoma that secretes a monoclonal antibody that has binding specificity for human CCL20, comprising administering lymphocytes of a CCL20 transgenic mouse to a non-transgenic mouse having the same strain (e.g., CD1) as the human CCL20 transgenic mouse, thereby producing an immunized, non-transgenic mouse.

Splenocytes of the immunized, non-transgenic mouse are contacted with immortalized cells, thereby producing fused cells, and the fused cells are maintained under conditions in which hybridomas that secrete a monoclonal antibody having binding specificity for human CCL20 are produced, thereby producing a hybridoma that secretes a monoclonal antibody that has binding specificity for human CCL20.

The present invention also provides methods of preparing mutated forms of the anti-CCL20 antibodies and antigen-binding portions thereof of the invention. In some embodiments, the antibodies or portions are mutated in the variable domains of the heavy and/or light chains. In certain embodiments, said mutation alters one or more binding properties of the antibody or portion. In particular embodiments, a mutation is made in one or more of the CDR regions to increase or decrease the $K_D$ of the anti-CCL20 antibody or portion, to increase or decrease $k_{off}$, or to alter the binding specificity of the antibody or portion. Techniques in site-directed mutagenesis are well-known in the art. See e.g. Sambrook et al. and Ausubel et al., supra. In another embodiment, one or more mutations are made at an amino acid residue that is known to be changed compared to the germline in a monoclonal antibody of the invention. In certain embodiments, the mutations are made in a CDR region or framework region of a variable domain, or in a constant domain. In a particular embodiment, the mutations are made in a variable domain. In some embodiments, one or more mutations are made at an amino acid residue that is known to be changed compared to the germline in a CDR region or framework region of a variable domain of an antibody or portion of the invention.

In another embodiment, the framework region is mutated so that the resulting framework region(s) have the amino acid sequence of the corresponding germline gene. In certain embodiments, one or more mutations are made in a framework region or constant domain to increase the half-life of the anti-CCL20 antibody or portion. See e.g. PCT Publication WO 00/09560. In certain embodiments, a mutation in a framework region or constant domain is made to alter the immunogenicity of the antibody, or to provide a site for covalent or non-covalent binding to another molecule. According to the invention, a single antibody or portion may have mutations in any one or more of the CDRs or framework regions of the variable domain or in the constant domain.

Anti-CCL20 antibodies or antigen-binding portions thereof of the invention also can be produced transgenically through the generation of a mammal or plant that is transgenic for the antibody heavy and light chain sequences of interest and production of the antibody in a recoverable form therefrom. In some embodiments, the anti-CCL20 antibodies or portions are produced in, and recovered from, the milk of goats, cows, or other mammals. See, e.g., U.S. Pat. Nos. 5,827,690, 5,756,687, 5,750,172, and 5,741,957. In some embodiments, non-human transgenic animals that comprise human antibody loci are immunized with human CCL20 or an immunogenic portion thereof, as described above. Methods for making antibodies in plants are described, e.g., in U.S. Pat. Nos. 6,046,037 and 5,959,177.

In some embodiments, non-human transgenic animals or plants are produced by introducing one or more nucleic acid molecules encoding an anti-CCL20 antibody or portion of the invention into the animal or plant by standard transgenic techniques. See Hogan and U.S. Pat. No. 6,417,429, supra. In certain embodiments, transgenic cells used for making the transgenic animal can be embryonic stem cells or somatic cells or a fertilized egg. In some embodiments, the non-human transgenic animals or plants are chimeric, nonchimeric heterozygotes, or nonchimeric homozygotes. See, e.g., Hogan et al., *Manipulating the Mouse Embryo: A Laboratory Manual* 2nd ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). In some embodiments, the non-human transgenic animals or plants have a targeted disruption and replacement by a targeting construct that encodes a heavy chain and/or a light chain of interest. In certain embodiments, the transgenic animals or plants comprise and express nucleic acid molecules encoding heavy and light chains that specifically bind to human CCL20. The anti-CCL20 antibodies or portions may be made in any non-human transgenic animal or plant. In particular embodiments, the non-human animals are mice, rats, sheep, pigs, goats, cattle or horses. The non-human transgenic animal may express the encoded polypeptides in blood, milk, urine, saliva, tears, mucus and other bodily fluids.

The antibodies and antigen-binding portions thereof of the invention are useful in neutralizing CCL20-induced chemoattraction of, e.g., CCR6+ cells such as immature dendritic cells (DC), effector/memory T-cells, and B-cells. The antibodies and portions may thus be useful in treating a variety of diseases and conditions such as inflammation, autoimmune diseases, and cancer. Examples of diseases and conditions that can be treated with the antibodies or antigen-binding portions of this invention include, without limitation, Grave's disease, vitiligo, hyperthyroidism, rheumatoid arthritis, psoriasis, atopic dermatitis, contact dermatitis, Crohn's disease, inflammatory bowel disease, B-cell malignancies, breast adenocarcinoma, chronic hepatitis, contact dermatitis, glioblastoma, hepatocellular carcinoma, human papillomavirus infection of the cervix, mycosis fungoides, pancreatic adenocarcinoma, periodontal disease, thyroid papillary carcinoma, pustulosis palmaris et plantaris, conditions associated with maculopapular exanthema, epidermolysis bullosa, alopecia areata, multiple sclerosis, polymyositis, dermatomyositis, Behcet's disease, acute generalized exanthematous pustulosis, vasculitides, juvenile idiopathic arthritis, sarcoidosis, bronchial asthma, allergic rhinitis, renal allograft rejection, graft-versus-host disease, liver allograft rejection, chronic obstructive pulmonary disease, cystic fibrosis, glomerulonephritis, respiratory syncytial virus infection, multiple myeloma, and Langerhans cell histiocytosis. In some embodiments, the invention provides methods for treating any CCR6-associated condition.

Accordingly, the invention provides methods for treating inflammation, an autoimmune disease, or cancer by administering an effective amount of an antibody or portion of the invention to a subject in need thereof. In some embodiments, the subject is a human patient having or at risk for having an autoimmune disease, a cancer, and/or inflammation. In some embodiments, the antibody or portion is administered prophylactically to prevent onset or relapse of inflammation, autoimmune disease, or cancer.

Antibodies and antigen-binding portions thereof of this invention can be administered to an individual (e.g., a human) alone or in conjunction with another agent in a combination therapy. The antibodies or portions can be administered before, as an admixture with, separately but concurrently with, or subsequent to administration of the additional agent. In some embodiments, the additional agent is selected from the group including, but not limited to: inhibitors of immuno-stimulatory cytokines (e.g., anti-TNF-α MAbs), immune cell eliminators (e.g., anti-CD20 MAbs), blockers of accessory molecules (e.g. Abatacept), disease-modifying agents for rheumatic diseases (e.g., non-steroidal anti-inflammatory drugs (NSAIDs), methotrexate, retinoic acids, and vitamin D3 analogs), and immunosuppressants (e.g., calcineurin inhibitors). In some embodiments, the additional agent is selected from the group including, but not limited to: steroidal agents, immunomodulatory agents, somatostatic agents, conventional immunotherapeutic agents, cytokines or cytokine antagonists, and/or growth factors or growth factor antagonists. In some embodiments, anti-CCL20 antibody therapy can be used in conjunction with standard-of-care cancer treatment such as chemotherapy, surgery, or radiation, or with another targeted therapy such as anti-VEGF antibody therapy. In some embodiments, anti-CCL20 antibody therapy can be used in conjunction with a prophylactic regimen. In one embodiment, a synthetic peptide mimetic can be administered in conjunction with an antibody of the present invention. In another embodiment, hormone therapy can be administered in conjunction with an antibody or portion of the present invention.

In one embodiment, the antibodies or antigen-binding portions of the invention are administered alone or in combination with an anti-inflammatory agent. Anti-inflammatory agents that may be administered with the antibodies of the invention include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., balsalazide, celecoxib, diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, olsalazine, oxaprozin, phenylbutazone, piroxicam, salsalate, sulindac, tenoxicam, tiaprofenic acid, and tolmetin), as well as acetaminophen, antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives (e.g. sulfasalazone and mesalamine), thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Conventional nonspecific immunosuppressive agents that may be administered in combination with the antibodies of the invention include, but are not limited to, steroids, cyclosporine, cyclosporine analogs, cyclophosphamide methylprednisone, prednisone, azathioprine, FK-506, 15-deoxyspergualin, natalizumab, and other immunosuppressive agents that act by suppressing the function of responding T cells.

In some embodiments, the antibodies or antigen-binding portions of the invention are administered in combination with immunosuppressants. Immunosuppressant preparations that may be administered with the antibodies of the invention include, but are not limited to, ORTHOCLONE™ (OKT3), SANDIMMUNE™/NEORAL™/SANGDYA™ (cyclosporin), PROGRAF™ (tacrolimus), CELLCEPT$^M$ (mycophenolate), Azathioprine, glucorticosteroids, AVONEX™ (interferon-beta 1A), and RAPAMUNE™ (sirolimus). In one embodiment, immunosuppressants may be used to prevent rejection of organ or bone marrow transplantation.

In some embodiments, the antibodies or antigen-binding portions of the invention are administered in combination with a chemotherapeutic agent. Chemotherapeutic agents that may be administered with the antibodies of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, and vincristine sulfate); hormones (e.g., medroxyprogesterone, estramustine phosphate sodium, ethinyl estradiol, estradiol, epinephrine, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, rituximab, and etoposide).

In some embodiments, the antibodies or antigen-binding portions of the invention are administered in combination with a TNF antagonist. TNF antagonists that may be administered with the antibodies or antigen-binding portions of the invention include, but are not limited to, infliximab (REMICADE™), adalimumab (HUMIRA™), certolizumab pegol (CIMZIA™), golimumab (SIMPONI™), etanercept (ENBREL™), xanthine deriviatives (e.g. pentoxifyline) and bupropion (WELLBURTIN™, ZYBAN™).

In some embodiments, the antibodies or antigen-binding portions of the invention are administered alone or in combination with one or more intravenous immune globulin preparations.

Intravenous immune globulin preparations that may be administered with the antibodies or portions of the invention include, but not limited to, GAMMAR™, IVEEGAM™, SANDOGLOBULIN™, GAMMAGARD S/D™, and GAMIMUNE™. In some embodiments, the antibodies or antigen-binding portions of the invention are administered in combination with intravenous immune globulin preparations in transplantation therapy (e.g., bone marrow transplant).

In some embodiments, the antibodies or antigen-binding portions of the invention are administered in combination with cytokines or cytokine antagonists. In some embodiments, the antibodies or antigen-binding portions of the invention may be administered with any cytokine or cytokine antagonist, including, but not limited to, IL2, IL3, IL4, IL5, IL6, IL7, IL10, IL12, IL13, IL15, anti-CD40, CD40L, IFN-γ and TNF-α or any antagonist thereof. In some embodiments, the antibodies or antigen-binding portions of the invention may be administered with any interleukin or interleukin antagonist, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21 or any antagonist thereof.

In some embodiments, the antibodies or antigen-binding portions of the invention are administered in combination with one or more chemokines or chemokine antagonists. In specific embodiments, the antibodies or antigen-binding portions of the invention are administered in combination with an α(CxC) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1α), macrophage inflammatory protein-1 beta (MIP-1β), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin; or any antagonist thereof.

In some embodiments, the antibodies or antigen-binding portions of the invention are administered with chemokine beta-8, chemokine beta-1, and/or macrophage inflammatory protein-4, or any antagonist thereof. In a preferred embodiment, the antibodies or antigen-binding portions of the invention are administered with chemokine beta-8 or an antagonist thereof.

In some embodiments, the antibodies or antigen-binding portions of the invention are administered in combination with an IL-4 antagonist. IL-4 antagonists that may be administered with the antibody and antibody compositions of the invention include, but are not limited to: soluble IL-4 receptor polypeptides, multimeric forms of soluble IL-4 receptor polypeptides, anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the anti-IL4 antibodies employed according to this method are monoclonal antibodies; antigen-binding portions thereof may also be employed.

In some embodiments, the antibodies or antigen-binding portions of the invention are administered in combination with members of the TNF family, or antagonists thereof. In some embodiments, the antibodies or antigen-binding portions of the invention are administered in combination with agents that include, but are not limited to, soluble forms of TNF-α, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), OPG, neutrokine-alpha (International Publication No. WO 98/18921), OX40, nerve growth factor (NGF), soluble forms of Fas, CD30, CD27, CD40 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, and soluble forms CD154, CD70, and CD153; or any antagonist thereof.

As used herein, the term "therapeutically effective amount" refers to an amount of the administered therapeutic agent that will relieve or prevent to some extent one or more of the symptoms of the disorder being treated. An effective amount of anti-CCL20 antibody or antigen-binding portion thereof for treating a disease is an amount that helps the treated subject to reach one or more desired clinical end points.

In some embodiments, to minimize immunogenicity, a humanized antibody or portion is used to treat a human patient in therapeutic methods and compositions of this invention. In cases where repeated administration is not necessary, in some embodiments, it may also be appropriate to administer a mouse or chimeric antibody or portion of the invention to a human patient.

In some embodiments, the antibodies or antigen-binding portions thereof of the invention may be used to treat an individual who has previously been treated with, e.g., inhibitors of immuno-stimulatory cytokines (e.g., anti-TNF-α MAbs), immune cell eliminators (e.g., anti-CD20 MAbs), and/or blockers of accessory molecules (e.g. Abatacept). In some embodiments, the antibodies or portions are used to treat a patient who has developed primary non-responsiveness or a gradual decline in response rate to these other treatments.

The antibody or antigen-binding portion thereof of this invention can be administered in a single unit dose or multiple doses at any time point deemed appropriate by a health care provider. The dosage can be determined by methods known in the art and can be dependent, for example, upon the individual's age, sensitivity, tolerance and overall well-being. Any administration method accepted in the art may be employed suitably for the antibodies and portions of the invention, including, but not necessarily limited to, parenteral (e.g., intravenous, intraarterial, intramuscular, intrathecal, intraperitoneal, subcutaneous injection), oral (e.g., dietary), locally, topical, inhalation (e.g., intrabronchial, intranasal or oral inhalation, intranasal drops), or rectal, depending on the disease or condition to be treated. In one embodiment, the antibody or portion is administered parenterally.

Formulation will vary according to the route of administration selected (e.g., solution, emulsion). An appropriate composition comprising the antibody or portion to be administered can be prepared in a physiologically acceptable vehicle or carrier. The composition can comprise multiple doses or be a single unit dose composition. For solutions or emulsions, suitable carriers include, for example, aqueous or alcoholic/aqueous solutions, emulsions, or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Sciences,* 17th Edition, Mack Publishing Co., PA, 1985). For inhalation, the compound can be solubilized and loaded into a suitable dispenser for administration (e.g., an atomizer, nebulizer or pressurized aerosol dispenser).

Dosage regimens may be adjusted to provide the optimum desired response. In certain embodiments, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. The present invention thus encompasses intra-patient dose-escalation as determined by the skilled artisan. Methods of determining appropriate dosages and regimens are well-known in the relevant art and would be understood to be encompassed by the skilled artisan once provided with the teachings disclosed herein.

In some embodiments, for administration to human subjects, the total monthly dose of the antibodies or antibody portion of the invention is in the range 0.5-1200 mg per patient, depending, of course, on the mode of administration. In certain embodiments, an intravenous monthly dose requires about 1-1000 mg/patient. The total monthly dose may be administered in single or divided doses and may, at the physician's discretion, fall outside of the typical range given herein.

In certain embodiments, a range for a therapeutically or prophylactically effective amount of an antibody or antibody portion of the invention is 1-1000 mg/kg/patient/month. In one embodiment, the antibody or portion thereof of the invention may be administered at about 1-200 or 1-150 mg/patient/month. In certain embodiments, the antibody or portion is administered in a 1, 2, 3, 4, 5, 6, 7, 8, 9, or 10 mg/kg/patient shot 1, 2, 3, 4, 5, 6, 7, 8, 9, or 10 times a month. In a particular embodiment, the antibody or portion is administered in a 1 to 5 mg/kg/patient shot 1 or 2 times a month.

The antibodies and antigen-binding portions thereof of the present invention also are useful in a variety of processes with applications in research and diagnosis. In some embodiments, the antibodies and portions are used to detect, isolate, and/or purify human CCL20 or variants thereof (e.g., by affinity purification or other suitable methods such as flow cytometry, e.g., for cells, such as lymphocytes, in suspension), and to study human CCL20 structure (e.g., conformation) and function. For in vitro applications, wherein immunogenicity of the antibody is not a concern, the mouse and chimeric antibodies and antigen-binding portions thereof of this invention will be useful in addition to humanized antibodies.

The antibodies or antigen-binding portions thereof of the present invention can be used in diagnostic applications (e.g., in vitro, ex vivo). In some embodiments, the humanized antibodies or portions of the present invention are used to detect and/or measure the level of human CCL20 in a sample. In certain embodiments, the sample comprises, e.g., cells or tissues expressing human CCL20, and/or body fluids such as an inflammatory exudate, blood, serum, and/or bowel fluid bearing human CCL20. A sample can be obtained from an individual and an antibody or portion described herein can be used in a suitable immunological method to detect and/or measure human CCL20 expression, including methods such as flow cytometry (e.g., for cells in suspension such as lymphocytes), enzyme-linked immunosorbant assays (ELISA), including chemiluminescence assays, radioimmunoassay, and immunohistology.

In one embodiment, a method of detecting human CCL20 in a sample comprises contacting the sample with an antibody or portion of the present invention under conditions suitable for specific binding of the antibody or portion to human CCL20 and detecting antibody-CCL20 complexes which are formed. In one embodiment, the antibodies or portions described herein can be used to analyze normal versus inflamed tissues (e.g., from a human) for human CCL20 reactivity and/or expression (e.g., immunohistologically) to detect associations between increased expression of human CCL20 (e.g., in affected tissues) and one or more disorders selected from, but not limited to, Grave's disease, vitiligo, hyperthyroidism, rheumatoid arthritis, psoriasis, atopic dermatitis, contact dermatitis, Crohn's disease, inflammatory bowel disease, B-cell malignancies, breast adenocarcinoma, chronic hepatitis, contact dermatitis, glioblastoma, hepatocellular carcinoma, human papillomavirus infection of the cervix, mycosis fungoides, pancreatic adenocarcinoma, periodontal disease, thyroid papillary carcinoma, pustulosis palmaris et plantaris, conditions associated with maculopapular exanthema, epidermolysis bullosa, alopecia areata, multiple sclerosis, polymyositis, dermatomyositis, Behcet's disease, acute generalized exanthematous pustulosis, vasculitides, juvenile idiopathic arthritis, sarcoidosis, bronchial asthma, allergic rhinitis, renal allograft rejection, graft-versus-host disease, liver allograft rejection, chronic obstructive pulmonary disease, cystic fibrosis, glomerulonephritis, respiratory syncytial virus infection, multiple myeloma, Langerhans cell histiocytosis, or other conditions. Thus, the antibodies of the present invention permit immunological methods of assessment of the presence of human CCL20 in normal and inflamed tissues, through which the presence of disease, disease progress and/or the efficacy of anti-human CCL20 therapy in the treatment of disease, e.g., inflammatory and/or immune disease, can be assessed.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

In order that this invention may be better understood, the following examples are set forth. These examples are for purposes of illustration only and are not to be construed as limiting the scope of the invention in any manner.

Example 1: Involvement of CCL20 in Autoimmune/Inflammatory Disorders

To obtain evidence for the involvement of CCL20 in autoimmune and inflammatory conditions, we studied the effects of knocking out the CCL20 receptor CCR6 in a type II collagen-induced arthritis (CIA) mouse rheumatoid arthritis (RA) model. CCR6 wild type mice, CCR6$^{-/-}$ (heterozygous) mice, and CCR6$^{-/-}$ (homozygous) knock-out mice (each n=10) were immunized at the base of the tail with bovine type II collagen (150 μg/mouse) emulsified in complete Freund's adjuvant (Chondrex, #7001). Three weeks later, a booster injection of the same amount of bovine type II collagen emulsion in incomplete adjuvant was administered at the base of the tail. We graded the severity of arthritic symptoms in the paws of each mouse as described in Griswold et al., *Arthritis & Rheumatism* 31(11):1406-1412 (1988). Briefly, we graded the articular lesions of the extremities distal to the elbow or knee on a scale of 0 to 4 based on the number of joints involved and the degree of erythema and swelling. Arthritis scores were calculated as the sum of the scores of all four paws for each animal. CCR6 wild type animals developed arthritis, while CCR6$^{-/-}$ animals showed strong resistance to the disease (FIG. 1). Interestingly, CCR6$^{-/-}$ animals also exhibited some levels of resistance, indicating that total abrogation of CCL20 function is not required to counteract the arthritic phenotype.

Figure 2:
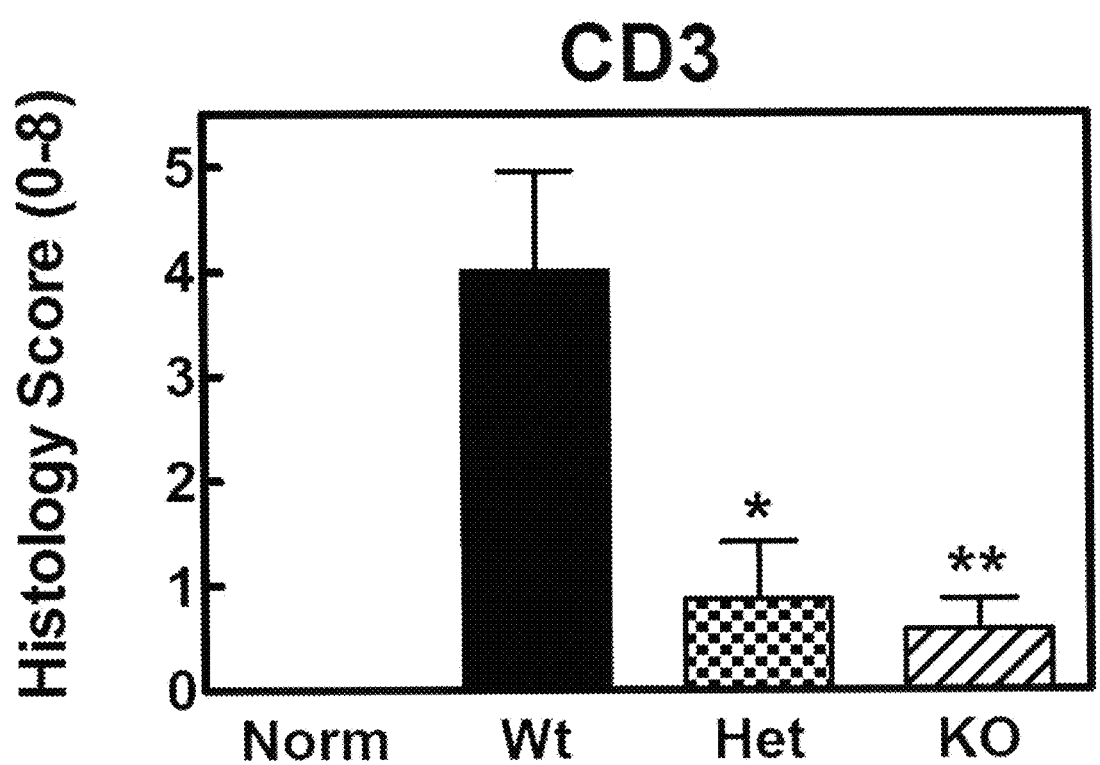
FIG. 2 is a graph showing that CCR6 deficient mice exhibit impaired infiltration of T-cells (as indicated by CD3 levels) in collagen-induced arthritic lesions in comparison to wild-type mice. Data shown are means±SEM from one experiment (n=7 mice per group). *$p<0.05$, **$p<0.01$. See Example 1.
Figure 3:
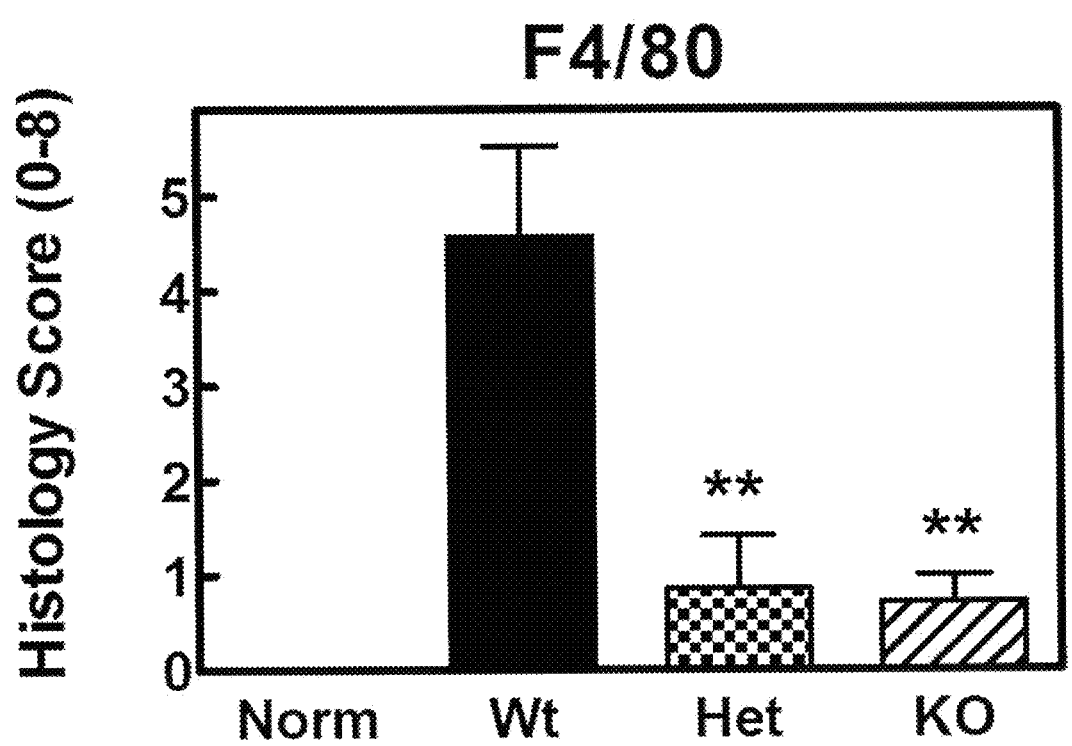
FIG. 3 is a graph showing that CCR6 deficient mice exhibit impaired infiltration of macrophages (as indicated by F4/80 levels) in collagen-induced arthritic lesions in comparison to wild-type mice. Data shown are means±SEM from one experiment (n=7 mice per group). **$p<0.01$. See Example 1.

In addition, we immunohistochemically analyzed the hind paws of mice for the presence of CD3-positive T-cells or F4/80-positive macrophages. On day 43, mice were harvested and their hind paws were fixed in formalin. The paws were then sectioned and placed on slides. After decalcification of the paw samples, the slides were stained immunohistochemically with anti-CD3 (#N1580, DAKO) and F4/80 antibodies (Clone CI:A3-1, AbD Serotec). The intensity of staining was scored by two independent observers by scanning the samples with an Aperio instrument (Aperio Technologies). The scoring scale was as follows: 0, normal; 1, light staining throughout the paw or intense staining in one digit; 2, moderate staining in multiple digits; 3, intense staining in multiple digits or moderate throughout; 4, intense staining throughout all digits and paw. The number of T-cells (FIG. 2) and macrophages (FIG. 3) infiltrating the CIA-induced lesions were strongly reduced in both CCR6$^{+/-}$ and CCR6$^{-/-}$ mice.

Figure 4:
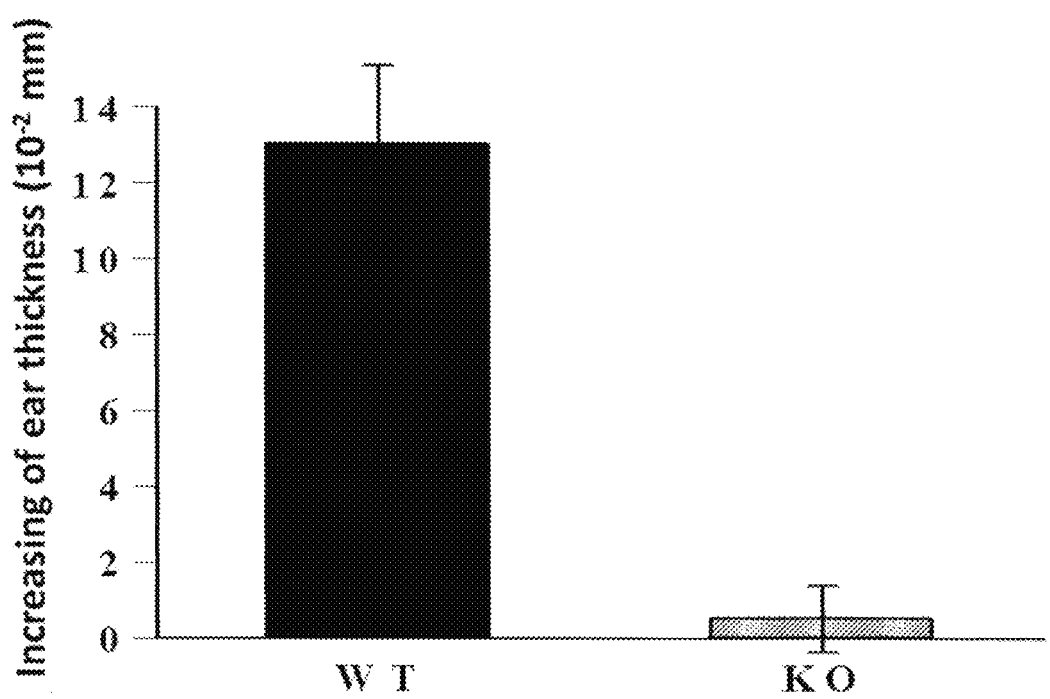
FIG. 4 is a graph showing that in comparison to wild-type mice, CCR6 deficient mice are resistant to increased ear thickness in a dinitrofluorobenzene (DNFB)-induced allergic contact dermatitis model. WT, wild-type mice; KO, CCR6 deficient mice. See Example 1.

We also studied the effects of knocking out CCR6 in a dinitrofluorobenzene (DNFB)-induced allergic contact dermatitis mouse model. Two groups of six mice each (one group of mice wild-type for CCR6 and one group CCR6 deficient) were sensitized by brushing 25 μl of 0.4% DNFB solution (in 4:1 acetone:olive oil) on the shaved abdomen for two successive days (days 0 and 1). On day 5, mice were re-challenged by applying 20 μl of 0.1% DNFB (in 4:1 acetone:olive oil) to one side of one ear. As an indicator of edema, ear thickness was measured before DNFB challenge and at 24 hr after the last challenge on Day 5 by using a thickness gauge. CCR6 deficient mice demonstrated almost no increased ear thickness after treatment with DNFB, indicating resistance against DNFB-induced contact hypersensitivity (FIG. 4).

These data support a role for CCR6 and CCL20 in autoimmune/inflammatory disorders.

Example 2: Inhibition of CCL20-Induced Chemotaxis by Hamster Anti-Mouse CCL20 2F5-5 MAb To further explore the role of CCL20 as a potential therapeutic target, we performed experiments using a hamster anti-mouse CCL20 antibody (2F5-5). We first characterized the ability of the 2F5-5 MAb to bind to mouse, human, and rhesus CCL20. Soluble CCL20-secreted alkaline phosphatase (SEAP) antigens of each species were prepared as follows. The cDNAs encoding the CCL20s of human, cynomolgus monkey, rhesus monkey, rat, and mouse were amplified and subcloned into a pcDNA3.1 (+) dSalI SEAP vector, which contains SEAP cDNA and has its SalI site deleted (pcDNA 3.1 (+) purchased from Invitrogen; SEAP cDNA derived from a pSEAP-Enhancer vector, Clontech). The expression vectors were transfected into the human embryo kidney cell line HEK293EBNA (HEK293E, Invitrogen). The HEK293E cells were inoculated with DMEM (Invitrogen) supplemented with 10% fetal bovine serum on the day before transfection. On the day of transfection, the culture medium was replaced with OPTI-MEM II serum free media (Invitrogen). The expression vectors were transfected using TransIT LT1 (TAKARA Bio Inc., Shiga, Japan) according to the manufacturer's protocol. After 3 days of incubation at 5% $CO_2$ and 37° C., culture supernatants were harvested. The concentration of CCL20-SEAP in each culture was measured by using the Great EscAPe SEAP Chemiluminescence Kit 2.0 (Clontech).

We then performed surface plasmon resonance (Biacore™) binding studies to measure the binding of the 2F5-5 MAb to mouse, human, rhesus, and cynomolgus CCL20-SEAP antigens. Anti-SEAP (monoclonal anti-mouse placental alkaline phosphatase, Thermo Scientific, Cat # MAI-19354, Lot # KL12748M) was immobilized on a CM5 sensor chip (GE Healthcare) using a standard NHS/EDC amine coupling procedure. SEAP-tagged mouse CCL20 (100 nM in supernatant, ID735, Lot #091130) was diluted to 5 nM with TBS-P containing 0.005% Tween-20 and captured on the CM5 sensor chip. 0.2 nM to 80 nM dilutions of hamster anti-mouse CCL20 (2F5-5, Lot #060215, 2 mg/ml) in TBS-P were injected over the sensor chip at a flow rate of 30 µl/min. Association and dissociation of hamster anti-mouse CCL20 with mouse CCL20 were monitored for 4 min and 16 min, respectively. The chip surface was regenerated between injections using 10 mM glycine, pH 2.25. Sensograms were double referenced by subtracting hamster anti-mouse CCL20 injections into a reference cell without captured mouse CCL20 and a TBS-P injection over captured mouse CCL20. The sensograms were analyzed using a 1:1 Langmuir binding model in BIAevaluation software (GE Healthcare, version 3.2). In this assay, 2F5-5 MAb binds to mouse CCL20 with an affinity of 32 pM, but does not bind to human, rhesus, or cynomolgus CCL20 (Table 1).

TABLE 1

2F5-5 MAb binding affinity to CCL20 orthologs

| CCL20 Ortholog | $k_a$ ($\times 10^5$ $M^{-1}sec^{-1}$) | $k_d$ ($\times 10^{-5}$ $sec^{-1}$) | $K_D$ ($\times 10^{-11}$ M) |
|---|---|---|---|
| Mouse | 9.63 | 0.474 | 0.492 |
| Human | Not detectable | Not detectable | Not detectable |
| Rhesus | Not detectable | Not detectable | Not detectable |
| Cynomolgus | Not detectable | Not detectable | Not detectable |

Figure 5:
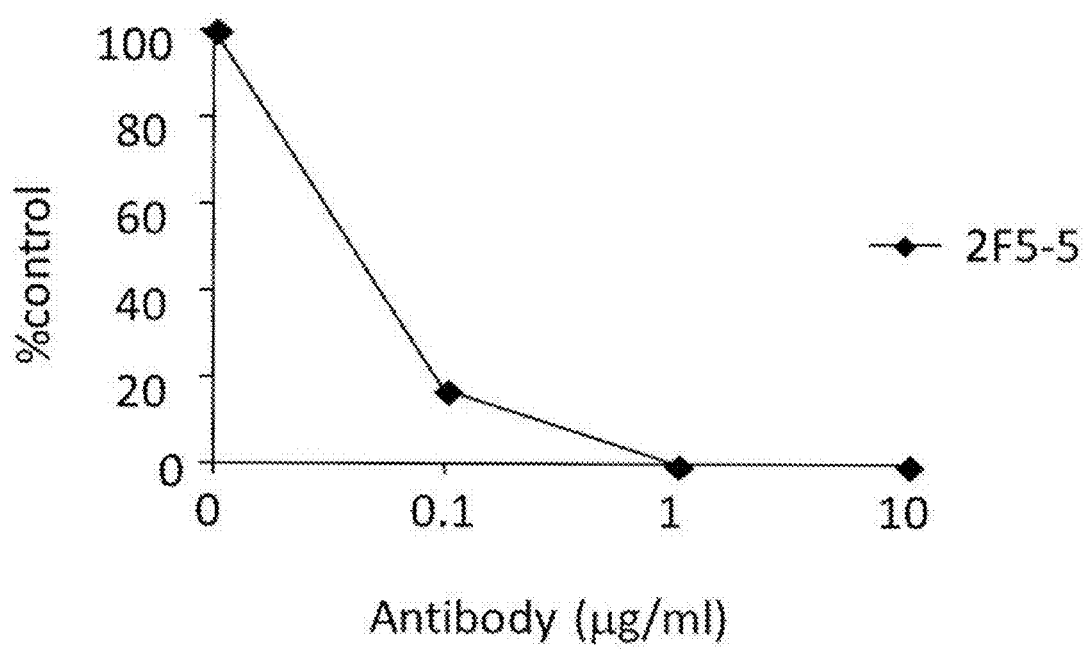
FIG. 5 is a graph showing that 2F5-5 MAb inhibits CCL20-induced chemotaxis. See Example 2.

To test the effect of 2F5-5 MAb on CCL20 function, we evaluated its neutralizing activity against mouse CCL20 using an in vitro chemotaxis assay. CCR6-transduced B300.19 cells and recombinant mouse CCL20 (1 nM) were added to transwell culture plates. Four hours later, the cells that migrated into the lower chamber were counted by fluorescence-activated cell sorting (FACS). 2F5-5 MAb completely inhibited chemotaxis at 1 µg/ml with an estimated $IC_{50}$ value of 0.04 µg/ml (0.27 nM) (FIG. 5). By contrast, a control hamster antibody (10 µg/ml) did not inhibit chemotaxis (100% control; data not shown).

Example 3: Humanization of Mouse Anti-CCL20 MAbs

To obtain monoclonal antibodies against human CCL20, we generated a panel of mouse anti-human CCL20 antibodies. Recombinant human CCL20 (R&D, #360-MP-025/CF, 17.5 µg/head) emulsified with Freund's complete adjuvant (Mitsubishi-Kagaku Yatron, RM606-1) was injected subcutaneously into the footpads of the mice. Two consecutive injections were then administered every three days. Three days after the final immunization, the animals were sacrificed and the inguinal lymph-node cells were fused with P3U1 myeloma cells at a 2:1 to 10:1 ratio in the presence of 50% polyethylene glycol. The cells were then cultured in 96-well plastic plates.

Sandwich ELISA was used for primary screening. A 96-well plate was coated with a polyclonal anti-human IgG antibody (Jackson, #709-005-149, 2 µg/ml in PBS (−)). After overnight incubation at 4° C., the wells were blocked with 1× Block-Ace (Dainippon Sumitomo Pharma, UK-B80) for 1 hour at room temperature. The wells were then washed with 0.02% Tween 20/PBS (−), after which 1 nM human CCL20-hIgG Fc chimera protein in 0.02% Tween 20/PBS (−) was added to the wells (50 µl/well). After a one hour incubation at room temperature, three additional washes were performed as described above. Culture supernatants from each hybridoma were then diluted twofold with 20% FBS and 200 µg/ml human IgG (Mitsubishi Welpharma) in 0.02% Tween 20/PBS (−), added to the wells, and incubated for one hour at room temperature. After three further washes, the wells were incubated with horseradish peroxidase-conjugated anti-mouse IgG antibody (Jackson, #715-035-150, 5000 fold dilution with 0.02% Tween 20/PBS (−)) for one hour at room temperature. The wells were then washed three times and incubated in a TMBZ (3,3',5,5'-tetramethylbenzidine) solution for 15-30 minutes. An equal volume of 2 M $H_2SO_4$ was then added to stop the reaction, and the optical density was read at 450 nm by ARVO (PerkinElmer). The sandwich ELISA identified 24 positive wells.

We then performed a chemotaxis assay as a secondary screen. The chemotaxis assay was performed in transwell culture plates (MultiScreen pore 5 µm, Millipore, #MAMIC 5S10). First, 50 µl/well of 300 ng/ml recombinant human CCL20 (R&D, #360-MP-025/CF) in chemotaxis buffer (0.5% BSA, 0.5% FBS, 20 mM HEPES (pH 7.4), 50 pM 2-mercaptoethanol in RPMI1640 (Invitrogen)) was pre-incubated with 100 µl/well of culture supernatants from the hybridomas at room temperature for 30 minutes (for a final CCL20 concentration of 100 ng/ml) in the lower wells of the plates. After 30 minutes, B300.19 cells transfected with human CCR6 (SEQ ID NO: 104) ($2 \times 10^5$ cells/75 µl) were applied to the upper wells and incubated in a 5% $CO_2$ incubator at 37° C. for 4 hours. Following the incubation, 150 µl from the lower wells were harvested and fixed with 50 μl of 4% PFA/PBS (−). 30 μl of each sample were applied to the FACSCantoII cell analyzer (BD Biosciences) to count migrated cells. Neutralizing activity was found in four wells.

We then used standard limiting dilution to obtain hybridoma clones from the four positive wells. We confirmed the neutralizing activity of supernatant from each clone using the in vitro chemotaxis assay. Three of the mouse anti-human CCL20 monoclonal antibodies produced by these clones (antibodies 36F7C10 (Table 2), 42G5B10 (Table 3), and 40-1C10B9 (Table 4)) demonstrated neutralizing activity against human CCL20.

TABLE 2

Amino acid and nucleotide sequences of 36F7C10

| DESCRIPTION | SEQUENCE |
|---|---|
| Heavy Chain Signal Sequence (Amino Acid) (SEQ ID NO: 33) | MRWSCIILFLVATATGVNS |
| Light Chain Signal Sequence (Amino Acid) (SEQ ID NO: 34) | MGVPTQLLLLWLTVVVVRC |
| Heavy Chain Variable Domain Amino Acid Sequence (SEQ ID NO: 39) | QVQLQQPGAELVKPGASVKMSCKASGYT FTNYWMHWVKQRPGQGLEWIGVIDPSDS YTTYNQKFKGKATLTVDTSSSTAYMQLS SLTSEDSAVYYCTRGNYGVDYAMDYWGQ GTSVTVSS |
| Light Chain Variable Domain Amino Acid Sequence (SEQ ID NO: 40) | DIQMTQSPASLSASVGETVTITCGASEN IYGALNWYQRKQGKSPQLLIYGATNLAD GMSSRFSGSGSGRQYSLKISSLHPDDVA TYYCQNVLITPYTFGGGTKLEIK |
| Heavy Chain Signal Sequence (Nucleotide) (SEQ ID NO: 45) | ATGAGATGGAGCTGTATCATCCTCTTCT TGGTAGCAACAGCTACAGGTGTCAACTC C |
| Light Chain Signal Sequence (Nucleotide) (SEQ ID NO: 46) | ATGGGTGTACCCACTCAGCTCCTGTTGC TGTGGCTTACAGTCGTAGTTGTCAGATG T |
| Heavy Chain Variable Domain Nucleotide Sequence (SEQ ID NO: 51) | CAGGTCCAACTGCAGCAGCCTGGGGCTG AGCTGGTGAAGCCTGGGGCTTCAGTGAA GATGTCCTGCAAGGCTTCTGGCTACACC TTCACCAACTACTGGATGCACTGGGTGA AGCAGAGGCCTGGACAAGGCCTTGAGTG GATCGGAGTGATTGATCCTTCTGATAGT TATACTACCTACAATCAAAAGTTCAAGG GCAAGGCCACATTGACTGTAGACACATC CTCCAGCACAGCCTACATGCAGCTCAGC AGCCTGACATCTGAGGACTCTGCGGTCT ATTACTGTACAAGAGGTAACTACGGAGT AGACTATGCTATGGACTACTGGGGTCAA GGAACCTCAGTCACCGTCTCCTCG |
| Light Chain Variable Domain Nucleotide Sequence (SEQ ID NO: 52) | GACATCCAGATGACTCAGTCTCCAGCTT CACTGTCTGCATCTGTGGGAGAAACTGT CACCATCACATGTGGAGCAAGTGAGAAT ATTTACGGTGCTTTAAATTGGTATCAGC GGAAACAGGGAAAATCCCTCAGCTCCT GATCTATGGTGCAACCAACTTGGCAGAT GGCATGTCATCGAGGTTCAGTGGCAGTG GATCTGGTAGACAGTATTCTCTCAAGAT CAGTAGCCTGCATCCTGACGATGTTGCA ACGTATTACTGTCAAAATGTGTTAATTA CTCCGTACACGTTCGGAGGGGGGACCAA GCTGGAAATAAAA |

TABLE 3

Amino acid and nucleotide sequences of 42G5B10

| DESCRIPTION | SEQUENCE |
|---|---|
| Heavy Chain Signal Sequence (Amino Acid) (SEQ ID NO: 37) | MRWSCIILFLVATATGVNS |
| Light Chain Signal Sequence (Amino Acid) (SEQ ID NO: 38) | MGVPTQLLLLWLTVVVVRC |
| Heavy Chain Variable Domain Amino Acid Sequence (SEQ ID NO: 43) | QVQLQQPGAELVKPGASVKMSCKASGYT FTSYWMHWVKQRPGQGLEWIGLIDPSDK YTNYNQKFKGKATLTVDTSSSTAYMQLS SLTSEDSAVYYCTRGNYGVDYGMDYWGQ GTSVTVSS |
| Light Chain Variable Domain Amino Acid Sequence (SEQ ID NO: 44) | DIQMTQSPASLSASVGETVTITCGASEN IYGALNWYQRKQGKSPQLLIYGATNLAD GMSSRFSGSGSGRQYSLKISSLHPDDVA TYYCQNVLSTPYTFGGGTKLEIK |
| Heavy Chain Signal Sequence (Nucleotide) (SEQ ID NO: 49) | ATGAGATGGAGCTGTATCATCCTCTTCT TGGTAGCAACAGCTACAGGTGTCAACTC C |
| Light Chain Signal Sequence (Nucleotide) (SEQ ID NO: 50) | ATGGGTGTACCCACTCAGCTCCTGTTGC TGTGGCTTACAGTCGTAGTTGTCAGATG T |
| Heavy Chain Variable Domain Nucleotide Sequence (SEQ ID NO: 55) | CAGGTCCAACTGCAGCAGCCTGGGGCTG AGCTGGTGAAGCCTGGGGCTTCAGTGAA GATGTCCTGCAAGGCTTCTGGCTACACC TTCACCAGCTACTGGATGCACTGGGTGA AGCAGAGGCCTGGACAAGGCCTTGAGTG GATCGGACTGATTGATCCTTCTGATAAG TATACTAACTACAATCAAAAGTTCAAGG GCAAGGCCACATTGACTGTAGACACATC CTCCAGCACAGCCTACATGCAGCTCAGC AGCCTGACATCTGAGGACTCTGCGGTCT ATTACTGTACAAGAGGTAACTACGGAGT AGACTATGGTATGGACTACTGGGGTCAA GGAACCTCAGTCACCGTCTCCTCA |
| Light Chain Variable Domain Nucleotide Sequence (SEQ ID NO: 56) | GACATCCAGATGACTCAGTCTCCAGCTT CACTGTCTGCATCTGTGGGAGAAACTGT CACCATCACATGTGGAGCAAGTGAGAAT ATTTACGGTGCTTTAAATTGGTATCAGC GGAAACAGGGAAAATCCCTCAGCTCCT GATCTATGGTGCAACCAACTTGGCAGAT GGCATGTCATCGAGGTTCAGTGGCAGTG GATCTGGTAGACAGTATTCTCTCAAGAT CAGTAGCCTGCATCCTGACGATGTTGCA ACGTATTACTGTCAAAATGTGTTAAGTA CTCCGTACACGTTCGGAGGGGGGACCAA GCTGGAAATAAAA |

TABLE 4

Amino acid and nucleotide sequences of 40-1C10B9

| DESCRIPTION | SEQUENCE |
|---|---|
| Heavy Chain Signal Sequence (Amino Acid) (SEQ ID NO: 35) | MEWSWVFLFLLSVIAGVQS |

TABLE 4-continued

Amino acid and nucleotide sequences of 40-1C10B9

| DESCRIPTION | SEQUENCE |
|---|---|
| Light Chain Signal Sequence (Amino Acid) (SEQ ID NO: 36) | MGVPTQLLLLWLTVVVVRC |
| Heavy Chain Variable Domain Amino Acid Sequence (SEQ ID NO: 41) | QVQLQQSGAELVRPGASVTLSCKASGYT FTDYEMHWVKQTPVHGLEWIGAIDPETT STAYNQKFKGKATLTADKSSSTAYMELR SLTSEDSAVYYCTKCYYGSADYAMDYWG QGTSVTVSS |
| Light Chain Variable Domain Amino Acid Sequence (SEQ ID NO: 42) | DIQMTQSPASLSASVGETVTITCGASEN IYGALNWYQRKQGKSPQLLIYGATNLAD GMSSRFSGSGSGRQYSLKISSLHPDDVA TYYCQNVLSTPWTFGGGTKLEIK |
| Heavy Chain Signal Sequence (Nucleotide) (SEQ ID NO: 47) | ATGGAATGGAGCTGGGTCTTTCTCTTCC TCCTGTCAGTAATTGCAGGTGTCCAATC C |
| Light Chain Signal Sequence (Nucleotide) (SEQ ID NO: 48) | ATGGGTGTACCCACTCAGCTCCTGTTGC TGTGGCTTACAGTCGTAGTTGTCAGATG T |
| Heavy Chain Variable Domain Nucleotide Sequence (SEQ ID NO: 53) | CAGGTTCAACTGCAGCAGTCTGGGGCTG AGCTGGTGAGGCCTGGGGCTTCAGTGAC GCTGTCCTGCAAGGCTTCGGGCTACACA TTTACTGACTATGAAATGCACTGGGTGA AGCAGACACCTGTGCATGGCCTGGAATG GATTGGAGCTATTGATCCTGAAACTACT AGTACTGCCTACAATCAGAAGTTCAAGG GCAAGGCCACACTGACTGCAGACAAATC CTCCAGCACAGCCTACATGGAGCTCCGC AGCCTGACATCTGAGGACTCTGCCGTCT ATTACTGTACCAAATGTTACTACGGTAG CGCGGACTATGCTATGGACTACTGGGGT CAAGGAACCTCAGTCACCGTCTCCTCA |
| Light Chain Variable Domain Nucleotide Sequence (SEQ ID NO: 54) | GACATCCAGATGACTCAGTCTCCAGCTT CACTGTCTGCATCTGTGGGAGAAACTGT CACCATCACATGTGGAGCAAGTGAGAAT ATTTACGGTGCTTTAAATTGGTATCAGC GGAAACAGGGAAAATCTCCTCAGCTCCT GATCTATGGTGCAACCAACTTGGCAGAT GGCATGTCATCGAGGTTCAGTGGCAGTG GATCTGGTAGACAGTATTCTCTCAAGAT CAGTAGCCTGCATCCTGACGATGTTGCA ACGTATTACTGTCAAAATGTGTTAAGTA CTCCGTGGACGTTCGGTGGAGGCACCAA GCTGGAAATCAAA |

The 36F7C10, 42G5B10, and 40-1C10B9 mouse antibodies were then used to produce humanized antibody heavy and light chains. The humanization method involved grafting mouse complementarity determining regions (CDRs), as identified by Kabat and/or Chothia definition methods according to Kabat numbering, into the human heavy and light chain germline sequences representing the best framework matches with the original mouse sequences from which the CDRs were derived (FIGS. 6A-C; bolding denotes residues that differ between the mouse antibody and the human germline sequence; underlining and bolding denotes grafted mouse CDRs; italicizing and bolding denotes framework residues substituted with corresponding mouse antibody residues; and underlining, italicizing and bolding denotes CDR residues substituted with corresponding human germline residues). Framework matches were identified using the IgBlast database, according to the methods described in Altschul et al., Nucl. Acids Res. 25:3389-3402 (1997). To derive alternative humanized chain versions, we used two methods: 1) 3D modeling techniques to predict critical murine residues within the framework interacting with the CDR residues, and 2) sequence alignments to identify murine residues immediately adjacent to the canonical CDR sequences.

The humanized sequences were constructed into expression vectors and transfected into mammalian cell lines (e.g., HEK293E cells (Invitrogen)) for antibody production. Antibodies obtained by this process were then characterized in functional and physiochemical assays.

Example 4: In Vitro Chemotaxis Assays Demonstrating Neutralization Activity of Humanized Anti-Human CCL20 Abs We identified humanized antibodies that actively neutralize the human CCL20 ligand by performing in vitro chemotaxis assays using CCR6-transduced B300.19 cells. Upon determination of $IC_{50}$, $IC_{90}$, and $IC_{95}$ values (FIGS. 7A-C), antibodies demonstrating a reduced value in the $IC_{95}$ table were deemed to possess significant neutralizing activity (FIG. 7C). Of the 14 humanized heavy chains and 26 humanized light chains produced, we tested 41 combinations. Eight of these combinations were shown to significantly neutralize chemotaxis. These eight humanized antibodies are listed below:

36LK3/36HKK3
36LK3/42HKK1
36LK3/42HKK2
36LK3/42HKK3
36LK3/36HC2
36LK3/36HC3
36LC3/36HKK3
36LC3/36HC2

The amino acid and nucleotide sequences of humanized heavy chains HC2, HC3, 36HKK3, 42HKK1, 42HKK2, and 42HKK3, and of humanized light chains LC3 and LK3, are shown in Tables 5-12. The amino acid sequences encoded by the human germline genes utilized by these heavy and light chains are shown in Table 13.

TABLE 5

Amino acid and nucleotide sequences of humanized anti-human CCL20 antibody heavy chain 36HC2 ("HC2")

| DESCRIPTION | SEQUENCE (signal sequence underlined, variable domain in bold) |
|---|---|
| Heavy Chain Amino Acid Sequence with the signal sequence (SEQ ID NO: 1) | <u>MGWSCIILFLVATATGVHS</u>QVQLVQSGA EVKKPGASVKVSCKASGYTFTNYWMHWV RQAPGQGLEWMGVIDPSDSYTTYAQKFQ GRVTMTVDTSTSTVYMELSSLRSEDTAV YYCARGNYGVDYAMDYWGQGTLVTVSSA STKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKRVEPKSCDKTHTCPPCP APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQ PREPQVYTLPPSREEMTKNQVSLTCLVK GFYPSDIAVEWESNGQPENNYKTTPPVL DSDGSFFLYSKLTVDKSRWQQGNVFSCS VMHEALHNHYTQKSLSLSPGK |

TABLE 5-continued

Amino acid and nucleotide sequences of humanized anti-human CCL20 antibody heavy chain 36HC2 ("HC2")

| DESCRIPTION | SEQUENCE (signal sequence underlined, variable domain in bold) |
|---|---|
| Heavy Chain Amino Acid Sequence without the signal sequence (SEQ ID NO: 108) | QVQLVQSGAEVKKPGASVKVSCKASGYT FTNYWMHWVRQAPGQGLEWMGVIDPSDS YTTYAQKFQGRVTMTVDTSTSTVYMELS SLRSEDTAVYYCARGNYGVDYAMDYWGQ GTLVTVSSASTKGPSVFPLAPSSKSTSG GTAALGCLVKDYFPEPVTVSWNSGALTS GVHTFPAVLQSSGLYSLSSVVTVPSSSL GTQTYICNVNHKPSNTKVDKRVEPKSCD KTHTCPPCPAPELLGGPSVFLFPPKPKD TLMISRTPEVTCVVVDVSHEDPEVKFNW YVDGVEVHNAKTKPREEQYNSTYRVVSV LTVLHQDWLNGKEYKCKVSNKALPAPIE KTISKAKGQPREPQVYTLPPSREEMTKN QVSLTCLVKGFYPSDIAVEWESNGQPEN NYKTTPPVLDSDGSFFLYSKLTVDKSRW QQGNVFSCSVMHEALHNHYTQKSLSLSP GK |
| Heavy Chain Variable Domain Amino Acid Sequence (SEQ ID NO: 9) | QVQLVQSGAEVKKPGASVKVSCKASGYT FTNYWMHWVRQAPGQGLEWMGVIDPSDS YTTYAQKFQGRVTMTVDTSTSTVYMELS SLRSEDTAVYYCARGNYGVDYAMDYWGQ GTLVTVSS |
| Heavy Chain Nucleotide Sequence with the signal sequence (SEQ ID NO: 17) | <u>ATGGGCTGGTCCTGCATCATTCTGTTCC TGGTGGCCACTGCTACCGGAGTGCACAG CC</u>AGGTGCAGCTGGTGCAGTCTGGGCT GAGGTGAAGAAACCCGGTGCAAGTGTGA AGGTGTCATGTAAAGCATCCGGCTATAC ATTCACTAACTACTGGATGCATTGGGTG AGGCAGGCTCCAGGACAGGGACTGGAAT GGATGGGCGTGATCGACCCTTCAGATTC CTACACCACATATGCCCAGAAGTTTCAG GGCAGGGTGACCATGACAGTGGACACTA GCACCTCTACAGTGTACATGGAGCTGTC CAGCCTGAGAAGTGAAGATACAGCAGTG TACTATTGCGCCCGCGGCAATTACGGAG TGGACTATGCCATGGATTACTGGGGCA GGGTACTCTGGTGACCGTGTCTAGTGCT TCTACCAAGGGCCCATCGGTCTTCCCCC TGGCACCCTCCTCCAAGAGCACCTCTGG GGGCACAGCGGCCCTGGGCTGCCTGGTC AAGGACTACTTCCCCGAACCGGTGACGG TGTCGTGGAACTCAGGCGCCCTGACCAG CGGCGTGCACACCTTCCCGGCTGTCCTA CAGTCCTCAGGACTCTACTCCCTCAGCA GCGTGGTGACCGTGCCCTCCAGCAGCTT GGGCACCCAGACCTACATCTGCAACGTG AATCACAAGCCCAGCAACACCAAGGTGG ACAAGAGAGTTGAGCCCAAATCTTGTGA CAAAACTCACACATGCCCACCGTGCCCA GCACCTGAACTCCTGGGGGGACCGTCAG TCTTCCTCTTCCCCCCAAAACCCAAGGA CACCCTCATGATCTCCCGGACCCCTGAG GTCACATGCGTGGTGGTGGACGTGAGCC ACGAAGACCCTGAGGTCAAGTTCAACTG GTACGTGGACGGCGTGGAGGTGCATAAT GCCAAGACAAAGCCGCGGGAGGAGCAGT ACAACAGCACGTACCGTGTGGTCAGCGT CCTCACCGTCCTGCACCAGGACTGGCTG AATGGCAAGGAGTACAAGTGCAAGGTCT CCAACAAAGCCCTCCCAGCCCCCATCGA GAAAACCATCTCCAAAGCCAAAGGGCAG CCCCGAGAACCACAGGTGTACACCCTGC CCCCATCCCGGGAGGAGATGACCAAGAA CCAGGTCAGCCTGACCTGCCTGGTCAAA GGCTTCTATCCCAGCGACATCGCCGTGG AGTGGGAGAGCAATGGGCAGCCGGAGAA CAACTACAAGACCACGCCTCCCGTGCTG GACTCCGACGGCTCCTTCTTCCTCTATA GCAAGCTCACCGTGGACAAGAGCAGGTG GCAGCAGGGGAACGTCTTCTCATGCTCC GTGATGCATGAGGCTCTGCACAACCACT ACACGCAGAAGAGCCTCTCCCTGTCTCC CGGGAAATGA |
| Heavy Chain Nucleotide Sequence without the signal sequence (SEQ ID NO: 109) | CAGGTGCAGCTGGTGCAGTCTGGGGCTG AGGTGAAGAAACCCGGTGCAAGTGTGAA GGTGTCATGTAAAGCATCCGGCTATACA TTCACTAACTACTGGATGCATTGGGTGA GGCAGGCTCCAGGACAGGGACTGGAATG GATGGGCGTGATCGACCCTTCAGATTCC TACACCACATATGCCCAGAAGTTTCAGG GCAGGGTGACCATGACAGTGGACACTAG CACCTCTACAGTGTACATGGAGCTGTCC AGCCTGAGAAGTGAAGATACAGCAGTGT ACTATTGCGCCCGCGGCAATTACGGAGT GGACTATGCCATGGATTACTGGGGGCAG GGTACTCTGGTGACCGTGTCTAGTGCTT CTACCAAGGGCCCATCGGTCTTCCCCCT GGCACCCTCCTCCAAGAGCACCTCTGGG GGCACAGCGGCCCTGGGCTGCCTGGTCA AGGACTACTTCCCCGAACCGGTGACGGT GTCGTGGAACTCAGGCGCCCTGACCAGC GGCGTGCACACCTTCCCGGCTGTCCTAC AGTCCTCAGGACTCTACTCCCTCAGCAG CGTGGTGACCGTGCCCTCCAGCAGCTTG GGCACCCAGACCTACATCTGCAACGTGA ATCACAAGCCCAGCAACACCAAGGTGGA CAAGAGAGTTGAGCCCAAATCTTGTGAC AAAACTCACACATGCCCACCGTGCCCAG CACCTGAACTCCTGGGGGGACCGTCAGT CTTCCTCTTCCCCCCAAAACCCAAGGAC ACCCTCATGATCTCCCGGACCCCTGAGG TCACATGCGTGGTGGTGGACGTGAGCCA CGAAGACCCTGAGGTCAAGTTCAACTGG TACGTGGACGGCGTGGAGGTGCATAATG CCAAGACAAAGCCGCGGGAGGAGCAGTA CAACAGCACGTACCGTGTGGTCAGCGTC CTCACCGTCCTGCACCAGGACTGGCTGA ATGGCAAGGAGTACAAGTGCAAGGTCTC CAACAAAGCCCTCCCAGCCCCCATCGAG AAAACCATCTCCAAAGCCAAAGGGCAGC CCCGAGAACCACAGGTGTACACCCTGCC CCCATCCCGGGAGGAGATGACCAAGAAC CAGGTCAGCCTGACCTGCCTGGTCAAAG GCTTCTATCCCAGCGACATCGCCGTGGA GTGGGAGAGCAATGGGCAGCCGGAGAAC AACTACAAGACCACGCCTCCCGTGCTGG ACTCCGACGGCTCCTTCTTCCTCTATAG CAAGCTCACCGTGGACAAGAGCAGGTGG CAGCAGGGGAACGTCTTCTCATGCTCCG TGATGCATGAGGCTCTGCACAACCACTA CACGCAGAAGAGCCTCTCCCTGTCTCCC GGGAAATGA |
| Heavy Chain Variable Domain Nucleotide Sequence (SEQ ID NO: 25) | CAGGTGCAGCTGGTGCAGTCTGGGGCTG AGGTGAAGAAACCCGGTGCAAGTGTGAA GGTGTCATGTAAAGCATCCGGCTATACA TTCACTAACTACTGGATGCATTGGGTGA GGCAGGCTCCAGGACAGGGACTGGAATG GATGGGCGTGATCGACCCTTCAGATTCC TACACCACATATGCCCAGAAGTTTCAGG GCAGGGTGACCATGACAGTGGACACTAG CACCTCTACAGTGTACATGGAGCTGTCC AGCCTGAGAAGTGAAGATACAGCAGTGT ACTATTGCGCCCGCGGCAATTACGGAGT GGACTATGCCATGGATTACTGGGGGCAG GGTACTCTGGTGACCGTGTCTAGT |

TABLE 6

Amino acid and nucleotide sequences of humanized anti-human CCL20 antibody heavy chain 36HC3 ("HC3")

| DESCRIPTION | SEQUENCE (signal sequence underlined, variable domain in bold) |
|---|---|
| Heavy Chain Amino Acid Sequence (SEQ ID NO: 2) | <u>MGWSCIILFLVATATGVHS</u>QVQLVQSGA EVKKPGASVKVSCKASGYTFTNYWMHWV KQAPGQGLEWIGVIDPSDSYTTYNQKFK GKATMTRDTSTSTVYMELSSLRSEDTAV YYCTRGNYGVDYAMDYWGQGTSVTVSSASTKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKRVEPKSCDKTHTCPPCP APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQ PREPQVYTLPPSREEMTKNQVSLTCLVK GFYPSDIAVEWESNGQPENNYKTTPPVL DSDGSFFLYSKLTVDKSRWQQGNVFSCS VMHEALHNHYTQKSLSLSPGK |
| Heavy Chain Variable Domain Amino Acid Sequence (SEQ ID NO: 10) | QVQLVQSGAEVKKPGASVKVSCKASGYT FTNYWMHWVKQAPGQGLEWIGVIDPSDS YTTYNQKFKGKATMTRDTSTSTVYMELS SLRSEDTAVYYCTRGNYGVDYAMDYWGQ GTSVTVSS |
| Heavy Chain Nucleotide Sequence (SEQ ID NO: 18) | <u>ATGGGCTGGTCCTGCATCATTCTGTTCC TGGTGGCAACTGCCACCGGAGTGCACAG C</u>CAGGTGCAGCTGGTGCAGTCTGGGGCT GAGGTGAAGAAACCCGGTCAAGTGTGA AAGTGTCATGCAAGGCATCCGGCTATAC ATTCACTAACTACTGGATGCATTGGGTG AAGCAGGCACCAGGACAGGGACTGGAAT GGATCGGCGTGATCGACCCTTCAGATTC CTACACCACATATAATCAGAAGTTTAAA GGCAAGGCTACCATGACAAGGGACACTA GCACCTCTACAGTGTACATGGAGCTGTC CAGCCTGAGGTCCGAAGATACAGCCGTG TACTATTGCACTCGGGGCAACTACGGAG TGGACTATGCTATGGATTACTGGGGCA GGGTACTAGTGTGACCGTGTCTAGTGCA TCTACCAAGGGCCCATCGGTCTTCCCCC TGGCACCCTCCTCCAAGAGCACCTCTGG GGGCACAGCGGCCCTGGGCTGCCTGGTC AAGGACTACTTCCCCGAACCGGTGACGG TGTCGTGGAACTCAGGCGCCCTGACCAG CGGCGTGCACACCTTCCCGGCTGTCCTA CAGTCCTCAGGACTCTACTCCCTCAGCA GCGTGGTGACCGTGCCCTCCAGCAGCTT GGGCACCCAGACCTACATCTGCAACGTG AATCACAAGCCCAGCAACACCAAGGTGG ACAAGAGAGTTGAGCCCAAATCTTGTGA CAAAACTCACACATGCCCACCGTGCCCA GCACCTGAACTCCTGGGGGGACCGTCAG TCTTCCTCTTCCCCCCAAAACCCAAGGA CACCCTCATGATCTCCCGGACCCCTGAG GTCACATGCGTGGTGGTGGACGTGAGCC ACGAAGACCCTGAGGTCAAGTTCAACTG GTACGTGGACGGCGTGGAGGTGCATAAT GCCAAGACAAAGCCGCGGGAGGAGCAGT ACAACAGCACGTACCGTGTGGTCAGCGT CCTCACCGTCCTGCACCAGGACTGGCTG AATGGCAAGGAGTACAAGTGCAAGGTCT CCAACAAAGCCCTCCCAGCCCCCATCGA GAAAACCATCTCCAAAGCCAAAGGGCAG CCCCGAGAACCACAGGTGTACACCCTGC CCCCATCCCGGGAGGAGATGACCAAGAA CCAGGTCAGCCTGACCTGCCTGGTCAAA GGCTTCTATCCCAGCGACATCGCCGTGG AGTGGGAGAGCAATGGGCAGCCGGAGAA CAACTACAAGACCACGCCTCCCGTGCTG GACTCCGACGGCTCCTTCTTCCTCTATA GCAAGCTCACCGTGGACAAGAGCAGGTG GCAGCAGGGGAACGTCTTCTCATGCTCC |

TABLE 6-continued

Amino acid and nucleotide sequences of humanized anti-human CCL20 antibody heavy chain 36HC3 ("HC3")

| DESCRIPTION | SEQUENCE (signal sequence underlined, variable domain in bold) |
|---|---|
| | GTGATGCATGAGGCTCTGCACAACCACT ACACGCAGAAGAGCCTCTCCCTGTCTCC CGGGAAATGA |
| Heavy Chain Variable Domain Nucleotide Sequence (SEQ ID NO: 26) | CAGGTGCAGCTGGTGCAGTCTGGGGCTG AGGTGAAGAAACCCGGTCAAGTGTGAA AGTGTCATGCAAGGCATCCGGCTATACA TTCACTAACTACTGGATGCATTGGGTGA AGCAGGCACCAGGACAGGGACTGGAATG GATCGGCGTGATCGACCCTTCAGATTCC TACACCACATATAATCAGAAGTTTAAAG GCAAGGCTACCATGACAAGGGACACTAG CACCTCTACAGTGTACATGGAGCTGTCC AGCCTGAGGTCCGAAGATACAGCCGTGT ACTATTGCACTCGGGGCAACTACGGAGT GGACTATGCTATGGATTACTGGGGCAG GGTACTAGTGTGACCGTGTCTAGT |

TABLE 7

Amino acid and nucleotide sequences of humanized anti-human CCL20 antibody heavy chain 36HKK3

| DESCRIPTION | SEQUENCE (signal sequence underlined, variable domain in bold) |
|---|---|
| Heavy Chain Amino Acid Sequence (SEQ ID NO: 3) | <u>MDWTWRILFLVAAATGAHS</u>QVQLVQSGA EVKKPGASVKVSCKASGYTFTNYWMHWV RQAPGQGLEWMGVIDPSDSYTTYNQKFK GKATLTVDTSTSTAYMELSSLRSEDTAV YYCTRGNYGVDYAMDYWGQGTLVTVSSASTKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKRVEPKSCDKTHTCPPCP APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQ PREPQVYTLPPSREEMTKNQVSLTCLVK GFYPSDIAVEWESNGQPENNYKTTPPVL DSDGSFFLYSKLTVDKSRWQQGNVFSCS VMHEALHNHYTQKSLSLSPGK |
| Heavy Chain Variable Domain Amino Acid Sequence (SEQ ID NO: 11) | QVQLVQSGAEVKKPGASVKVSCKASGYT FTNYWMHWVRQAPGQGLEWMGVIDPSDS YTTYNQKFKGKATLTVDTSTSTAYMELS SLRSEDTAVYYCTRGNYGVDYAMDYWGQ GTLVTVSS |
| Heavy Chain Nucleotide Sequence (SEQ ID NO: 19) | <u>ATGGACTGGACATGGAGAATCCTGTTCC TGGTGGCCGCTGCAACCGGAGCACACAG C</u>CAGGTGCAGCTGGTGCAGTCTGGAGCA GAGGTGAAGAAACCCGGTGCTAGTGTGA AAGTGTCATGCAAGGCCTCCGGGTATAC TTTCACCAACTACTGGATGCATTGGGTG AGGCAGGCTCCAGGACAGGGACTGGAAT GGATGGGCGTGATTGACCCTTCAGATTC CTACACCACATATAATCAGAAGTTTAAA GGAAAGGCAACACTGACTGTGGACACCA GCACATCTACTGCCTACATGGAGCTGTC CAGCCTGAGGTCCGAAGATACTGCCGTG TACTATTGTACCCGGGGCAACTACGGAG TGGACTATGCAATGGATTACTGGGGCA GGGTACCCTGGTGACAGTGTCTAGTGCT AGCACCAAGGGCCCATCGGTCTTCCCCC TGGCACCCTCCTCCAAGAGCACCTCTGG |

TABLE 7-continued

Amino acid and nucleotide sequences of humanized anti-human CCL20 antibody heavy chain 36HKK3

| DESCRIPTION | SEQUENCE (signal sequence underlined, variable domain in bold) |
|---|---|
| | GGGCACAGCGGCCCTGGGCTGCCTGGTC<br>AAGGACTACTTCCCCGAACCGGTGACGG<br>TGTCGTGGAACTCAGGCGCCCTGACCAG<br>CGGCGTGCACACCTTCCCGGCTGTCCTA<br>CAGTCCTCAGGACTCTACTCCCTCAGCA<br>GCGTGGTGACCGTGCCCTCCAGCAGCTT<br>GGGCACCCAGACCTACATCTGCAACGTG<br>AATCACAAGCCCAGCAACACCAAGGTGG<br>ACAAGAGAGTTGAGCCCAAATCTTGTGA<br>CAAAACTCACACATGCCCACCGTGCCCA<br>GCACCTGAACTCCTGGGGGGACCGTCAG<br>TCTTCCTCTTCCCCCCAAAACCCAAGGA<br>CACCCTCATGATCTCCCGGACCCCTGAG<br>GTCACATGCGTGGTGGTGGACGTGAGCC<br>ACGAAGACCCTGAGGTCAAGTTCAACTG<br>GTACGTGGACGGCGTGGAGGTGCATAAT<br>GCCAAGACAAAGCCGCGGGAGGAGCAGT<br>ACAACAGCACGTACCGTGTGGTCAGCGT<br>CCTCACCGTCCTGCACCAGGACTGGCTG<br>AATGGCAAGGAGTACAAGTGCAAGGTCT<br>CCAACAAAGCCCTCCCAGCCCCCATCGA<br>GAAAACCATCTCCAAAGCCAAAGGGCAG<br>CCCCGAGAACCACAGGTGTACACCCTGC<br>CCCCATCCCGGGAGGAGATGACCAAGAA<br>CCAGGTCAGCCTGACCTGCCTGGTCAAA<br>GGCTTCTATCCCAGCGACATCGCCGTGG<br>AGTGGGAGAGCAATGGGCAGCCGGAGAA<br>CAACTACAAGACCACGCCTCCCGTGCTG<br>GACTCCGACGGCTCCTTCTTCCTCTATA<br>GCAAGCTCACCGTGGACAAGAGCAGGTG<br>GCAGCAGGGGAACGTCTTCTCATGCTCC<br>GTGATGCATGAGGCTCTGCACAACCACT<br>ACACGCAGAAGAGCCTCTCCCTGTCTCC<br>GGGTAAATGA |
| Heavy Chain Variable Domain Nucleotide Sequence (SEQ ID NO: 27) | CAGGTGCAGCTGGTGCAGTCTGGAGCAG<br>AGGTGAAGAAACCCGGTGCTAGTGTGAA<br>AGTGTCATGCAAGGCCTCCGGGTATACT<br>TTCACCAACTACTGGATGCATTGGGTAC<br>GGCAGGCTCCAGGACAGGGACTGGAATG<br>GATGGGCGTGATTGACCCTTCAGATTCC<br>TACACCACATATAATCAGAAGTTTAAAG<br>GAAAGGCAACACTGACTGTGGACACCAG<br>CACATCTACTGCCTACATGGAGCTGTCC<br>AGCCTGAGGTCCGAAGATACTGCCGTGT<br>ACTATTGTACCCGGGGCAACTACGGAGT<br>GGACTATGCAATGGATTACTGGGGGCAG<br>GGTACCCTGGTGACAGTGTCTAGT |

TABLE 8

Amino acid and nucleotide sequences of humanized anti-human CCL20 antibody heavy chain 42HKK1

| DESCRIPTION | SEQUENCE (signal sequence underlined, variable domain in bold) |
|---|---|
| Heavy Chain Amino Acid Sequence (SEQ ID NO: 4) | <u>MDWTWRILFLVAAATGAHS</u>QVQLVQSGA<br>EVKKPGASVKVSCKASGYTFTSYWMHWV<br>RQAPGQGLEWMGLIDPSDKYTNYNQKFK<br>GRVTMTRDTSTSTVYMELSSLRSEDTAV<br>YYCARGNYGVDYGMDYWGQGTLVTVSSA<br>STKGPSVFPLAPSSKSTSGGTAALGCLV<br>KDYFPEPVTVSWNSGALTSGVHTFPAVL<br>QSSGLYSLSSVVTVPSSSLGTQTYICNV<br>NHKPSNTKVDKRVEPKSCDKTHTCPPCP<br>APELLGGPSVFLFPPKPKDTLMISRTPE |

TABLE 8-continued

Amino acid and nucleotide sequences of humanized anti-human CCL20 antibody heavy chain 42HKK1

| DESCRIPTION | SEQUENCE (signal sequence underlined, variable domain in bold) |
|---|---|
| | VTCVVVDVSHEDPEVKFNWYVDGVEVHN<br>AKTKPREEQYNSTYRVVSVLTVLHQDWL<br>NGKEYKCKVSNKALPAPIEKTISKAKGQ<br>PREPQVYTLPPSREEMTKNQVSLTCLVK<br>GFYPSDIAVEWESNGQPENNYKTTPPVL<br>DSDGSFFLYSKLTVDKSRWQQGNVFSCS<br>VMHEALHNHYTQKSLSLSPGK |
| Heavy Chain Variable Domain Amino Acid Sequence (SEQ ID NO: 12) | QVQLVQSGAEVKKPGASVKVSCKASGYT<br>FTSYWMHWVRQAPGQGLEWMGLIDPSDK<br>YTNYNQKFKGRVTMTRDTSTSTVYMELS<br>SLRSEDTAVYYCARGNYGVDYGMDYWGQ<br>GTLVTVSS |
| Heavy Chain Nucleotide Sequence (SEQ ID NO: 20) | <u>ATGGACTGGACCTGGCGAATCCTGTTCC<br>TGGTGGCCGCTGCAACAGGAGCACACTC</u>A<br>CAGGTGCAGCTGGTGCAGTCCGGGGCA<br>GAGGTGAAGAAACCCGGTGCCAGCGTGA<br>AGGTGTCTTGCAAAGCTAGTGGCTATAC<br>CTTCACAAGCTACTGGATGCATTGGGTG<br>CGGCAGGCACCAGGACAGGGACTGGAAT<br>GGATGGGCCTGATTGACCCTTCTGATAA<br>GTACACTAACTACAACCAGAAGTTTAAA<br>GGAAGGGTGACTATGACCCGGGACACAT<br>CAACTTCCACCGTGTACATGGAGCTGTC<br>CAGCCTGAGATCCGAAGATACCGCCGTG<br>TACTATTGTGCTCGCGGCAACTACGGAG<br>TGGACTATGGCATGGATTACTGGGGGCA<br>GGGTACACTGGTGACCGTGTCCAGTGCT<br>AGCACCAAGGGCCCATCGGTCTTCCCCC<br>TGGCACCCTCCTCCAAGAGCACCTCTGG<br>GGGCACAGCGGCCCTGGGCTGCCTGGTC<br>AAGGACTACTTCCCCGAACCGGTGACGG<br>TGTCGTGGAACTCAGGCGCCCTGACCAG<br>CGGCGTGCACACCTTCCCGGCTGTCCTA<br>CAGTCCTCAGGACTCTACTCCCTCAGCA<br>GCGTGGTGACCGTGCCCTCCAGCAGCTT<br>GGGCACCCAGACCTACATCTGCAACGTG<br>AATCACAAGCCCAGCAACACCAAGGTGG<br>ACAAGAGAGTTGAGCCCAAATCTTGTGA<br>CAAAACTCACACATGCCCACCGTGCCCA<br>GCACCTGAACTCCTGGGGGGACCGTCAG<br>TCTTCCTCTTCCCCCCAAAACCCAAGGA<br>CACCCTCATGATCTCCCGGACCCCTGAG<br>GTCACATGCGTGGTGGTGGACGTGAGCC<br>ACGAAGACCCTGAGGTCAAGTTCAACTG<br>GTACGTGGACGGCGTGGAGGTGCATAAT<br>GCCAAGACAAAGCCGCGGGAGGAGCAGT<br>ACAACAGCACGTACCGTGTGGTCAGCGT<br>CCTCACCGTCCTGCACCAGGACTGGCTG<br>AATGGCAAGGAGTACAAGTGCAAGGTCT<br>CCAACAAAGCCCTCCCAGCCCCCATCGA<br>GAAAACCATCTCCAAAGCCAAAGGGCAG<br>CCCCGAGAACCACAGGTGTACACCCTGC<br>CCCCATCCCGGGAGGAGATGACCAAGAA<br>CCAGGTCAGCCTGACCTGCCTGGTCAAA<br>GGCTTCTATCCCAGCGACATCGCCGTGG<br>AGTGGGAGAGCAATGGGCAGCCGGAGAA<br>CAACTACAAGACCACGCCTCCCGTGCTG<br>GACTCCGACGGCTCCTTCTTCCTCTATA<br>GCAAGCTCACCGTGGACAAGAGCAGGTG<br>GCAGCAGGGGAACGTCTTCTCATGCTCC<br>GTGATGCATGAGGCTCTGCACAACCACT<br>ACACGCAGAAGAGCCTCTCCCTGTCTCC<br>GGGTAAATGA |
| Heavy Chain Variable Domain Nucleotide Sequence (SEQ ID NO: 28) | CAGGTGCAGCTGGTGCAGTCCGGGGCAG<br>AGGTGAAGAAACCCGGTGCCAGCGTGAA<br>GGTGTCTTGCAAAGCTAGTGGCTATACC<br>TTCACAAGCTACTGGATGCATTGGGTGC<br>GGCAGGCACCAGGACAGGGACTGGAATG<br>GATGGGCCTGATTGACCCTTCTGATAAG |

TABLE 8-continued

Amino acid and nucleotide sequences of humanized anti-human CCL20 antibody heavy chain 42HKK1

| DESCRIPTION | SEQUENCE (signal sequence underlined, variable domain in bold) |
| --- | --- |
| | TACACTAACTACAACCAGAAGTTTAAAG GAAGGGTGACTATGACCCGGGACACATC AACTTCCACCGTGTACATGGAGCTGTCC AGCCTGAGATCCGAAGATACCGCGTGT ACTATTGTGCTCGCGGCAACTACGGAGT GGACTATGGCATGGATTACTGGGGCAG GGTACACTGGTGACCGTGTCCAGT |

TABLE 9

Amino acid and nucleotide sequences of humanized anti-human CCL20 antibody heavy chain 42HKK2

| DESCRIPTION | SEQUENCE (signal sequence underlined, variable domain in bold) |
| --- | --- |
| Heavy Chain Amino Acid Sequence (SEQ ID NO: 5) | <u>MDWTWRILFLVAAATGAHS</u>QVQLVQSGA EVKKPGASVKVSCKASGYTFTSYWMHWV RQAPGQGLEWMGLIDPSDKYTNYNQKFK GRVTLTVDTSTSTVYMELSSLRSEDTAV YYCTRGNYGVDYGMDYWGQGTLVTVSSASTKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKRVEPKSCDKTHTCPPCP APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQ PREPQVYTLPPSREEMTKNQVSLTCLVK GFYPSDIAVEWESNGQPENNYKTTPPVL DSDGSFFLYSKLTVDKSRWQQGNVFSCS VMHEALHNHYTQKSLSLSPGK |
| Heavy Chain Variable Domain Amino Acid Sequence (SEQ ID NO: 13) | QVQLVQSGAEVKKPGASVKVSCKASGYT FTSYWMHWVRQAPGQGLEWMGLIDPSDK YTNYNQKFKGRVTLTVDTSTSTVYMELS SLRSEDTAVYYCTRGNYGVDYGMDYWGQ GTLVTVSS |
| Heavy Chain Nucleotide Sequence (SEQ ID NO: 21) | <u>ATGGACTGGACTTGGAGGATCCTGTTCC TGGTGGCCGCTGCAACGGAGCTCACTC</u>ACAGGTGCAGCTGGTGCAGTCCGGAGCA GAGGTGAAGAAACCCGGTGCCTCCGTGA AGGTGTCTTGCAAAGCAAGTGGCTATAC CTTCACAAGCTACTGGATGCATTGGGTG AGACAGGCACCAGGACAGGGACTGGAAT GGATGGGCCTGATTGACCCTTCTGATAA GTACACCAACTACAACCAGAAGTTTAAA GGACGCGTGACTCTGACCGTGGACACAT CAACTTCCACCGTGTACATGGAGCTGTC CAGCCTGAGGTCCGAAGATACCGCAGTG TACTATTGTACACGGGGCAACTACGGAG TGGACTATGGCATGGATTACTGGGGCA GGGTACACTGGTGACCGTGTCCAGTGCT AGCACCAAGGGCCCATCGGTCTTCCCCC TGGCACCCTCCTCCAAGAGCACCTCTGG GGGCACCGCGGCCCTGGGCTGCCTGGTC AAGGACTACTTCCCCGAACCGGTGACGG TGTCGTGGAACTCAGGCGCCCTGACCAG CGGCGTGCACACCTTCCCGGCTGTCCTA CAGTCCTCAGGACTCTACTCCCTCAGCA GCGTGGTGACCGTGCCCTCCAGCAGCTT GGGCACCCAGACCTACATCTGCAACGTG AATCACAAGCCCAGCAACACCAAGGTGG ACAAGAGAGTTGAGCCCAAATCTTGTGA CAAAACTCACACATGCCCACCGTGCCCA |

TABLE 9-continued

Amino acid and nucleotide sequences of humanized anti-human CCL20 antibody heavy chain 42HKK2

| DESCRIPTION | SEQUENCE (signal sequence underlined, variable domain in bold) |
| --- | --- |
| | GCACCTGAACTCCTGGGGGGACCGTCAG TCTTCCTCTTCCCCCCAAAACCCAAGGA CACCCTCATGATCTCCCGGACCCCTGAG GTCACATGCGTGGTGGTGGACGTGAGCC ACGAAGACCCTGAGGTCAAGTTCAACTG GTACGTGGACGGCGTGGAGGTGCATAAT GCCAAGACAAAGCCGCGGGAGGAGCAGT ACAACAGCACGTACCGTGTGGTCAGCGT CCTCACCGTCCTGCACCAGGACTGGCTG AATGGCAAGGAGTACAAGTGCAAGGTCT CCAACAAAGCCCTCCCAGCCCCCATCGA GAAAACCATCTCCAAAGCCAAAGGGCAG CCCCGAGAACCACAGGTGTACACCCTGC CCCCATCCCGGGAGGAGATGACCAAGAA CCAGGTCAGCCTGACCTGCCTGGTCAAA GGCTTCTATCCCAGCGACATCGCCGTGG AGTGGGAGAGCAATGGGCAGCCGGAGAA CAACTACAAGACCACGCCTCCCGTGCTG GACTCCGACGGCTCCTTCTTCCTCTATA GCAAGCTCACCGTGGACAAGAGCAGGTG GCAGCAGGGGAACGTCTTCTCATGCTCC GTGATGCATGAGGCTCTGCACAACCACT ACACGCAGAAGAGCCTCTCCCTGTCTCC GGGTAAATGA |
| Heavy Chain Variable Domain Nucleotide Sequence (SEQ ID NO: 29) | CAGGTGCAGCTGGTGCAGTCCGGAGCAG AGGTGAAGAAACCCGGTGCCTCCGTGAA GGTGTCTTGCAAAGCAAGTGGCTATACC TTCACAAGCTACTGGATGCATTGGGTGA GACAGGCACCAGGACAGGGACTGGAATG GATGGGCCTGATTGACCCTTCTGATAAG TACACCAACTACAACCAGAAGTTTAAAG GACGCGTGACTCTGACCGTGGACACATC AACTTCCACCGTGTACATGGAGCTGTCC AGCCTGAGGTCCGAAGATACCGCAGTGT ACTATTGTACACGGGGCAACTACGGAGT GGACTATGGCATGGATTACTGGGGCAG GGTACACTGGTGACCGTGTCCAGT |

TABLE 10

Amino acid and nucleotide sequences of humanized anti-human CCL20 antibody heavy chain 42HKK3

| DESCRIPTION | SEQUENCE (signal sequence underlined, variable domain in bold) |
| --- | --- |
| Heavy Chain Amino Acid Sequence (SEQ ID NO: 6) | <u>MDWTWRILFLVAAATGAHS</u>QVQLVQSGA EVKKPGASVKVSCKASGYTFTSYWMHWV RQAPGQGLEWMGLIDPSDKYTNYNQKFK GKATLTVDTSTSTAYMELSSLRSEDTAV YYCTRGNYGVDYGMDYWGQGTLVTVSSASTKGPSVFPLAPSSKSTSGGTAALGCLV KDYFPEPVTVSWNSGALTSGVHTFPAVL QSSGLYSLSSVVTVPSSSLGTQTYICNV NHKPSNTKVDKRVEPKSCDKTHTCPPCP APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAKGQ PREPQVYTLPPSREEMTKNQVSLTCLVK GFYPSDIAVEWESNGQPENNYKTTPPVL DSDGSFFLYSKLTVDKSRWQQGNVFSCS VMHEALHNHYTQKSLSLSPGK |

TABLE 10-continued

Amino acid and nucleotide sequences of humanized anti-human CCL20 antibody heavy chain 42HKK3

| DESCRIPTION | SEQUENCE (signal sequence underlined, variable domain in bold) |
|---|---|
| Heavy Chain Variable Domain Amino Acid Sequence (SEQ ID NO: 14) | QVQLVQSGAEVKKPGASVKVSCKASGYT FTSYWMHWVRQAPGQGLEWMGLIDPSDK YTNYNQKFKGKATLTVDTSTSTAYMELS SLRSEDTAVYYCTRGNYGVDYGMDYWGQ GTLVTVSS |
| Heavy Chain Nucleotide Sequence (SEQ ID NO: 22) | <u>ATGGACTGGACTTGGAGAATCCTGTTCC TGGTGGCCGCTGCAACCGGAGCTCACTC A</u>CAGGTGCAGCTGGTGCAGTCCGGAGCA GAGGTGAAGAAACCCGGTGCCTCCGTGA AAGTGTCTTGCAAGGCTAGTGGCTATAC CTTCACAAGCTACTGGATGCATTGGGTG AGGCAGGCACCAGGACAGGGACTGGAAT GGATGGGCCTGATTGACCCTTCTGATAA GTACACCAACTACAACCAGAAGTTTAAA GGAAAGGCAACTCTGACCGTGGACACAT CAACTTCCACCGCCTACATGGAGCTGTC CAGCCTGAGGTCCGAAGATACCGCCGTG TACTATTGTACACGGGGCAACTACGGAG TGGACTATGGCATGGATTACTGGGGGCA GGGTACACTGGTGACCGTGTCCAGTGCT AGCACCAAGGGCCCATCGGTCTTCCCCC TGGCACCCTCCTCCAAGAGCACCTCTGG GGGCACAGCGGCCCTGGGCTGCCTGGTC AAGGACTACTTCCCCGAACCGGTGACGG TGTCGTGGAACTCAGGCGCCCTGACCAG CGGCGTGCACACCTTCCCGGCTGTCCTA CAGTCCTCAGGACTCTACTCCCTCAGCA GCGTGGTGACCGTGCCCTCCAGCAGCTT GGGCACCCAGACCTACATCTGCAACGTG AATCACAAGCCCAGCAACACCAAGGTGG ACAAGAGAGTTGAGCCCAAATCTTGTGA CAAAACTCACACATGCCCACCGTGCCCA GCACCTGAACTCCTGGGGGGACCGTCAG TCTTCCTCTTCCCCCCAAAACCCAAGGA CACCCTCATGATCTCCCGGACCCCTGAG GTCACATGCGTGGTGGTGGACGTGAGCC ACGAAGACCCTGAGGTCAAGTTCAACTG GTACGTGGACGGCGTGGAGGTGCATAAT GCCAAGACAAAGCCGCGGGAGGAGCAGT ACAACAGCACGTACCGTGTGGTCAGCGT CCTCACCGTCCTGCACCAGGACTGGCTG AATGGCAAGGAGTACAAGTGCAAGGTCT CCAACAAAGCCCTCCCAGCCCCCATCGA GAAAACCATCTCCAAAGCCAAAGGGCAG CCCCGAGAACCACAGGTGTACACCCTGC CCCCATCCCGGGAGGAGATGACCAAGAA CCAGGTCAGCCTGACCTGCCTGGTCAAA GGCTTCTATCCCAGCGACATCGCCGTGG AGTGGGAGAGCAATGGGCAGCCGGAGAA CAACTACAAGACCACGCCTCCCGTGCTG GACTCCGACGGCTCCTTCTTCCTCTATA GCAAGCTCACCGTGGACAAGAGCAGGTG GCAGCAGGGGAACGTCTTCTCATGCTCC GTGATGCATGAGGCTCTGCACAACCACT ACACGCAGAAGAGCCTCTCCCTGTCTCC GGGTAAATGA |
| Heavy Chain Variable Domain Nucleotide Sequence (SEQ ID NO: 30) | CAGGTGCAGCTGGTGCAGTCCGGAGCAG AGGTGAAGAAACCCGGTGCCTCCGTGAA AGTGTCTTGCAAGGCTAGTGGCTATACC TTCACAAGCTACTGGATGCATTGGGTGA GGCAGGCACCAGGACAGGGACTGGAATG GATGGGCCTGATTGACCCTTCTGATAAG TACACCAACTACAACCAGAAGTTTAAAG GAAAGGCAACTCTGACCGTGGACACATC AACTTCCACCGCCTACATGGAGCTGTCC AGCCTGAGGTCCGAAGATACCGCCGTGT |

TABLE 10-continued

Amino acid and nucleotide sequences of humanized anti-human CCL20 antibody heavy chain 42HKK3

| DESCRIPTION | SEQUENCE (signal sequence underlined, variable domain in bold) |
|---|---|
| | ACTATTGTACACGGGGCAACTACGGAGT GGACTATGGCATGGATTACTGGGGGCAG GGTACACTGGTGACCGTGTCCAGT |

TABLE 11

Amino acid and nucleotide sequences of humanized anti-human CCL20 antibody light chain LC3

| DESCRIPTION | SEQUENCE (signal sequence underlined, variable domain in bold) |
|---|---|
| Light Chain Amino Acid Sequence with the signal sequence (SEQ ID NO: 7) | <u>MGWSCIILFLVATATGVHS</u>DIQMTQSPS SLSASVGDRVTITCRASENIYGALNWYQ QKPGKAPKLLIYGATNLADGVPSRFSGS GSGRQYSLTISSLQPEDFATYYCQNVLI TPYTFGGGTKLEIKRTVAAPSVFIFPPS DEQLKSGTASVVCLLNNFYPREAKVQWK VDNALQSGNSQESVTEQDSKDSTYSLSS TLTLSKADYEKHKVYACEVTHQGLSSPV TKSFNRGEC |
| Light Chain Amino Acid Sequence without the signal sequence (SEQ ID NO: 110) | DIQMTQSPSSLSASVGDRVTITCRASEN IYGALNWYQQKPGKAPKLLIYGATNLAD GVPSRFSGSGSGRQYSLTISSLQPEDFA TYYCQNVLITPYTFGGGTKLEIKRTVAA PSVFIFPPSDEQLKSGTASVVCLLNNFY PREAKVQWKVDNALQSGNSQESVTEQDS KDSTYSLSSTLTLSKADYEKHKVYACEV THQGLSSPVTKSFNRGEC |
| Light Chain Variable Domain Amino Acid Sequence (SEQ ID NO: 15) | DIQMTQSPSSLSASVGDRVTITCRASEN IYGALNWYQQKPGKAPKLLIYGATNLAD GVPSRFSGSGSGRQYSLTISSLQPEDFA TYYCQNVLITPYTFGGGTKLEIK |
| Light Chain Nucleotide Sequence with the signal sequence (SEQ ID NO: 23) | <u>ATGGGCTGGTCCTGCATCATTCTGTTCC TGGTGGCAACCGCCACAGGAGTGCACAG C</u>GACATCCAGATGACCCAGTCTCCATCC AGCCTGAGTGCCTCAGTGGGCGATAGGG TGACTATCACCTGTCGGGCCAGCGAGAA CATCTACGGCGCTCTGAATTGGTATCAG CAGAAGCCAGGAAAAGCTCCCAAGCTGC TGATCTACGGGGCTACAAACCTGGCAGA CGGTGTGCCCAGTCGATTCTCCGGTAGC GGCTCTGGACGACAGTATTCACTGACTA TCTCTAGTCTGCAGCCTGAAGATTTCGC CACTTACTATTGCCAGAATGTGCTGATT ACTCCATATACCTTTGGCGGAGGGACAA AACTGGAGATCAAGAGAACTGTGGCCGC TCCCAGTGTGTTCATTTTTCCCCCTTCA GACGAACAGCTGAAATCAGGGACCGCTT CCGTGGTGTGTCTGCTGAACAATTTCTA CCCTCGCGAGGCAAAAGTGCAGTGGAAG GTGGATAACGCCCTGCAGAGTGGCAATT CACAGGAGTCCGTGACCGAACAGGACAG CAAAGATTCTACATATAGTCTGTCATCC ACCCTGACACTGAGCAAGGCTGATTACG AGAAGCACAAAGTGTATGCATGCGAAGT GACTCATCAGGGGCTGAGCTCTCCCGTG ACCAAGTCTTTTAACCGGGGTGAATGTT GA |

TABLE 11-continued

Amino acid and nucleotide sequences of humanized anti-human CCL20 antibody light chain LC3

| DESCRIPTION | SEQUENCE (signal sequence underlined, variable domain in bold) |
| --- | --- |
| Light Chain Nucleotide Sequence without the signal sequence (SEQ ID NO: 111) | GACATCCAGATGACCCAGTCTCCATCCAGCCTGAGTGCCTCAGTGGGCGATAGGGTGACTATCACCTGTCGGGCCAGCGAGAACATCTACGGCGCTCTGAATTGGTATCAGCAGAAGCCAGGAAAAGCTCCCAAGCTGCTGATCTACGGGGCTACAAACCTGGCAGACGGTGTGCCCAGTCGATTCTCCGGTAGCGGCTCTGGACGACAGTATTCACTGACTATCTCTAGTCTGCAGCCTGAAGATTTCGCCACTTACTATTGCCAGAATGTGCTGATTACTCCATATACCTTTGGCGGAGGGACAAAACTGGAGATCAAGAGAACTGTGGCCGCTCCCAGTGTGTTCATTTTTCCCCCTTCAGACGAACAGCTGAAATCAGGGACCGCTTCCGTGGTGTGTCTGCTGAACAATTTCTACCCTCGCGAGGCAAAAGTGCAGTGGAAGGTGGATAACGCCCTGCAGAGTGGCAATTCACAGGAGTCCGTGACCGAACAGGACAGCAAAGATTCTACATATAGTCTGTCATCCACCCTGACACTGAGCAAGGCTGATTACGAGAAGCACAAAGTGTATGCATGCGAAGTGACTCATCAGGGGCTGAGCTCTCCCGTGACCAAGTCTTTTAACCGGGGTGAATGTTGA |
| Light Chain Variable Domain Nucleotide Sequence (SEQ ID NO: 31) | GACATCCAGATGACCCAGTCTCCATCCAGCCTGAGTGCCTCAGTGGGCGATAGGGTGACTATCACCTGTCGGGCCAGCGAGAACATCTACGGCGCTCTGAATTGGTATCAGCAGAAGCCAGGAAAAGCTCCCAAGCTGCTGATCTACGGGGCTACAAACCTGGCAGACGGTGTGCCCAGTCGATTCTCCGGTAGCGGCTCTGGACGACAGTATTCACTGACTATCTCTAGTCTGCAGCCTGAAGATTTCGCCACTTACTATTGCCAGAATGTGCTGATTACTCCATATACCTTTGGCGGAGGGACAAAACTGGAGATCAAG |

TABLE 12

Amino acid and nucleotide sequences of humanized anti-human CCL20 antibody light chain LK3

| DESCRIPTION | SEQUENCE (signal sequence underlined, variable domain in bold) |
| --- | --- |
| Light Chain Amino Acid Sequence with the signal sequence (SEQ ID NO: 8) | <u>MDMRVPAQLLGLLLLWLRGARC</u>DIQMTQSPSSLSASVGDRVTITCGASENIYGALNWYQRKPGKAPKLLIYGATNLADGVPSRFSGSGSGRDYTLTISSLQPEDFATYYCQNVLITPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Light Chain Amino Acid Sequence without the signal sequence (SEQ ID NO: 112) | DIQMTQSPSSLSASVGDRVTITCGASENIYGALNWYQRKPGKAPKLLIYGATNLADGVPSRFSGSGSGRDYTLTISSLQPEDFATYYCQNVLITPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 12-continued

Amino acid and nucleotide sequences of humanized anti-human CCL20 antibody light chain LK3

| DESCRIPTION | SEQUENCE (signal sequence underlined, variable domain in bold) |
| --- | --- |
| Light Chain Variable Domain Amino Acid Sequence (SEQ ID NO: 16) | DIQMTQSPSSLSASVGDRVTITCGASENIYGALNWYQRKPGKAPKLLIYGATNLADGVPSRFSGSGSGRDYTLTISSLQPEDFATYYCQNVLITPYTFGQGTKLEIK |
| Light Chain Nucleotide Sequence with the signal sequence (SEQ ID NO: 24) | <u>ATGGACATGAGGGTGCCTGCTCAGCTGCTGGGACTGCTGCTGCTGTGGCTGAGGGGAGCACGATGC</u>GACATCCAGATGACTCAGAGCCCATCCAGCCTGTCAGCCTCCGTGGGCGACAGGGTGACCATCACATGTGGAGCATCCGAGAACATCTACGGGGCCCTGAATTGGTATCAGAGGAAGCCCGGCAAAGCTCCTAAGCTGCTGATCTACGGTGCCACAAACCTGGCTGATGGCGTGCCCTCCAGATTCAGCGGCTCTGGAAGTGGGCGCGACTATACTCTGACCATTTCTAGTCTGCAGCCAGAGGATTTCGCCACCTACTATTGCCAGAATGTGCTGATCACACCCTACACTTTTGGTCAGGGCACAAAACTGGAAATTAAGCGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTGA |
| Light Chain Nucleotide Sequence without the signal sequence (SEQ ID NO: 113) | GACATCCAGATGACTCAGAGCCCATCCAGCCTGTCAGCCTCCGTGGGCGACAGGGTGACCATCACATGTGGAGCATCCGAGAACATCTACGGGGCCCTGAATTGGTATCAGAGGAAGCCCGGCAAAGCTCCTAAGCTGCTGATCTACGGTGCCACAAACCTGGCTGATGGCGTGCCCTCCAGATTCAGCGGCTCTGGAAGTGGGCGCGACTATACTCTGACCATTTCTAGTCTGCAGCCAGAGGATTTCGCCACCTACTATTGCCAGAATGTGCTGATCACACCCTACACTTTTGGTCAGGGCACAAAACTGGAAATTAAGCGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTGA |
| Light Chain Variable Domain Nucleotide Sequence (SEQ ID NO: 32) | GACATCCAGATGACTCAGAGCCCATCCAGCCTGTCAGCCTCCGTGGGCGACAGGGTGACCATCACATGTGGAGCATCCGAGAACATCTACGGGGCCCTGAATTGGTATCAGAGGAAGCCCGGCAAAGCTCCTAAGCTGCTGATCTACGGTGCCACAAACCTGGCTGATGGCGTGCCCTCCAGATTCAGCGGCTCTGGAAGTGGGCGCGACTATACTCTGACCATTTCTAGTCTGCAGCCAGAGGATTTCGCCACCTACTATTGCCAGAATGTGCTGATCACACCCTACACTTTTGGTCAGGGCACAAAACTGGAAATTAAG |

TABLE 13

Amino acid sequences encoded by human germline genes

| DESCRIPTION | SEQUENCE |
|---|---|
| IGHV1-46*03 (SEQ ID NO: 57) | QVQLVQSGAEVKKPGASVKVSCKASGYT FTSYYMHWVRQAPGQGLEWMGIINPSGG STSYAQKFQGRVTMTRDTSTSTVYMELS SLRSEDTAVYYCAR |
| JH4 (SEQ ID NO: 117) | WGQGTLVTVSS |
| IGKV1D-39*01 (SEQ ID NO: 59) | DIQMTQSPSSLSASVGDRVTITCRASQS ISSYLNWYQQKPGKAPKLLIYAASSLQS GVPSRFSGSGSGTDFTLTISSLQPEDFA TYYCQQSYSTPP |

Based on the evaluation results, we selected 36LK3/36HC2 ("HC2/LK3") and 36LC3/36HC2 ("HC2/LC3") for further studies. For these two antibodies, in vitro chemotaxis assays were performed in parallel with parental mouse clone 36F7C10 and its chimeric form (comprising a human Fc portion). In this assay, we employed transwell culture plates with B300.19 CCR6+ cells seeded in the upper layer and recombinant human CCL20 ligand in the lower layer. Recombinant human CCL20 (10 nM final, R&D Systems) was pre-incubated with the humanized anti-CCL20 antibodies at room temperature. After 30 min, human CCR6-transduced murine pre-B cells (B300.19, provided by Dr. H. Kawasaki at Tokyo University) were applied to the upper layer and chemotaxis was developed at 37° C. for 4 hrs. At the end of incubation, FACS was used to measure migrated cells. The 50%, 90%, and 95% inhibitory concentrations ($IC_{50}$, $IC_{90}$, and $IC_{95}$, respectively) for HC2/LK3 and HC2/LC3 were then calculated (Table 14). Neither of the humanized antibodies lost neutralization activity in comparison with the parental mouse MAb, and $IC_{50}$ values were calculated at around 1 nM.

TABLE 14

Neutralizing activity of HC2/LK3 and HC2/LC3 against human CCL20 in a chemotaxis assay (in nM)

| | Mouse MAb | Chimeric MAb |
|---|---|---|
| $IC_{50}$ | 1.697 ± 0.464 | 1.438 ± 0.216 |
| $IC_{90}$ | 3.944 ± 0.593 | 3.510 ± 0.601 |
| $IC_{95}$ | 7.680 ± 2.966 | 5.480 ± 1.179 |

HuMAb HC2/LK3

| | Assay-1 | -2 | -3 | Average |
|---|---|---|---|---|
| $IC_{50}$ | 0.65 | 1.09 | 1.30 | 1.014 ± 0.330 |
| $IC_{90}$ | 3.55 | 3.35 | 6.79 | 4.564 ± 1.928 |
| $IC_{95}$ | 7.59 | 5.41 | 13.91 | 8.972 ± 4.417 |

HuMAb HC2/LC3

| | Assay-1 | -2 | -3 | Average |
|---|---|---|---|---|
| $IC_{50}$ | 0.90 | 1.26 | 1.20 | 1.117 ± 0.193 |
| $IC_{90}$ | 4.64 | 5.82 | 5.30 | 5.251 ± 0.591 |
| $IC_{95}$ | 11.77 | >66.77 | 10.33 | — |

Figure 8A:
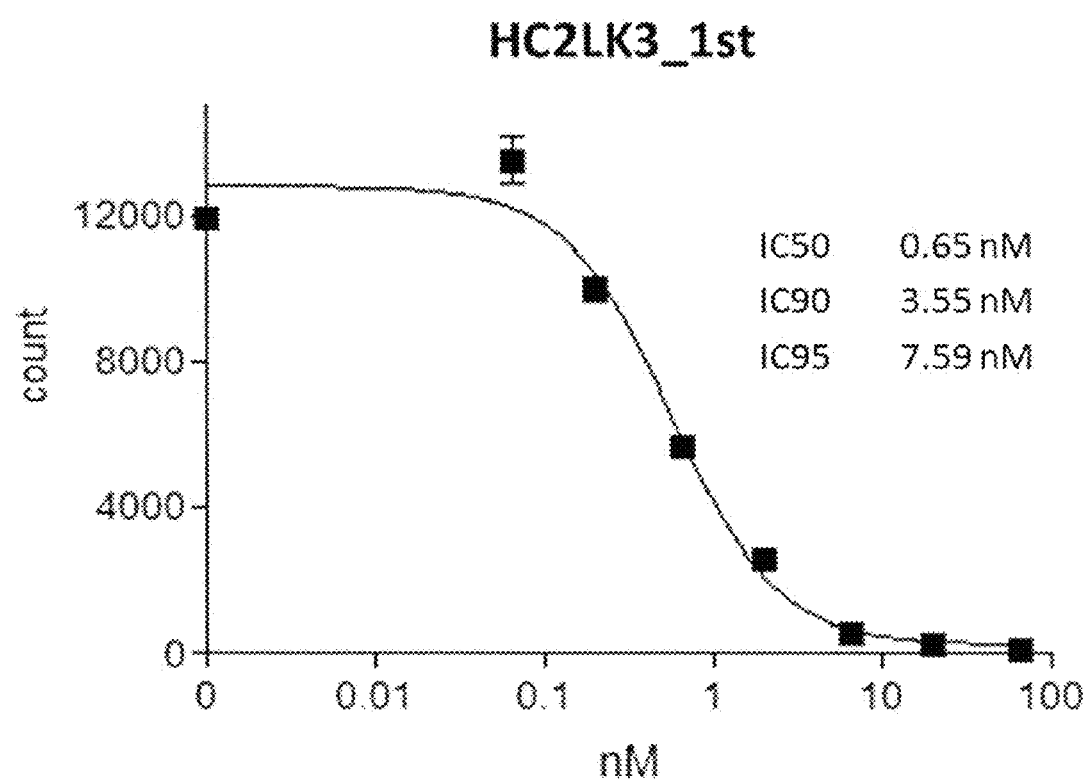
FIGS. 8A-C depict three independent trials performed to assess the inhibitory effect of the humanized HC2/LK3 anti-human CCL20 antibody. The HC2/LK3 antibody is shown to inhibit CCL20-induced chemotaxis. Values for $IC_{50}$, $IC_{90}$, and $IC_{95}$ are shown for each experiment. See Example 4.
Figure 8B:
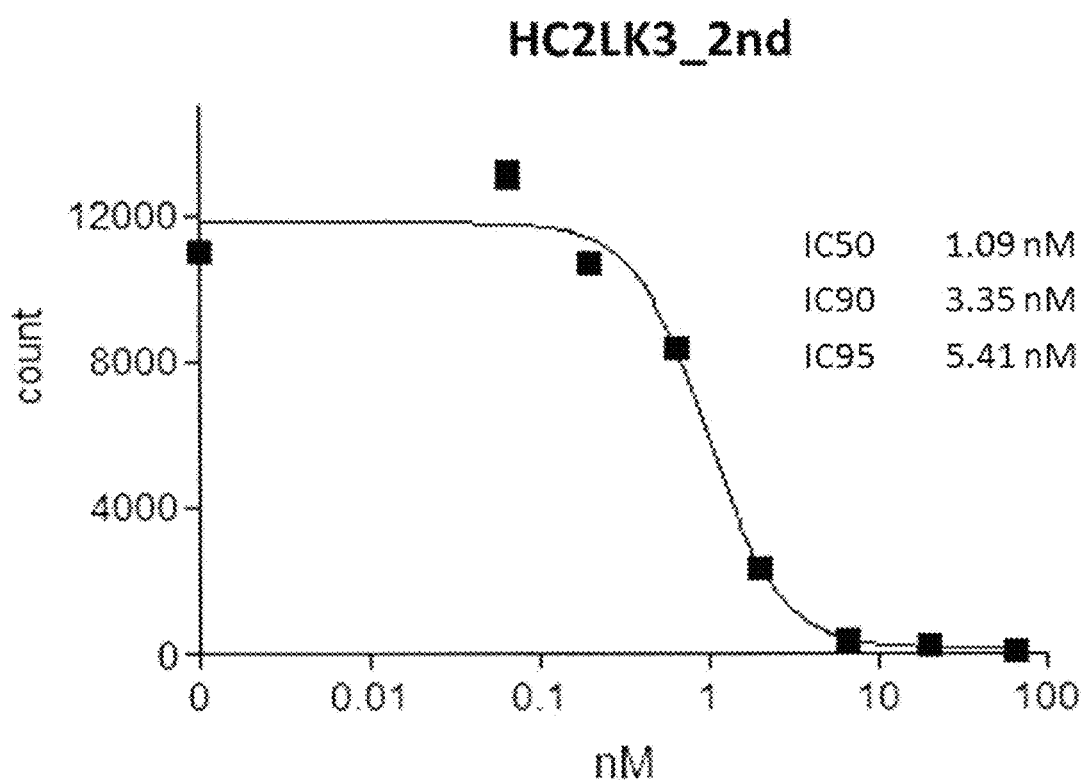
Figure 8C:
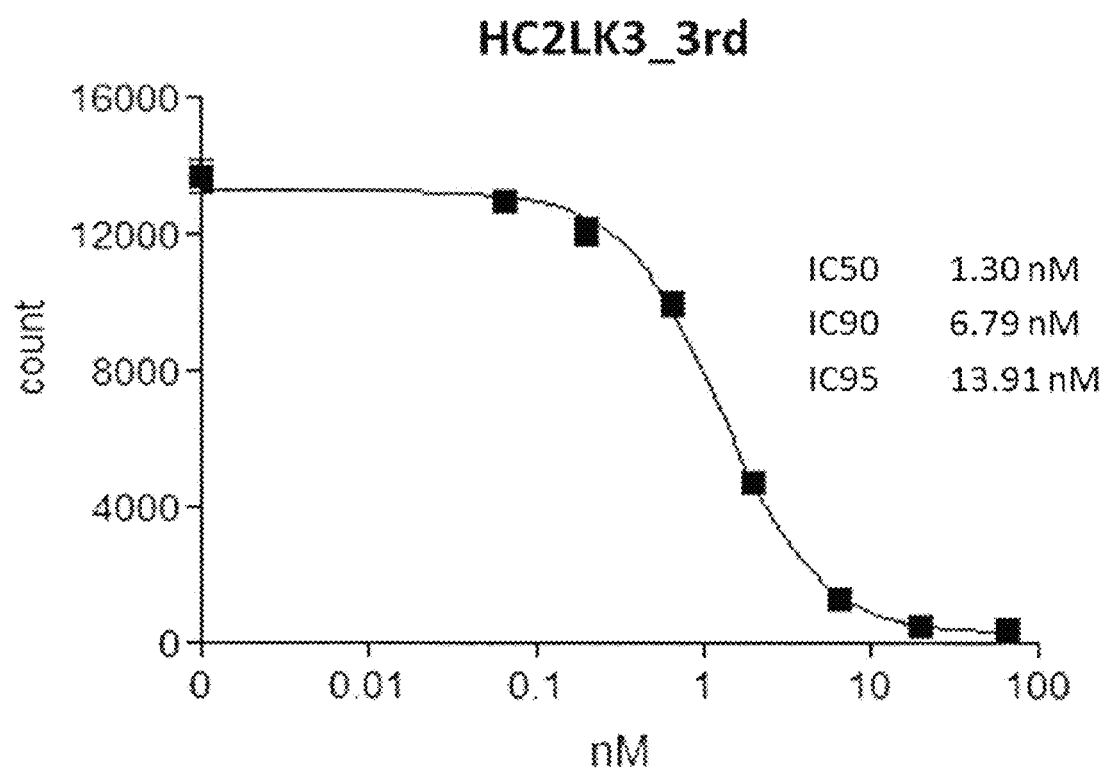

The dose responses for a representative trial with the HC2/LK3 antibody are shown in FIGS. 8A-C. Three independent experiments are depicted.

Figure 9A:
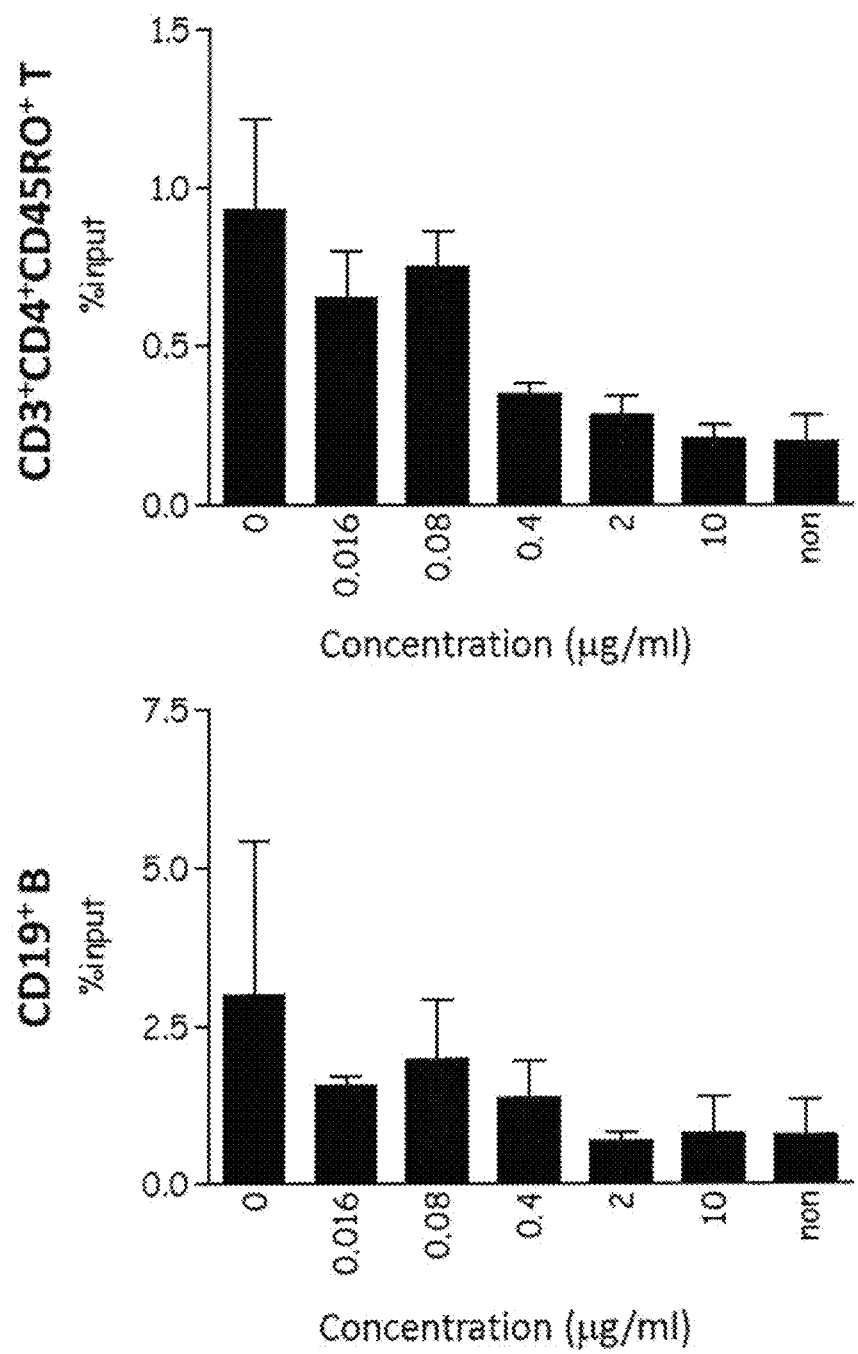
FIGS. 9A-C depict a series of graphs showing that humanized antibodies B) HC2/LK3 and C) HC2/LC3 demonstrate dose dependent inhibition of cell migration comparable to that of A) mouse antibody 36F7C10 in a transendothelial migration assay. See Example 4.
Figure 9B:
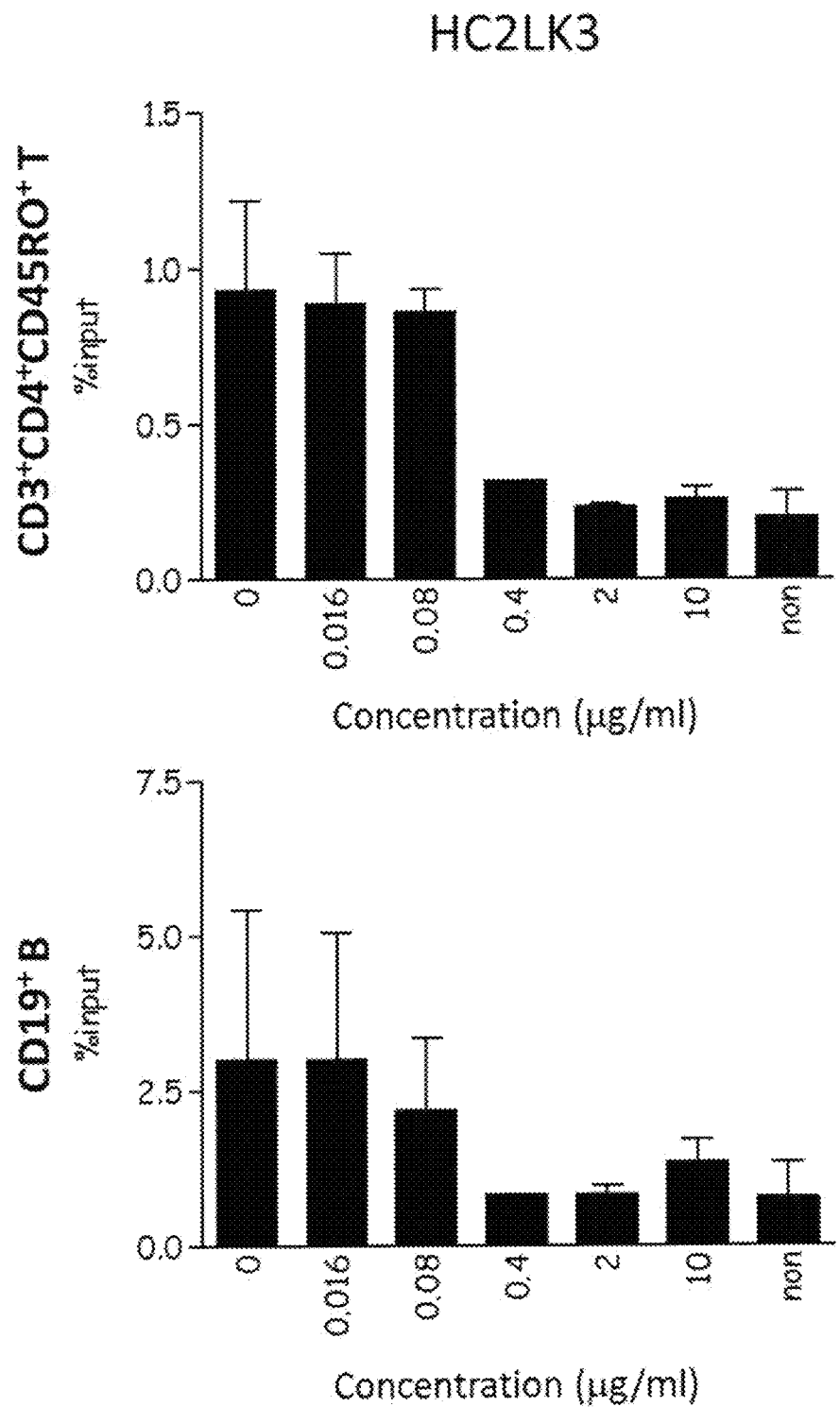
Figure 9C:
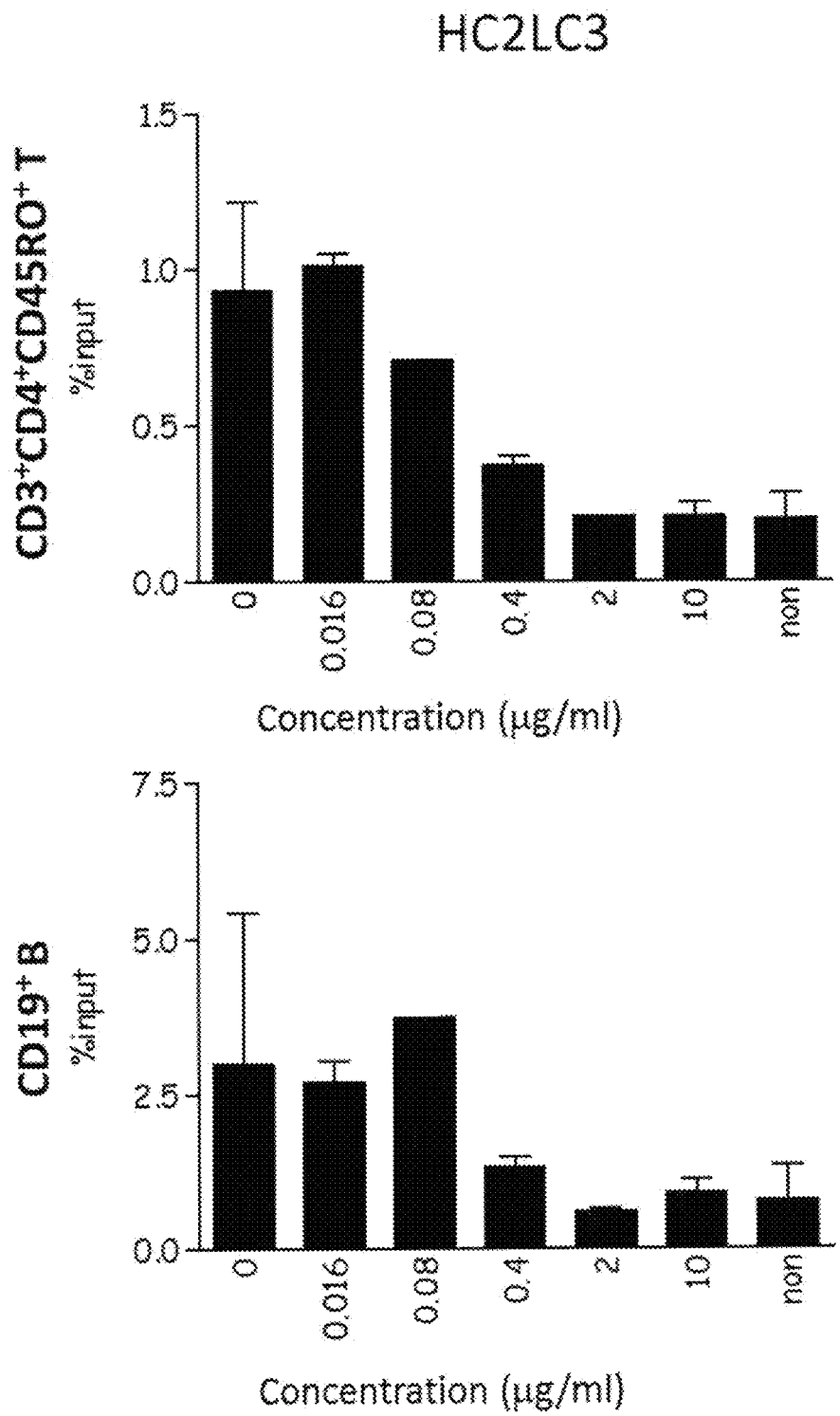

We further confirmed the neutralizing activity of HC2/LK3 and HC2/LC3 using a transendothelial migration (TEM) assay in which freshly isolated human peripheral blood mononuclear cells were used instead of CCR6-transduced artificial cells. Because CD3+CD4+CD45RO+ memory T cells and CD19+B cells are well known to be enriched with CCR6-positive cells, we measured the migrated cell numbers of these populations in the presence or absence of the HC2/LK3 and HC2/LC3 antibodies, as well as the parental mouse antibody 36F7C10. Both humanized antibodies (FIGS. 9B and C) demonstrated dose dependent inhibition of cell migration comparable to that of 36F7C10 (FIG. 9A), providing further evidence of their neutralizing activity.

Example 5: Binding of Humanized Anti-Human CCL20 MAbs to Human CCL20

Figure 10A:
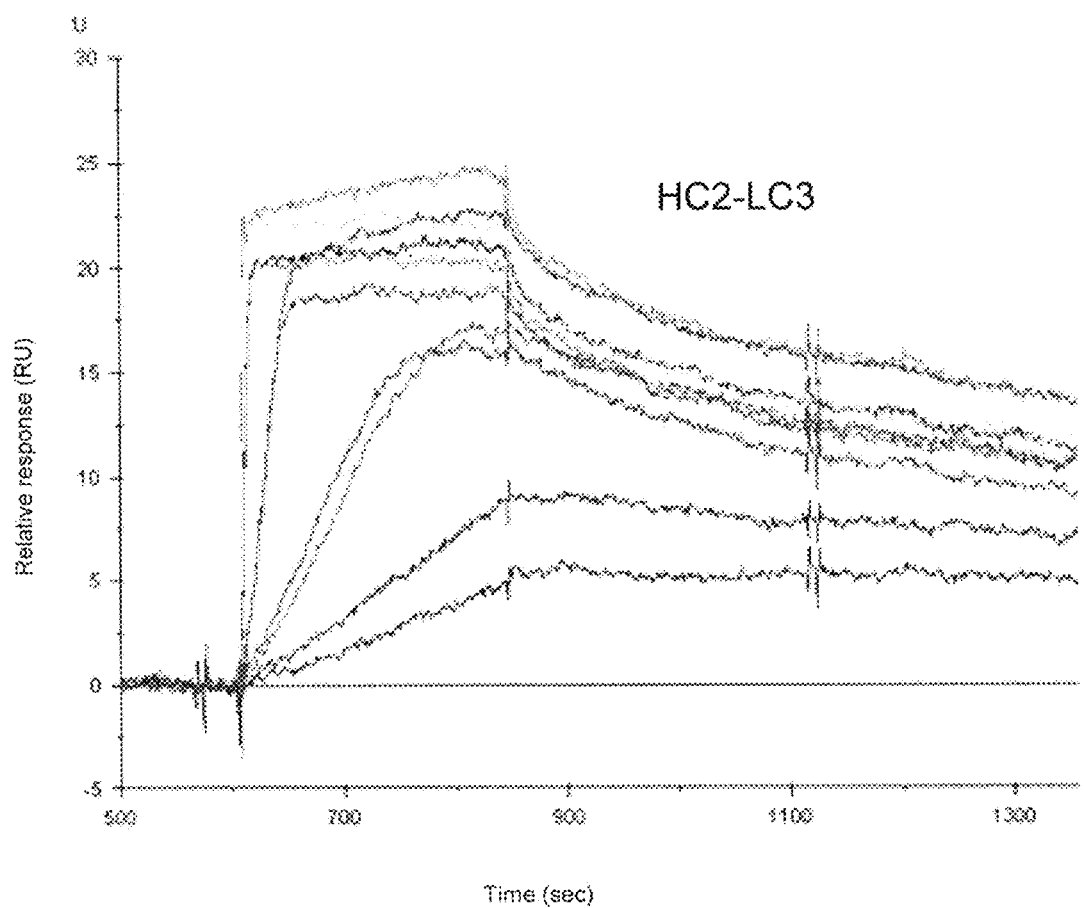
FIGS. 10A and B depict Biacore™ sensograms demonstrating that the A) HC2/LC3 and B) HC2/LK3 humanized antibodies bind to human CCL20 in a concentration-dependent manner. See Example 5.
Figure 10B:
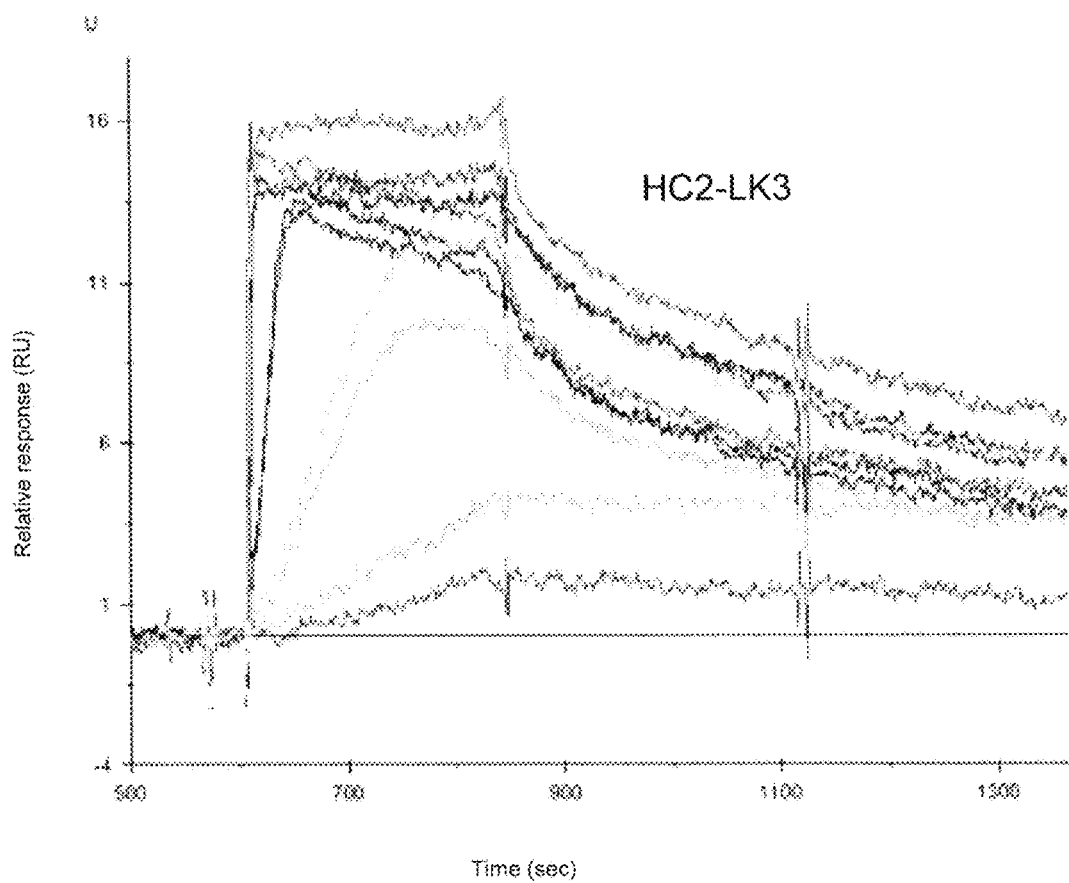

To measure the binding affinity of humanized antibodies HC2/LC3 and HC2/LK3 by surface plasmon resonance (Biacore™), we expressed and purified the antibodies from conditioned media of transiently-transfected HEK293F cells, and captured the antibodies on a CM5 chip coated with anti-human Fc monoclonal antibodies using HBS-EP as the running buffer. We then injected several dilutions (100, 20, 4, 0.8, 0.16, and 0 nM) of human CCL20 protein (R&D Systems) over the coated chip surface, and observed dissociation of bound CCL20 for up to 20 minutes (FIGS. 10A and B). We fitted binding data globally to a 1:1 Langmuir model. The results are shown in Table 15 and represent the average of two independent experiments. Affinity between CCL20 and its receptor, CCR6, has been reported as 500 pM in primary human cells (Liao et al., J. Immunol. 168(10): 4871-4880 (2002)); these data demonstrate that the affinities of the HC2/LC3 and HC2/LK3 antibodies for CCL20 are approximately 10 times higher than the affinity of CCR6 for CCL20.

TABLE 15

SPR results of humanized anti-CCL20 antibodies of the invention

| Heavy chain/ Light chain | $k_a$ ($\times 10^5$ $M^{-1}$ $sec^{-1}$) | $k_d$ ($\times 10^{-5}$ $sec^{-1}$) | $K_D$ (pM) | Standard deviation |
|---|---|---|---|---|
| HC2/LC3 | 145 | 61 | 44 | 15 |
| HC2/LK3 | 166 | 117 | 70 | 7 |

Example 6: Cross-Reactivity of Humanized Anti-Human CCL20 MAbs to Chemokine Paralogs We examined HC2/LK3 and HC2/LC3 for their specificity for human CCL20 by analyzing their cross-reactivity against a chemokine panel (Table 16) using an enzyme-linked immunosorbant assay (ELISA).

TABLE 16

Recombinant human chemokines used in ELISA assay

| Chemokine | Maker | Cat. No. |
|---|---|---|
| CCL20 | MIP-3a/LARC | R&D | #360-MP-025/CF |
| XCL1 | Ltn | R&D | #695-LT-025/CF |
| CCL28 | | R&D | #717-VC-025/CF |
| CCL27 | CTACK | R&D | #376-CT-025/CF |
| CCL25 | TECK | GT | #2234X |
| CCL24 | Eotaxin-2/MPIF-2 | GT | #2343X |
| CCL22 | MDC | R&D | #336-MD-025/CF |
| CCL21 | 6Ckine/SLC | R&D | #366-6C-025/CF |

TABLE 16-continued

Recombinant human chemokines used in ELISA assay

| Chemokine | Maker | Cat. No. |
|---|---|---|
| CCL19 | MIP-3b | R&D | #361-MI-025/CF |
| CCL17 | TARC | GT | #2364 |
| CCL16 | HCC-4 | R&D | #802-HC-025/CF |
| CCL13 | MCP-4 | GT | #2327X |
| CCL11 | Eotaxin | R&D | #320-EO-020/CF |
| CCL7 | MARC | R&D | #282-P3-010/CF |
| CCL5 | Rantes | CHEMICON | #GF020 |
| CCL4 | MIP-1β | R&D | #271-BME-010/CF |
| CCL3 | MIP-1a | GT | #2270X |
| CCL2 | MCP-1/MCAF/JE | PEPRO TECH | #300-04 |
| CCL1 | TCA3/I-309 | GT | #2272 |
| CXCL16 | CXCL16 | GT | #2976X |
| CXCL13 | BCA-1/BLC | R&D | #801-CX-025/CF |
| CXCL12 | SDF-1/PBSF | R&D | #350-NS-010/CF |
| CXCL10 | IP-10 | PEPRO TECH | #300-12 |
| CXCL9 | MIG | GT | #2392X |
| CXCL8 | IL-8 | PEPRO TECH | #200-08M |
| CXCL4 | PF4 | R&D | #795-P4-025/CF |
| CXCL2 | GROβ | R&D | #276-GB-010/CF |
| CXCL1 | GROα | R&D | #275-GR-010/CF |
| CX3CL1 (Chemokine Domain) | FKN | R&D | #362-CX-025/CF |
| CX3CL1 (Extracellular Domain) | FKN | R&D | #365-FR-025/CF |

The wells of a 96-well plate were coated with 1 μg/ml of the recombinant human chemokines in PBS (−). After overnight incubation at 4° C., the wells were blocked with 1× Block-Ace (Dainippon Sumitomo Pharma, UK-B80) for 1 hour at room temperature. After washing twice with 0.02% Tween 20/PBS (−), we added 50 μl of 10 μg/ml purified 36F7C10, chimeric 36F710, HC2/LK3, or HC2/LC3 in 0.02% Tween 20/PBS (−) to each well. The wells were incubated for 1 hour at room temperature and washed three times as described in Example 3. Horseradish peroxidase (HRP)-conjugated anti-mouse IgG antibody (Jackson, #715-035-150, for 36F7C10) or HRP-conjugated anti-human IgG Fcγ fragment (Jackson, #109-035-098, for chimeric and humanized mAbs) was then added (in a 5000 fold dilution with 0.02% Tween 20/PBS (−)) and the wells were incubated for 1 hour at room temperature. After washing five times, a TMBZ (3,3′,5,5′-tetramethylbenzidine) solution (1%, in N,N-Dimethylformamide) was added to the wells and incubated for 15-30 minutes. The reaction was stopped by adding an equal volume of a 2 M $H_2SO_4$ stopping solution, and the optical density was read at 450 nm by ARVO (PerkinElmer). As demonstrated in FIG. 11B, HC2/LK3 and HC2/LC3 bind specifically to human CCL20 over the other chemokines in the panel.

Figure 11A:
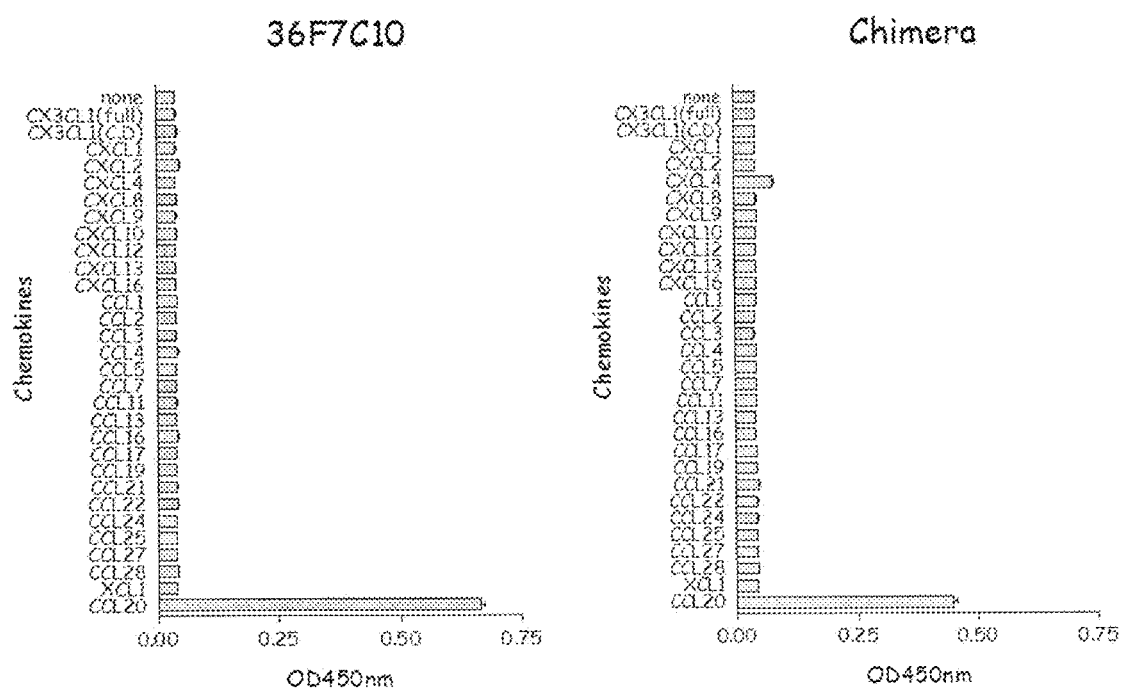
FIGS. 11A-D demonstrate that anti-human CCL20 antibodies specifically bind to human CCL20. An ELISA assay with plate-bound CCL20 and other chemokines (at 1 μg/ml) was used to detect binding of A) 36F7C10 and chimeric antibodies, and B) humanized HC2LK3 and HC2LC3 antibodies. C) An ELISA assay with His-tag anchored CCL20 was used to detect binding. D) Biacore™ experiments confirm that anti-human CCL20 antibodies bind to human CCL20, and exhibit negligible binding to CXCL4. See Example 6.
Figure 11B:
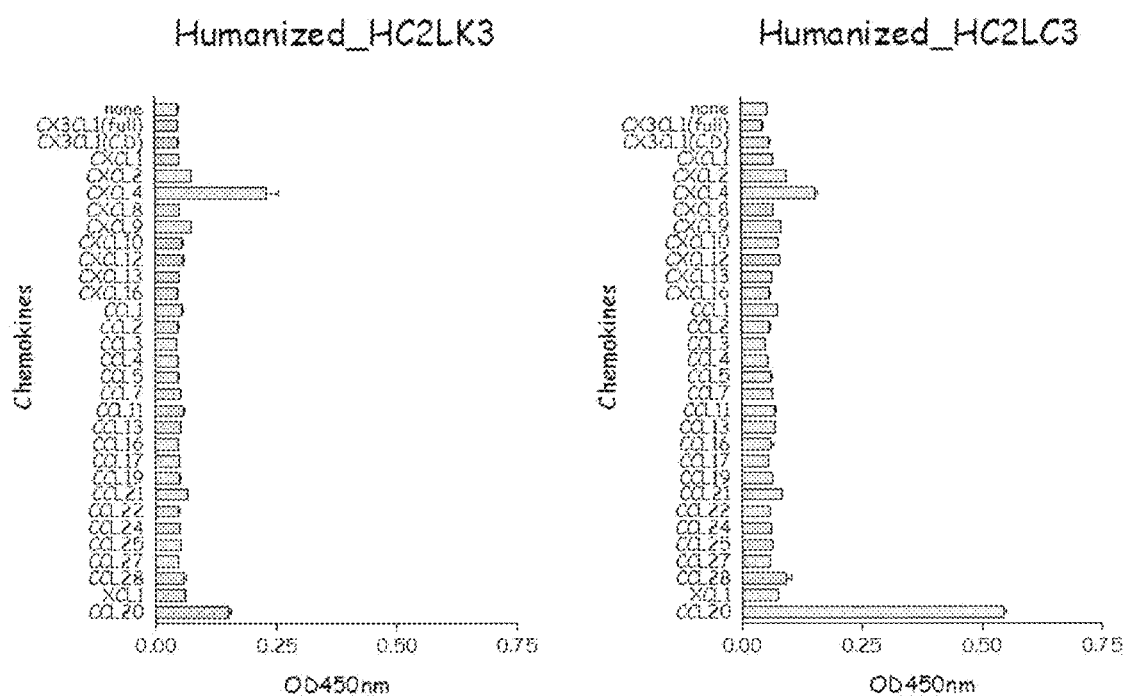
Figure 11C:
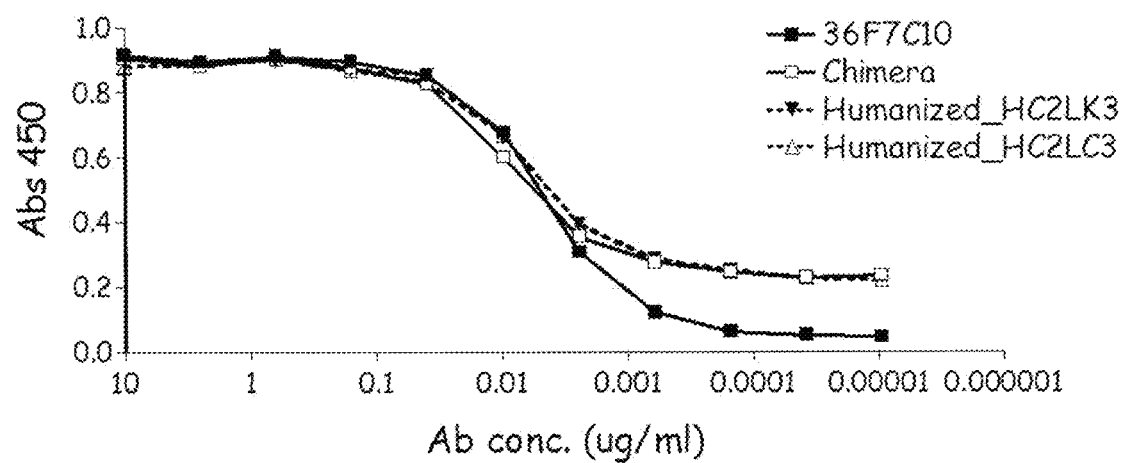
Figure 11D:
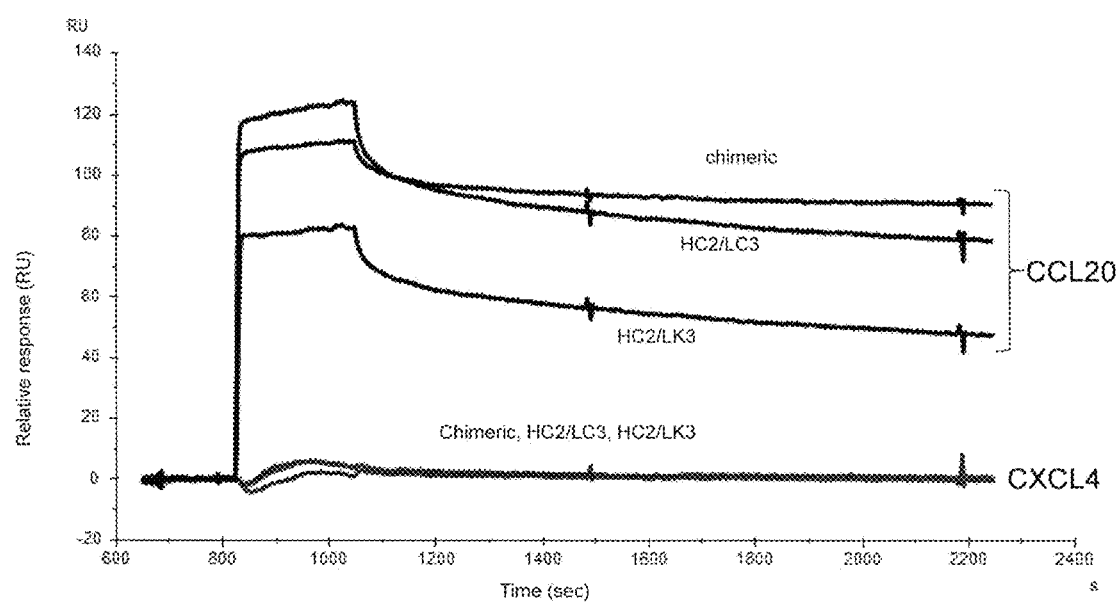

In these assays, although HC2/LK3 was reactive against plate-bound human CCL20, it appeared less potent than the mouse 36F7C10 or chimeric 36F7C10-hFc antibodies (FIG. 11A). However, the HC2/LK3 showed clear and strong binding against CCL20 anchored via a His-tag in ELISA assays (FIG. 11C), which allowed exposure of all CCL20 portions to the solvent. This may indicate that the CCL20 epitope(s) for HC2/LK3 are buried or occluded in the procedure used to bind CCL20 to the plate surface in the first assay format. To avoid this possible artifact, we employed Biacore™ analysis in which free CCL20 was applied over MAbs captured on a sensor chip. In the Biacore™ assays, HC2/LK3 and HC2/LC3 showed strong CCL20 binding comparable to that of the 36F7C10-hFc chimeric antibody (FIG. 11D). Further, the small reaction against CXCL4 observed in FIG. 11B was found to be negligible in the Biacore™ assays (FIG. 11D).

Phylogenetic analysis by Dereeper et al., (*Nucleic Acids Res.* 1(36):W465-469 (2008)) indicates that CCL16 is the chemokine closest in sequence to CCL20, although the percent identity between CCL20 and CCL16 is less than 37.5% (homology in only 56 out of 70 amino acids comprising the mature CCL20 peptide (SIM—Alignment Tool for protein sequences, Swiss Institute of Bioinformatics)) (FIG. 12). We used Biacore™ analysis to test whether HC2/LK3 and HC2/LC3 cross-react with CCL16. Monoclonal mouse anti-human Fc was immobilized on all four flow cells of a CM5 chip at a flow rate of 25 μl/min with HBS-EP buffer containing 0.2 mg/mL BSA. Subsequently, 50 μl of a 1 μg/ml solution of chimeric, HC2/LC3, or HC2/LK3 antibody in HBS-EP buffer with 0.2 mg/ml BSA was injected over flow cells 2, 3, and 4, respectively. 150 μl of a 100 nM solution of CCL20 or CCL16 in HBS-EP buffer (or buffer alone) with 0.2 mg/ml BSA was then injected over all four flow cells at a flow rate of 40 μl/min. Dissociation followed for 20 min. Flow cell 1 (anti-human Fc antibody alone) was used as a reference for all flow cells.

Figure 13A:
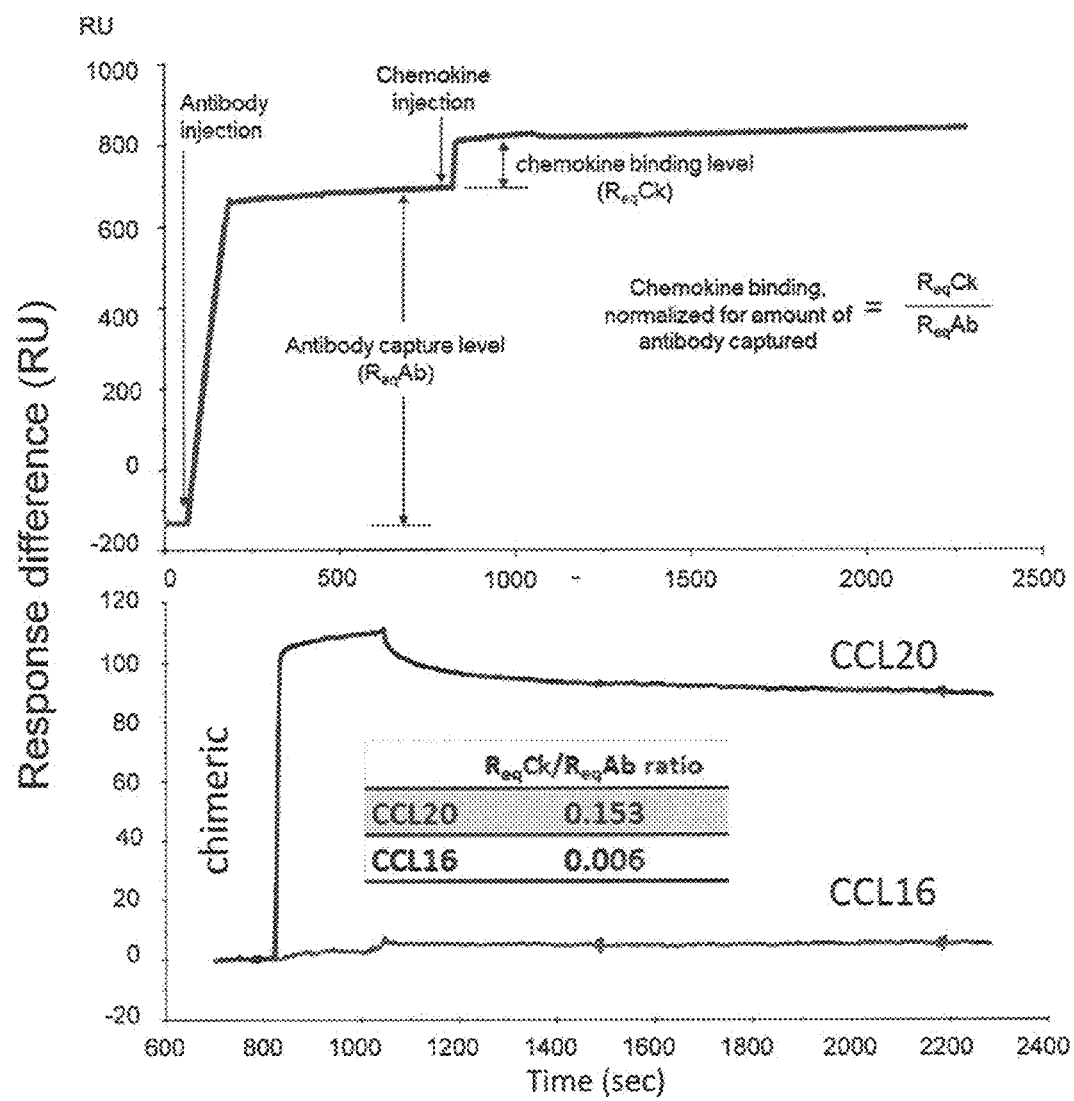
FIGS. 13A and B are a series of graphs showing that A) chimeric and B) humanized anti-human CCL20 antibodies react specifically with CCL20 and do not react with CCL16. See Example 6.
Figure 13B:
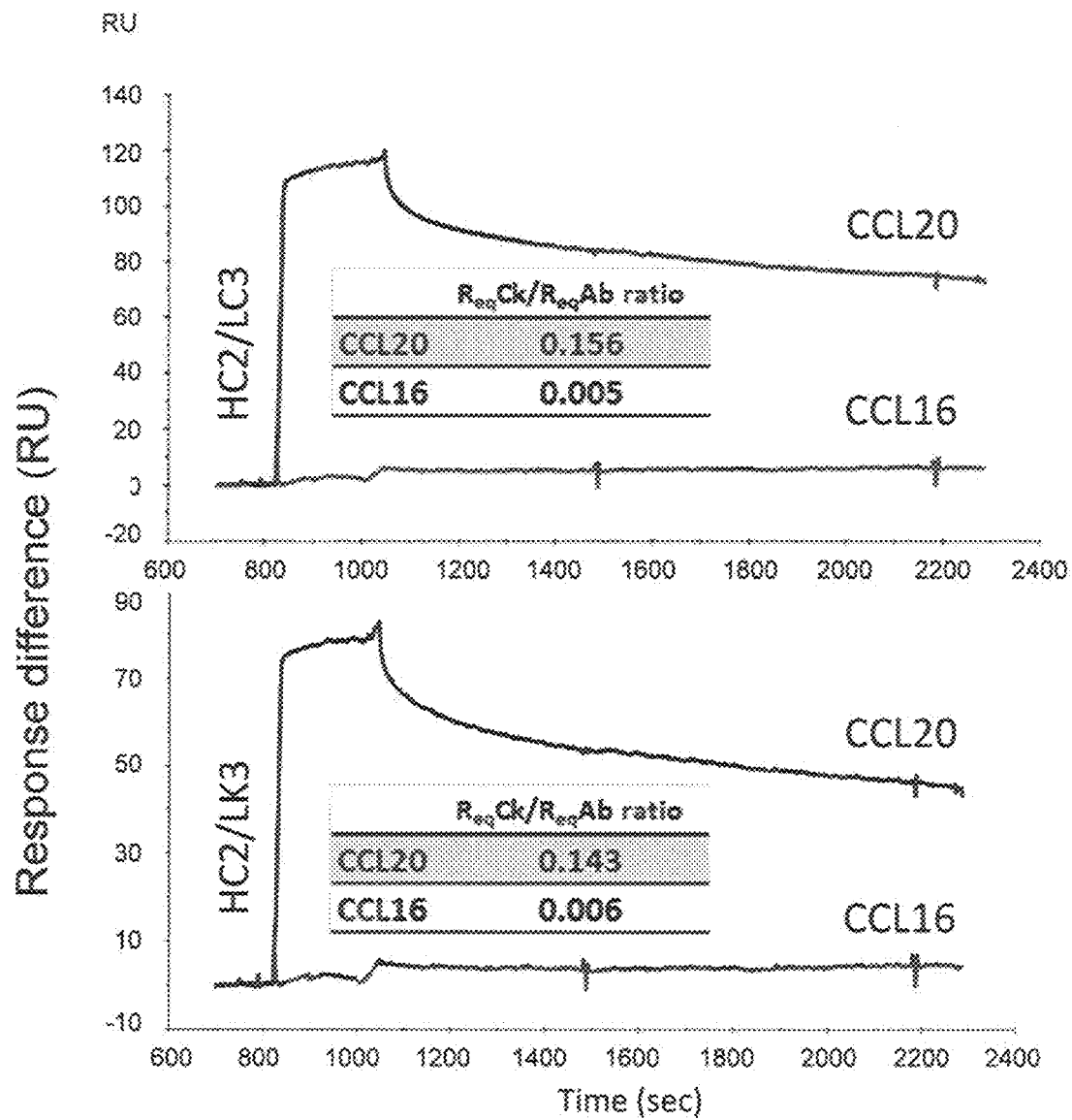

Under these conditions, human CCL20 bound to the chimeric (FIG. 13A), HC2/LC3 (FIG. 13B), and HC2/LK3 (FIG. 13B) antibodies captured on the chip with similar strength. By contrast, no significant binding was detected when human CCL16 was run through the chip, indicating that although CCL16 is the chemokine closest in sequence to CCL20, CCL20 and CCL16 do not possess sufficient homology (<37%, as discussed above) to allow the humanized anti-CCL20 antibodies to cross-react with CCL16.

These data indicate that HC2/LK3 and HC2/LC3 are specific for human CCL20 over other chemokines.

Example 7: Cross-Reactivity of Humanized Anti-Human CCL20 MAbs to Species Orthologs We then determined the cross-reactivity of the HC2/LC3 and HC2/LK3 MAbs to CCL20 from other species. Amino acid sequence alignments among CCL20 orthologs (obtained using SIM—alignment tool for protein sequences (Swiss Institute of Bioinformatics)) indicate that the identity between cynomolgus/rhesus and human CCL20 is 86%, while the homology between mouse and human CCL20 is 64% (FIG. 14; human CCL20—SEQ ID NO: 85; rhesus CCL20—SEQ ID NO: 86; cynomolgus CCL20—SEQ ID NO: 87; partial mouse CCL20—SEQ ID NO: 88 (the entire mouse CCL20 amino acid sequence may be found in SEQ ID NO: 102; residues 1-27 constitute the signal sequence; see Table 18)).

Figure 15:
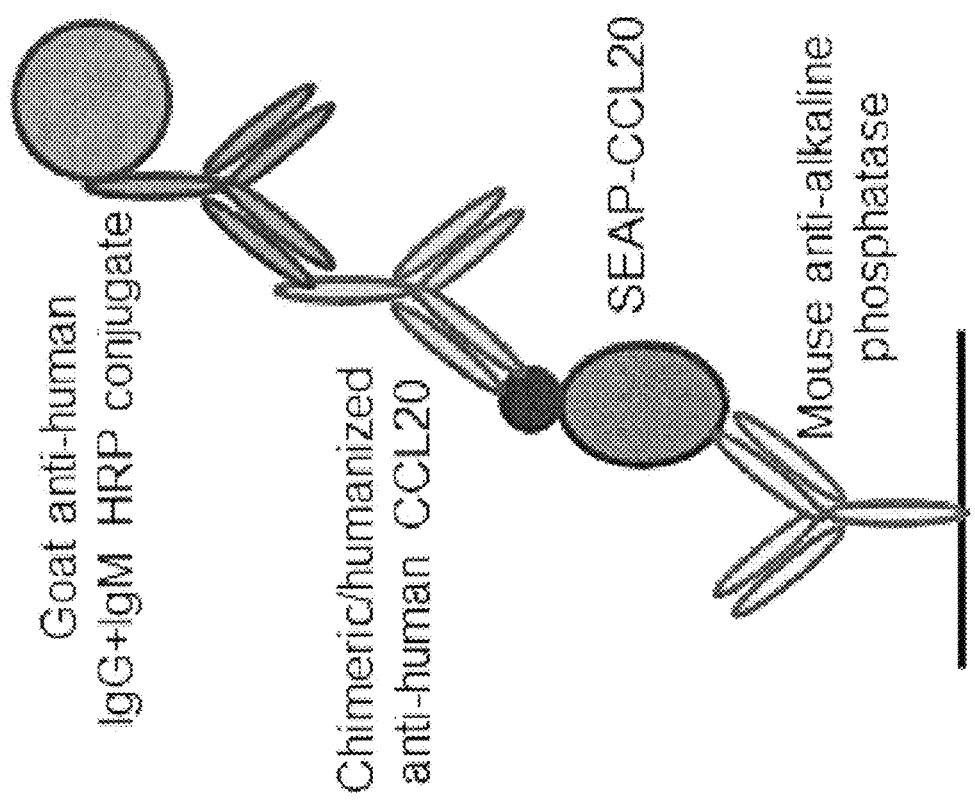
FIG. 15 is a schematic representation of anti-human CCL20 antibody detection in ELISA assays. See Example 7.
Figure 16A:
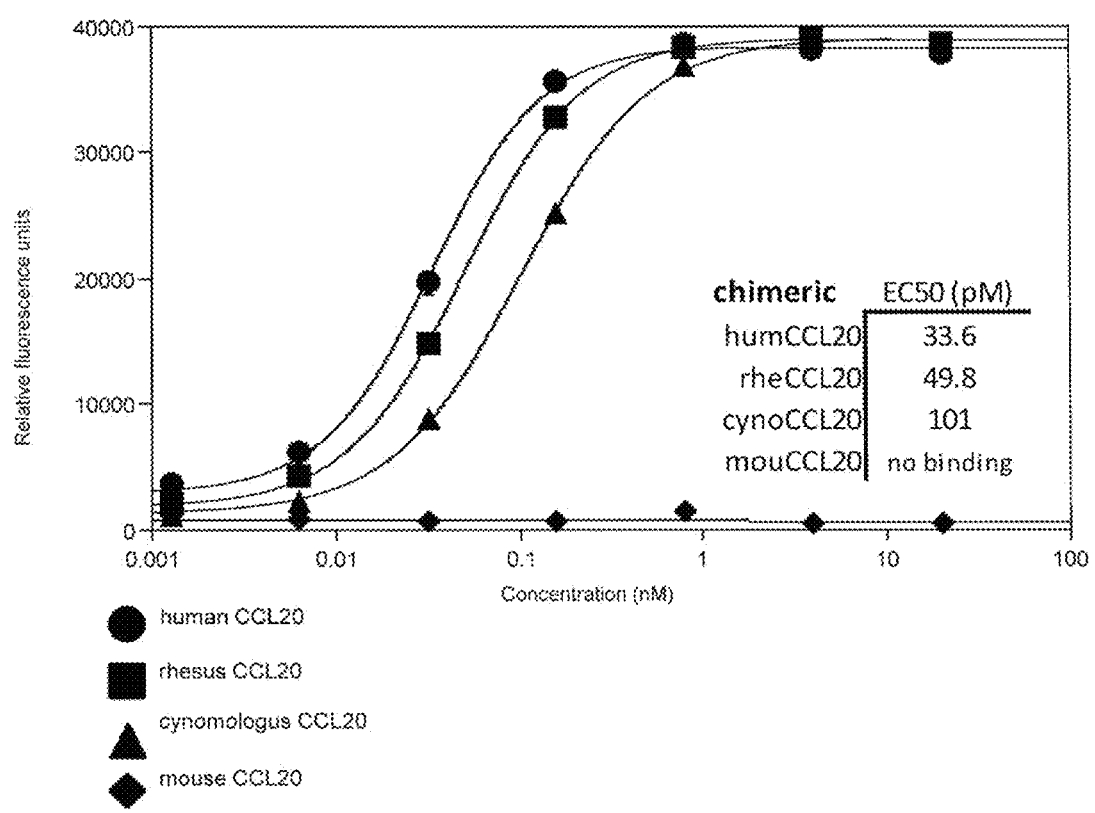
FIGS. 16A-C depict a series of graphs demonstrating that A) chimeric and B), C) humanized anti-human CCL20 antibodies bind effectively to human, rhesus, and cynomolgus CCL20, but not to mouse CCL20. See Example 7.
Figure 16B:
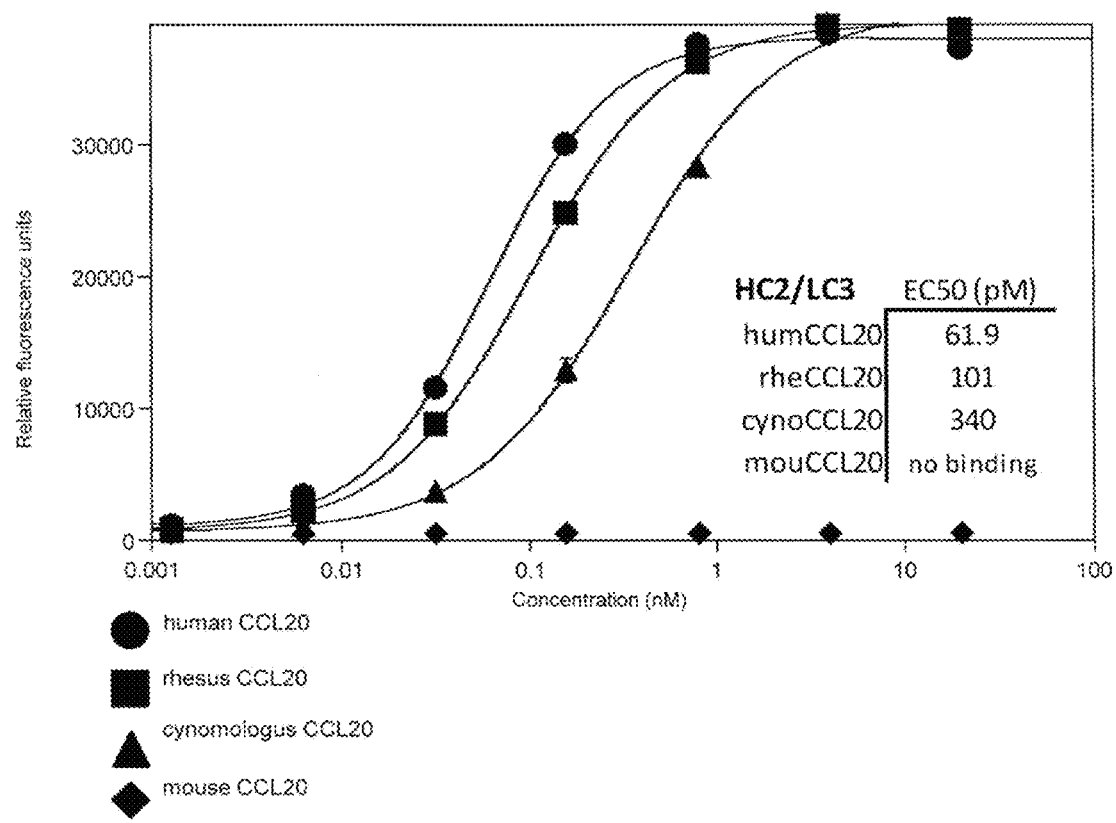
Figure 16C:
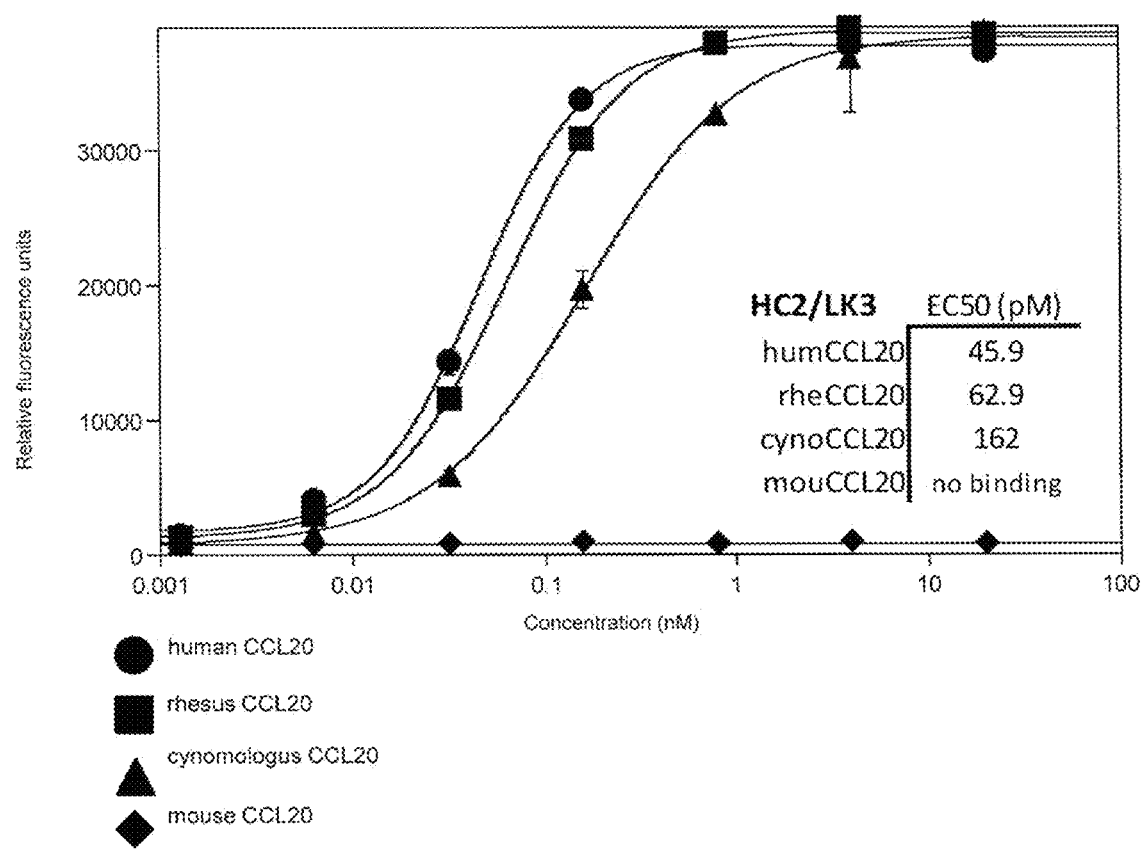
Figure 17B:
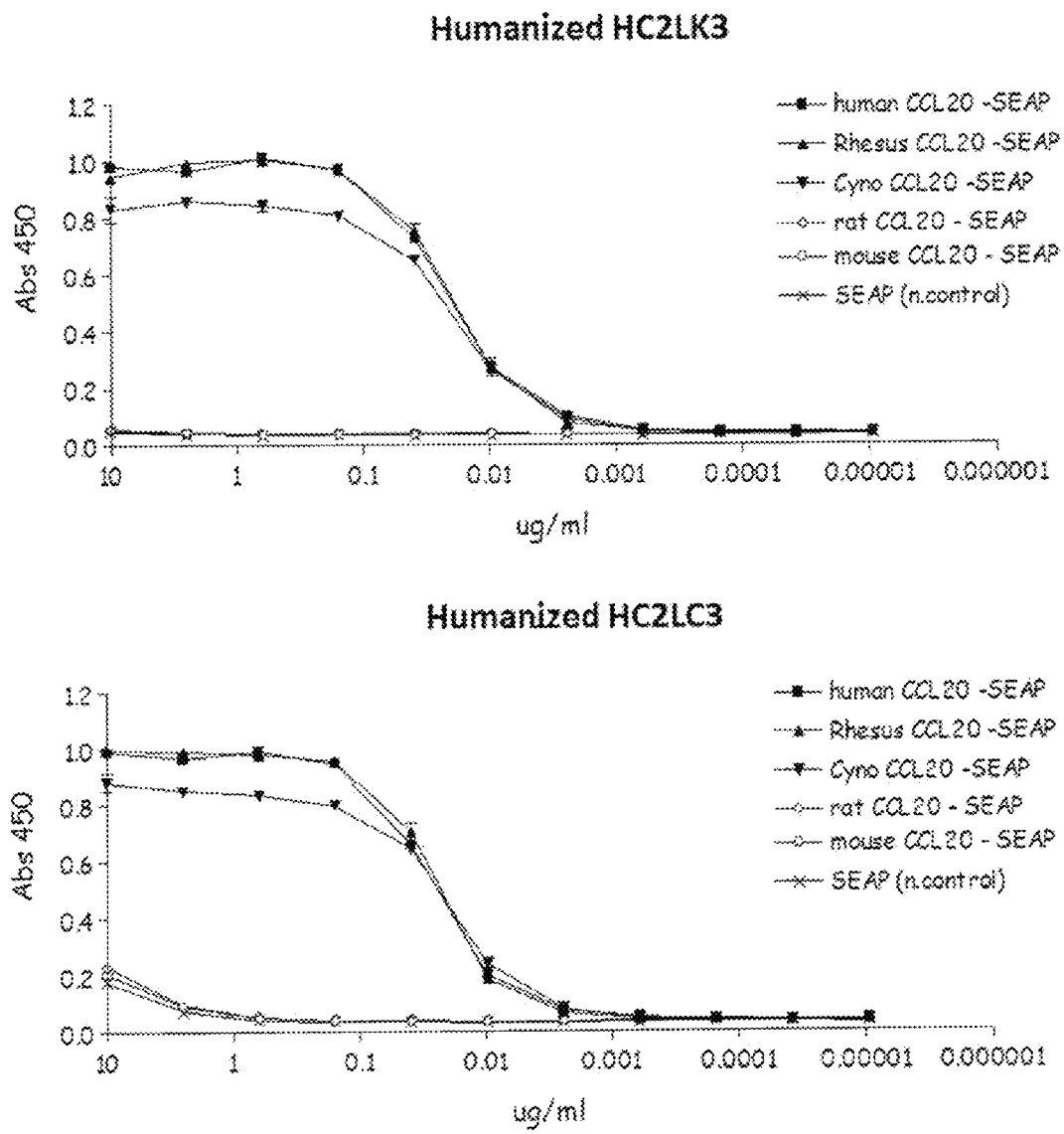
FIGS. 17A and B depict graphs demonstrating that humanized and chimeric anti-human CCL20 antibodies bind effectively to human, rhesus, and cynomolgus CCL20, but not to rat or mouse CCL20. The B) humanized and A) chimeric antibodies retain the binding specificity of A) mouse antibody 36F7C10, from which they are derived. See Example 7.

To test whether the chimeric and humanized antibodies can bind to mouse, cynomolgus, or rhesus macaque CCL20 orthologs, we used ELISA assays as illustrated in FIG. 15. Recombinant secreted alkaline phosphatase (SEAP)-chemokine fusion proteins were engineered as described in Example 2, expressed and purified for all of the CCL20 orthologs tested. Nunc MaxiSorb flat-bottom black plates were coated with 1 μg/ml mouse anti-placental alkaline phosphatase antibody (Pierce, cat#MA1-19354) in 50 mM sodium bicarbonate, pH 9.4, overnight at 4° C. Plates were then blocked using 1× phosphate buffered saline with Tween-20 (PBST) with 5% bovine serum albumin (BSA) for 2 hours at room temperature. 20 nM SEAP-CCL20 fusion proteins were serially diluted 5-fold in Opti-MEM medium (Invitrogen). Chimeric and humanized (HC2/LC3 and HC2/

LK3) antibodies were diluted to 1 μg/ml in 1×PBST with 5% BSA, added to the plates, and incubated for 1 hr at room temperature. The plates were then washed with 1×PBST with 5% BSA three times. Goat anti-human IgG+IgM (H+L) HRP conjugate (Jackson ImmunoResearch cat#109-035-127) was diluted to 80 ng/ml, added to the plate, and incubated for 1 hour at room temperature. QuantaBlu fluorescent HRP substrate (Pierce cat#15169) was added for detection of bound antibody by measuring fluorescence in a Molecular Devices M5 (Excitation 325 nm/Emission 420 nm) plate reader.

While the hamster anti-mouse CCL20 antibody 2F5-5 MAb bound mouse CCL20 with a 50% effective dose ($EC_{50}$) of 64 pM (data not shown), neither the chimeric nor humanized anti-human CCL20 antibodies bound detectably to mouse CCL20 or rat CCL20 under the conditions described above. By contrast, both the chimeric and humanized antibodies effectively bound to human, rhesus, and cynomolgus CCL20 (FIGS. 16A-C, 17A and B). While the $EC_{50}$ for human and rhesus CCL20 appeared similar (for example, 62 and 101 pM for HC2/LC3), the $EC_{50}$ for cynomolgus CCL20 was 340 pM for HC2/LC3, a 5.4 fold difference versus human CCL20. Similar results were seen for HC2/LK3. This suggests that a much greater concentration of antibody was required to achieve the same amount of binding to cynomolgus CCL20 as to human or rhesus CCL20.

Example 8: Surface Plasmon Resonance Assays for Cross-Reactivity of Humanized Anti-CCL20 MAbs to CCL20 Species Orthologs We also used surface plasmon resonance (Biacore™) analysis to test whether HC2/LC3 and HC2/LK3 can bind to mouse, cynomolgus, or rhesus macaque CCL20 orthologs. Monoclonal mouse anti-human placental alkaline phosphatase was immobilized on all four flow cells of a CM5 chip at a flow rate of 25 μl/min. 25 μl of a 2 nM solution of human, rhesus, cynomolgus, or mouse CCL20-SEAP in HBS-EP buffer was injected over flow cell 2, 3, or 4. For antibody binding, 240 μl of 0-80 nM dilutions of HC2/LC3, HC2/LK3, or 2F5-5 MAb in HBS-EP buffer (or buffer alone) was injected over all four flow cells at a flow rate of 50 μl/min. Dissociation followed for 45 min. Flow cell 1 (anti-SEAP alone) was used as a reference for all flow cells. Regeneration of the flow cells was performed with 10 mM glycine at pH 2.25. Due to regeneration effects on the capturing capacity of the chips, antibody injections were performed sequentially from low to high concentration. Data fitting was performed using a 1:1 Langmuir model.

Under the above conditions, hamster anti-mouse CCL20 antibody 2F5-5 bound mouse CCL20 with a (bivalent) $K_D$ of 4.9 pM, but did not significantly bind human, rhesus, or cynomolgus CCL20. In contrast, chimeric, HC2/LC3, and HC2/LK3 antibodies effectively bound to human, rhesus, and cynomolgus CCL20 (Table 17).

The apparent affinity values measured were higher in this assay than previously detected in Example 5 (for example 4.7 pM for HC2/LC3 in the present assay vs. 44 pM in Table 3) due to the bivalent (higher affinity) nature of the assay format used (versus the monovalent format used for the data shown in Table 15). The $K_D$ values for rhesus and cynomolgus CCL20 were generally higher (3-fold) than for human CCL20, indicating that the antibodies bound more specifically to human CCL20. In contrast to the ELISA data from Example 7, however, we observed no significant difference between binding affinity for rhesus and cynomolgus CCL20.

TABLE 17

Assessment of anti-CCL20 humanized monoclonal antibody binding to CCL20 orthologs by Biacore™

| Antibody | Ligand | $k_a$ (×$10^5$ $M^{-1}sec^{-1}$) | $k_d$ (×$10^{-5}$ $sec^{-1}$) | $K_D$ (pM) |
|---|---|---|---|---|
| Chimeric clone 36F7C10[a] | hCCL20 | 29 | 2.08 | 7.16 |
| | rCCL20 | 29.4 | 1.78 | 6.05 |
| | cCCL20 | 38.3 | 5.04 | 13.2 |
| HC2/LC3 | hCCL20 | 56.9 | 2.68 | 4.71 |
| | rCCL20 | 41.3 | 7.51 | 18.2 |
| | cCCL20 | 86.4 | 13.4 | 15.5 |
| HC2/LK3 | hCCL20 | 28.8 | 3.39 | 11.8 |
| | rCCL20 | 26.3 | 8.21 | 31.2 |
| | cCCL20 | 52.8 | 14.9 | 28.3 |
| Hamster anti-mouse 2F5-5[b] | hCCL20 | No binding | No binding | No binding |
| | rCCL20 | No binding | No binding | No binding |
| | cCCL20 | No binding | No binding | No binding |
| | mCCL20 | 9.63 | 0.474 | 4.92 |

[a]Previously shown not to bind mCCL20
[b]Hamster anti-mouse data from earlier chip

Example 9: Epitope Mapping for Mouse Anti-Human CCL20 Clone 36F7C10

Figure 18A:
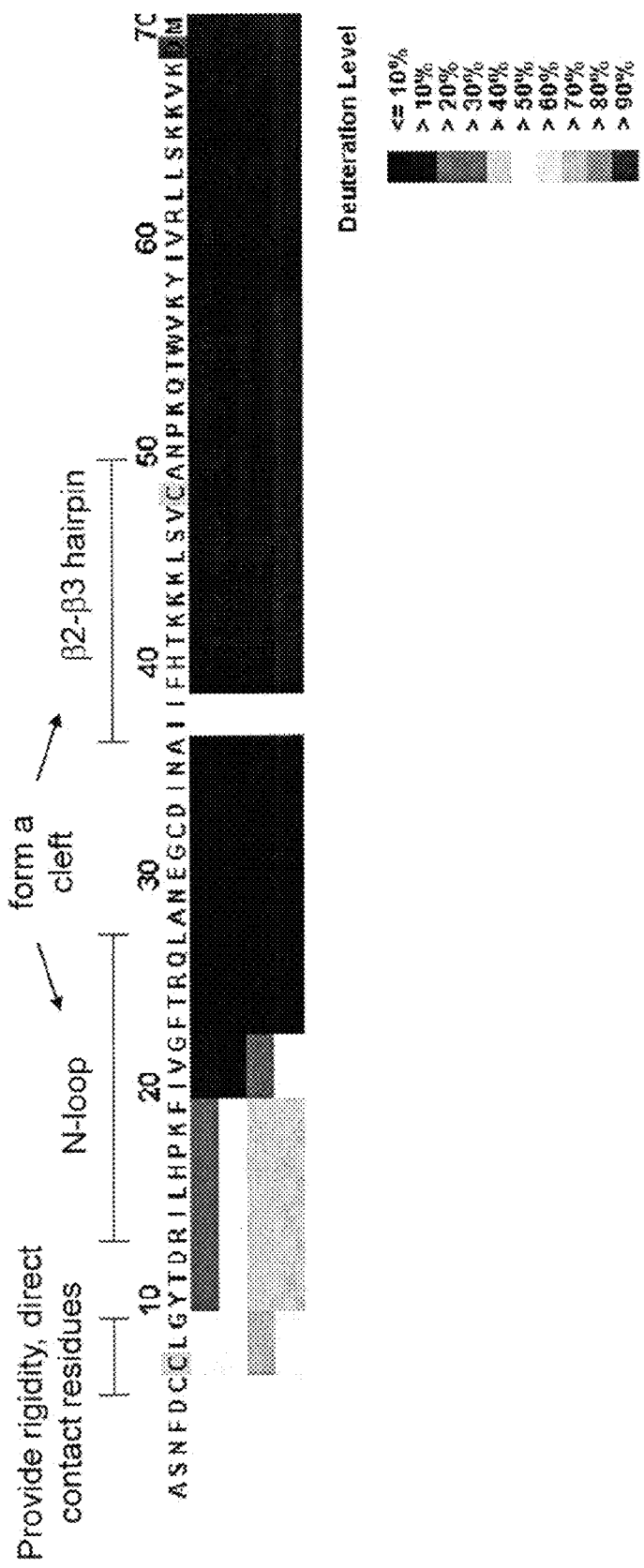
FIGS. 18A and B show the results of epitope mapping of human CCL20 by hydrogen/deuterium exchange. This experiment utilized a variant of human CCL20 (SEQ ID NO: 84) from R&D Systems in which the second to last residue is a D instead of the N shown in the wild-type sequence. A) The deuteration level of each residue of CCL20 is indicated at four time points (from top: 150 s, 500 s, 1500 s, and 5000 s). B) Structure of human CCL20, indicating an epitope bound by antibodies of the invention. See Example 9.

To determine the human CCL20 epitope(s) to which mouse anti-human CCL20 monoclonal antibody 36F7C10 binds, we used a hydrogen/deuterium exchange method in which antibody binding protects and thus preserves deuteration of the epitope. As shown in FIG. 18A, we observed very strong perturbations near the N-terminus of human CCL20 at residues 7-9, 10-19, and 20-22, possibly representing the epitope(s). Marginal protection was also observed near the C-terminus at residues 39-55, 56-67, and 61-70. These segments may be peripheral to the epitope, or their breathing motions may be conjugated to the epitope. The deuteration level of each indicated amino acid is shown at four timepoints: from top to bottom, 150, 500, 1,500, and 5,000 s.

Figure 18B:
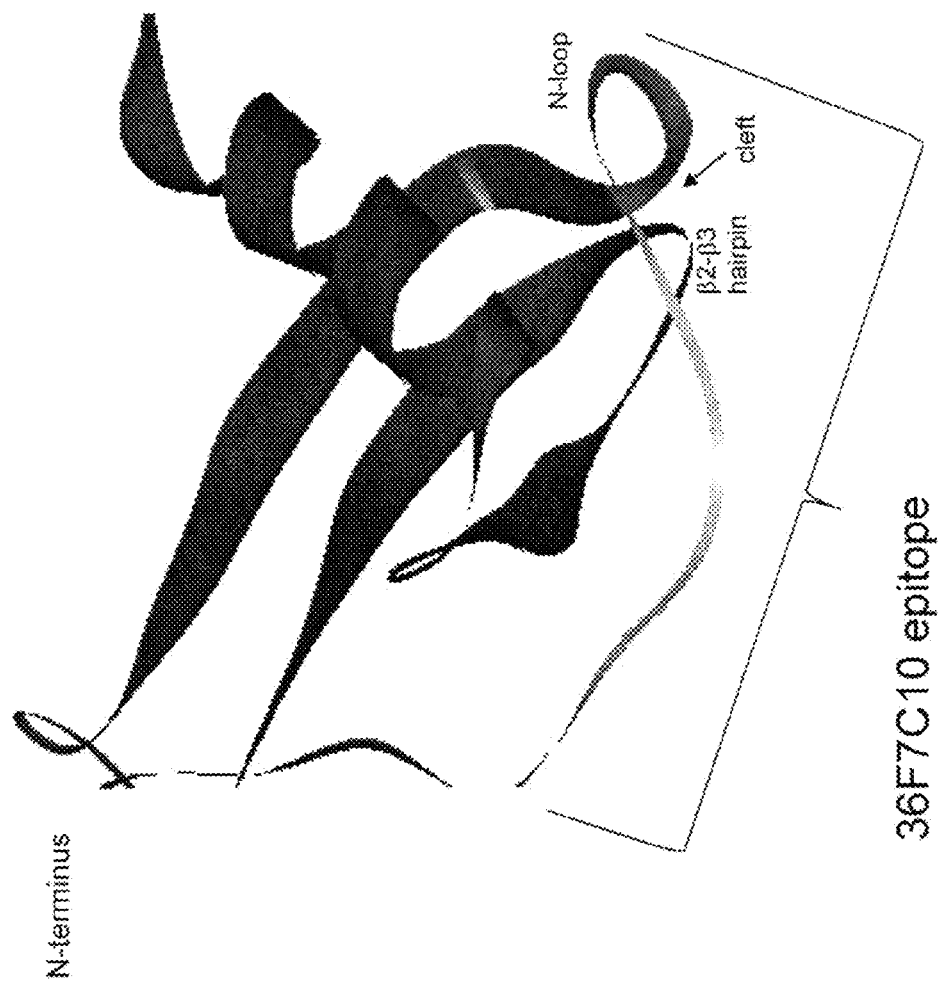

The regions identified as the epitope for 36F7C10 fall within the N-terminal and loop regions of CCL20, which are known to be critical for CCR6 binding and signaling (Malik et al., Acta Cryst F62:631-634 (2006))(FIG. 18B). Chimeric and humanized antibodies derived from 36F7C10, especially antibodies with the same heavy and light chain CDR1, CDR2 and CDR3 amino acid sequences as 36F7C10, or similar heavy and light chain CDR1, CDR2 and CDR3 amino acid sequences as 36F7C10 (e.g., with less than 3, 2 or 1 amino acid substitutions as compared to the CDRs of 36F7C10) are expected to bind to the same epitope. The identification of this epitope may thus explain the ability of the 36F7C10 MAb and chimeric and humanized antibodies derived therefrom to neutralize CCL20 activity.

Figure 20:
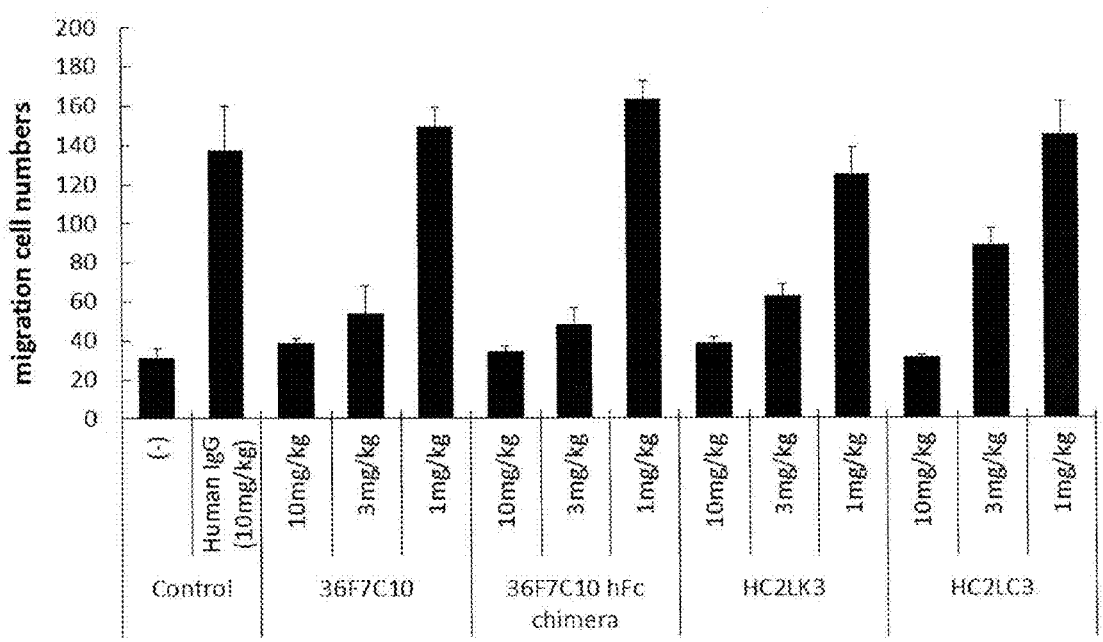
FIG. 20 is a graph showing that mouse, chimeric, and humanized anti-human CCL20 antibodies inhibit mouse T-cell migration toward human CCL20 in vivo in a dose-dependent fashion. See Example 10.

Example 10: In Vivo Chemotaxis Assay for Humanized Anti-Human CCL20 Antibodies To test whether HC2/LC3 and HC2/LK3 can inhibit CCL20-induced chemotaxis in vivo, we took advantage of the fact that human CCL20 can interact with mouse CCR6 (SEQ ID NO: 106) to induce chemotaxis of mouse T cells (FIG. 19). We used a hybrid in vivo system measuring the migration of mouse T cells towards intradermally injected human CCL20 (FIG. 20).

Recombinant human CCL20 (10 ng/head) and vehicle were intradermally injected into the shaved skin on the right and left sides, respectively, of the backs of the test mice (groups of n=3). Calcein-AM-labeled mouse splenic T cells ($5 \times 10^6$ cells/mouse) were then transferred intravenously into the tail vein, with simultaneous injection of the indicated antibodies into the tail vein at the dosages described in FIG. 20. After one hour, the fluorescent positive cells were counted using a stereoscopic microscope at the site of the intradermal injections.

Both HC2/LK3 and HC2/LC3 significantly inhibited cell migration to the CCL20-injected sites at a level comparable to that of parental mouse antibody 36F7C10 and its chimeric form. Because the chemotaxis of T cells is a key step in the inflammatory cascade, prevention of this migration has clinical implications for the treatment of autoimmune and inflammatory conditions.

Example 11: Effect of 2F5-5 MAb on Type II Collagen-Induced Arthritis

Figure 21:
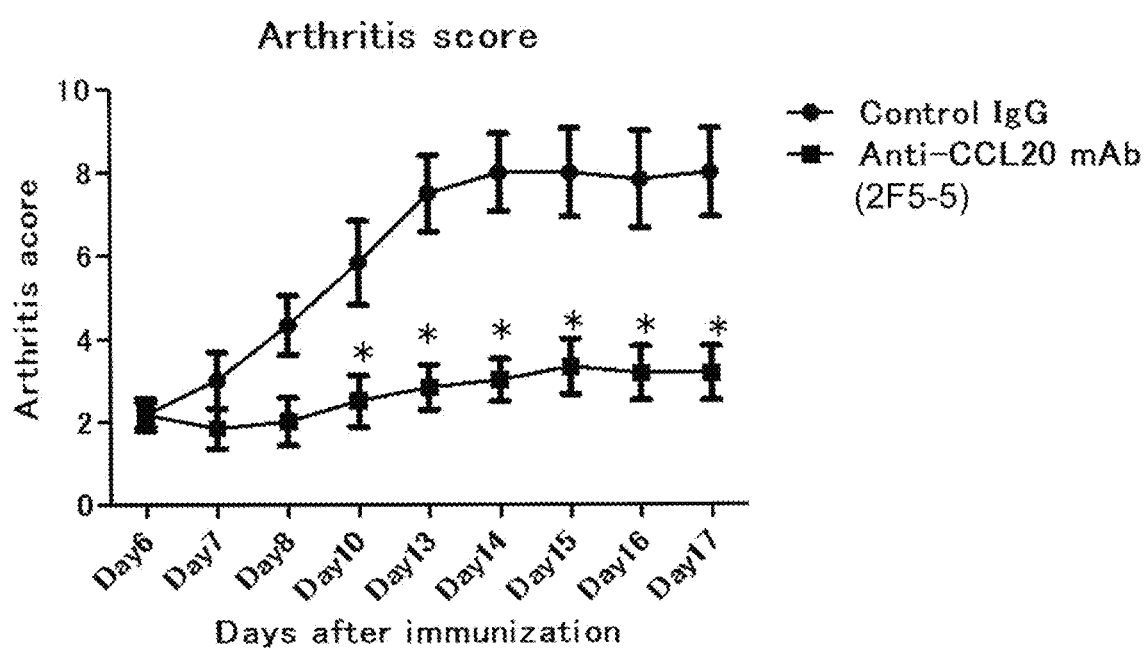
FIG. 21 is a graph showing that hamster anti-mouse CCL 20 MAb 2F5-5 reduces collagen-induced arthritis symptoms in mice. See Example 11.

To further evaluate the use of anti-CCL20 antibodies for therapeutic indications, we performed further in vivo studies in mice using the hamster anti-mouse 2F5-5 MAb. First, we evaluated the ability of 2F5-5 to neutralize CCL20-mediated chemotaxis in CIA mice (an animal model of rheumatoid arthritis). CIA was induced essentially as described in Example 1. After the development of arthritis (arthritis score 1-3), mice were randomized and treated with 500 µg/mouse of either 2F5-5 MAb or a control IgG antibody. In both cases, the antibody was administered intravenously every other day. Compared to the control IgG, 2F5-5 MAb inhibited the further development of arthritis symptoms (FIGS. 21, 22).

Figure 23:
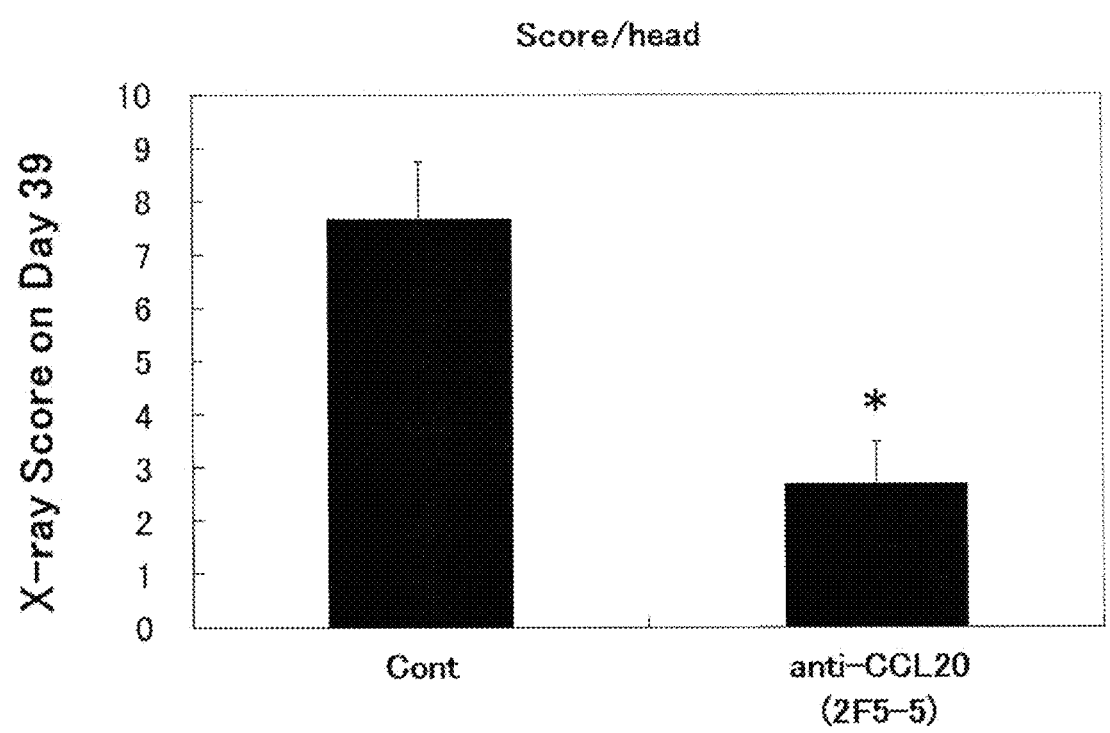
FIG. 23 is a graph depicting the grading of mouse paws by X-ray scoring. 2F5-5 MAb is shown to reduce bone pathology in mice with collagen-induced arthritis. Cont: control IgG. See Example 11.
Figure 24:
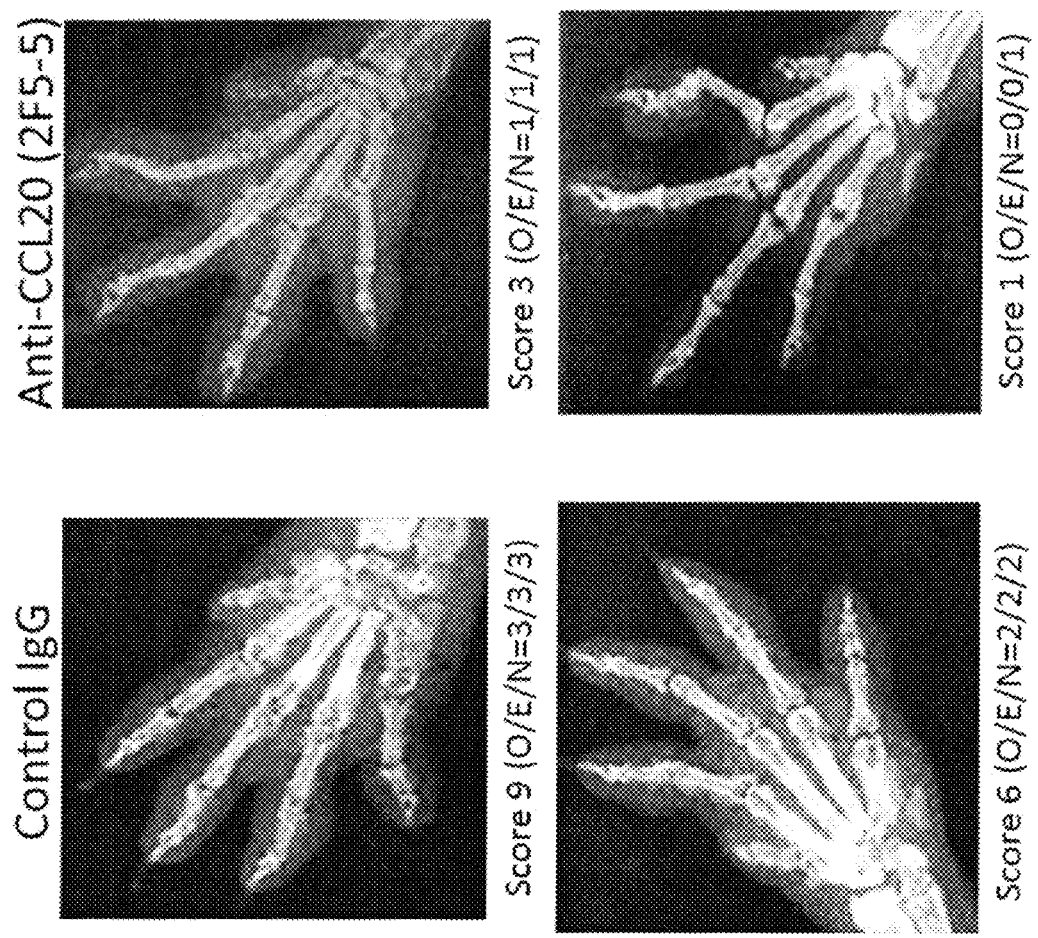
FIG. 24 depicts examples of scored X-rays indicating bone pathology in the paws of mice with collagen-induced arthritis. O: osteoporosis, E: bone erosion, N: new bone formation. See Example 11.

We also used X-ray scoring to determine the effects of 2F5-5 MAb on bone lesions, which are frequently seen in rheumatoid arthritis. Scoring was performed as described in Inoue et al., *Agents Actions* 39:187-194 (1993). Briefly, each paw of a CIA mouse was graded on a scale of 0 to 3 based on the severity of osteoporosis (O), bone erosion (E), and new bone formation (N) according to X-ray images. The scale used was: 0, no change; 1, slight change; 2, moderate change; and 3, severe change. The scores for each factor were added to develop a cumulative X-ray score for bone lesions. Mice treated with 2F5-5 MAb demonstrated remarkably less severe X-ray scores on day 39, as compared to mice treated with a control IgG (FIGS. 23, 24).

Figure 25A:
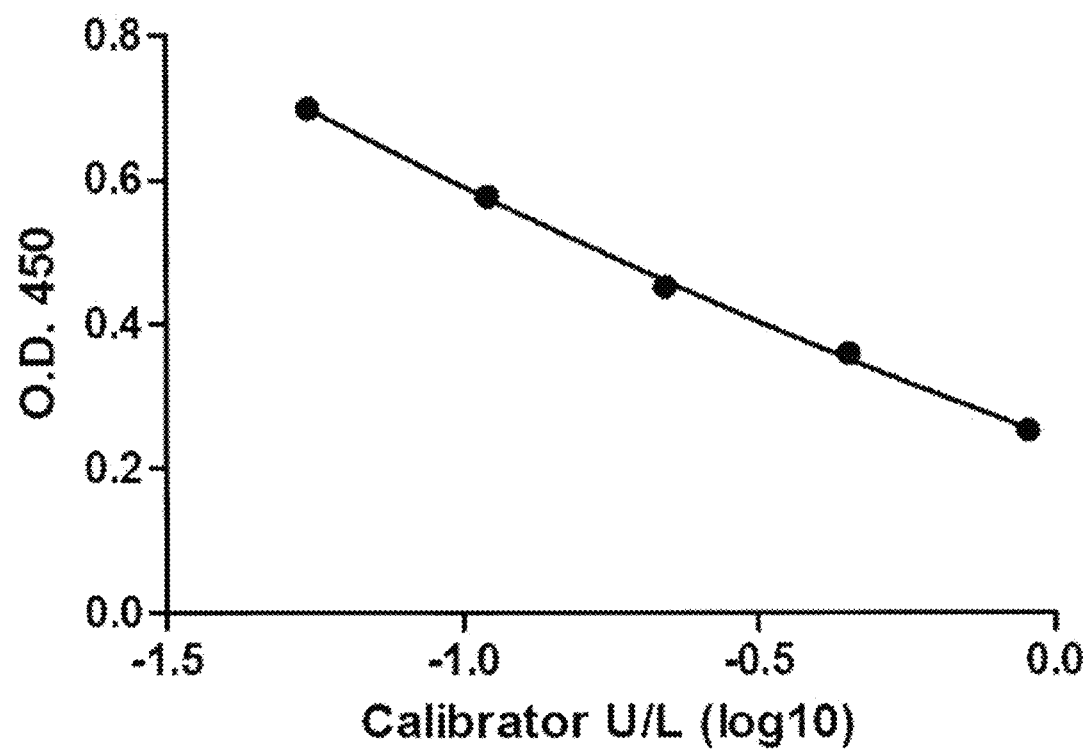
Figure 25C:
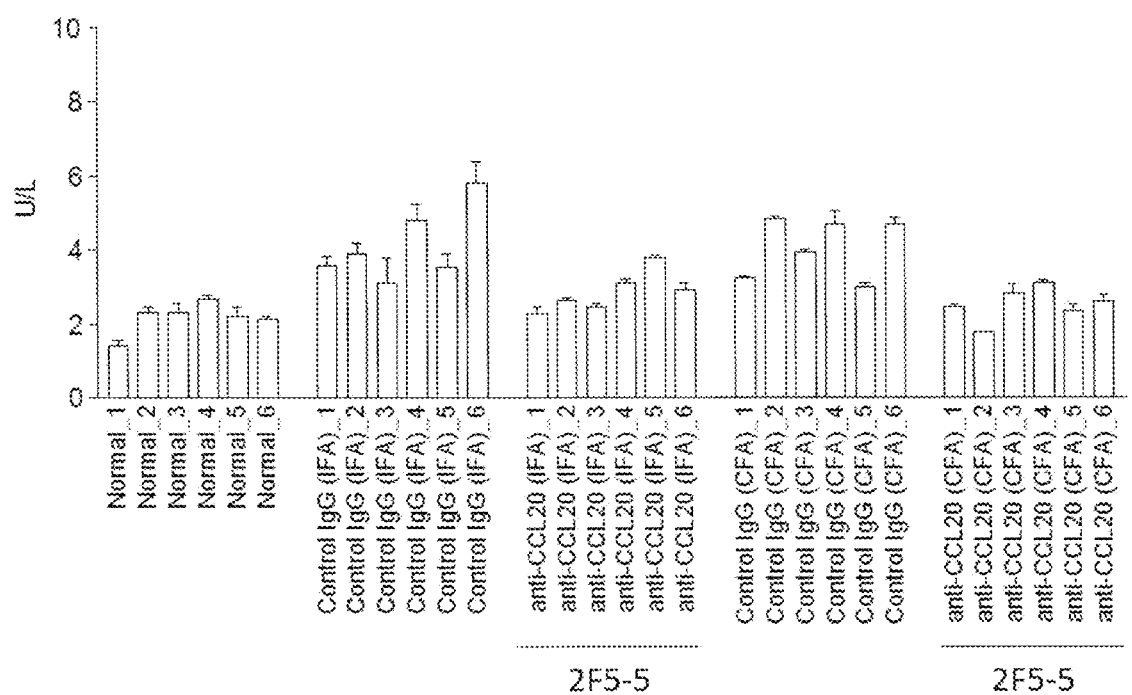
Figure 26:
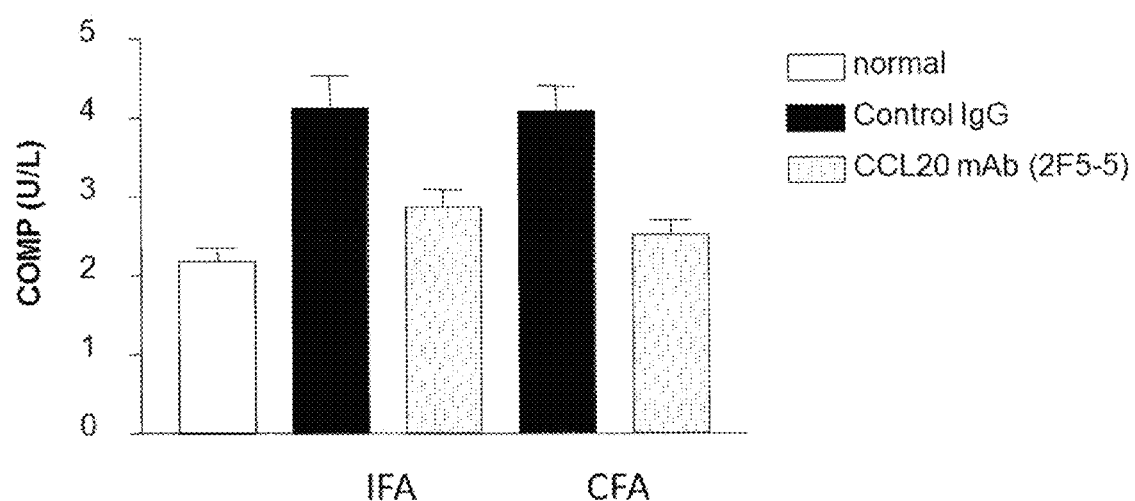
FIG. 26 is a graph showing that 2F5-5 MAb decreases serum levels of COMP in mice. Ctrl IgG: isotype-matched antibody; CCL20 mAb: 2F5-5 MAb. See Example 11.

We confirmed the effect of 2F5-5 MAb treatment on bone pathology by analyzing several biomarkers using ELISA. CIA mice were immunized and treated with 500 µg of 2F5-5 or control IgG antibody as described above. Plasma samples were prepared from the mice on day 11 or 12 after the second immunization. A marker of cartilage destruction, serum cartilage oligomeric matrix protein (COMP), was quantified using the Animal COMP ELISA Enzyme immunoassay kit (AnaMar Medical) according to the manufacturer's instructions (incorporated herein by reference), except that animal plasma samples were diluted 1:20. Because COMP is pre-coated on the plate, this is a competition ELISA, whereby addition of the COMP standard or COMP-containing plasma results in a decrease in $OD_{450}$ (FIG. 25A). Raw data from a sample assay is shown in FIGS. 25B and 25C. COMP serum levels in CIA mice were reduced almost to normal levels by treatment with 2F5-5 MAb (FIG. 26), demonstrating the ability of 2F5-5 to inhibit cartilage destruction.

Because the formation and differentiation of osteoclasts is responsible for RA-related osteoporosis and erosion, we measured the levels of osteoclast induction molecule receptor activator for nuclear factor κB ligand (RANKL), and osteoclast markers such as the receptor activator for nuclear factor κB (RANK), tartrate resistant acid phosphatase (TRAP), and cathepsin K, as indicators for arthritic therapy. We evaluated mRNA expression levels of these markers by quantitative PCR using total RNA isolated from homogenized mouse paws. The paws were first homogenized with a homogenizer after soaking in a tissue lysing buffer containing Trizol reagent (Invitrogen, CA, USA). After adding chloroform, samples were centrifuged at 14,000 rpm for 15 minutes at 4° C. to separate the solution into aqueous and organic phases. The aqueous phase was removed and isopropanol added to it, followed by centrifugation at 14,000 rpm for 15 minutes at 4° C. to obtain RNA pellets. RNA pellets dissolved with RNAse free water were used in an RNAeasy mini kit (QIAGEN, Valencia, Calif., USA) to isolate the RNA and treated with DNAse to remove any DNA. Complimentary DNA (cDNA) was generated from the RNA with an RT reaction kit (RNA PCR Kit, TAKARA Bio, Inc. Shiga, Japan) according to the manufacturer's protocol. Quantitative real time PCR for each cDNA species was performed and compared to the level of a housekeeping gene, hypoxanthine guanine phosphoribosyl transferase (HPRT). The following forward and reverse primer sets were used in the PCR reactions:

```
RANKL,
                                 (SEQ ID NO: 89)
5'-CATTTGCACACCTCACCATC-3'
and (SEQ ID NO: 90)
5'-TCCGTTGCTTAACGTCATGT-3';

RANK,
                                 (SEQ ID NO: 91)
5'-CGGCGTTTACTACAGGAAGG-3'
and (SEQ ID NO: 92)
5'-TTCTTGCTGACTGGAGGTTG-3';

TRAP,
                                 (SEQ ID NO: 93)
5'-GCTGGAAACCATGATCACCT-3'
and (SEQ ID NO: 94)
5'-GGTAGTAAGGGCTGGGGAAG-3';

Cathepsin K,
                                 (SEQ ID NO: 95)
5'-CAGTGTTGGTGGTGGGCTAT-3'
and (SEQ ID NO: 96)
5'-CCGAGCCAAGAGAGCATATC-3';
and HPRT,
                                 (SEQ ID NO: 97)
5'-CAGGCCAGACTTTGTTGGAT-3'
and (SEQ ID NO: 98)
5'-TTGCGCTCATCTTAGGCTTT-3'.
```

All primers were designed using web-based software Primer 3 (Whitehead Institute for Biomedical Research, Cambridge, Mass., USA) to avoid non-specific amplification of RNA. Reaction mixtures with cDNA template, primers, uracil DNA glycosylase (Invitrogen, CA, USA), and QuantiTect SYBR Green PCR Master Mix (QIAGEN, Valencia, Calif., USA) were used in the amplification reaction in an ABI PRISM 7700 Sequence Detection System (Applied Biosystems, Foster, Calif., USA). Expression levels were automatically quantified by ABI PRISM 7700 Sequence Detector Software.

Figure 27A:
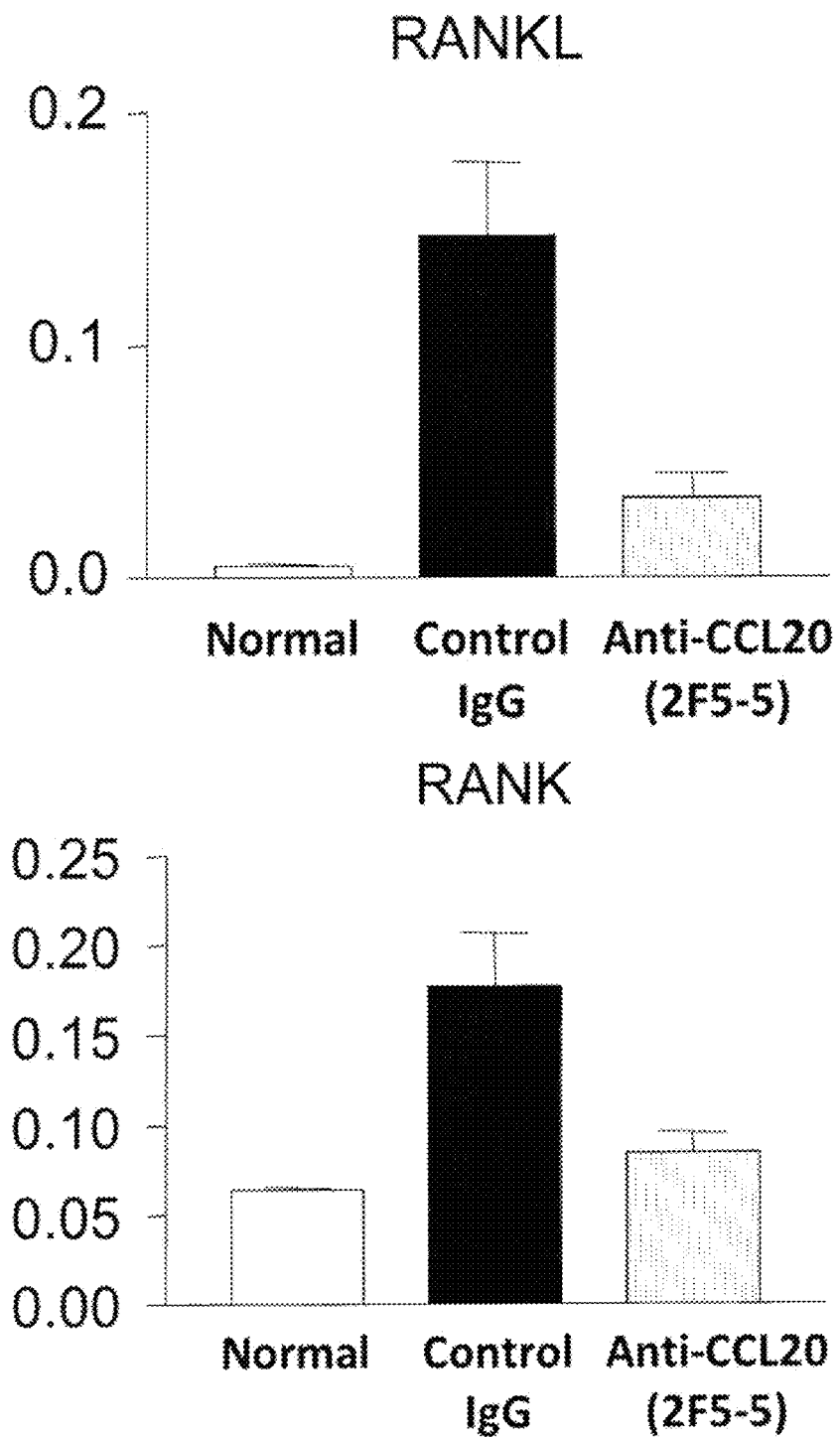
FIGS. 27A and B are graphs showing that 2F5-5 MAb reduces mRNA expression of osteoclast markers A) RANKL and RANK, and B) TRAP and Cathepsin K. Ctrl IgG: isotype-matched antibody; CCL20 mAb: 2F5-5MAb; Y axis: quantitative PCR units. See Example 11.
Figure 27B:
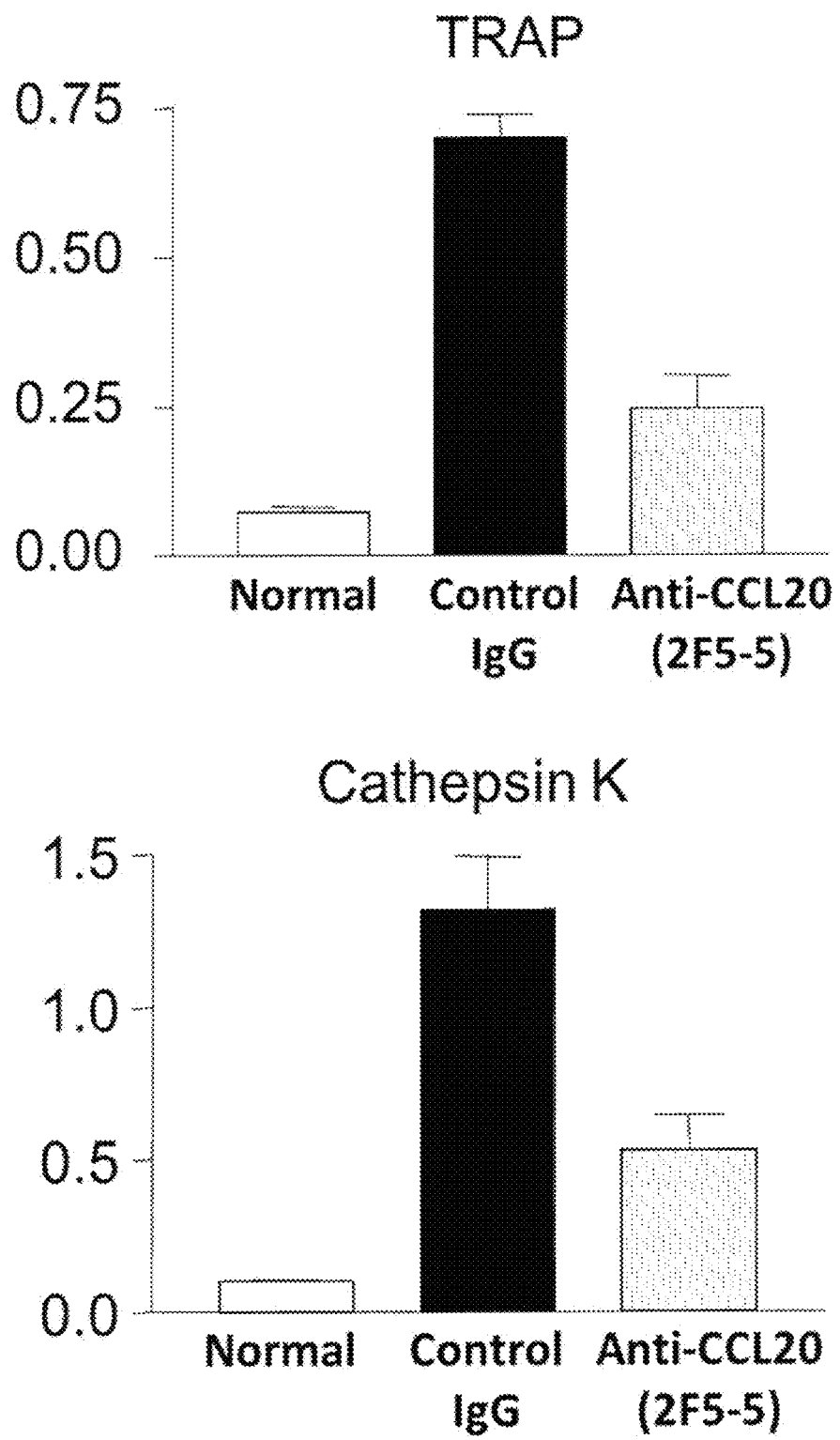

Following 2F5-5 MAb treatment, mRNA levels were suppressed for all markers in the joint tissue (FIGS. 27A and B; show fold change in expression level compared to housekeeping gene HPRT), providing further evidence that 2F5-5 inhibits bone pathology in vivo.

Figure 28:
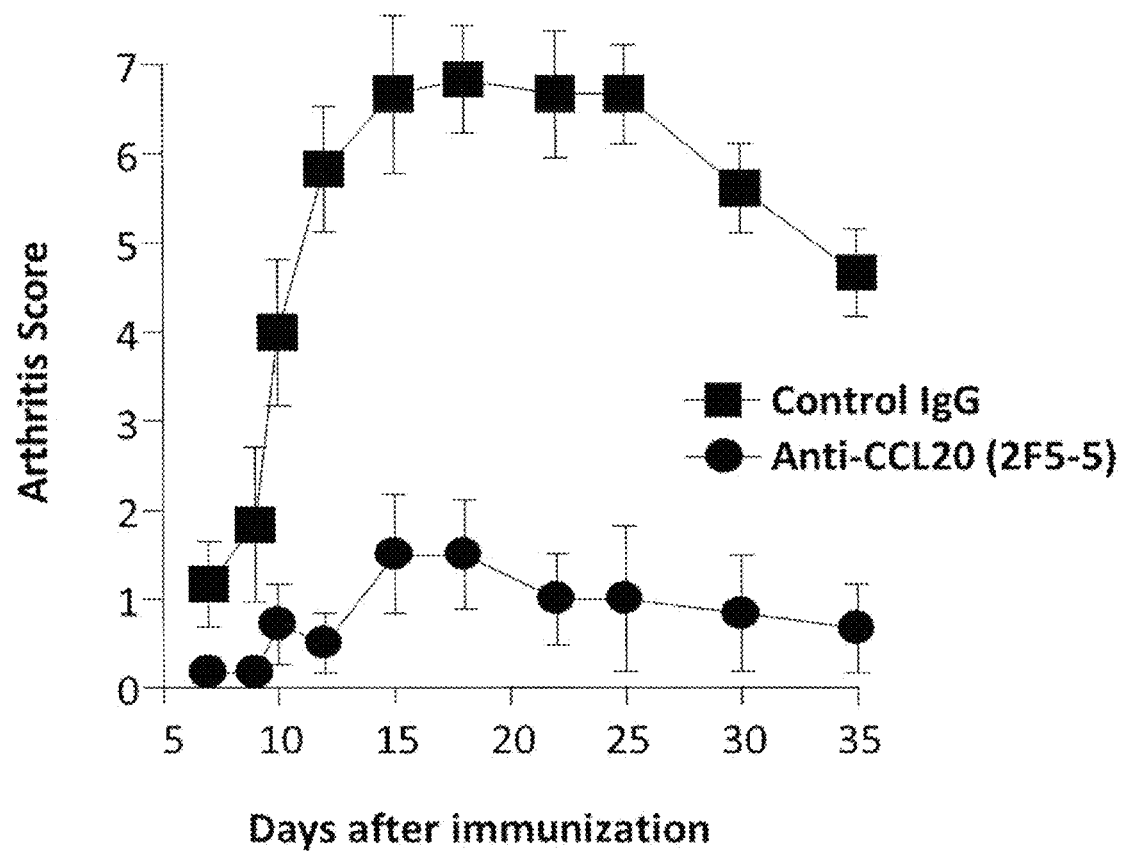
FIG. 28 is a graph showing that 2F5-5 MAb has a prophylactic effect on glucose-6-phosphate isomerase-induced arthritis in mice. See Example 12.

Example 12: Effects of 2F5-5 MAb on Glucose-6-Phosphate Isomerase-Induced Arthritis We tested the anti-arthritic effects of 2F5-5 MAb treatment in mice with glucose-6-phosphate isomerase (G6PI)-induced arthritis, another mouse model for RA. Arthritis was induced by intradermal sensitization with recombinant GST-G6PI (300 μg/mouse) emulsified in complete Freund's adjuvant and injected at the base of the tail of DBA/1 mice. Six days after the G6PI immunization and just prior to the onset of joint swelling, mice were randomized and treated with 500 fig/mouse of either isotype-matched antibody or 2F5-5 MAb. The severity of arthritic symptoms in the paws of each mouse was graded as described previously in Example 1. Mice treated with 2F5-5 MAb exhibited significantly lower arthritic scores than mice treated with isotype-matched antibodies, showing that 2F5-5 strongly suppresses arthritis development compared to the control (FIG. 28).

These data demonstrate the efficacy of anti-CCL20 antibody treatment in in vivo arthritis models, and suggest that the use of anti-CCL20 antibodies may be beneficial in the treatment of rheumatoid arthritis.

Example 13: Effect of 2F5-5 MAb on Oxazolone-Induced Atopic Dermatitis

Figure 29:
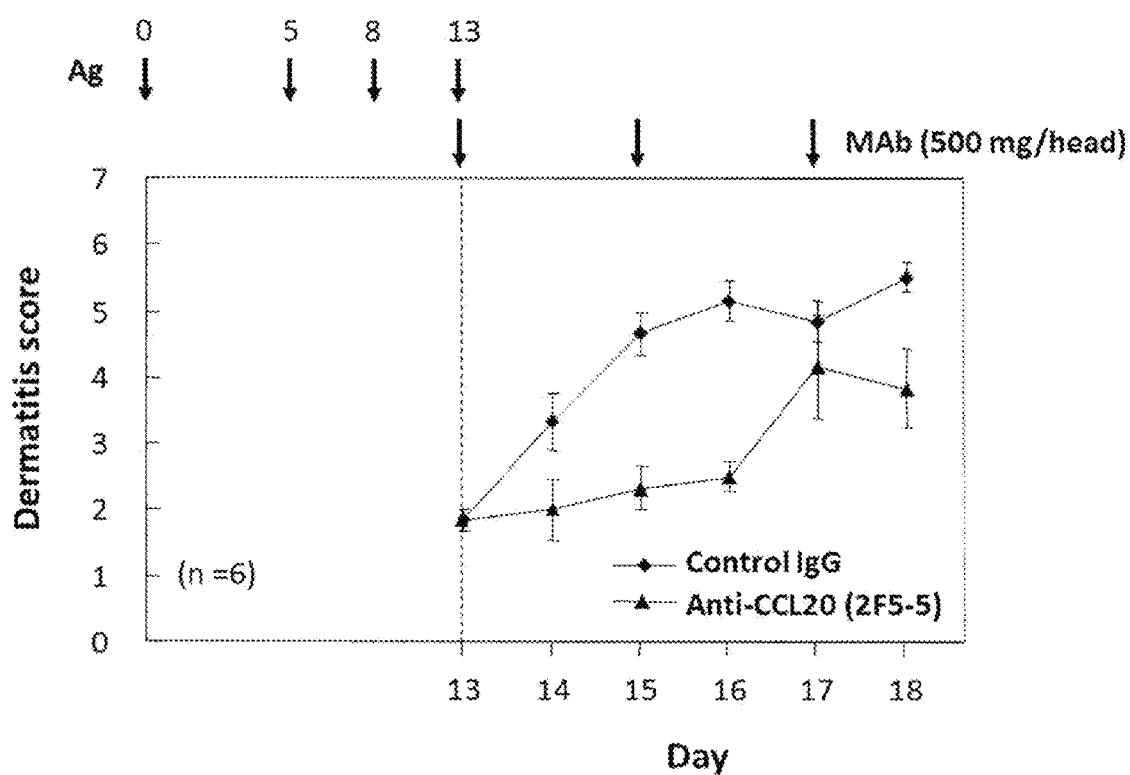
FIG. 29 is a graph showing that 2F5-5 MAb suppresses the progression of oxazolone-induced atopic dermatitis in mice. See Example 13.

We then evaluated the effect of 2F5-5 MAb treatment in mouse models of dermatitis. In one model, oxazolone was used to induce atopic dermatitis in mice prone to the disease (NC/Nga strain). The abdominal skin of the mice was shaved and exposed to oxazolone on days 0, 5, and 8. On day 13, mice showing signs of dermatitis (score 2) were selected and immunized again with oxazolone. Mice were thereafter randomized in groups of six for treatment with either 2F5-5 MAb or an isotype-matched control IgG antibody (500 μg/mouse, administered intravenously every other day). We assayed dermatitis scores in a blind study as follows: each dermatitis symptom such as dryness, scale, erythema, oozing/crusting, and excoriation was scored on a scale of 0 to 3 (0=none, 1=slight, 2=moderate, 3=severe); these scores were then added for a cumulative dermatitis score (as described in Leung et al., *J. Allergy Clin. Immunol.* 85(5): 927-933 (1990)). We compared the magnitude of disease suppression between the two groups by quantifying the area under the curve ("AUC") from day 13 to day 18. In this dermatitis model, 2F5-5 MAb induced a statistically significant (p<0.05) suppression of disease progression compared to control IgG (FIG. 29).

Example 14: Effect of 2F5-5 MAb on DNFB-Induced Allergic Contact Dermatitis

Figure 30:
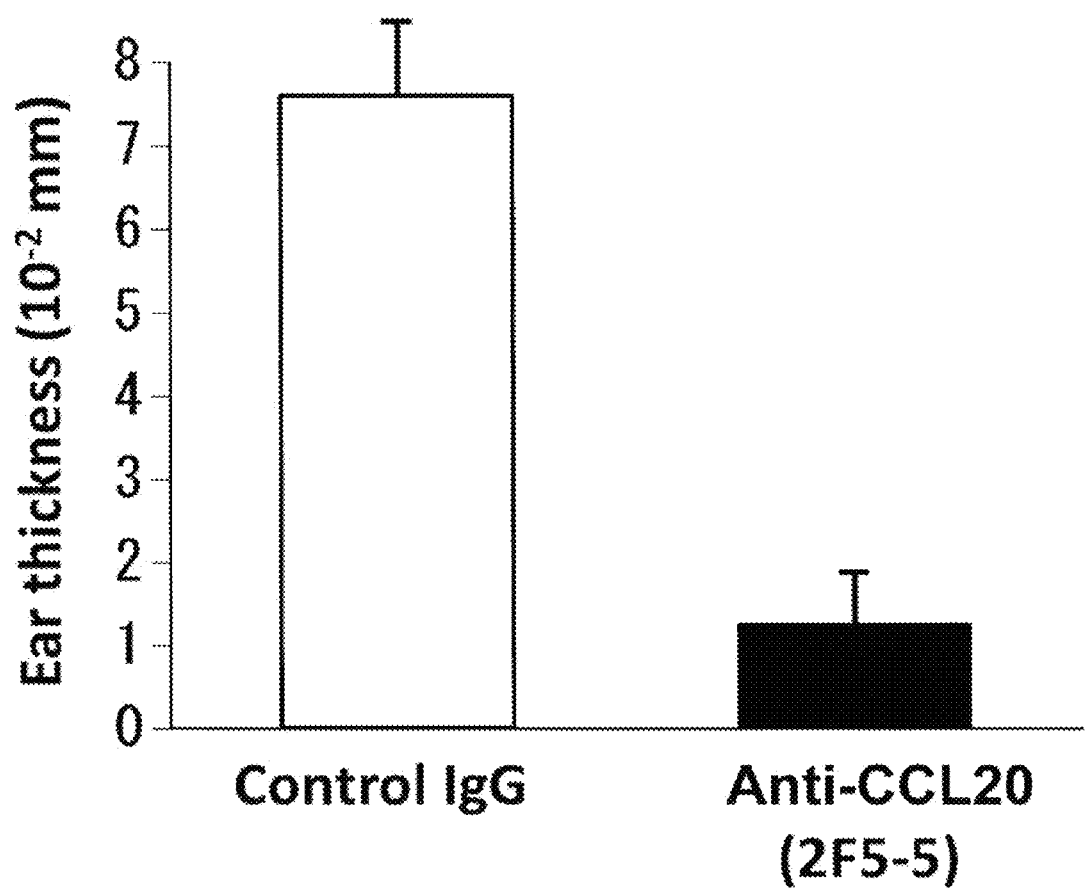
FIG. 30 is a graph showing that 2F5-5 MAb inhibits dinitrofluorobenzene-induced allergic contact dermatitis (as measured by ear thickness) in mice. See Example 14.

We tested the effect of 2F5-5 MAb treatment in dinitrofluorobenzene (DNFB)-induced allergic contact dermatitis, a second mouse model of dermatitis. Mice were divided into groups of 6 and sensitized by brushing 25 μl of DNFB solution (0.4% DNFB in a 4:1 solution of acetone:olive oil) on the shaved abdomen for two successive days (days 0 and 1). One group was treated with 2F5-5 MAb, while the other group was treated with an isotype-matched control antibody (500 μg/mouse intravenously on days 0, 2, and 5). On day 5, the mice were re-challenged by applying 20 μl of 0.2% DNFB solution (in 4:1 acetone:olive oil) to one side of one ear. Ear thickness was measured as an indicator of edema on day 6 using a thickness gauge. Treatment with 2F5-5 MAb reduced car thickness, indicating successful prevention of dermatitis development (FIG. 30).

All publications, patents, and patent applications cited in this specification are incorporated herein by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 18

Amino acid and nucleotide sequences for human and mouse CCL20 and CCR6

| Description | Sequence Type | Sequence (signal sequences underlined) | SEQ ID NO: |
|---|---|---|---|
| Human CCL20 with signal sequence | Amino Acid | mcctkslllaalmsvlllhlcgeseaasnfdcclgytdri lhpkfivgftrqlanegcdinaiifhtkkklsvcanpkqt wykyivrllskkvknm | 85 |
| | Nucleotide | atgtgctgtaccaagagtttgctcctggctgctttgatgt cagtgctgctactccacctctgcggcgaatcagaagcagc aagcaactttgactgctgtcttggatacacagaccgtatt cttcatcctaaatttattgtgggcttcacacggcagctgg ccaatgaaggctgtgacatcaatgctatcatctttcacac aaagaaaagttgtctgtgtgcgcaaatccaaaacagact tgggtgaaatatattgtgcgtctcctcagtaaaaaagtca agaacatg | 101 |
| Human CCL20 without signal sequence | Amino Acid | asnfdcclgytdrilhpkfivgftrqlanegodinaiifh tkkklsvcanpkqtwvkyivrllskkvknm | 99 |
| | Nucleotide | gcaagcaactttgactgctgtcttggatacacagaccgta ttcttcatcctaaatttattgtgggcttcacacggcagct ggccaatgaaggctgtgacatcaatgctatcatctttcac | 100 |

TABLE 18-continued

Amino acid and nucleotide sequences
for human and mouse CCL20 and CCR6

| Description | Sequence Type | Sequence (signal sequences underlined) | SEQ ID NO: |
|---|---|---|---|
| | | acaaagaaaaagttgtctgtgtgcgcaaatccaaaacaga<br>cttgggtgaaatatattgtgcgtctcctcagtaaaaaagt<br>caagaacatg | |
| Mouse CCL20 with signal sequence | Amino Acid | macqgkrliflalawvllahlcsqaeaasnydcclsyiqt<br>plpsraivgftrqmadeacdinaiifhtkkrksvcadpkq<br>nwvkravnllslrvkkm | 102 |
| | Nucleotide | atggcctgcggtggcaagcgtctgctcttccttgctttgg<br>catgggtactgctggctcacctctgcagccaggcagaagc<br>agcaagcaactacgactgttgcctctcgtacatacagacg<br>cctcttccttccagagctattgtgggtttcacaagacaga<br>tggccgatgaagcttgtgacattaatgctatcatctttca<br>cacgaagaaaagaaatctgtgtgcgctgatccaaagcag<br>aactgggtgaaaagggctgtgaacctcctcagcctaagag<br>tcaagaagatg | 103 |
| Human CCR6 | Amino Acid | msgesmnfsdvfdssedyfvsvntsyysvdsemllcslqe<br>vrqfsrlfvpiayslicvfgllgnilvvitfafykkarsm<br>tdvyllnmaiadilfvltlpfwayshatgawvfsnatckl<br>lkgiyainfncgmllltcismdryiaivqatksfrlrsrt<br>lprskiiclvvwglsviisssstfvfnqkyntqgsdvcepk<br>yqtvsepirwkllmlglellfgffiplmfmifcytfivkt<br>lvqaqnskrhkairviiavvlvflacqiphnmvllvtaan<br>lgkmnrscqsekligytktvtevlaflhcclnpvlyafig<br>qkfrnyflkilkdlwcvrrkykssgfscagrysenisrqt<br>setadndnassftm | 104 |
| | Nucleotide | atgagcggggaatcaatgaatttcagcgatgttttcgact<br>ccagtgaagattattttgtgtcagtcaatacttcatatta<br>ctcagttgattctgagatgttactgtgctccttgcaggag<br>gtcaggcagttctccaggctatttgtaccgattgcctact<br>ccttgatctgtgtctttggcctcctggggaatattctggt<br>ggtgatcacctttgctttttataagaaggccaggtctatg<br>acagacgtctatctcttgaacatggccattgcagacatcc<br>tctttgttcttactctcccattctgggcagtgagtcatgc<br>caccggtgcgtgggttttcagcaatgccacgtgcaagttg<br>ctaaaaggcatctatgccatcaactttaactgcgggatgc<br>tgctcctgacttgcattagcatggaccggtacatcgccat<br>tgtacaggcgactaagtcattccggctccgatccagaaca<br>ctaccgcgcagcaaaatcatctgccttgttgtgtgggggc<br>tgtcagtcatcatctccagctcaacttttgtcttcaacca<br>aaaatacaacacccaaggcagcgatgtctgtgaacccaag<br>taccagactgtctcggagcccatcaggtggaagctgctga<br>tgttggggcttgagctactctttggtttctttatccctt<br>gatgttcatgatatttgttacacgttcattgtcaaaacc<br>ttggtgcaagctcagaattctaaaaggcacaaagccatcc<br>gtgtaatcatagctgtggtgcttgtgtttctggcttgtca<br>gattcctcataacatggtcctgcttgtgacggctgcaaat<br>ttgggtaaaatgaaccgatcctgccagagcgaaaagctaa<br>ttggctatacgaaaactgtcacagaagtcctggctttcct<br>gcactgctgcctgaaccctgtgctctacgctttattggg<br>cagaagttcagaaactactttctgaagatcttgaaggacc<br>tgtggtgtgagaaggaagtacaagtcctcaggcttctc<br>ctgtgccgggaggtactcagaaaacatttctcggcagacc<br>agtgagaccgcagataacgacaatgcgtcgtccttcacta<br>tg | 105 |
| Mouse CCR6 | Amino Acid | mnstesyfgtddydnteyysippdhgpcsleevrnftkvf<br>vpiayslicvfgllgnimvvmtfafykkarsmtdvyllnm<br>aitdilfvltlpfwavthatntwvfsdalcklmkgtyavn<br>fncgmlllacismdryiaivqatksfrvrsrtlthskvic<br>vavwfisiiisssptfifnkkyelqdrdvcepryrsysepi<br>twkllgmglelffgfftpllfmvfcylfiiktivqaqnsk<br>rhrairvviavvlvflacqiphnmvllvtavntgkvgrsc<br>stekvlaytrnvaevlaflhcclnpvlyafigqkfrnyfm<br>kimkdvwcmrrknkmpgflcarvysesyisrqtsetvend<br>nassftm | 106 |
| | Nucleotide | atgaattccacagagtcctactttggaacggatgattatg<br>acaacacagagtattattctattcctccagaccatgggcc<br>atgctcccttagaagaggtcagaaacttcaccaaggtattt<br>gtgccaattgcctactccttaatatgtgtctttggcctcc<br>tgggcaacattatggtggtgatgacctttgccttctacaa<br>gaaagccagatccatgactgacgtctacctgttgaacatg<br>gccatcacagacatactctttgtcctcaccctaccgttct<br>gggcagttactcatgccaccaacacttgggttttcagcga | 107 |

TABLE 18-continued

Amino acid and nucleotide sequences
for human and mouse CCL20 and CCR6

| Description | Sequence Type | Sequence (signal sequences underlined) | SEQ ID NO: |
|---|---|---|---|
| | | tgcactgtgtaaactgatgaaaggcacatatgcggtcaac<br>tttaactgtgggatgctgctcctggcctgtatcagcatgg<br>accggtacattgccatcgtccaggcaaccaaatctttccg<br>ggtacgctccagaacactgacgcacagtaaggtcatctgt<br>gtggcagtgtggttcatctccatcatcatctcaagcccta<br>catttatcttcaacaagaaatacgagctgcaggatcgtga<br>tgtctgtgagccacggtacaggtctgtctcagagcccatc<br>acgtggaagctgctgggtatgggactggagcgttctttg<br>ggttcttcaccccttgctgtttatggtgttctgctatct<br>gttcattatcaagaccttggtgcaggcccagaactccaag<br>aggcacagagcaatccgagtcgtgatcgctgtggttctcg<br>tgttcctggcttgtcagatccctcacaacatggtcctcct<br>cgtgactgcggtcaacacgggcaaagtgggccggagctgc<br>agcaccgagaaagtcctcgcctacaccaggaacgtggccg<br>aggtcctggctttcctgcattgctgcctcaaccccgtgtt<br>gtatgcgtttattggacagaaattcagaaactacttcatg<br>aagatcatgaaggatgtgtggtgtatgagaaggaagaata<br>agatgcctggcttcctctgtgcccgggtttactcggaaag<br>ctacatctccaggcagaccagtgagaccgtcgaaaatgat<br>aatgcatcgtcctttaccatg | |

TABLE 19

Sequence Identification Numbers

| SEQ ID NO | | Description | |
|---|---|---|---|
| 1 | HC2 | Full-Length | Amino Acid |
| 2 | HC3 | Heavy Chain | Sequence |
| 3 | 36HKK3 | (HC) | |
| 4 | 42HKK1 | | |
| 5 | 42HKK2 | | |
| 6 | 42HKK3 | | |
| 7 | LC3 | Full-Length | |
| 8 | LK3 | Light Chain | |
| 9 | HC2 | (LC) | |
| 10 | HC3 | | |
| 11 | 36HKK3 | Heavy Chain | |
| 12 | 42HKK1 | Variable | |
| 13 | 42HKK2 | Domain (VH) | |
| 14 | 42HKK3 | | |
| 15 | LC3 | Light Chain Variable | |
| 16 | LK3 | Domain (VL) | |
| 17 | HC2 | Full-Length | Nucleotide |
| 18 | HC3 | Heavy Chain | Sequence |
| 19 | 36HKK3 | (HC) | |
| 20 | 42HKK1 | | |
| 21 | 42HKK2 | | |
| 22 | 42HKK3 | | |
| 23 | LC3 | Full-Length | |
| 24 | LK3 | Light Chain (LC) | |
| 25 | HC2 | Heavy Chain | |
| 26 | HC3 | Variable | |
| 27 | 36HKK3 | Domain (VH) | |
| 28 | 42HKK1 | | |
| 29 | 42HKK2 | | |
| 30 | 42HKK3 | | |
| 31 | LC3 | Light Chain Variable | |
| 32 | LK3 | Domain (VL) | |
| 33 | 36F7C10 | Heavy Chain Signal Sequence | Amino Acid |
| 34 | | Light Chain Signal Sequence | Sequence |
| 35 | 40-1C10B9 | Heavy Chain Signal Sequence | |
| 36 | | Light Chain Signal Sequence | |
| 37 | 42G5B10 | Heavy Chain Signal Sequence | |
| 38 | | Light Chain Signal Sequence | |
| 39 | 36F7C10 | VH | |
| 40 | | VL | |

TABLE 19-continued

Sequence Identification Numbers

| SEQ ID NO | Description | | |
|---|---|---|---|
| 41 | 40-1C10B9 | VH | |
| 42 | | VL | |
| 43 | 42G5B10 | VH | |
| 44 | | VL | |
| 45 | 36F7C10 | Heavy Chain Signal Sequence | Nucleotide |
| 46 | | Light Chain Signal Sequence | Sequence |
| 47 | 40-1C10B9 | Heavy Chain Signal Sequence | |
| 48 | | Light Chain Signal Sequence | |
| 49 | 42G5B10 | Heavy Chain Signal Sequence | |
| 50 | | Light Chain Signal Sequence | |
| 51 | 36F7C10 | VH | |
| 52 | | VL | |
| 53 | 40-1C10B9 | VH | |
| 54 | | VL | |
| 55 | 42G5B10 | VH | |
| 56 | | VL | |
| 57 | | IGHV1-46*03 Germline Sequence | |
| 58 | | JH4 Germline Sequence | |
| 59 | | IGKV1D-39*01 Germline Sequence | |
| 60 | Mouse 36F7C10<br>HC2<br>HC3<br>36HKK3 | H-CDR1<br>(Kabat) | NYWMH |
| 61 | Mouse 42G5B10<br>42HKK1<br>42HKK2<br>42HKK3 | | SYWMH |
| 62 | IGHV1-46*03/<br>ABM67212 | | SYYMH |
| 63 | Mouse 36F7C10<br>HC3<br>36HKK3 | H-CDR2<br>(Kabat) | VIDPSDSYTTYNQKFKG |
| 64 | HC2 | | VIDPSDSYTTYAQKFQG |
| 65 | Mouse 42G5B10<br>42HKK1<br>42HKK2<br>42HKK3 | | LIDPSDKYTNYNQKFKG |
| 66 | IGHV1-46*03/<br>ABM67212 | | IINPSGGSTSYAQKFQG |
| 67 | Mouse 36F7C10<br>HC2<br>HC3<br>36HKK3 | H-CDR3<br>(Kabat or Chothia) | GNYGVDYAMDY |
| 68 | Mouse 42G5B10<br>42HKK1<br>42HKK2<br>42HKK3 | | GNYGVDYGMDY |
| 69 | ABM67212 | | EGDGYIQAFDY |
| 70 | Mouse 36F7C10<br>LK3 | L-CDR1<br>(Kabat or Chothia) | GASENIYGALN |
| 71 | LC3 | | RASENIYGALN |
| 72 | IGKV1D-39*01/<br>BAH04867.1 | | RASQSISSYLN |
| 73 | Mouse 36F7C10<br>LC3<br>LK3 | L-CDR2<br>(Kabat or Chothia) | GATNLAD |
| 74 | IGKV1D-39*01/<br>BAH04867.1 | | AASSLQS |
| 75 | Mouse 36F7C10<br>LC3<br>LK3 | L-CDR3<br>(Kabat or Chothia) | QNVLITPYT |
| 76 | BAH04867.1 | | QQSYSTPYT |
| 77 | Mouse 36F7C10<br>HC2<br>HC3<br>36HKK3 | H-CDR1<br>(Chothia) | GYTFTNY |

TABLE 19-continued

Sequence Identification Numbers

| SEQ ID NO | Description | | |
|---|---|---|---|
| 78 | Mouse 42G5B10<br>42HKK1<br>42HKK2<br>42HKK3<br>IGHV1-46*03/<br>ABM67212 | | GYTFTSY |
| 79 | Mouse 36F7C10<br>HC2<br>HC3<br>36HKK3 | H-CDR2<br>(Chothia) | VIDPSDSYTT |
| 80 | Mouse 42G5B10<br>42HKK1<br>42HKK2<br>42HKK3 | | LIDPSDKYTN |
| 81 | IGHV1-46*03/<br>ABM67212 | | IINPSGGSTS |
| 82 | ABM67212 | VH | |
| 83 | BAH04867.1 | VL | |
| 84 | Human CCL20 variant (without signal sequence) amino acid sequence | | |
| 85 | Human CCL20 (with signal sequence) amino acid sequence | | |
| 86 | Rhesus CCL20 amino acid sequence | | |
| 87 | Cynomolgus CCL20 amino acid sequence | | |
| 88 | Mouse CCL20 amino acid sequence (partial) | | |
| 89 | 5'-CATTTGCACACCTCACCATC-3' | RANKL | Primers |
| 90 | 5'-TCCGTTGCTTAACGTCATGT-3' | | |
| 91 | 5'-CGGCGTTTACTACAGGAAGG-3' | RANK | |
| 92 | 5'-TTCTTGCTGACTGGAGGTTG-3' | | |
| 93 | 5'-GCTGGAAACCATGATCACCT-3' | TRAP | |
| 94 | 5'-GGTAGTAAGGGCTGGGGAAG-3' | | |
| 95 | 5'-CAGTGTTGGTGGTGGGCTAT-3' | Cathepsin K | |
| 96 | 5'-CCGAGCCAAGAGAGCATATC-3' | | |
| 97 | 5'-CAGGCCAGACTTTGTTGGAT-3' | HPRT | |
| 98 | 5'-TTGCGCTCATCTTAGGCTTT-3' | | |
| 99 | Human CCL20 (without signal sequence) amino acid sequence | | |
| 100 | Human CCL20 (without signal sequence) nucleotide sequence | | |
| 101 | Human CCL20 (with signal sequence) nucleotide sequence | | |
| 102 | Mouse CCL20 (with signal sequence) amino acid sequence | | |
| 103 | Mouse CCL20 (with signal sequence) nucleotide sequence | | |
| 104 | Human CCR6 amino acid sequence | | |
| 105 | Human CCR6 nucleotide sequence | | |
| 106 | Mouse CCR6 amino acid sequence | | |
| 107 | Mouse CCR6 nucleotide sequence | | |
| 108 | HC2 full-length amino acid sequence (without signal sequence) | | |
| 109 | HC2 full-length nucleotide sequence (without signal sequence) | | |
| 110 | LC3 full-length amino acid sequence (without signal sequence) | | |
| 111 | LC3 full-length nucleotide sequence (without signal sequence) | | |
| 112 | LK3 full-length amino acid sequence (without signal sequence) | | |

TABLE 19-continued

Sequence Identification Numbers

| SEQ ID NO | Description |
|---|---|
| 113 | LK3 full-length nucleotide sequence (without signal sequence) |
| 114 | partial CCL20 amino acid sequence |
| 115 | partial CCL16 amino acid sequence |

TABLE 20

Humanized and Mouse Antibody Sequences

| | | Amino Acid Sequences | | | | H-CDR | | | L-CDR | | | Nucleotide Sequences | | | |
|---|---|---|---|---|---|---|---|---|---|---|---|---|---|---|---|
| | | HC | LC | VH | VL | 1 | 2 | 3 | 1 | 2 | 3 | HC | LC | VH | VL |
| Humanized Anti-Human CCL20 Ab Chains | HC2 | 1 | | 9 | | K: 60 C: 77 | K: 64 C: 79 | K: 67 C: 67 | | | | 17 | | 25 | |
| | HC3 | 2 | | 10 | | K: 60 C: 77 | K: 63 C: 79 | K: 67 C: 67 | | | | 18 | | 26 | |
| | 36HKK3 | 3 | | 11 | | K: 60 C: 77 | K: 63 C: 79 | K: 67 C: 67 | | | | 19 | | 27 | |
| | 42HKK1 | 4 | | 12 | | K: 61 C: 78 | K: 65 C: 80 | K: 68 C: 68 | | | | 20 | | 28 | |
| | 42HKK2 | 5 | | 13 | | K: 61 C: 78 | K: 65 C: 80 | K: 68 C: 68 | | | | 21 | | 29 | |
| | 42HKK3 | 6 | | 14 | | K: 61 C: 78 | K: 65 C: 80 | K: 68 C: 68 | | | | 22 | | 30 | |
| | LC3 | | 7 | | 15 | | | | 71 | 73 | 75 | | 23 | | 31 |
| | LK3 | | 8 | | 16 | | | | 70 | 73 | 75 | | 24 | | 32 |
| Mouse Anti-Human CCL20 Abs | 36F7C10 | | | 39 | 40 | K: 60 C: 77 | K: 63 C: 79 | K: 67 C: 67 | 70 | 73 | 75 | | | 51 | 52 |
| | 40-1C10B9 | | | 41 | 42 | | | | | | | | | 53 | 54 |
| | 42G5B10 | | | 43 | 44 | K: 61 C: 78 | K: 65 C: 80 | K: 68 C: 68 | | | | | | 55 | 56 |

What is claimed is:

1. A monoclonal anti-human CCL20 antibody or an antigen-binding portion thereof, whose heavy chain complementarity determining region 1 (CDR1), complementarity determining region 2 (CDR2), and complementarity determining region 3 (CDR3) and whose light chain CDR1, CDR2, and CDR3 comprise the amino acid sequences of:
   a) SEQ ID NOS: 60, 64, 67, 70, 73, and 75, respectively;
   b) SEQ ID NOS: 60, 64, 67, 71, 73, and 75, respectively;
   c) SEQ ID NOS: 77, 79, 67, 70, 73, and 75, respectively; or
   d) SEQ ID NOS: 77, 79, 67, 71, 73, and 75, respectively;
   wherein said monoclonal antibody or antigen-binding portion further comprises a detectable label.

2. The antibody or antigen-binding portion of claim 1, wherein the heavy chain variable domain of the antibody comprises the amino acid sequence of SEQ ID NO: 9.

3. The antibody or antigen-binding portion of claim 2, wherein the light chain variable domain of the antibody comprises the amino acid sequence shown in SEQ ID NO: 15 or SEQ ID NO: 16.

4. The antibody or antigen-binding portion of claim 1, wherein:
   the heavy chain of the antibody comprises the amino acid sequence of SEQ ID NO: 108, or the amino acid sequence of SEQ ID NO: 108 without the C-terminal lysine; or
   the light chain of the antibody comprises the amino acid sequence of SEQ ID NO: 110 or 112.

5. The antibody or antigen-binding portion of claim 4, wherein said heavy chain and said light chain comprise amino acid sequences selected from the group consisting of:
   a) SEQ ID NO: 1 and SEQ ID NO: 7, respectively;
   b) SEQ ID NO: 1 and SEQ ID NO: 8, respectively;
   c) SEQ ID NO: 108 and SEQ ID NO: 110, respectively;
   d) SEQ ID NO: 108 and SEQ ID NO: 112, respectively;
   e) SEQ ID NO: 108 without the C-terminal lysine and SEQ ID NO: 110, respectively; and
   f) SEQ ID NO: 108 without the C-terminal lysine and SEQ ID NO: 112, respectively.

6. A monoclonal antibody whose heavy chain and light chain comprise the amino acid sequences of SEQ ID NO: 108 and SEQ ID NO: 110, respectively, wherein said monoclonal antibody further comprises a detectable label.

7. The antibody or antigen-binding portion of any one of claims 2, 5, and 6, wherein said detectable label is selected from the group consisting of: a radioisotope, a positron emitting label, a paramagnetic ion, an epitope label, an affinity label, a spin label, an enzyme, a fluorescent group, and a chemiluminescent group.

\* \* \* \* \*

SEQUENCE LISTING

<160> NUMBER OF SEQ ID NOS: 117

<210> SEQ ID NO 1
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asn Tyr Trp Met His Trp Val Arg Gln Ala Pro Gly Gln Gly Leu
        50                  55                  60

Glu Trp Met Gly Val Ile Asp Pro Ser Asp Ser Tyr Thr Thr Tyr Ala
65                  70                  75                  80

Gln Lys Phe Gln Gly Arg Val Thr Met Thr Val Asp Thr Ser Thr Ser
                85                  90                  95

-continued

Thr Val Tyr Met Glu Leu Ser Ser Leu Arg Ser Glu Asp Thr Ala Val
            100                 105                 110

Tyr Tyr Cys Ala Arg Gly Asn Tyr Gly Val Asp Tyr Ala Met Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 2
<211> LENGTH: 469
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 2

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Lys Gln Ala Pro Gly Gln Gly Leu
    50                  55                  60

Glu Trp Ile Gly Val Ile Asp Pro Ser Asp Ser Tyr Thr Thr Tyr Asn
65                  70                  75                  80

Gln Lys Phe Lys Gly Lys Ala Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Thr Arg Gly Asn Tyr Gly Val Asp Tyr Ala Met Asp Tyr
        115                 120                 125

Trp Gly Gln Gly Thr Ser Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400
```

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 3
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Gly Leu
    50                  55                  60

Glu Trp Met Gly Val Ile Asp Pro Ser Asp Ser Tyr Thr Thr Tyr Asn
65                  70                  75                  80

Gln Lys Phe Lys Gly Lys Ala Thr Leu Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asn Tyr Gly Val Asp Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val

```
                275                 280                 285
Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 4
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Met Gly Leu Ile Asp Pro Ser Asp Lys Tyr Thr Asn Tyr Asn
65                  70                  75                  80

Gln Lys Phe Lys Gly Arg Val Thr Met Thr Arg Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Ala Arg Gly Asn Tyr Gly Val Asp Tyr Gly Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160
```

-continued

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

```
Thr Ser Tyr Trp Met His Trp Val Arg Gln Ala Pro Gly Gln Gly Leu
        50                  55                  60

Glu Trp Met Gly Leu Ile Asp Pro Ser Asp Lys Tyr Thr Asn Tyr Asn
65                  70                  75                  80

Gln Lys Phe Lys Gly Arg Val Thr Leu Thr Val Asp Thr Ser Thr Ser
                85                  90                  95

Thr Val Tyr Met Glu Leu Ser Ser Leu Arg Ser Glu Asp Thr Ala Val
            100                 105                 110

Tyr Tyr Cys Thr Arg Gly Asn Tyr Gly Val Asp Tyr Gly Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460
```

```
Leu Ser Pro Gly Lys
465

<210> SEQ ID NO 6
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Trp Met His Trp Val Arg Gln Ala Pro Gly Gln Gly Leu
    50                  55                  60

Glu Trp Met Gly Leu Ile Asp Pro Ser Asp Lys Tyr Thr Asn Tyr Asn
65              70                  75                  80

Gln Lys Phe Lys Gly Lys Ala Thr Leu Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Thr Arg Gly Asn Tyr Gly Val Asp Tyr Gly Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350
```

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 7
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Glu Asn Ile
        35                  40                  45

Tyr Gly Ala Leu Asn Trp Tyr Gln Gln Lys Pro Gly Lys Ala Pro Lys
    50                  55                  60

Leu Leu Ile Tyr Gly Ala Thr Asn Leu Ala Asp Gly Val Pro Ser Arg
65                  70                  75                  80

Phe Ser Gly Ser Gly Ser Gly Arg Gln Tyr Ser Leu Thr Ile Ser Ser
                85                  90                  95

Leu Gln Pro Glu Asp Phe Ala Thr Tyr Tyr Cys Gln Asn Val Leu Ile
            100                 105                 110

Thr Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys

```
225                 230

<210> SEQ ID NO 8
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Gly Ala Ser
            35                  40                  45

Glu Asn Ile Tyr Gly Ala Leu Asn Trp Tyr Gln Arg Lys Pro Gly Lys
        50                  55                  60

Ala Pro Lys Leu Leu Ile Tyr Gly Ala Thr Asn Leu Ala Asp Gly Val
65                  70                  75                  80

Pro Ser Arg Phe Ser Gly Ser Gly Ser Gly Arg Asp Tyr Thr Leu Thr
                85                  90                  95

Ile Ser Ser Leu Gln Pro Glu Asp Phe Ala Thr Tyr Tyr Cys Gln Asn
                100                 105                 110

Val Leu Ile Thr Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Val Ile Asp Pro Ser Asp Ser Tyr Thr Thr Tyr Ala Gln Lys Phe
```

```
                    50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asn Tyr Gly Val Asp Tyr Ala Met Asp Tyr Trp Gly Gln
            100                 105                 110

Gly Thr Leu Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Met His Trp Val Lys Gln Ala Pro Gly Gln Gly Leu Glu Trp Ile
            35                  40                  45

Gly Val Ile Asp Pro Ser Asp Ser Tyr Thr Thr Tyr Asn Gln Lys Phe
        50                  55                  60

Lys Gly Lys Ala Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Gly Asn Tyr Gly Val Asp Tyr Ala Met Asp Tyr Trp Gly Gln
            100                 105                 110

Gly Thr Ser Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Trp Met His Trp Val Arg Gln Ala Pro Gly Gln Gly Leu Glu Trp Met
            35                  40                  45

Gly Val Ile Asp Pro Ser Asp Ser Tyr Thr Thr Tyr Asn Gln Lys Phe
        50                  55                  60

Lys Gly Lys Ala Thr Leu Thr Val Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Gly Asn Tyr Gly Val Asp Tyr Ala Met Asp Tyr Trp Gly Gln
```

```
                100                 105                 110
Gly Thr Leu Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile Asp Pro Ser Asp Lys Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Gly Val Asp Tyr Gly Met Asp Tyr Trp Gly Gln
            100                 105                 110

Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile Asp Pro Ser Asp Lys Tyr Thr Asn Tyr Asn Gln Lys Phe
    50                  55                  60

Lys Gly Arg Val Thr Leu Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Asn Tyr Gly Val Asp Tyr Gly Met Asp Tyr Trp Gly Gln
            100                 105                 110

Gly Thr Leu Val Thr Val Ser Ser
        115                 120

<210> SEQ ID NO 14
<211> LENGTH: 120
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Leu Ile Asp Pro Ser Asp Lys Tyr Thr Asn Tyr Asn Gln Lys Phe
    50                  55                  60

Lys Gly Lys Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asn Tyr Gly Val Asp Tyr Gly Met Asp Tyr Trp Gly Gln
            100                 105                 110

Gly Thr Leu Val Thr Val Ser Ser
        115                 120
```

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Gln Tyr Ser Leu Thr Ile Ser Ser Leu Gln Pro
65                  70                  75                  80

Glu Asp Phe Ala Thr Tyr Tyr Cys Gln Asn Val Leu Ile Thr Pro Tyr
                85                  90                  95

Thr Phe Gly Gly Gly Thr Lys Leu Glu Ile Lys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30
```

```
Leu Asn Trp Tyr Gln Arg Lys Pro Gly Lys Ala Pro Lys Leu Leu Ile
         35                  40                  45

Tyr Gly Ala Thr Asn Leu Ala Asp Gly Val Pro Ser Arg Phe Ser Gly
     50                  55                  60

Ser Gly Ser Gly Arg Asp Tyr Thr Leu Thr Ile Ser Ser Leu Gln Pro
 65                  70                  75                  80

Glu Asp Phe Ala Thr Tyr Tyr Cys Gln Asn Val Leu Ile Thr Pro Tyr
                 85                  90                  95

Thr Phe Gly Gln Gly Thr Lys Leu Glu Ile Lys
             100                 105
```

<210> SEQ ID NO 17
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atgggctggt cctgcatcat tctgttcctg gtggccactg ctaccggagt gcacagccag      60
gtgcagctgg tgcagtctgg ggctgaggtg aagaaacccg gtgcaagtgt gaaggtgtca     120
tgtaaagcat ccggctatac attcactaac tactggatgc attgggtgag gcaggctcca     180
ggacagggac tggaatggat gggcgtgatc gacccttcag attcctacac cacatatgcc     240
cagaagtttc agggcagggt gaccatgaca gtggacacta gcacctctac agtgtacatg     300
gagctgtcca gcctgagaag tgaagataca gcagtgtact attgcgcccg cggcaattac     360
ggagtggact atgccatgga ttactggggg cagggtactc tggtgaccgt gtctagtgct     420
tctaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtctcc gggaaatga                                      1410
```

<210> SEQ ID NO 18
<211> LENGTH: 1410
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 18

| | | | | | |
|---|---|---|---|---|---|
| atgggctggt | cctgcatcat | tctgttcctg | gtggcaactg | ccaccggagt | gcacagccag | 60 |
| gtgcagctgg | tgcagtctgg | ggctgaggtg | aagaaaccccg | gtgcaagtgt | gaaagtgtca | 120 |
| tgcaaggcat | ccggctatac | attcactaac | tactggatgc | attgggtgaa | gcaggcacca | 180 |
| ggacagggac | tggaatggat | cggcgtgatc | gacccttcag | attcctacac | cacatataat | 240 |
| cagaagttta | aggcaaggc | taccatgaca | agggacacta | gcacctctac | agtgtacatg | 300 |
| gagctgtcca | gcctgaggtc | cgaagataca | gccgtgtact | attgcactcg | gggcaactac | 360 |
| ggagtggact | atgctatgga | ttactgggggg | cagggtacta | gtgtgaccgt | gtctagtgca | 420 |
| tctaccaagg | gcccatcggt | cttccccctg | gcaccctcct | ccaagagcac | ctctgggggc | 480 |
| acagcggccc | tgggctgcct | ggtcaaggac | tacttccccg | aaccggtgac | ggtgtcgtgg | 540 |
| aactcaggcg | ccctgaccag | cggcgtgcac | accttcccgg | ctgtcctaca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagagagt | tgagcccaaa | 720 |
| tcttgtgaca | aaactcacac | atgcccaccg | tgcccagcac | ctgaactcct | gggggggaccg | 780 |
| tcagtcttcc | tcttccccccc | aaaacccaag | gacaccctca | tgatctcccg | gacccctgag | 840 |
| gtcacatgcg | tggtggtgga | cgtgagccac | gaagaccctg | aggtcaagtt | caactggtac | 900 |
| gtggacggcg | tggaggtgca | taatgccaag | acaaagccgc | gggaggagca | gtacaacagc | 960 |
| acgtaccgtg | tggtcagcgt | cctcaccgtc | ctgcaccagg | actggctgaa | tggcaaggag | 1020 |
| tacaagtgca | aggtctccaa | caaagccctc | ccagccccca | tcgagaaaac | catctccaaa | 1080 |
| gccaaagggc | agccccgaga | accacaggtg | tacaccctgc | ccccatcccg | ggaggagatg | 1140 |
| accaagaacc | aggtcagcct | gacctgcctg | gtcaaaggct | tctatcccag | cgacatcgcc | 1200 |
| gtggagtggg | agagcaatgg | gcagccggag | aacaactaca | agaccacgcc | tcccgtgctg | 1260 |
| gactccgacg | gctccttctt | cctctatagc | aagctcaccg | tggacaagag | caggtggcag | 1320 |
| caggggaacg | tcttctcatg | ctccgtgatg | catgaggctc | tgcacaacca | ctacacgcag | 1380 |
| aagagcctct | ccctgtctcc | cgggaaatga | | | | 1410 |

<210> SEQ ID NO 19
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | | | | |
|---|---|---|---|---|---|
| atggactgga | catggagaat | cctgttcctg | gtggccgctg | caaccggagc | acacagccag | 60 |
| gtgcagctgg | tgcagtctgg | agcagaggtg | aagaaaccccg | gtgctagtgt | gaaagtgtca | 120 |
| tgcaaggcct | ccgggtatac | tttcaccaac | tactggatgc | attgggtgag | gcaggctcca | 180 |
| ggacagggac | tggaatggat | gggcgtgatt | gacccttcag | attcctacac | cacatataat | 240 |
| cagaagttta | aggaaaggc | aacactgact | gtggacacca | gcacatctac | tgcctacatg | 300 |
| gagctgtcca | gcctgaggtc | cgaagatact | gccgtgtact | attgtacccg | ggcaactac | 360 |
| ggagtggact | atgcaatgga | ttactgggggg | cagggtaccc | tggtgacagt | gtctagtgct | 420 |

```
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctatagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                    1410

<210> SEQ ID NO 20
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggactgga cctggcgaat cctgttcctg gtggccgctg caacaggagc acactcacag     60
gtgcagctgg tgcagtccgg ggcagaggtg aagaaacccg gtgccagcgt gaaggtgtct    120
tgcaaagcta gtggctatac cttcacaagc tactggatgc attgggtgcg gcaggcacca    180
ggacagggac tggaatggat gggcctgatt gaccctttct ataagtacac taactacaac    240
cagaagttta aggaagggt gactatgacc cgggacacat caacttccac cgtgtacatg    300
gagctgtcca gcctgagatc cgaagatacc gccgtgtact attgtgctcg cggcaactac    360
ggagtggact atggcatgga ttactggggg cagggtacac tggtgaccgt gtccagtgct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
```

```
tacaagtgca aggtctccaa caaagccctc ccagccccca tcgagaaaac catctccaaa    1080 gccaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                    1410
```

<210> SEQ ID NO 21
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atggactgga cttggaggat cctgttcctg gtggccgctg caaccggagc tcactcacag    60
gtgcagctgg tgcagtccgg agcagaggtg aagaaacccg gtgcctccgt gaaggtgtct    120
tgcaaagcaa gtggctatac cttcacaagc tactggatgc attgggtgag acaggcacca    180
ggacagggac tggaatggat gggcctgatt gacccttctg ataagtacac aactacaac    240 cagaagttta aggacgcgt gactctgacc gtggacacat caacttccac cgtgtacatg    300
gagctgtcca gcctgaggtc cgaagatacc gcagtgtact attgtacacg gggcaactac    360
ggagtggact atggcatgga ttactggggg cagggtacac tggtgaccgt gtccagtgct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tgagcccaaa    720
tcttgtgaca aaactcacac atgcccaccg tgcccagcac ctgaactcct ggggggaccg    780
tcagtcttcc tcttccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080 gccaagggc agccccgaga accacaggtg tacaccctgc ccccatcccg ggaggagatg    1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                    1410
```

<210> SEQ ID NO 22
<211> LENGTH: 1410
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atggactgga cttggagaat cctgttcctg gtggccgctg caaccggagc tcactcacag      60
gtgcagctgg tgcagtccgg agcagaggtg aagaaacccg gtgcctccgt gaaagtgtct     120
tgcaaggcta gtggctatac cttcacaagc tactggatgc attgggtgag gcaggcacca     180
ggacagggac tggaatggat gggcctgatt gaccccttctg ataagtacac caactacaac     240
cagaagttta aggaaaggc aactctgacc gtggacacat caacttccac cgcctacatg      300
gagctgtcca gcctgaggtc cgaagatacc gccgtgtact attgtacacg gggcaactac     360
ggagtggact atggcatgga ttactggggg caggtacac tggtgaccgt gtccagtgct      420
agcaccaagg gcccatcggt cttccccctg gcaccctcct ccaagagcac ctctggggc      480
acagcggccc tgggctgcct ggtcaaggac tacttcccg aaccggtgac ggtgtcgtgg      540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagagagt tgagcccaaa     720
tcttgtgaca aaactcacac atgcccaccg tgcccagcac ctgaactcct ggggggaccg     780
tcagtcttcc tcttcccccc aaaacccaag gacacctca tgatctcccg gacccctgag      840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg      1140
accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctatagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 23
<211> LENGTH: 702
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
atgggctggt cctgcatcat tctgttcctg gtggcaaccg ccacaggagt gcacagcgac      60
atccagatga cccagtctcc atccagcctg agtgcctcag tgggcgatag ggtgactatc     120
acctgtcggg ccagcgagaa catctacggc gctctgaatt ggtatcagca gaagccagga     180
aaagctccca gctgctgat ctacgggct acaaacctgg cagacggtgt gcccagtcga      240
ttctccggta gcggctctgg acgacagtat tcactgacta tctctagtct gcagcctgaa     300
gatttcgcca cttactattg ccagaatgtg ctgattactc catatacctt tggcggaggg     360
acaaaactgg agatcaagag aactgtggcc gctcccagtg tgttcatttt tccccttca      420
```

```
gacgaacagc tgaaatcagg gaccgcttcc gtggtgtgtc tgctgaacaa tttctaccct    480
cgcgaggcaa aagtgcagtg gaaggtggat aacgccctgc agagtggcaa ttcacaggag    540
tccgtgaccg aacaggacag caaagattct acatatagtc tgtcatccac cctgacactg    600
agcaaggctg attacgagaa gcacaaagtg tatgcatgcg aagtgactca tcagggctg    660 agctctcccg tgaccaagtc ttttaaccgg ggtgaatgtt ga                       702
```

<210> SEQ ID NO 24
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggacatga gggtgcctgc tcagctgctg ggactgctgc tgctgtggct gaggggagca    60
cgatgcgaca tccagatgac tcagagccca tccagcctgt cagcctccgt gggcgacagg    120
gtgaccatca catgtggagc atccgagaac atctacgggg ccctgaattg gtatcagagg    180
aagcccggca agctcctaa gctgctgatc tacggtgcca caaacctggc tgatggcgtg    240
ccctccagat tcagcggctc tggaagtggg cgcgactata ctctgaccat ttctagtctg    300
cagccagagg atttcgccac ctactattgc cagaatgtgc tgatcacacc ctacactttt    360
ggtcagggca caaaactgga aattaagcgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgttg a             711
```

<210> SEQ ID NO 25
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
caggtgcagc tggtgcagtc tggggctgag gtgaagaaac ccggtgcaag tgtgaaggtg    60
tcatgtaaag catccggcta tacattcact aactactgga tgcattgggt gaggcaggct    120
ccaggacagg gactggaatg gatgggcgtg atcgaccctt cagattccta caccacatat    180
gcccagaagt ttcagggcag ggtgaccatg acagtggaca ctagcacctc tacagtgtac    240
atggagctgt ccagcctgag aagtgaagat acagcagtgt actattgcgc ccgcggcaat    300
tacggagtgg actatgccat ggattactgg gggcaggta ctctggtgac cgtgtctagt    360
```

<210> SEQ ID NO 26
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
caggtgcagc tggtgcagtc tggggctgag gtgaagaaac ccggtgcaag tgtgaaagtg      60
tcatgcaagg catccggcta tacattcact aactactgga tgcattgggt gaagcaggca     120
ccaggacagg gactggaatg gatcggcgtg atcgacccct cagattccta caccacatat     180
aatcagaagt ttaaaggcaa ggctaccatg acaaggaca ctagcacctc tacagtgtac      240
atggagctgt ccagcctgag gtccgaagat acagccgtgt actattgcac tcggggcaac    300
tacggagtgg actatgctat ggattactgg gggcagggta ctagtgtgac cgtgtctagt    360
```

<210> SEQ ID NO 27
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
caggtgcagc tggtgcagtc tggagcagag gtgaagaaac ccggtgctag tgtgaaagtg      60
tcatgcaagg cctccgggta actttcacc aactactgga tgcattgggt gaggcaggct      120
ccaggacagg gactggaatg gatgggcgtg attgacccct cagattccta caccacatat     180
aatcagaagt ttaaaggaaa ggcaacactg actgtggaca ccagcacatc tactgcctac    240
atggagctgt ccagcctgag gtccgaagat actgccgtgt actattgtac ccggggcaac    300
tacggagtgg actatgcaat ggattactgg ggcagggta ccctggtgac agtgtctagt     360
```

<210> SEQ ID NO 28
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
caggtgcagc tggtgcagtc cggggcagag gtgaagaaac ccggtgccag cgtgaaggtg      60
tcttgcaaag ctagtggcta taccttcaca agctactgga tgcattgggt gcggcaggca     120
ccaggacagg gactggaatg gatgggcctg attgacccct ctgataagta cactaactac    180
aaccagaagt ttaaaggaag ggtgactatg acccgggaca catcaacttc caccgtgtac     240
atggagctgt ccagcctgag atccgaagat accgccgtgt actattgtgc tcgcggcaac    300
tacggagtgg actatggcat ggattactgg gggcagggta cactggtgac cgtgtccagt    360
```

<210> SEQ ID NO 29
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
caggtgcagc tggtgcagtc cggagcagag gtgaagaaac ccggtgcctc cgtgaaggtg      60
tcttgcaaag caagtggcta taccttcaca agctactgga tgcattgggt gagacaggca    120
ccaggacagg gactggaatg gatgggcctg attgacccct ctgataagta caccaactac    180
aaccagaagt ttaaaggacg cgtgactctg accgtggaca catcaacttc caccgtgtac     240
atggagctgt ccagcctgag gtccgaagat accgcagtgt actattgtac acggggcaac    300
```

```
tacggagtgg actatggcat ggattactgg gggcaggta cactggtgac cgtgtccagt        360

<210> SEQ ID NO 30
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caggtgcagc tggtgcagtc cggagcagag gtgaagaaac ccggtgcctc cgtgaaagtg        60
tcttgcaagg ctagtggcta taccttcaca agctactgga tgcattgggt gaggcaggca       120
ccaggacagg gactggaatg gatgggcctg attgaccctt ctgataagta caccaactac       180
aaccagaagt ttaaaggaaa ggcaactctg accgtggaca catcaacttc caccgcctac       240
atggagctgt ccagcctgag gtccgaagat accgccgtgt actattgtac acggggcaac       300
tacggagtgg actatggcat ggattactgg gggcagggta cactggtgac cgtgtccagt       360

<210> SEQ ID NO 31
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gacatccaga tgacccagtc tccatccagc ctgagtgcct cagtgggcga tagggtgact        60
atcacctgtc gggccagcga gaacatctac ggcgctctga attggtatca gcagaagcca       120
ggaaaagctc ccaagctgct gatctacggg gctacaaaac tggcagacgg tgtgcccagt       180
cgattctccg gtagcggctc tggacgacag tattcactga ctatctctag tctgcagcct       240
gaagatttcg ccacttacta ttgccagaat gtgctgatta ctccatatac ctttggcgga       300
gggacaaaac tggagatcaa g                                                 321

<210> SEQ ID NO 32
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gacatccaga tgactcagag cccatccagc ctgtcagcct ccgtgggcga cagggtgacc        60
atcacatgtg gagcatccga gaacatctac ggggccctga attggtatca gaggaagccc       120
ggcaaagctc ctaagctgct gatctacggt gccacaaacc tggctgatgg cgtgccctcc       180
agattcagcg gctctggaag tgggcgcgac tatactctga ccatttctag tctgcagcca       240
gaggatttcg ccacctacta ttgccagaat gtgctgatca caccctacac ttttggtcag       300
ggcacaaaac tggaaattaa g                                                 321

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 33

Met Arg Trp Ser Cys Ile Ile Leu Phe Leu Val Ala Thr Ala Thr Gly
1               5                   10                  15

Val Asn Ser

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Gly Val Pro Thr Gln Leu Leu Leu Leu Trp Leu Thr Val Val Val
1               5                   10                  15

Val Arg Cys

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Glu Trp Ser Trp Val Phe Leu Phe Leu Leu Ser Val Ile Ala Gly
1               5                   10                  15

Val Gln Ser

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Gly Val Pro Thr Gln Leu Leu Leu Leu Trp Leu Thr Val Val Val
1               5                   10                  15

Val Arg Cys

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Arg Trp Ser Cys Ile Ile Leu Phe Leu Val Ala Thr Ala Thr Gly
1               5                   10                  15

Val Asn Ser

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 38

Met Gly Val Pro Thr Gln Leu Leu Leu Leu Trp Leu Thr Val Val
1               5                   10                  15

Val Arg Cys

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Thr Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Asn Tyr Gly Val Asp Tyr Ala Met Asp Tyr Trp Gly Gln
            100                 105                 110

Gly Thr Ser Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ile Thr Pro Tyr
                85                  90                  95

Thr Phe Gly Gly Gly Thr Lys Leu Glu Ile Lys
            100                 105

<210> SEQ ID NO 41
<211> LENGTH: 121

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Thr Ser Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Lys Cys Tyr Tyr Gly Ser Ala Asp Tyr Ala Met Asp Tyr Trp Gly
            100                 105                 110

Gln Gly Thr Ser Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro Trp
                85                  90                  95

Thr Phe Gly Gly Gly Thr Lys Leu Glu Ile Lys
            100                 105

<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
```

```
            20                  25                  30
Trp Met His Trp Val Lys Gln Arg Pro Gly Gln Gly Leu Glu Trp Ile
        35                  40                  45
Gly Leu Ile Asp Pro Ser Asp Lys Tyr Thr Asn Tyr Asn Gln Lys Phe
    50                  55                  60
Lys Gly Lys Ala Thr Leu Thr Val Asp Thr Ser Ser Thr Ala Tyr
65                  70                  75                  80
Met Gln Leu Ser Ser Leu Thr Ser Glu Asp Ser Ala Val Tyr Tyr Cys
                85                  90                  95
Thr Arg Gly Asn Tyr Gly Val Asp Tyr Gly Met Asp Tyr Trp Gly Gln
                100                 105                 110
Gly Thr Ser Val Thr Val Ser Ser
            115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ala Ser Leu Ser Ala Ser Val Gly
1               5                   10                  15
Glu Thr Val Thr Ile Thr Cys Gly Ala Ser Glu Asn Ile Tyr Gly Ala
            20                  25                  30
Leu Asn Trp Tyr Gln Arg Lys Gln Gly Lys Ser Pro Gln Leu Leu Ile
        35                  40                  45
Tyr Gly Ala Thr Asn Leu Ala Asp Gly Met Ser Ser Arg Phe Ser Gly
    50                  55                  60
Ser Gly Ser Gly Arg Gln Tyr Ser Leu Lys Ile Ser Ser Leu His Pro
65                  70                  75                  80
Asp Asp Val Ala Thr Tyr Tyr Cys Gln Asn Val Leu Ser Thr Pro Tyr
                85                  90                  95
Thr Phe Gly Gly Gly Thr Lys Leu Glu Ile Lys
                100                 105

<210> SEQ ID NO 45
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
atgagatgga gctgtatcat cctcttcttg gtagcaacag ctacaggtgt caactcc      57

<210> SEQ ID NO 46
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
atgggtgtac ccactcagct cctgttgctg tggcttacag tcgtagttgt cagatgt      57
```

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggaatgga gctgggtctt tctcttcctc ctgtcagtaa ttgcaggtgt ccaatcc    57

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atgggtgtac ccactcagct cctgttgctg tggcttacag tcgtagttgt cagatgt    57

<210> SEQ ID NO 49
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atgagatgga gctgtatcat cctcttcttg gtagcaacag ctacaggtgt caactcc    57

<210> SEQ ID NO 50
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgggtgtac ccactcagct cctgttgctg tggcttacag tcgtagttgt cagatgt    57

<210> SEQ ID NO 51
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggtccaac tgcagcagcc tggggctgag ctggtgaagc ctggggcttc agtgaagatg    60
tcctgcaagg cttctggcta caccttcacc aactactgga tgcactgggt gaagcagagg   120
cctggacaag gccttgagtg gatcggagtg attgatcctt ctgatagtta tactacctac   180
aatcaaaagt tcaagggcaa ggccacattg actgtagaca catcctccag cacagcctac   240
atgcagctca gcagcctgac atctgaggac tctgcggtct attactgtac aagaggtaac   300
tacggagtag actatgctat ggactactgg ggtcaaggaa cctcagtcac cgtctcctcg   360

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52

```
gacatccaga tgactcagtc tccagcttca ctgtctgcat ctgtgggaga aactgtcacc    60
atcacatgtg gagcaagtga gaatatttac ggtgctttaa attggtatca gcggaaacag   120
ggaaaatctc ctcagctcct gatctatggt gcaaccaact ggcagatgg catgtcatcg    180
aggttcagtg gcagtggatc tggtagacag tattctctca agatcagtag cctgcatcct   240
gacgatgttg caacgtatta ctgtcaaaat gtgttaatta ctccgtacac gttcggaggg   300
gggaccaagc tggaaataaa a                                             321
```

<210> SEQ ID NO 53
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53

```
caggttcaac tgcagcagtc tggggctgag ctggtgaggc ctggggcttc agtgacgctg    60
tcctgcaagg cttcgggcta cacatttact gactatgaaa tgcactgggt gaagcagaca   120
cctgtgcatg gcctggaatg gattggagct attgatcctg aaactactag tactgcctac   180
aatcagaagt tcaagggcaa ggccacactg actgcagaca atcctccag cacagcctac    240
atggagctcc gcagcctgac atctgaggac tctgccgtct attactgtac caaatgttac    300
tacggtagcg cggactatgc tatggactac tggggtcaag aacctcagt caccgtctcc    360
tca                                                                 363
```

<210> SEQ ID NO 54
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54

```
gacatccaga tgactcagtc tccagcttca ctgtctgcat ctgtgggaga aactgtcacc    60
atcacatgtg gagcaagtga gaatatttac ggtgctttaa attggtatca gcggaaacag   120
ggaaaatctc ctcagctcct gatctatggt gcaaccaact ggcagatgg catgtcatcg    180
aggttcagtg gcagtggatc tggtagacag tattctctca agatcagtag cctgcatcct   240
gacgatgttg caacgtatta ctgtcaaaat gtgttaagta ctccgtggac gttcggtgga   300
ggcaccaagc tggaaatcaa a                                             321
```

<210> SEQ ID NO 55
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55

```
caggtccaac tgcagcagcc tggggctgag ctggtgaagc ctggggcttc agtgaagatg    60
```

```
tcctgcaagg cttctggcta caccttcacc agctactgga tgcactgggt gaagcagagg    120
cctggacaag gccttgagtg gatcggactg attgatcctt ctgataagta tactaactac    180
aatcaaaagt tcaagggcaa ggccacattg actgtagaca catcctccag cacagcctac    240
atgcagctca gcagcctgac atctgaggac tctgcggtct attactgtac aagaggtaac    300
tacggagtag actatggtat ggactactgg ggtcaaggaa cctcagtcac cgtctcctca    360
```

<210> SEQ ID NO 56
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
gacatccaga tgactcagtc tccagcttca ctgtctgcat ctgtgggaga aactgtcacc    60
atcacatgtg agcaagtga gaatatttac ggtgctttaa attggtatca gcggaaacag    120
ggaaaatctc ctcagctcct gatctatggt gcaaccaact ggcagatggg catgtcatcg    180
aggttcagtg gcagtggatc tggtagacag tattctctca agatcagtag cctgcatcct    240
gacgatgttg caacgtatta ctgtcaaaat gtgttaagta ctccgtacac gttcggaggg    300
gggaccaagc tggaaataaa a                                             321
```

<210> SEQ ID NO 57
<211> LENGTH: 98
<212> TYPE: PRT
<213> ORGANISM: Homo sapiens

<400> SEQUENCE: 57

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 58
<211> LENGTH: 15
<212> TYPE: PRT
<213> ORGANISM: Homo sapiens

<400> SEQUENCE: 58

```
Tyr Phe Asp Tyr Trp Gly Gln Gly Thr Leu Val Thr Val Ser Ser
1               5                   10                  15
```

<210> SEQ ID NO 59
<211> LENGTH: 96
<212> TYPE: PRT
<213> ORGANISM: Homo sapiens

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Tyr Trp Met His
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Trp Met His
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Tyr Tyr Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Ile Asp Pro Ser Asp Ser Tyr Thr Thr Tyr Asn Gln Lys Phe Lys
1               5                   10                  15

Gly

<210> SEQ ID NO 64
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Ile Asp Pro Ser Asp Ser Tyr Thr Thr Tyr Ala Gln Lys Phe Gln
1               5                   10                  15
Gly

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Ile Asp Pro Ser Asp Lys Tyr Thr Asn Tyr Asn Gln Lys Phe Lys
1               5                   10                  15
Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Ile Asn Pro Ser Gly Gly Ser Thr Ser Tyr Ala Gln Lys Phe Gln
1               5                   10                  15
Gly

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Asn Tyr Gly Val Asp Tyr Ala Met Asp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Asn Tyr Gly Val Asp Tyr Gly Met Asp Tyr
1               5                   10

<210> SEQ ID NO 69
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 69

Glu Gly Asp Gly Tyr Ile Gln Ala Phe Asp Tyr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ala Ser Glu Asn Ile Tyr Gly Ala Leu Asn
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ala Ser Glu Asn Ile Tyr Gly Ala Leu Asn
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ala Ser Gln Ser Ile Ser Ser Tyr Leu Asn
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ala Thr Asn Leu Ala Asp
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Ala Ser Ser Leu Gln Ser
1               5
```

```
<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Asn Val Leu Ile Thr Pro Tyr Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln Ser Tyr Ser Thr Pro Tyr Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Thr Phe Thr Asn Tyr
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Tyr Thr Phe Thr Ser Tyr
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Val Ile Asp Pro Ser Asp Ser Tyr Thr Thr
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Leu Ile Asp Pro Ser Asp Lys Tyr Thr Asn
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Ile Asn Pro Ser Gly Gly Ser Thr Ser
1               5                   10

<210> SEQ ID NO 82
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Gly Tyr Ile Gln Ala Phe Asp Tyr Trp Gly Gln
            100                 105                 110

Gly Thr Leu Val Thr Val Ser Ser
        115                 120

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 84
<211> LENGTH: 70
<212> TYPE: PRT
<213> ORGANISM: Homo sapiens

<400> SEQUENCE: 84

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asp Met
65                  70

<210> SEQ ID NO 85
<211> LENGTH: 96
<212> TYPE: PRT
<213> ORGANISM: Homo sapiens

<400> SEQUENCE: 85

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 86
<211> LENGTH: 96
<212> TYPE: PRT
<213> ORGANISM: Macaca mulatta

<400> SEQUENCE: 86

Met Cys Cys Thr Lys Ser Leu Leu Leu Ala Ala Leu Met Ser Val Leu
1               5                   10                  15

Leu Leu Tyr Leu Cys Ser Glu Ser Glu Ala Ala Ser Asn Phe Asp Cys
            20                  25                  30

Cys Leu Arg Tyr Thr Asp Arg Ile Leu His Pro Lys Phe Ile Val Gly
        35                  40                  45

Phe Thr Gln Gln Leu Ala Asn Glu Thr Cys Asp Ile Asn Ala Val Val
    50                  55                  60

Phe His Thr Lys Lys Gly Leu Ser Val Cys Ala Asn Pro Lys Gln Thr
65                  70                  75                  80
```

```
Trp Val Lys Leu Ile Val Arg Arg Leu Ser Lys Lys Ile Asn Lys Met
                85                  90                  95
```

<210> SEQ ID NO 87
<211> LENGTH: 96
<212> TYPE: PRT
<213> ORGANISM: Macaca fascicularis

<400> SEQUENCE: 87

```
Met Cys Cys Ser Lys Ser Leu Leu Leu Ala Ala Leu Met Ser Val Leu
 1               5                  10                  15

Leu Leu Tyr Leu Cys Ser Glu Ser Glu Ala Ala Ser Asn Phe Asp Cys
                20                  25                  30

Cys Leu Arg Tyr Thr Asp Arg Ile Leu His Pro Lys Phe Ile Val Gly
            35                  40                  45

Phe Thr Gln Gln Leu Ala Asn Glu Thr Cys Asp Ile Asn Ala Val Ile
        50                  55                  60

Phe His Thr Lys Lys Gly Leu Ser Val Cys Ala Asn Pro Lys Gln Thr
65                  70                  75                  80

Trp Val Lys Leu Ile Val Arg Arg Leu Ser Lys Lys Ile Asn Lys Met
                85                  90                  95
```

<210> SEQ ID NO 88
<211> LENGTH: 95
<212> TYPE: PRT
<213> ORGANISM: Mus musculus

<400> SEQUENCE: 88

```
Cys Gly Gly Lys Arg Leu Leu Phe Leu Ala Leu Ala Trp Val Leu Leu
 1               5                  10                  15

Ala His Leu Cys Ser Gln Ala Glu Ala Ala Ser Asn Tyr Asp Cys Cys
                20                  25                  30

Leu Ser Tyr Ile Gln Thr Pro Leu Pro Ser Arg Ala Ile Val Gly Phe
            35                  40                  45

Thr Arg Gln Met Ala Asp Glu Ala Cys Asp Ile Asn Ala Ile Ile Phe
        50                  55                  60

His Thr Lys Lys Arg Lys Ser Val Cys Ala Asp Pro Lys Gln Asn Trp
65                  70                  75                  80

Val Lys Arg Ala Val Asn Leu Leu Ser Leu Arg Val Lys Lys Met
                85                  90                  95
```

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
catttgcaca cctcaccatc                                        20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
tccgttgctt aacgtcatgt                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
cggcgtttac tacaggaagg                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ttcttgctga ctggaggttg                                               20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gctggaaacc atgatcacct                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggtagtaagg gctggggaag                                               20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cagtgttggt ggtgggctat                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccgagccaag agagcatatc                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
caggccagac tttgttggat                                                       20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ttgcgctcat cttaggcttt                                                       20

<210> SEQ ID NO 99
<211> LENGTH: 70
<212> TYPE: PRT
<213> ORGANISM: Homo sapiens

<400> SEQUENCE: 99

Ala Ser Asn Phe Asp Cys Cys Leu Gly Tyr Thr Asp Arg Ile Leu His
1               5                   10                  15

Pro Lys Phe Ile Val Gly Phe Thr Arg Gln Leu Ala Asn Glu Gly Cys
            20                  25                  30

Asp Ile Asn Ala Ile Ile Phe His Thr Lys Lys Leu Ser Val Cys
        35                  40                  45

Ala Asn Pro Lys Gln Thr Trp Val Lys Tyr Ile Val Arg Leu Leu Ser
    50                  55                  60

Lys Lys Val Lys Asn Met
65                  70

<210> SEQ ID NO 100
<211> LENGTH: 210
<212> TYPE: DNA
<213> ORGANISM: Homo sapiens

<400> SEQUENCE: 100
gcaagcaact ttgactgctg tcttggatac acagaccgta ttcttcatcc taaatttatt           60
gtgggcttca cacggcagct ggccaatgaa ggctgtgaca tcaatgctat catctttcac          120
acaaagaaaa agttgtctgt gtgcgcaaat ccaaaacaga cttgggtgaa atatattgtg          180
cgtctcctca gtaaaaaagt caagaacatg                                           210

<210> SEQ ID NO 101
<211> LENGTH: 288
<212> TYPE: DNA
<213> ORGANISM: Homo sapiens

<400> SEQUENCE: 101
atgtgctgta ccaagagttt gctcctggct gctttgatgt cagtgctgct actccacctc           60
tgcggcgaat cagaagcagc aagcaacttt gactgctgtc ttggatacac agaccgtatt          120
cttcatccta aatttattgt gggcttcaca cggcagctgg ccaatgaagg ctgtgacatc          180

```
aatgctatca tctttcacac aaagaaaaag ttgtctgtgt gcgcaaatcc aaaacagact    240
tgggtgaaat atattgtgcg tctcctcagt aaaaaagtca agaacatg                288
```

<210> SEQ ID NO 102
<211> LENGTH: 97
<212> TYPE: PRT
<213> ORGANISM: Mus musculus

<400> SEQUENCE: 102

```
Met Ala Cys Gly Gly Lys Arg Leu Leu Phe Leu Ala Leu Ala Trp Val
1               5                   10                  15

Leu Leu Ala His Leu Cys Ser Gln Ala Glu Ala Ala Ser Asn Tyr Asp
            20                  25                  30

Cys Cys Leu Ser Tyr Ile Gln Thr Pro Leu Pro Ser Arg Ala Ile Val
        35                  40                  45

Gly Phe Thr Arg Gln Met Ala Asp Glu Ala Cys Asp Ile Asn Ala Ile
    50                  55                  60

Ile Phe His Thr Lys Lys Arg Lys Ser Val Cys Ala Asp Pro Lys Gln
65                  70                  75                  80

Asn Trp Val Lys Arg Ala Val Asn Leu Leu Ser Leu Arg Val Lys Lys
                85                  90                  95

Met
```

<210> SEQ ID NO 103
<211> LENGTH: 291
<212> TYPE: DNA
<213> ORGANISM: Mus musculus

<400> SEQUENCE: 103

```
atggcctgcg gtggcaagcg tctgctcttc cttgctttgg catgggtact gctggctcac     60
ctctgcagcc aggcagaagc agcaagcaac tacgactgtt gcctctcgta catacagacg    120
cctcttcctt ccagagctat tgtgggtttc acaagacaga tggccgatga agcttgtgac    180
attaatgcta tcatctttca cacgaagaaa agaaaatctg tgtcgctga tccaaagcag     240 aactgggtga aagggctgt gaacctcctc agcctaagag tcaagaagat g              291
```

<210> SEQ ID NO 104
<211> LENGTH: 374
<212> TYPE: PRT
<213> ORGANISM: Homo sapiens

<400> SEQUENCE: 104

```
Met Ser Gly Glu Ser Met Asn Phe Ser Asp Val Phe Asp Ser Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
                100                 105                 110
```

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Leu Gly Lys Met Asn Arg Ser Cys
        275                 280                 285

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320

Gln Lys Phe Arg Asn Tyr Phe Leu Lys Ile Leu Lys Asp Leu Trp Cys
                325                 330                 335

Val Arg Arg Lys Tyr Lys Ser Ser Gly Phe Ser Cys Ala Gly Arg Tyr
            340                 345                 350

Ser Glu Asn Ile Ser Arg Gln Thr Ser Glu Thr Ala Asp Asn Asp Asn
        355                 360                 365

Ala Ser Ser Phe Thr Met
    370

<210> SEQ ID NO 105
<211> LENGTH: 1122
<212> TYPE: DNA
<213> ORGANISM: Homo sapiens

<400> SEQUENCE: 105
atgagcgggg aatcaatgaa tttcagcgat gttttcgact ccagtgaaga ttattttgtg     60
tcagtcaata cttcatatta ctcagttgat tctgagatgt tactgtgctc cttgcaggag    120
gtcaggcagt tctccaggct atttgtaccg attgcctact ccttgatctg tgtctttggc    180
ctcctgggga atattctggt ggtgatcacc tttgcttttt ataagaaggc caggtctatg    240
acagacgtct atctcttgaa catggccatt gcagacatcc tctttgttct tactctccca    300
ttctgggcag tgagtcatgc caccggtgcg tgggttttca gcaatgccac gtgcaagttg    360
ctaaaaggca tctatgccat caactttaac tgcgggatgc tgctcctgac ttgcattagc    420
atggaccggt acatcgccat tgtacaggcg actaagtcat tccggctccg atccagaaca    480
ctaccgcgca gcaaaatcat ctgccttgtt gtgtgggggc tgtcagtcat catctccagc    540 tcaactttg tcttcaacca aaaatacaac acccaaggca gcgatgtctg tgaacccaag    600

```
taccagactg tctcggagcc catcaggtgg aagctgctga tgttggggct tgagctactc    660
tttggtttct ttatcccttt gatgttcatg atattttgtt acacgttcat tgtcaaaacc    720
ttggtgcaag ctcagaattc taaaaggcac aaagccatcc gtgtaatcat agctgtggtg    780
cttgtgtttc tggcttgtca gattcctcat aacatggtcc tgcttgtgac ggctgcaaat    840
ttgggtaaaa tgaaccgatc ctgccagagc gaaaagctaa ttggctatac gaaaactgtc    900
acagaagtcc tggctttcct gcactgctgc ctgaaccctg tgctctacgc ttttattggg    960
cagaagttca gaaactactt tctgaagatc ttgaaggacc tgtggtgtgt gagaaggaag   1020
tacaagtcct caggcttctc ctgtgccggg aggtactcag aaaacatttc tcggcagacc   1080
agtgagaccg cagataacga caatgcgtcg tccttcacta tg                     1122
```

<210> SEQ ID NO 106
<211> LENGTH: 367
<212> TYPE: PRT
<213> ORGANISM: Mus musculus

<400> SEQUENCE: 106

```
Met Asn Ser Thr Glu Ser Tyr Phe Gly Thr Asp Asp Tyr Asp Asn Thr
1               5                   10                  15

Glu Tyr Tyr Ser Ile Pro Pro Asp His Gly Pro Cys Ser Leu Glu Glu
            20                  25                  30

Val Arg Asn Phe Thr Lys Val Phe Val Pro Ile Ala Tyr Ser Leu Ile
        35                  40                  45

Cys Val Phe Gly Leu Leu Gly Asn Ile Met Val Val Met Thr Phe Ala
    50                  55                  60

Phe Tyr Lys Lys Ala Arg Ser Met Thr Asp Val Tyr Leu Leu Asn Met
65                  70                  75                  80

Ala Ile Thr Asp Ile Leu Phe Val Leu Thr Leu Pro Phe Trp Ala Val
                85                  90                  95

Thr His Ala Thr Asn Thr Trp Val Phe Ser Asp Ala Leu Cys Lys Leu
            100                 105                 110

Met Lys Gly Thr Tyr Ala Val Asn Phe Asn Cys Gly Met Leu Leu Leu
        115                 120                 125

Ala Cys Ile Ser Met Asp Arg Tyr Ile Ala Ile Val Gln Ala Thr Lys
    130                 135                 140

Ser Phe Arg Val Arg Ser Arg Thr Leu Thr His Ser Lys Val Ile Cys
145                 150                 155                 160

Val Ala Val Trp Phe Ile Ser Ile Ile Ser Ser Pro Thr Phe Ile
                165                 170                 175

Phe Asn Lys Lys Tyr Glu Leu Gln Asp Arg Asp Val Cys Glu Pro Arg
            180                 185                 190

Tyr Arg Ser Val Ser Glu Pro Ile Thr Trp Lys Leu Leu Gly Met Gly
        195                 200                 205

Leu Glu Leu Phe Phe Gly Phe Pro Thr Pro Leu Leu Phe Met Val Phe
    210                 215                 220

Cys Tyr Leu Phe Ile Ile Lys Thr Leu Val Gln Ala Gln Asn Ser Lys
225                 230                 235                 240

Arg His Arg Ala Ile Arg Val Val Ile Ala Val Val Leu Val Phe Leu
                245                 250                 255

Ala Cys Gln Ile Pro His Asn Met Val Leu Leu Val Thr Ala Val Asn
            260                 265                 270

Thr Gly Lys Val Gly Arg Ser Cys Ser Thr Glu Lys Val Leu Ala Tyr
```

```
                275                 280                 285
Thr Arg Asn Val Ala Glu Val Leu Ala Phe Leu His Cys Cys Leu Asn
        290                 295                 300

Pro Val Leu Tyr Ala Phe Ile Gly Gln Lys Phe Arg Asn Tyr Phe Met
305                 310                 315                 320

Lys Ile Met Lys Asp Val Trp Cys Met Arg Arg Lys Asn Lys Met Pro
                    325                 330                 335

Gly Phe Leu Cys Ala Arg Val Tyr Ser Glu Ser Tyr Ile Ser Arg Gln
                340                 345                 350

Thr Ser Glu Thr Val Glu Asn Asp Asn Ala Ser Ser Phe Thr Met
            355                 360                 365

<210> SEQ ID NO 107
<211> LENGTH: 1101
<212> TYPE: DNA
<213> ORGANISM: Mus musculus

<400> SEQUENCE: 107
atgaattcca cagagtccta ctttggaacg atgattatg acaacacaga gtattattct      60
attcctccag accatgggcc atgctcccta aagaggtca gaaacttcac caaggtattt     120
gtgccaattg cctactcctt aatatgtgtc tttggcctcc tgggcaacat tatggtggtg     180
atgacctttg ccttctacaa gaaagccaga tccatgactg acgtctacct gttgaacatg     240
gccatcacag acatactctt tgtcctcacc ctaccgttct gggcagttac tcatgccacc     300
aacacttggg ttttcagcga tgcactgtgt aaactgatga aggcacata tgcggtcaac     360 tttaactgtg ggatgctgct cctggcctgt atcagcatgg accggtacat tgccatcgtc     420
caggcaacca atctttccg ggtacgctcc agaacactga cgcacagtaa ggtcatctgt     480
gtggcagtgt ggttcatctc catcatcatc tcaagccctat catttatctt caacaagaaa     540
tacgagctgc aggatcgtga tgtctgtgag ccacggtaca ggtctgtctc agagcccatc     600
acgtggaagc tgctgggtat gggactggag ctgttctttg ggttcttcac ccctttgctg     660
tttatggtgt tctgctatct gttcattatc aagaccttgg tgcaggccca gaactccaag     720
aggcacagag caatccgagt cgtgatcgct gtggttctcg tgttcctggc ttgtcagatc     780
cctcacaaca tggtcctcct cgtgactgcg gtcaacacgg gcaaagtggg ccggagctgc     840
agcaccgaga agtcctcgc ctacaccagg aacgtggccg aggtcctggc tttcctgcat     900
tgctgcctca cccgtgttt gtatgcgttt attggacaga aattcagaaa ctacttcatg     960
aagatcatga aggatgtgtg gtgtatgaga aggaagaata gatgcctgg cttcctctgt    1020 gcccgggttt actcggaaag ctacatctcc aggcagacca gtgagaccgt cgaaaatgat    1080
aatgcatcgt cctttaccat g                                              1101

<210> SEQ ID NO 108
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

```
Trp Met His Trp Val Arg Gln Ala Pro Gly Gln Gly Leu Glu Trp Met
        35                  40                  45
Gly Val Ile Asp Pro Ser Asp Ser Tyr Thr Thr Tyr Ala Gln Lys Phe
50                  55                  60
Gln Gly Arg Val Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Asn Tyr Gly Val Asp Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 109
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109

| | | | | | |
|---|---|---|---|---|---|
| caggtgcagc | tggtgcagtc | tggggctgag | gtgaagaaac | ccggtgcaag | tgtgaaggtg | 60 |
| tcatgtaaag | catccggcta | tacattcact | aactactgga | tgcattgggt | gaggcaggct | 120 |
| ccaggacagg | gactggaatg | gatgggcgtg | atcgaccctt | cagattccta | caccacatat | 180 |
| gcccagaagt | tcagggcag | ggtgaccatg | acagtggaca | ctagcacctc | tacagtgtac | 240 |
| atggagctgt | ccagcctgag | aagtgaagat | acagcagtgt | actattgcgc | ccgcggcaat | 300 |
| tacggagtgg | actatgccat | ggattactgg | ggcagggta | ctctggtgac | cgtgtctagt | 360 |
| gcttctacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagag | agttgagccc | 660 |
| aaatcttgtg | acaaaactca | cacatgccca | ccgtgcccag | cacctgaact | cctgggggga | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcgggagga | gcagtacaac | 900 |
| agcacgtacc | gtgtggtcag | cgtcctcacc | gtcctgcacc | aggactggct | gaatggcaag | 960 |
| gagtacaagt | gcaaggtctc | caacaaagcc | ctcccagccc | ccatcgagaa | aaccatctcc | 1020 |
| aaagccaaag | ggcagccccg | agaaccacag | gtgtacaccc | tgcccccatc | ccgggaggag | 1080 |
| atgaccaaga | accaggtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctat | agcaagctca | ccgtggacaa | gagcaggtgg | 1260 |
| cagcagggga | acgtcttctc | atgctccgtg | atgcatgagg | ctctgcacaa | ccactacacg | 1320 |
| cagaagagcc | tctccctgtc | tcccgggaaa | tga | | | 1353 |

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

-continued

```
Tyr Gly Ala Thr Asn Leu Ala Asp Gly Val Pro Ser Arg Phe Ser Gly
         50                  55                  60
Ser Gly Ser Gly Arg Gln Tyr Ser Leu Thr Ile Ser Ser Leu Gln Pro
 65                  70                  75                  80
Glu Asp Phe Ala Thr Tyr Tyr Cys Gln Asn Val Leu Ile Thr Pro Tyr
                 85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 111
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
gacatccaga tgacccagtc tccatccagc ctgagtgcct cagtgggcga tagggtgact    60
atcacctgtc gggccagcga gaacatctac ggcgctctga attggtatca gcagaagcca   120
ggaaaagctc ccaagctgct gatctacggg gctacaaacc tggcagacgg tgtgcccagt   180
cgattctccg gtagcggctc tggacgacag tattcactga ctatctctag tctgcagcct   240
gaagatttcg ccacttacta ttgccagaat gtgctgatta ctccatatac ctttggcgga   300
gggacaaaac tggagatcaa gagaactgtg gccgctccca gtgtgttcat ttttccccct   360
tcagacgaac agctgaaatc agggaccgct tccgtggtgt gtctgctgaa caatttctac   420
cctcgcgagg caaaagtgca gtggaaggtg gataacgccc tgcagagtgg caattcacag   480
gagtccgtga ccgaacagga cagcaaagat tctacatata gtctgtcatc caccctgaca   540
ctgagcaagg ctgattacga gaagcacaaa gtgtatgcat gcgaagtgac tcatcagggg   600
ctgagctctc ccgtgaccaa gtcttttaac cggggtgaat gttga                   645
```

<210> SEQ ID NO 112
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Asp Ile Gln Met Thr Gln Ser Pro Ser Ser Leu Ser Ala Ser Val Gly

```
              1               5              10              15
Asp Arg Val Thr Ile Thr Cys Gly Ala Ser Glu Asn Ile Tyr Gly Ala
                           20              25              30

Leu Asn Trp Tyr Gln Arg Lys Pro Gly Lys Ala Pro Lys Leu Leu Ile
                35              40              45

Tyr Gly Ala Thr Asn Leu Ala Asp Gly Val Pro Ser Arg Phe Ser Gly
     50              55              60

Ser Gly Ser Gly Arg Asp Tyr Thr Leu Thr Ile Ser Ser Leu Gln Pro
 65              70              75              80

Glu Asp Phe Ala Thr Tyr Tyr Cys Gln Asn Val Leu Ile Thr Pro Tyr
                     85              90              95

Thr Phe Gly Gln Gly Thr Lys Leu Glu Ile Lys Arg Thr Val Ala Ala
                100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 113
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gacatccaga tgactcagag cccatccagc ctgtcagcct ccgtgggcga cagggtgacc      60
atcacatgtg gagcatccga gaacatctac ggggccctga attggtatca gaggaagccc     120
ggcaaagctc ctaagctgct gatctacggt gccacaaacc tggctgatgg cgtgccctcc     180
agattcagcg gctctggaag tgggcgcgac tatactctga ccatttctag tctgcagcca     240
gaggatttcg ccacctacta ttgccagaat gtgctgatca cccctacac ttttggtcag      300 ggcacaaaac tggaaattaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacctgacg      540 ctgagcaaag cagactacga gaaacacaaa gtctacgcct gcgaagtcac ccatcagggc     600
ctgagctcgc ccgtcacaaa gagcttcaac aggggagagt gttga                    645

<210> SEQ ID NO 114
<211> LENGTH: 56
<212> TYPE: PRT
<213> ORGANISM: Homo sapiens
```

-continued

```
<400> SEQUENCE: 114

Cys Cys Leu Gly Tyr Thr Asp Arg Ile Leu His Pro Lys Phe Ile Val
1               5                   10                  15

Gly Phe Thr Arg Gln Leu Ala Asn Glu Gly Cys Asp Ile Asn Ala Ile
            20                  25                  30

Ile Phe His Thr Lys Lys Lys Leu Ser Val Cys Ala Asn Pro Lys Gln
        35                  40                  45

Thr Trp Val Lys Tyr Ile Val Arg
    50                  55

<210> SEQ ID NO 115
<211> LENGTH: 53
<212> TYPE: PRT
<213> ORGANISM: Homo sapiens

<400> SEQUENCE: 115

Cys Cys Leu Lys Tyr Tyr Glu Lys Val Leu Pro Arg Arg Leu Val Val
1               5                   10                  15

Gly Tyr Arg Lys Ala Leu Asn Cys His Leu Pro Ala Ile Ile Phe Val
            20                  25                  30

Thr Lys Arg Asn Arg Glu Val Cys Thr Asn Pro Asn Asp Asp Trp Val
        35                  40                  45

Gln Glu Tyr Ile Lys
    50

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Gly Gly Gly Ser Gly Gly Gly Ser Gly Gly Gly Gly Ser
1               5                   10                  15

<210> SEQ ID NO 117
<211> LENGTH: 11
<212> TYPE: PRT
<213> ORGANISM: Homo sapiens

<400> SEQUENCE: 117

Trp Gly Gln Gly Thr Leu Val Thr Val Ser Ser
1               5                   10
```